(12) United States Patent
Polyak et al.

(10) Patent No.: US 9,556,430 B2
(45) Date of Patent: Jan. 31, 2017

(54) GENE METHYLATION AND EXPRESSION

(75) Inventors: Kornelia Polyak, Brookline, MA (US); Min Hu, Brighton, MA (US); Noga Qimron, Brighton, MA (US); Jun Yao, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1565 days.

(21) Appl. No.: 11/915,645

(22) PCT Filed: May 30, 2006

(86) PCT No.: PCT/US2006/020843
§ 371 (c)(1),
(2), (4) Date: Jun. 13, 2008

(87) PCT Pub. No.: WO2006/128140
PCT Pub. Date: Nov. 30, 2006

(65) Prior Publication Data
US 2009/0280478 A1    Nov. 12, 2009

Related U.S. Application Data

(60) Provisional application No. 60/685,104, filed on May 27, 2005.

(51) Int. Cl.
*C12Q 1/68* (2006.01)
*C12N 15/10* (2006.01)

(52) U.S. Cl.
CPC ......... *C12N 15/1093* (2013.01); *C12Q 1/6855* (2013.01); *C12Q 1/6881* (2013.01); *C12Q 2600/154* (2013.01); *C12Q 2600/158* (2013.01)

(58) Field of Classification Search
USPC .......................................... 546/113; 514/300
See application file for complete search history.

(56) References Cited

U.S. PATENT DOCUMENTS

| 2004/0096892 | A1 | 5/2004 | Wang | |
| 2004/0234960 | A1* | 11/2004 | Olek | C12Q 1/6827 435/6.11 |
| 2007/0054295 | A1* | 3/2007 | Spivack et al. | 435/6 |

FOREIGN PATENT DOCUMENTS

| DE | WO 0218632 A2 * | 3/2002 | ........... C12Q 1/6827 |
| WO | WO 2004/085621 A | 10/2004 | |
| WO | WO 2005/010180 | 2/2005 | |

OTHER PUBLICATIONS

Hu et al. Nature Genetics. 2005. 37(8); 899-905.*
Qui et al. Nature Genetics. 2008. 40(5):650-655.*
Bock. Epigenomics. 2009. 1(1): 99-110.*
Michels. Experimental Gerontology. 2010. 45: 297-301.*
Ying et al. Cardiovascular Research. 2000. 46: 172-179.*
Feng et al. PNAS. 2010. 107(19): 8689-8694.*
Nguyen. Journal of the National Cancer Institute. 2001. 93(19): 1465-1472.*
Lehmann. The American Journal of Pathology. 2002. 160(2): 605-612.*
Umbricht. Oncogene. 2001. 20: 3348-3353.*
Fackler. Cancer Research. 2004. 64: 4442-4452.*
Kurose. Human Molecular Genetics. 2001. 10(18): 1907-1913.*
Moinfar. Cancer Research. 2000. 60: 2562-2566.*
Tan. Carcinogenesis. 2002. 23(2): 231-236.*
AF327440.1 (Retrieved on May 16, 2013 from the internet: <http://www.ncbi.nlm.nih.gov/nucleotide/13195440?report=genbank&log$=nuclalign&blast_rank=9&RID=T9XJ8UHH01R>).*
NM_018266.1 (Retrieved on May 16, 2013 from the internet: <http://www.ncbi.nlm.nih.gov/nuccore/8922755?sat=24&satkey=6846816>).*
NM_138460.1 (Retrieved on May 16, 2013 from the internet: <http://www.ncbi.nlm.nih.gov/nuccore/61097911?sat=34&satkey=7335851>).*
U52112.2 (Retrieved on May 16, 2013 from the internet: <http://www.ncbi.nlm.nih.gov/nuccore/U52112.2?report=genbank&log$=seqview>).*
AC106738.3 (Retrieved on May 16, 2013 from the internet: <http://www.ncbi.nlm.nih.gov/nucleotide/24022394?report=genbank&log$=nuclalign&blast_rank=6&RID=T9Z9X2PS014>).*
Lehmann et al. American Journal of Pathology. 2002. 160(2): 605-612.*
Cullen et al. Contemporary Endocrinology of Breast Cancer. 1999. 11: 155-168.*
Rush et al. Analytical Biochemistry. 2002. 307: 191-201.*
Strichman-Almashanu et al. Genome Research. 2002. 12: 543-554.*
NCBI Reference Sequence: NM_031918.1 (Oct. 27, 2004).*
Dunn et al., Genomic signature tags (GSTs): A system for profiling genomic DNA; Genome Research, Cold Spring Harbor Laboratory Press, 12(11):1756-1765, Nov. 2002.
Saha et al., Using the Transcriptome to 1-10 Annotate the Genome, Nature Biotechnol., 20(5):508-512, May 2002.
Sidransky, Emerging Molecular Markers of Cancer, Nature Rev. Cancer, Natur Publishing Group, London, 2(3):210-219, Mar. 2002.
Cantile et al., "In vivo expression of the whole HOX gene network in human breast cancer", Eur. J. Can., 39:257-264 (2003).
Dai et al., "An AscI Boundary Library for the Studies of Genetic and Epigenetic alterations in CpG Islands", Genome Research, 12:1591-1598 (2002).
Evron et al., "Loss of Cyelin D2 Expression in the Majority of Breast Cancers Is Associated with Promoter Hypermethylation", Can. Res., 61:2782-2787 (2001).
Hu et al., "Distinct epigenetic changes in the stromal cells of breast cancers", Nature Genetics, 37(8):899-905 (2005).
Huang et al., "Methylation profiling of CpG islands in human breast cancer cells", Human Mol. Genetics., 8(3):459-470 (1999).
Kominsky et al., Loss of the tight junction protein claudin-7 correlates with histological grade in both ductal carcinoma in situ and invasive ductal carcinoma of the breast:, Oncogene, 22:2021-2033 (2003).

(Continued)

*Primary Examiner* — Joseph G Dauner
(74) *Attorney, Agent, or Firm* — Fish & Richardson P.C.

(57) ABSTRACT

The invention provides a method of analyzing the methylation status of all or part of an entire genome. Moreover, the invention features methods of and reagents for characterizing biological cells containing DNA that is susceptible to methylation. Such methods include methods of diagnosing cancer, e.g., breast cancer.

4 Claims, 60 Drawing Sheets

(56) References Cited

OTHER PUBLICATIONS

Paz et al., "Genetic unmasking of epigenetically silenced tumor suppressor genes in colon cancer cells deficient in DNA methyltransferases", Human Mol. Genetics., 12(17):2209-2219 (2003).
Shi et al., "Expressed CpG Island Sequence Tag Microarray for Dual Screening of DNA Hypermethylation and Gene Silencing in Cancer Cells", Can. Res., 62:3214-3220 (2002).
Umbricht, et al., "Hypermethylation of 14-3-3 σ 9stratifin) is an early event in breast cancer", Oncogene, 20:3348-3353 (2001).
Wang et al., "Digital karyotyping", PNAS, 99(25):16156-16161 (2002).
Makiyama et al., "Aberrant expression of HOX genes in human invasive breast carcinoma", Oncol. Rep., 2005, 13(4):673-679.
Svingen et al., "Altered HOX Gene Expression in Human Skin and Breast Cancer Cells", Can. Biol. Ther., 2003, 2(5):518-523.
Widschwendter et al., "DNA methylation and breast carcinogenesis", Oncogene, 21:5462-5482 (2002).
Canadian Intellectual Property Office, Office Action Dated Feb. 5, 2014 in CA Application No. 2,609,512.

* cited by examiner

LHX3

```
catgcagccagctttctgccccttcactttgcacagcacttgttacccaagaagggccagggcaa
ggaca▓▓ggtgcaaagc▓agtgtgtg▓ggctgtgctgggtgcaggtggctgagtgtcagct
gctgc▓aag▓atcagggt▓tgtgtggcaggactggggaagggg▓g▓gcaggttaaggag
g▓gcccaccctgctggcatctggccagccctccaacaatgcctccattatttcccag▓tc▓t
ggtgatggaatggcccttggggagggtggttcagg▓ggagacacaggctgggtcccctgctgt
ggggtccagagacctgggc▓ggctgtgtgcaagagctga▓ggcactggtcac▓ggggaacct
agcacccctggt▓gcccat▓ccccccagctgtgcctg▓atgccccttttttctagggg
cctccactccaac▓ctgtcc▓cactcttgcaggccag▓tcaggccctccc▓ccaccctggg
atctggaaactcactctctgcagtttccatctctgtcc▓cctgcagag▓g▓ggactttct
ttgcctggc▓ctggcctgca▓caccccttcct▓▓cctctgc▓cccttgc▓tttctgt
cct_cagtgtcctgctggggcttaccc_▓agtcc▓cccaaggtgcaga▓g▓g▓gccc▓ggc
ct▓ct▓gt▓▓ct▓agccc▓tttccagcagcat▓▓gccaccaggc▓agtgg▓g▓ag
a▓▓ctcctcctaggtcag▓tcccctggagggtt▓gggctcccaagtcc▓c▓▓t▓tg▓
▓gggcagggagcc▓ggagccactgggcctgg▓ctgtc▓▓gtgctgaaggagg▓cc▓ctg
cc▓ccc▓cc▓▓▓cc▓cccacctcc▓gggcccctct▓t▓ccc▓gtcccacccc▓
cctctgccc▓tgt▓GG▓cctccctccctggctgggttgggc▓cactcaaggcagcccc▓
ccct_caccctctgagacccagggtggc_▓tgcc▓ctcctccctaagctccaggccctgctgag
g▓ctgggatt▓c▓agttt▓cagcaag▓ggt▓tccagc▓cagggcaggaggacactgac
cctaccttctgg▓tgcagcctctggaaggcagtgcccaggc▓tgccc▓gggcagccccatg
▓tgatcaac
```

FIG. 6A

LHX3, minus strand
▓agtcc▓c ccaaggtgca ga▓▓g▓▓g▓
gccc▓▓ggcc t▓ct▓▓gt▓▓▓▓ct▓▓agc cc▓▓tttcca gcagcat▓▓▓▓gccaccagg
c▓agtgg▓▓▓▓aga▓▓▓c tcctcctagg tcag▓▓tccc ctggagggtt ▓▓gggctccc
aagtcc▓▓c▓▓▓t▓tg▓ gggcagggag cc▓▓ggagcc actgggcctg g▓▓ctgtc▓
▓gtgctgaa ggagg▓▓cc▓▓ctgcc▓▓cc c▓▓cc▓▓▓▓▓cc▓▓cccac ctcc▓▓gggc
ccctct▓▓t▓▓ccc▓▓gtcc cacccc▓▓c ctctgccc▓▓ tgt▓▓gg▓▓▓▓cctccctcc
ctgctgggt tgggc▓▓cac tcaaggcagc ccc▓▓ccct

FIG. 6B

LMX-1A catgtt▓ggc▓ggc▓ggaggacctgtagaggagaagaaa▓atg▓tctga▓tc▓tgcc▓
▓ctgggact▓g▓ccagcagccac▓cactcctgggaaagaactgagggagtgtccaggg▓ac
cagaatcagccaggaggatagggtccagccaagagaatgtagggtgggaggagagatcagtcaca
g▓aactgctctggctgatctgatttcacttgaagtcaaca▓ttatgtacttaggcctc▓ccc
cccaactg▓tttctccttctctgcccctcacccccacctacatcccttgccccaggttttc
catcc▓aatc▓actc▓ccccaacctata▓aaggtgggccct▓gga▓tctctgcaggaa▓
▓cagctactggggtatattgggtatataaagagtgggtaccctccct▓ag▓ac▓ggtccagg
ca▓▓gga▓atggggtttgcaatcc▓▓▓tccagc▓ccc▓ttg▓gccctcacctgcccc
aggt▓agaaggggcactgtaagggacc▓gaggg▓tcc▓cc▓cttctggactcctgg▓ct
g▓ctctgttggggtg▓▓▓caggagc▓gtgtg▓ggg▓▓gggaggtcctcc▓ccagt▓
▓gccagtgc▓ggaatgtctgcagaagcaaaagagt▓cct▓gggaggagccc▓gctggcc
gctcactcttggatgcatttcaagtcaactttcagaaaca▓cc▓cc▓agccacagcctaggc
a▓ggcagccttacttacctggtagg▓agctctctcccagtgactggagcagagagaagttg▓
gag▓ctgctggaagcttctgcc▓ggaagg▓t▓cccc▓agactgcagc▓gaggagc▓cc
ct▓gctt▓gag▓c▓gggagggagc▓gag▓aa▓c▓gc▓ctggctctgctcct▓G▓
▓CCcaggctgggc▓gga▓tggt▓▓agctgc▓gcctcc▓gga▓tcctaccagcc▓
▓t▓ctcctcag▓ggaggagagggccagttgcttctccaaggctaggagggaaggcagaggccc
agggtcctgggt▓agt▓gccctgctt▓▓c▓ggg▓gatcctgcagcttctgacaggggc▓
▓g▓ctg▓tg▓▓▓g▓g▓gagag

FIG. 7A

LMX1A, minus strand
agagag
aagttg▓ga g▓ctgctgg aagcttctgc c▓ggaagg▓ t▓cccc▓ agactgcagc
▓gaggagc▓ccct▓gct t▓gag▓c▓gggagggag c▓gag▓aa ▓c▓gc▓c
tggctctgct cct▓g▓ cccaggctgg gc▓gga▓t ggt▓▓agc tgc▓gcctt
cc▓gga▓t cctaccagcc ▓t▓ctc ctcag▓gga ggagaggg

FIG. 7B

TCF7L1

```
catgcccagctcggcggcgggg  g  g  g  g  g  gcag  ggggagg  g  gctcca
   c  ggg  gc  g  gaggggga  acct  ggg  aa  a  agctgatcccttccagga
aggggggg  aggagcaggagc  agcag  atag  cct  g  cag  ggacctaga  aggtc
aagt  tccctggtcaa  agt  gagaaccagagcagcagct  gact  gaggtaaggaagca
c  gccacccc  ggggatcc  gccctg  tc  ctcacc  ctcttgcctttgtgtctcct
c  cagg  gagagg  cc  cagcc  tc  ggacactttccagaagc  ggactattt  c
 aaggtatgtgcc  ctgggacagcccccactct  attcc  ctg  ctc  ctgctcagcc
gg  gcccac  tcccccttgcttgggtgga  caccttgccctc  cctttattgg  gca
gcccc  tgggg   tgggggg  ctgggtcccagctcc  cct  agcccctgc
g  ctgtcagtcc  ggggcctggcctcacct  ccttggtcttgtt  cagtgagaaggcctc
aggacag  ttctttaaaggacccc  ta ccctgggtaccccttcctgatgatcc  gacctg
agcagcc  tacctctccaa  gaccctgtctcc  gaggag  cac  tgagtgcc  t
GG   gggagggtggaggc  gcc  caggatg  cccc  ggcttggccatggagtgg
gggatggggccttctg  c  atcccaagcagaacttgtttg  gagttgaactactctctgg
gc  ag  aggctg ctggccagtgcctggatgaaag taaagttactttaacttttcccctc
ttg  ggttgaggttttggagtccacctctgggatcttccttggcctccagaat
```

FIG. 8A

TCF7L1, plus strand

```
░g acctgagcag cc░tacctctccaa░gac ccctgtctcc ░gaggag░
░cac░tga gtgcc░t░ gg░░c░gggagggtggg aggc░░gc c░caggatg
░cccc░gg cttggccatg gagtgggggatgggccttc tg░c░atc ccaagcagaa
cttgtttg░ gagttgaact actctctgg░gc░ag░░aggctg░
```

FIG. 8B

PRDM14 caacc▓gttcctgcaaaacccattgaagttccctttccttccttcttctcagtcctacaaaact
▓ttggtagggtctgtgggagc▓▓gggccctgccaacct▓gggctgggc▓ggagc▓ag▓
caggg▓gt▓gagggcaatggagcaag▓acagctccagg▓ctcctgggccct▓gctgggagg
gaagagc▓aggaccctgggt▓cac▓▓cagatggaga▓▓ctcccaga*gccccgggcagg*
*tccagggaccc*▓▓acctgctctggccag▓gtgtgaccc▓▓ggtcctgg▓gtcctgact
gcc▓caggggaggc▓▓ccacttttggctgcctaggatg▓c▓cctgaacctcttttccc
t▓▓ggcag▓tc▓ccacattccc▓ggttcct▓gaaactccaatcattcta*ccaggactat*
*tggggcctggggtag*ccct▓ggagc▓▓tgga▓agccctggccaggtgggag▓aagagcc
t▓g▓actgccagtcctcc▓cccc▓cac▓c▓ggaaaggatgg▓ttttaatagacaggca
gcaagttcac▓aggctgaagaatgaagccccttcagggc▓g▓ggtcttgagatcaatgagcc
caataagaaa

FIG. 16A

PRDM14, minus strand
▓▓acctg ctctggccca g▓▓gtgtgac
cc▓▓ggtc ctgg▓▓gtcc tgactgcc▓ caggggaggg g▓▓▓ccact tttggctgcc
ctaggatg▓ c▓cctgaac ctcttttccc t▓▓ggcag ▓tc▓ccac attccc▓gg
ttcct▓gaa actccaatca ttcta

FIG. 16B

ZCCHC14

```
gg  gaggcttgggatgta  gtggaggcttggagaggtggggcacacatttggggtg  acata
gaggcttaggatggggcttgggata  ggctgggggct  tggtgcaggttggagacctgggtgg
gagctctcagtgcaggctggagg  tgggt  gggggt     gtgcaggctggaggcttggagtg
cagagttggggatgcagacttggggtacagggcagagt  ggg  ggca  caccttgtggcag
gctgggcaagtgggcag     c  cc  gcc  GG    ccttgc  c  tggcccc  c  c
ttcaggctgctctggatctg  tgagctcctgg  cagcacctgcttctggtggaagctgaagg
c  ggtggttgaggccatggtgaacagcagcaggaactcat  cc  tg  gccct  ttaagc
tgcagcc  tagttgtggatgatggagt  atgtg  tgag  tg  gtagagca  cc  c  c
ct     ctgctc  agcccagcag  ccag  acaccagcagcttctg  caccacct  tc
tcaggttggtgaggctgcccaggt  gc  ggttgttggccttgatctc  agt    cag  ag
tggtagtcct
```

FIG. 17A

ZCCHC14, minus strand
tgg agg■tgggt ■gggggt■ ■gtgcaggc
tggaggcttg gagtgcagag ttggggatgc agacttgggg tacagggcag agct■ggg■
■ggca■cac cttgtggcag gctgggcaag tgggcag■■■c■cc■gc c■gg■■■c
ccttgc■c■■tggcccc■ c■■c■ttca ggctgctctg gatctg■■tg agctcctgg■
■

FIG. 17B

Hoxd4

```
gcaggtcaggaccatgtggctggctgct■gctgtggg■caaaggggtggggatgggggggt
ggggaggactccattttcagagcagggggaaggctgtggaggag■ggggatttccaaaatgct
tgagggttc■gacctggtggtgggcccagaagaaggagcacatttggggatcc■caagcctgg
ggtatgtgggtgtgtttgaggaggtgggtgggagtgag■tgtg■c■gggagaggg■ggagg
gaggaagcaag■agcttgggag■■gggagggc■■ggcct■ggg■■ccaggaagtga
g■g■gagg■aggggcctaactagtggc■gg■ctgacctgcctgtcctgtctgttttgtc
t■cagtgaacccaactacac■gtggggaacccaag■gtcc■aa■gcctacacc■gcag
caagtcctagaactggaaaaagaatttcattttaacaggtatctgacaagg■c■t■gattga
aat■ctcacaccctgtgtctgt■gag■ccagatcaagatctggttccagaac■gaggatga
agtggaaaaaagatcataagctgcccaacactaaaggcaggtcat■tcctcatcttcctcctca
cttgctcct
```

FIG. 18A

HOXD4, plus strand
ag aagaaggagc acatttgggg
atcc■■caag cctggggtat gtgggtgtgt ttgaggaggt gggtgggagt gag■■tgtg■
■c■■gggaga ggg■■ggagg gaggaagcaa g■■agcttgg gag■■■■■g ggagggc■■
■ggcct■■gg g■■■■ccagg aagtgag■■g ■■gagg■■ag gggcctaact agtggc■■gg
■■

FIG. 18B

SLC9A3R1 gaactagctgggagtgggccctgcagtgaggcaggggtgggccagggagaacaaggcaagagga
gcttcattca*gggttcctgagcctttgtgagccac*tca tttttaccactcacttaac tctt
tgttgttggggtgaggggtcct agcctggatttgggtatgaaaacccaggcaagaaagacctg
cccaagcctttaaaggaatgcaaagtcatcctctagccaccccagagat aaaggctggggat
tgagtctcctgcagatggtgg gcctcctggggctggcaagtgggacagaggcccataagccc
tcctgGG ccttcccacccctct gccctctccactc*ccagctggggatttgggtttcag*ag
cagcctggcacacacaccccaccccaccagaatctcactcccagcttcctatgactattcatta
gtattcacaacaatgggaaagtctgggtgtgcacagggattttttacagttagaaagtgtttaa
gtcaatgacctcactgggcctcagcaaccctgggaggcagatggcagtcagaatgatccataaat
gacctgccccaggtcacacagctcctaaacaggggagctggaacctggctgggagccttgactat
ccactgctca

FIG. 19A

SLC9A3R1, plus strand
tca■tttttt accactcact
taac■tctt tgttgttggg gtgaggggtc ct■agcctg gatttgggta tgaaaaccca
ggcaagaaag acctgcccaa gcctttaaag gaatgcaaag tcatcctcta gccacccca
gagat■aaa ggctggggat tgagtctcct gcagatggtg g■gcctcct ggggctggca
agttgggaca gaggcccata agccctcctg gg■■cctt cccacccctc t■gccctct
ccactc

FIG. 19B

LOC389333

```
g   gctc  tcc  gg   caggcttgt       c  aat         ct     gaggctgggcca  gc
ct   gggccttgg   ggggc   aattatct   ta      aagtggc   agacttagccttctccag
gacca   tgggtgctg   ggc   tttcc   ggtctcaggttc   ac   ccc   tggacc   aagg
tgg   ctgct   gggc   gggcct   gggctcagttttctggccaa   c   tctgca   aagcc
      g   gcctgcagggggcccag   act   tccagggaac   gtg   caggagcagc   gggg
   G      gc   ccttggggactctgggc   gggg   cagct   atctga   cttgggca
ctgtc   gggcctgg   gg      g   ccctcctccagagccacctccacacact   aactg   ct
gggg   gcaggacttggccca   gggc   cagctctaggtaggtggcccagc   ggagccaccat
   gggacctgggactgg   tgggac      g   ggaga   ctggccc   g   gcaagggctgatga
aggc   gctc   tgaactgttgttg   cct   at   tctg   c   gagcagc   aacaggggt
c   a   c   a
```

FIG. 20A

Loc389333, minus strand
a
a■c■tctg ca■aagcc■■■g■gcct gcaggggcc cag■act■ tccagggaac
■gtg■cag gagcagc■g ggg■■g■ ■c■gc■c ccttggggga ctctggggc■
■gggg■cag ct■atctga ■cttgggca ctgtc■ggg cctgg■gg■■g■ccct
cctccagagc cacctccaca cact■aact g■ctgggg■■gcaggactt ggccca■gg
gc■

FIG. 20B

CDC42EP5 gcac░cctggcca░ccct░ggctctcttaaaggagc░caccccaccccagggcaatcat░
░gacc░gaccaggcctc░ggtgacacatc░gctctcagagg░ccaggaccctatcattcat
ccctttcca░tgcaaagtgaaaagt*cagagcccgggcacacaccttggc*░tttatgtatacag
aagtggggtgc░gg░ggaaggg░░gggaatgagggaacctagaggc░atga░t░ttca
gct░aggtc░░ttgggg░gcag░ggcctggggggctg░tcc░ggg░gggttc░░
t░ggcttgg░gcagc░cctc░GG░░c░c░tccatga░cccagcac░░*tccagcat
ggagggccccagatccagg*tggaaggacagcag░ggt░gcagg░aggg░ctg░gactg░
gga░g░gg░g░g░gggag░░gggcccc░░ggggg░cc░gggct░ggggg░gc
c░c░c░tgg░gctcaggaa░aggtgtccc░aagg░t░c░c░░ccca░tgcag
░tgtgc░gaagt░c░ag░g░░gagatggacaggg░c░░atcaggc░cttcttgg
gctg░░gg

FIG. 21A

CDC42Ep5, minus strand
■tttatgta tacagaagtg gggtgc■gg ■ggaaggg■■gggaatg agggaaccta
gaggc■atg a■t■ttca gct■aggtc ■■ttgggg ■gcag■gg cctgggggg
ctg■tcc■ ggg■gggtt c■■■t■gg cttgg■gca gc■cctc■ gg■■■c■
■tccatga■ cccagcac■ ■t

FIG. 21B

Cxorf12

```
catgg    gcag   g   c    g    gt   gg   aggagg   gagc   ggtga   tcac    cttccccc
cact    ccct    cac    ctt    ccctgggcccaagcctcttaaaggaccctg    ctgcct
  g    ggggtgggggt    g    ctgc         ctgggctaaagct    agt    ctcagatcaggtg
cagg    cagg    ccc    ccca    gcccccac    gg    agcctca    cctc    ccctggg
agc    ccatcttgccacttcccct    cc    gc    tc    gg    tcaatag    actttcagcaca
aacaaagatgg    g    g    gcatct    gaaatgcc    gatgagactgctaacccctc    a
ct    gccc    cccccttgggaa    gtctct    ggttgataaggga    ca    cc    aagaa
```

FIG. 22A

Cxorf12, plus strand
ccctg▮ctgcct▮▮g▮ggggtg ggggt▮g▮
ctgc▮    ctgggctaaa gct▮agt▮ ▮ctcagatc aggtgcagg▮cagg▮▮c
cc▮cccca▮gccccccca c▮gg▮agc ctcca▮cct c▮ccctggg agc▮ccatc
ttgccacttc ccct▮cc▮ gc▮tc▮▮ gg▮tcaata g▮a

FIG. 22B

FNDC1, plus strand

TGGGGCAGTGTTACAATTACAGAAAAGGGAGAGG■AGGTC■CTGAGTCCTTGGCCTGGGCAACAAGGCACACT
GAAAACTGGGTTCCTTTT■ACC■CAT■TG■■CCCTAGAAATGACAGCCAGA■GAGCAGGGTCTAAGGA■
■CTGAAAACCCCTGA■TGGG■■C■GGTG■GGTAGGGA■TGGAAGGACTGGGCTAGCCACAGGAACTACA
G■CTG■GAC■GGTGAGGGGTCC■GCC■AGTCCCCACTTGGGG■CAGAGGTGTTTCTGTAAGGGGACAAA
GGGCACTCCT■■G■■ATGGG■ACTTC

FIG. 30

FOXC1 plus strand

A■GGGCAAAGCCTTTCTTCCACACCCACAGCCAAGG■■■TC■TGCAGGGGCACA■CCTTCTGCTCCAGCC
CCAGGAAGG■CTTT■CCCTGCAGTCCTC■A■GC■GCTCC■C■CAC■■■CACCCTGGCTC■GCAGAC
TCTGGGGCCTGGGGACT■CCCACCCTG■■G■■CCCCCACATGAGC■AGGTTGGGAGGCTG■GGGCCT
CTGTCCTCCCAGGC■TGGAGTG■G■GC■CTCTGAGTC■CTGGGGA

FIG. 31

PACAP minus stran

AA■C■TCTGCA■AAGCC■■G■GCCTGCAGGGGGCCCAG■ACT■TCCAGGGAAC■GTG■CAGGAGC
AGC■GGGG■■G■■C■GC■CCCTTGGGGGACTCTGGGC■GGGG■CAGCT■ATCTGA■CTTGGGC
ACTGTC■GGGCCTGG■GG■■G■CCCTCCTCCAGAGCCACCTCCACACACT■AACTG■CTGGGG■GCA
GGACTTGGCCCA■GGGC■CAGCTCTAGGTAGGTGGCCCAG■GGAGCCACCAT■GGGACCTGGGACTGG■T
GGGAC■■G■GGAGA■CTGGCCC■G■G

FIG. 32

DDN, minus strand

```
TTAGGCCCAGCAGCTT■GGAGCCCAGGGCAGAGC■AGGGGT■GAAGTGG■GTGGTCCAG■G■■C■GC
■GGGCTGGG■■GACCCCAGGGCCCTA■C■GGGCCTG■AGAAGC■TGTCC■TATC■C■CCACACA
GCCCCTGACT■GACA■GA■AAGCTGAGGAGCTCAG■TCCATAG■GCTCCTCTGATGGAAG■ACACAGAA
GCCC■GG■CCTCCTGG■GAATGAGAGGACCCTGCC■AGGTTGGAAACAGTT■
```

FIG. 33

LHX1 plus stran

CTCTGGACTCCATCTCTCACTTCTCTCTGGATTCTGGGCTCTCCTGGCT█GCCTGGGTGCCCAAAGTGGCAGTG
TGGGCCTCTGTGGGATGGAGAGG███C█GGGCCTGACCTGAATGA███CATGTTGAGGC█GTCTCCTG██C
CAGCTGCT███GATGTGG█GGTGGGCTTGGGTGTAGCAG█AAGG██GCCTTCAG██T

FIG. 34

SOX13 plus strand

AATGG■■ATCT■GCCCACTGCAACCTCCCACTCC■GGTTCAAG■ATTCTCCTGCCTCAGCCTCC■AGTA
GGGGGTTACAGG■■CCACCA■CC■GCTAATTTTTGTATTTTTAGTAGAGA■GGGTTTCAC■TGTTAGC
CAGGATTGTCTCCATCTCCTGACCT■TGATC■CCCC■T■GCCTCCCAAAGTGCTGGGATTACAGG■TGAG
CCAC■■CC■GCAGAGATCAGGTTCTTAAGGGAAGTC■GAGAAATGGGGTTTTTAAAAAACC■AGT

FIG. 35

DTX1 plus strand
TGCTGCTCCTG▓GCTCTCAGCCAGCCCTTTGCACTCCCAACTG▓TCCCAGACCCTG▓CC▓GCTTCAGTGGG
GCTTCT▓CCTCCCTC▓GTCTGGGCCCCTTCTC▓A▓GCTCCTGC▓AAGGGGG▓TCCCTGCCCCCTTGTT
CCCTCTCCA▓GTGTCCTGGAAGGCCTGGGTGGC▓CAGAA▓CA▓GGGGAGGGGTG▓G▓TGGACCCT▓GG
▓G▓CCTGGACTG▓GCTC▓GAGCTGGGCTGGGGA▓AGGGGGA▓AGGGGGG▓GGGGCC▓TGGGCA▓
CCCCACCCCACT▓TGCT▓A

FIG. 36

HOXA10 minus strand

```
T  GGG  C  C  C  CTCTTTCTCCTCTGCTGC  C  C  TCTCC  GCAGC  C  C  C  C  CTGTC
 AACTTGAAGTTGC  G    CC  TTGCAGC  C   C   C  C    GAGGT  C  TGGC  C  GGGGCCCC
TTCT  G  CTCTTGTCCC  GGGTAGT  GAGGAGG  AGGTTTTC  GGGTGC  TAGGCTGTCT  AAAAAC
TGGT  AAAGCCTGTGGCAGGA  C  TTCCTGCCCA  GTGCTATAGAAATTGGA  AGACTG  GGGGTGGGG
TGGTGGTAGA  TTGGC  AGCTCTTGGCCAGCA  T  CCAGGCA  C  GC  CTGGG
```

FIG. 37

SLC9A3R1, plus strand
TCA█TTTTTACCACTCACTTAAC█TCTTTGTTGTTGGGGTGAGGGGTCCT█AGCCTGGATTTGGGTA
TGAAAACCCAGGCAAGAAAGACCTGCCCAAGCCTTTAAAGGAATGCAAAGTCATCCTCTAGCCACCCCA
GAGAT█AAAGGCTGGGGATTGAGTCTCCTGCAGATGGTGG█GCCTCCTGGGGCTGGCAAGTTGGGACA
GAGGCCCATAAGCCCTCCTGGG█ █CCTTCCCACCCCTCT█GCCCTCTCCACTC

FIG. 38

CDC42Ep5, minus strand

```
 TTTATGTATACAGAAGTGGGGTGC  GG  GGAAGGG     GGGAATGAGGGAACCTAGAGGC  ATGA   T
TTCAGCT  AGGTC    TTGGGG  GCAG  GGCCTGGGGGGCTG  TCC   GGG  GGGTTC     T  GG
CTTGG  GCAGC  CCTC  GG    C    TCCATGA  CCCAGCAC      T
```

FIG. 39

GENE METHYLATION AND EXPRESSION

CROSS REFERENCE TO RELATED APPLICATIONS

This application is a national phase filing under 35 U.S.C. §371 of international application number PCT/US2006/020843, filed May 30, 2006, which claims priority to U.S. Provisional Application No. 60/685,104, filed May 27, 2005. The entire content of the prior applications is incorporated herein by reference in its entirety.

STATEMENT REGARDING FEDERALLY SPONSORED RESEARCH

This invention was made with government support under grant numbers P50CA89393 and CA94074 awarded by The National Institutes of Health and DAMD 17-02-1-0692 and W81XWH-04-1-0452 awarded by the Department of The Army. The government has certain rights in the invention.

TECHNICAL FIELD

This invention relates to epigenetic gene regulation, and more particularly to DNA methylation and its effect on gene expression, and its use as a marker of a particular cell type and/or disease state.

BACKGROUND

Epigenetic changes (e.g., changes in the levels of DNA methylation), as well as genetic changes, can be detected in cancer cells and stromal cells within tumors. In order to develop more discriminatory diagnostic methods and more effective therapeutic methods it is important that these epigenetic effects be defined and characterized.

SUMMARY

The inventors have developed a method of assessing the level of methylation in an entire, or part of a, genome. They call this method Methylation Specific Digital Karyotyping (MSDK). The MSDK method can be adapted to establish a test genomic methylation profile for a test cell of interest. By comparing the test profile to control profiles obtained with defined cells types, the test cell can be identified. The MSDK method can also be used to identify genes in a test cell (e.g., a cancer cell) the methylation of which is altered (increased or decreased) relative to a corresponding control cell (e.g., a normal cell of the same tissue as the cancer cell). This information provides the basis for methods for discriminating whether a test cell of interest (a) is the same as a control cell (e.g., a normal cell) or (b) is different from a control cell but is, for example, a pathologic cell such as a cancer cell. Such methods include, for example, assessing the level of DNA methylation or the level of expression of genes of interest, or the level of DNA methylation in a particular chromosomal area in test cells and comparing the results to those obtained with control cells.

More specifically, the invention features a method of making a methylation specific digital karyotyping (MSDK) library. The method includes:
providing all or part of the genomic DNA of a test cell;
exposing the DNA to a methylation-sensitive mapping restriction enzyme (MMRE) to generate a plurality of first fragments;
conjugating to one terminus or to both termini of each of the first fragments a binding moiety, the binding moiety comprising a first member of an affinity pair, the conjugating resulting in a plurality of second fragments;
exposing the plurality of second fragments to a fragmenting restriction enzyme (FRE) to generate a plurality of third fragments, each third fragment containing at one terminus the first member of the affinity pair and at the other terminus the 5' cut sequence of the FRE or the 3' cut sequence of the FRE;
contacting the plurality of third fragments with an insoluble substrate having bound thereto a plurality of second members of the affinity pair to the contacting resulting in a plurality of bound third fragments, each bound third fragment being a third fragment bound via the first and second members of the affinity pair to the insoluble substrate;
conjugating to free termini of the bound third fragments a releasing moiety, the releasing moiety comprising a releasing restriction enzyme (RRE) recognition sequence and, 3' of the recognition sequence of the RRE, either the 5' cut sequence of the FRE or the 3' cut sequence of the FRE, the conjugating resulting in a plurality of bound fourth fragments, each bound fourth fragment (i) containing at one terminus the recognition sequence of the RRE and (ii) being bound via the first member of the affinity pair at the other terminus and the second member of the affinity pair to the insoluble substrate; and
exposing the bound fourth fragments to the RRE, the exposing resulting in the release from the insoluble substrate of a MSDK library, the library comprising a plurality of fifth fragments, each fifth fragment comprising the releasing moiety and a MSDK tag, the tag consisting of a plurality of base pairs of the genomic DNA. Thus, the method results in the production of a plurality of MSDK tags.

In the method, the MMRE can be, e.g., AscI, the FRE can be, e.g., NlaIII, and the RRE can be, e.g., MmeI. The binding moiety can further include a 5' or 3' cut sequence of the MMRE. The binding moiety can also further include, between the 5' or 3' recognition sequence of the MMRE and the first member of an affinity pair, a linker nucleic acid sequence comprising a plurality of base pairs. The releasing moiety can further include, 5' of the RRE recognition sequence, an extender nucleic acid sequence comprising a plurality of base pairs. The test cell can be a vertebrate cell and the vertebrate test cell can be a mammalian test cell, e.g., a human test cell. Moreover the test cell can be a normal cell or, for example, a cancer cell, e.g., a breast cancer cell. The first member of the affinity pair can be biotin, iminobiotin, avidin or a functional fragment of avidin, an antigen, a haptenic determinant, a single-stranded nucleotide sequence, a hormone, a ligand for adhesion receptor, a receptor for an adhesion ligand, a ligand for a lectin, a lectin, a molecule containing all or part of an immunoglobulin Fc region, bacterial protein A, or bacterial protein G. The insoluble substrate can include, or be, magnetic beads.

Also provided by the invention is a method of analyzing a MSDK library. The method includes: providing a MSDK library made by the above-described method; and identifying the nucleotide sequences of one tag, a plurality of tags, or all of the tags. Identifying the nucleotide sequences of a plurality of tags can involve: making a plurality of ditags, each ditag containing two fifth fragments ligated together; forming a concatamer containing a plurality of ditags or ditag fragments, wherein each ditag fragment contains two MSDK tags; determining the nucleotide sequence of the concatamer; and deducing, from the nucleotide sequence of the concatamer, the nucleotide sequences of one or more of the MSDK tags that the concatamer contains. The ditag fragments can be made by exposing the ditags to the FRE. The method can further include, after making a plurality of ditags and prior to forming the concatamers, the number (abundance) of individual ditags is increased by PCR. The method can further include determining the relative frequency of some or all of the tags.

Another aspect of the invention is an additional method of analyzing a MSDK library. The method includes: providing a MSDK library made by the above-described method; identifying a chromosomal site corresponding to the sequence of a tag selected from the library. The method can further involve determining a chromosomal location, in the genome of the test cell, of an unmethylated full recognition sequence of the MMRE closest to the identified chromosomal site. These two steps can be repeated with a plurality of tags obtained from the library in order to determine the chromosomal location of a plurality of unmethylated recognition sequences of the MMRE. The identification of the chromosomal site and the determination of the chromosomal location can be performed by a process that includes comparing the nucleotide sequence of the selected tag to a virtual tag library generated using the nucleotide sequence of the genome or the part of a genome, the nucleotide sequence of the full recognition sequence of the MMRE, the nucleotide sequence of the full recognition sequence of the FRE, and the number of nucleotides separating the full recognition sequence of the RRE from the RRE cutting site.

In another aspect, the invention provides a method of classifying a biological cell. The method includes: (a) identifying the nucleotide sequences of one tag, a plurality of tags, or all of the tags in an MSDK library made as described above and determining the relative frequency of some or all of the tags, thereby obtaining a test MSDK profile for the test cell; (b) comparing the test MSDK profile to separate control MSDK expression profiles for one or more control cell types; (c) selecting a control MSDK profile that most closely resembles the test MSKD profile; and (d) assigning to the test cell a cell type that matches the cell type of the control MSDK profile selected in step (c). The test and control cells can be vertebrate cells, e.g., mammalian cells such as human cells. The control cell types can include a control normal cell and a control cancer cell of the same tissue as the normal cell. The control normal cell and the control cancer cell can be breast cells or of a tissue selected from colon, lung, prostate, and pancreas. The test cell can be a breast cell or of a tissue selected from of colon, lung, prostate, and pancreas. The control cell types can include cells of different categories of a cancer of a single tissue and the different categories of a cancer of a single tissue can include, for example, a breast ductal carcinoma in situ (DCIS) cell and an invasive breast cancer cell. The different categories of a cancer of a single tissue can alternatively include, for example, two or more of: a high grade DCIS cell, an intermediate grade DCIS cell; and a low grade DCIS cell. The control cell types can include two or more of: a lung cancer cell; a breast cancer cell; a colon cancer cell; a prostate cancer cell; and a pancreatic cancer. In addition, the control cell types can include an epithelial cell obtained from non-cancerous tissue and a myoepithelial cell obtained from non-cancerous tissue. Furthermore, the control cells can also include stem cells and differentiated cells derived therefrom (e.g., epithelial cells or myoepithelial cells) of the same tissue type. The control stem and differentiated cells therefrom can be of breast tissue, or of a tissue selected from colon, lung, prostate, and pancreas. The control stem and differentiated cells derived therefrom can be normal or cancer cells (e.g., breast cancer cells) or obtained from a cancerous tissue (e.g., breast cancer).

Another embodiment of the invention is a method of diagnosis. The method includes: (a) providing a test breast epithelial cell; (b) determining the degree of methylation of one or more C residues in a DNA sequence (e.g., in a gene) in the test cell, wherein the DNA (e.g., the gene) is selected from the AscI sites identified by the MSDK tags listed in Table 5, wherein the one or more C residues are C residues in CpG sequences; and (c) comparing the degree of methylation of the one or more residues to the degree of methylation of corresponding one or more C residues in a corresponding gene in a control epithelial cell obtained from non-cancerous breast tissue, wherein an altered degree of methylation of the one or more C residues in the test epithelial cell compared to the control epithelial cell is an indication that the test epithelial cell is a cancer cell. The altered degree of methylation can be a lower degree of methylation or a higher degree of methylation. The altered degree of methylation can be in the promoter region of the gene, an exon of the gene, an intron of the gene, or a region outside of the gene (e.g., in an intergenic region). The gene can be, for example, PRDM14 or ZCCHC14.

The invention provides another method of diagnosis. The method includes:
(a) providing a test colon epithelial cell; (b) determining the degree of methylation of one or more C residues in a DNA sequence (e.g., in a gene) in the test cell, wherein the DNA sequence (e.g., the gene) is selected from those identified by the MSDK tags listed in Table 2, wherein the one or more C residues are C residues in CpG sequences; and (c) comparing the degree of methylation of the one or more residues to the degree of methylation of corresponding one or more C residues in a corresponding gene in a control epithelial cell obtained from non-cancerous colon tissue, wherein an altered degree of methylation of the one or more C residues in the test epithelial cell compared to the control epithelial cell is an indication that the test epithelial cell is a cancer cell. The altered degree of methylation can be a lower degree of methylation or a higher degree of methylation. In addition, the altered degree of methylation can be in the promoter region of the gene, an exon of the gene, an intron of the gene, or a region outside of the gene (e.g., an intergenic region). The gene can be, for example, LHX3, TCF7L1, or LMX-1A.

Another method of diagnosis featured by the invention involves: (a) providing a test myoepithelial cell obtained from a test breast tissue; (b) determining the degree of methylation of one or more C residues in a DNA sequence (e.g., in a gene) in the test cell, wherein the DNA sequence (e.g., the gene) is selected from those identified by the MSDK tags listed in Table 10, wherein the one or more C residues are C residues in CpG sequences; and (c) comparing the degree of methylation of the one or more residues to the degree of methylation of corresponding one or more C residues in a corresponding gene in a control myoepithelial cell obtained from non-cancerous breast tissue, wherein an altered degree of methylation of the one or more C residues in the test myoepithelial cell compared to the control myoepithelial cell is an indication that the test breast tissue is cancerous tissue. The altered degree of methylation can be a lower degree of methylation or a higher degree of methylation. In addition, the altered degree of methylation can be in the promoter region of the gene, an exon of the gene, an intron of the gene, or a region outside of the gene (e.g., an intergenic region). The gene is can be, for example, HOXD4, SLC9A3R1, or CDC42EP5.

Yet another method of diagnosis embodied by the invention involves:
(a) providing a test fibroblast obtained from a test breast tissue; (b) determining the degree of methylation of one or more C residues in a DNA sequence (e.g., in a gene) in the test cell, wherein the DNA sequence (e.g., the gene) is selected from those identified by the MSDK tags listed in Tables 7 and 8, wherein the one or more C residues are C residues in CpG sequences; and (c) comparing the degree of methylation of the one or more residues to the degree of methylation of corresponding one or more C residues in a corresponding gene in a control fibroblast obtained from non-cancerous breast tissue, wherein an altered degree of methylation of the one or more C residues in the test fibroblast compared to the control fibroblast is an indication that the test breast tissue is cancerous tissue. The altered degree of methylation can be a lower degree of methylation or a higher degree of methylation. In addition, the altered degree of methylation can be in the promoter region of the gene, an exon of the gene, an intron of the gene, or a region outside of the gene (e.g., an intergenic region). The gene can be, for example, Cxorf12.

In another aspect, the invention includes a method of determining the likelihood of a cell being an epithelial cell or a myoepithelial cell. The method involves:
(a) providing a test cell; (b) determining the degree of methylation of one or more C residues in a DNA sequence (e.g., in a gene) in the test cell, wherein the DNA sequence (e.g., the gene) is selected from those identified by the MSDK tags listed in Table 12, wherein the one or more C residues are C residues in CpG sequences; and (c) comparing the degree of methylation of the one or more residues to the degree of methylation of corresponding one or more C residues in a corresponding gene in a control myoepithelial cell and to the degree of methylation of corresponding one or more C residues in a corresponding gene in a control epithelial cell, wherein the test cell is: (i) more likely to be a myoepithelial cell if the degree of methylation in the test sample more closely resembles the degree of methylation in the control myoepithelial cell; or (ii) more likely to be an epithelial cell if the degree of methylation in the test sample more closely resembles the degree of methylation in the control epithelial cell. The C residues can be in the promoter region of the gene, an exon of the gene, an intron of the gene, or in a region outside of the gene (e.g., an intergenic region). The gene can be, for example, LOC389333 or CDC42EP5.

In another aspect, the invention includes a method of determining the likelihood of a cell being a stem cell, an differentiated luminal epithelial cell or a myoepithelial cell. The method involves: (a) providing a test cell; (b) determining the degree of methylation of one or more C residues in a DNA sequence (e.g., in a gene) in the test cell, wherein the DNA sequence (e.g., the gene) is selected from those identified by the MSDK tags listed in Table 15 or 16, wherein the one or more C residues are C residues in CpG sequences; and (c) comparing the degree of methylation of the one or more residues to the degree of methylation of corresponding one or more C residues in a corresponding gene in a control stem cell, to the degree of methylation of corresponding one or more C residues in a corresponding gene in a control differentiated luminal epithelial cell, and to the degree of methylation of corresponding one or more C residues in a corresponding gene in a control myoepithelial cell, wherein the test cell is: (i) more likely to be a stem cell if the degree of methylation in the test sample more closely resembles the degree of methylation in the control stem cell; (ii) more likely to be a differentiated luminal epithelial cell if the degree of methylation in the test sample more closely resembles the degree of methylation in the control epithelial cell; or (iii) more likely to be a myoepithelial cell if the degree of methylation in the test sample more closely resembles the degree of methylation in the control myoepithelial cell. The C residues can be in the promoter region of the gene, an exon of the gene, an intron of the gene, or in a region outside of the gene (e.g., an intergenic region). The gene can be, for example, SOX13, SLC9A3R1, FNDC1, FOXC1, PACAP, DDN, CDC42EP5, LHX1, and HOXA10.

The invention also features a method of diagnosis that involves: (a) providing a test cell from a test tissue; (b) determining the degree of methylation of one or more C residues in a PRDM14 gene in the test cell, wherein the one or more C residues are C residues in CpG sequences; and (c) comparing the degree of methylation of the one or more residues to the degree of methylation of corresponding one or more C residues in the PRDM14 gene in a control cell obtained from non-cancerous tissue of the same tissue as the test cell, wherein an altered degree of methylation of the one or more C residues in the test cell compared to the control cell is an indication that the test cell is a cancer cell. The altered degree of methylation can be a lower degree of methylation or a higher degree of methylation. In addition, the altered degree of methylation can be in the promoter region of the gene, an exon of the gene, an intron of the gene, or a region outside of the gene (e.g., an intergenic region). The test and control cells can be breast cells or of a tissue selected from colon, lung, prostate, and pancreas.

Another embodiment of the invention is a method of diagnosis that includes: (a) providing a test sample of breast tissue comprising a test epithelial cell; (b) determining the level of expression in the test epithelial cell of a gene selected from those listed in Table 5, wherein the gene is one that is expressed in a breast cancer epithelial cell at a substantially altered level compared to a compared to a normal breast epithelial cell; and (c) classifying the test cell as: (i) a normal breast epithelial cell if the level of expression of the gene in the test cell is not substantially altered compared to a control level of expression for a normal breast epithelial cell; or (ii) a breast cancer epithelial cell if the level of expression of the gene in the test cell is substantially altered compared to a control level of expression for a normal breast epithelial cell. The gene is can be, for example, PRDM14 or ZCCHC14. The alteration in the level of expression can be an increase in the level of expression or a decrease in the level of expression.

Another aspect of the invention is a method of diagnosis that includes:
(a) providing a test sample of colon tissue comprising a test epithelial cell;
(b) determining the level of expression in the test epithelial cell of a gene selected from those listed in Table 2, wherein the gene is one that is expressed in a colon cancer epithelial cell at a substantially altered level compared to a compared to a normal colon epithelial cell; and (c) classifying the test cell as: (i) a normal colon epithelial cell if the level of expression of the gene in the test cell is not substantially altered compared to a control level of expression for a normal colon epithelial cell; or (ii) a colon cancer epithelial cell if the level of expression of the gene in the test cell is substantially altered compared to a control level of expression for a normal colon epithelial cell. The gene can be, for example, LHX3, TCF7L1, or LMX-1A. The alteration in the level of expression can be an increase in the level of expression or a decrease in the level of expression.

Another method of diagnosis included in the invention involves: (a) providing a test sample of breast tissue comprising a test stromal cell; (b) determining the level of expression in the stromal cell of a gene selected from those listed in Tables 7, 8, and 10, wherein the gene is one that is expressed in a cell of the same type as the test stromal cell at a substantially altered level when present in breast cancer tissue than when present in normal breast tissue; and (c) classifying the test sample as: (i) normal breast tissue if the level of expression of the gene in the test stromal cell is not substantially altered compared to a control level of expression for a control cell of the same type as the test stromal cell in normal breast tissue; or (ii) breast cancer tissue if the level of expression of the gene in the test stromal cell is substantially altered compared to a control level of expression for a control cell of the same type as the test stromal cell in normal breast tissue. The test and control stromal cells can be myoepithelial cells and the genes can be those listed in Table 10, e.g., HOXD4, SLC9A3R1, or CDC32EP5. Alternatively, the test and control stromal cells can be fibroblasts and the genes can be those listed in Tables 7 and 8, e.g., Cxorf1. The alteration in the level of expression can be an increase in the level of expression or a decrease in the level of expression.

In another aspect, the invention includes a method of determining the likelihood of a cell being an epithelial cell or a myoepithelial cell. The method includes: (a) providing a test cell; (b) determining the level of expression in the test sample of a gene selected from the group consisting of those identified by the MSDK tags listed in Table 12; (c) determining whether the level of expression of the selected gene in the test sample more closely resembles the level of expression of the selected gene in (i) a control myoepithelial cell or (ii) a control epithelial cell; and (d) classifying the test cell as: (i) likely to be a myoepithelial cell if the level of expression of the gene in the test cell more closely resembles the level of expression of the gene in a control myoepithelial cell; or (ii) likely to be an epithelial cell if the level of expression of the gene in the test cell more closely resembles the level of expression of the gene in a control epithelial cell. The gene can be, for example, LOC389333 or CDC42EP5.

In another aspect, the invention includes a method of determining the likelihood of a cell being a stem cell, a differentiated luminal epithelial cell, or a myoepithelial cell. The method includes: (a) providing a test cell; (b) determining the level of expression in the test sample of a gene selected from the group consisting of those identified by the MSDK tags listed in Table 15 or 16; (c) determining whether the level of expression of the selected gene in the test sample more closely resembles the level of expression of the selected gene in (i) a control stem cell, (ii) a control differentiated luminal epithelial cell, or (iii) a control myoepithelial cell; and (d) classifying the test cell as: (i) likely to be a stem cell if the level of expression of the gene in the test cell more closely resembles the level of expression of the gene in a control stem cell; (ii) likely to be an differentiated luminal epithelial cell if the level of expression of the gene in the test cell more closely resembles the level of expression of the gene in a control differentiated luminal epithelial cell, or (iii) likely to be a myoepithelial cell if the level of expression of the gene in the test cell more closely resembles the level of expression of the gene in a control myoepithelial cell. The gene can be, for example, SOX13, SLC9A3R1, FNDC1, FOXC1, PACAP, DDN, CDC42EP5, LHX1, and HOXA10.

Also embodied by the invention is a method of diagnosis that includes:
(a) providing a test cell; (b) determining the level of expression in the test cell of a PRDM14 gene; and (c) classifying the test cell as: (i) a normal cell if the level of expression of the gene in the test cell is not substantially altered compared to a control level of expression for a control normal cell of the same tissue as the test cell; or (ii) a cancer cell if the level of expression of the gene in the test cell is substantially altered compared to a control level of expression for a control normal cell of the same tissue as the test cell. The alteration in the level of expression can be an increase in the level of expression or a decrease in the level of expression. The test and control cells can be breast cells or of a tissue selected from colon, lung, prostate, and pancreas.

The invention also provides a single stranded nucleic acid probe that includes: (a) the nucleotide sequence of a tag selected from those listed in Tables 2, 5, 7, 8, 10, 12, 15 and 16; (b) the complement of the nucleotide sequence; or (c) the AscI sites defined by the MSDK tags listed in Tables 2, 5, 7, 8, 10, 12, 15, and 16.

In another aspect, there is provided an array containing a substrate having at least 10, 25, 50, 100, 200, 500, or 1,000 addresses, wherein each address has disposed thereon a capture probe that includes: (a) a nucleic acid sequence consisting of a tag nucleotide sequence selected from those listed in Tables 2, 5, 7, 8, 10, 12, 15 and 16; (b) the complement of the nucleic acid sequence; or (c) the AscI sites defined by the MSDK tags listed in Tables 2, 5, 7, 8, 10, 12, 15, and 16.

The invention also features a kit comprising at least 10, 25, 50, 100, 200, 500, or 1,000 probes, each probe containing: (a) a nucleic acid sequence comprising a tag nucleotide sequence selected from those listed in Tables 2, 5, 7, 8, 10, 12, 15 and 16; (b) the complement of the nucleic acid sequence; (c) the AscI sites defined by the MSDK tags listed in Tables 2, 5, 7, 8, 10, 12, 15, and 16.

Another aspect of the invention is kit containing at least 10, 25, 50, 100, 200, 500, or 1,000 antibodies each of which is specific for a different protein encoded by a gene identified by a tag selected from the group consisting of the tags listed in Tables 2, 5, 7, 8, 10, 12, 15 and 16.

As used herein, an "affinity pair" is any pair of molecules that have an intrinsic ability to bind to each other. Thus, affinity pairs include, without limitation, any receptor/ligand pair, e.g., vitamins (e.g., biotin)/vitamin-binding proteins (e.g., avidin or streptavidin); cytokines (e.g., interleukin-2)/cytokine receptors (e.g., interleukin-2); hormones (e.g., steroid hormones)/hormone receptors (e.g., steroid hormone receptors); signal transduction ligands/signal transduction receptors; adhesion ligands/adhesion receptors; death domain molecule-binding ligands/death domain molecules; lectins (e.g., pokeweed mitogen, pea lectin, concanavalin A, lentil lectin, phytohemagglutinin (PHA) from Phaseolus vulgaris, peanut agglutinin, soybean agglutinin, Ulex europaeus agglutinin-I, Dolichos biflorus agglutinin, Vicia villosa agglutinin and Sophora japonica agglutinin/lectin receptors (e.g., carbohydrate lectin receptors); antigens or haptens (e.g., trinitrophenol or biotin)/antibodies (e.g., antibody specific for trinitrophenol or biotin); immunoglobulin Fc fragments/immunoglobulin Fc fragment binding proteins (e.g., bacterial protein A or protein G). Ligands can serve as first or second members of an affinity pair, as can receptors. Where a ligand is used as the first member of the affinity pair the corresponding receptor is used as the second member of the affinity pair and where a receptor is used as the first member of the affinity pair, the corresponding receptor is used as the second member of the affinity pair. Functional fragments of polypeptide first and second members of affinity pairs are fragments of the full-length, mature first or second members that are shorter than the full-length, mature first or second members but have at least 25% (e.g., at least: 30%; 40%; 50%; 60%; 70%; 80%; 90%; 95%; 98%; 99%; 99.5%; 100%; or even more) of the ability of the full-length, mature first or second members to bind to corresponding second or first members, respectively.

The nucleotide sequences of all the identified genes in Tables 2, 5, 7, 8, 10, 12, 15 and 16 are available on public genetic databases (e.g., GeneBank). These sequences are incorporated herein by reference.

As used herein, a "substantially altered" level of expression of a gene in a first cell (or first tissue) compared to a second cell (or second tissue) is an at least 2-fold (e.g., at least: 2-; 3-; 4-; 5-; 6-; 7-; 8-; 9-; 10-; 15-; 20-; 30-; 40-; 50-; 75-; 100-; 200-; 500-; 1,000-; 2000-; 5,000-; or 10,000-fold) altered level of expression of the gene. It is understood that the alteration can be an increase or a decrease.

As used herein, breast "stromal cells" are breast cells other than epithelial cells.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., assessing the methylation of an entire genome, will be apparent from the following description, from the drawings and from the claims.

DESCRIPTION OF DRAWINGS

FIG. 6A is a depiction of the nucleotide sequence (SEQ ID NO:3) of a region of the LHX3 gene containing the MSDK tag sequence (bold and underlined) that identified the relevant AscI recognition sequence (in capital letters and underlined) and multiple CpG dinucleotides (shaded). The segment of SEQ ID NO:3 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp −196 to bp +172 (relative to the LHX3 gene transcription initiation site) and thus the last 23 CpG in the sequenced segment are within the promoter region and the first 26 CpG are in exon 1.

FIG. 6B is a depiction of the nucleotide sequence (SEQ ID NO:1545) of a region of the LHX3 gene within SEQ ID NO:3 containing the relevant AscI site (bold and underlined) and multiple CpG dinucleotides (shaded).

FIG. 7A is a depiction of the nucleotide sequence (SEQ ID NO:5) of a region of the LMX-1A gene containing the MSDK tag sequence (bold and underlined) that identified the relevant AscI recognition sequence (in capital letters and underlined) and multiple CpG dinucleotides (shaded). The segment of SEQ ID NO:5 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp −842 to bp −609 (relative to the LMX-LA gene transcription initiation site) and thus the whole of the sequenced segment is within the promoter region.

FIG. 7B is a depiction of the nucleotide sequence (SEQ ID NO:1546) of a region of the LMX-1A gene within SEQ ID NO:5 containing the relevant AscI recognition sequence (in bold and underlined) and multiple CpG dinucleotides (shaded).

FIG. 8A is a depiction of the nucleotide sequence (SEQ ID NO:4) of a region of the TCF7L1 gene containing the MSDK tag sequence (bold and underlined) that identified the relevant AscI recognition sequence (in capital letters and underlined) and multiple CpG dinucleotides (shaded). The segment of SEQ ID NO:4 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp +782 to bp +1003 (relative to the TCF7L1 gene transcription initiation site) and thus the first six CpG in the sequenced segment are within exon 1 and the last 19 CpG are in intron 3-4.

FIG. 8B is a depiction of the nucleotide sequence (SEQ ID NO:1547) of a region of the TCF7L1 gene within SEQ ID NO:4 containing the relevant AscI recognition sequence (in bold and underlined) and multiple CpG dinucleotides (shaded).

FIG. 15 provides the above-listed information for the HCFC1 gene as well as the Cxorf12 gene. As can be seen for the figure, the two genes are located relatively close together on the X chromosome.

FIG. 16A is a depiction of the nucleotide sequence (SEQ ID NO:1) of a region of the PRDM14 gene containing the relevant AscI recognition sequence (in capital letters and underlined) and multiple CpG dinucleotides (shaded). The segment of SEQ ID NO:1 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp +666 to bp +839 (relative to the PRDM14 gene transcription initiation site) and thus the whole sequenced segment is within intron 1-2.

FIG. 16B is a depiction of the nucleotide sequence (SEQ ID NO:1548) of a region of the PRDM14 gene within SEQ ID NO:1 containing the relevant AscI recognition sequence (in bold and underlined) and multiple CpG dinucleotides (shaded).

FIG. 17A is a depiction of the nucleotide sequence (SEQ ID NO:2) of a region of the ZCCHC14 gene containing the relevant AscI recognition sequence (in capital letters and underlined) and multiple CpG dinucleotides (shaded). The segment of SEQ ID NO:2 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp +79 to bp +292 (relative to the ZCCHC14 gene transcription initiation site) and thus the last 14 CpG in the sequenced segment are within exon 1 and the first 7 CpG are in intron 1-2.

FIG. 17B is a depiction of the nucleotide sequence (SEQ ID NO:1549) of a region of the ZCCHC14 gene within SEQ ID NO:2 containing the relevant AscI recognition sequence (in bold and underlined) and multiple CpG dinucleotides (shaded).

FIG. 18A is a depiction of the nucleotide sequence (SEQ ID NO:6) of a region of the HOXD4 gene containing the relevant AscI recognition sequence (in capital letters and underlined) and multiple CpG dinucleotides (shaded). The segment of SEQ ID NO:6 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp +986 to bp +1,189 (relative to the HOXD4 gene transcription initiation site) and thus the whole sequenced segment is within intron 1-2.

FIG. 18B is a depiction of the nucleotide sequence (SEQ ID NO:1550) of a region of the HOXD4 gene within SEQ ID NO:6 containing the relevant AscI recognition sequence (in bold and underlined) and multiple CpG dinucleotides (shaded).

FIG. 19A is a depiction of the nucleotide sequence (SEQ ID NO:7) of a region of the SLC9A3R1 gene containing the relevant AscI recognition sequence (in capital letters and underlined) and multiple CpG dinucleotides (shaded). The segment of SEQ ID NO:7 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp +11,713 to bp +11,978 (relative to the SLC9A3R1 gene transcription initiation site) and thus the whole sequenced segment is within intron 1-2.

FIG. 19B is a depiction of the nucleotide sequence (SEQ ID NO:1551) of a region of the SLC9A3R1 gene within SEQ ID NO:7 containing the relevant AscI recognition sequence (in bold and underlined) and multiple CpG dinucleotides (shaded).

FIG. 20A is a depiction of the nucleotide sequence (SEQ ID NO:10) of a region of the LOC389333 gene containing the relevant AscI recognition sequence (in capital letters and underlined) and multiple CpG dinucleotides (shaded). The segment of SEQ ID NO:10 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp +518 to bp +762 (relative to the LOC389333 gene transcription initiation site) and thus the last 10 CpG in the sequenced segment are within exon 1 and the first 21 CpG are within intron 1-2.

FIG. 20B is a depiction of the nucleotide sequence (SEQ ID NO:1552) of a region of the LOC389333 gene within SEQ ID NO:10 containing the relevant AscI recognition sequence (in bold and underlined) and multiple CpG dinucleotides (shaded).

FIG. 21A is a depiction of the nucleotide sequence (SEQ ID NO:8) of a region of the CDC42EP5 gene containing the relevant AscI recognition sequence (in capital letters and underlined) and multiple CpG dinucleotides (shaded). The segment of SEQ ID NO:8 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp +7,991 to bp +8,193 (relative to the CDC42EP5 gene transcription initiation site) and thus the whole the sequenced segment is within exon 3.

FIG. 21B is a depiction of the nucleotide sequence (SEQ ID NO:1553) of a region of the CDC42EP5 gene within SEQ ID NO:8 containing the relevant AscI recognition sequence (in bold and underlined) and multiple CpG dinucleotides (shaded).

FIG. 22A is a depiction of the nucleotide sequence (SEQ ID NO:9) of a region of the Cxorf12 gene containing the MSDK tag sequence (bold and underlined) that identified the relevant AscI recognition sequence (in capital letters and underlined) and multiple CpG dinucleotides (shaded). The segment of SEQ ID NO:9 subjected to methylation-detecting sequence analysis starts at the nucleotide after the 3' end of the forward PCR primer target sequence (shown in italics and underlined) used for the sequencing analysis and ends at the nucleotide before the 3' end of the reverse PCR primer target sequence (shown in italics and underlined). The sequenced segment spans bp −838 to bp −639 (relative to the Cxorf12 gene transcription initiation site) and thus the whole sequenced segment is within the promoter region.

FIG. 22B is a depiction of the nucleotide sequence (SEQ ID NO:1555) of a region of the Cxorf12 gene within SEQ ID NO:9 containing the MSDK tag sequence (bold and underlined) that identified the relevant AscI recognition sequence (in capital letters and underlined) and multiple CpG dinucleotides (shaded).

The X-axis represents the ratio of normalized tags from the indicated libraries in the various comparisons. CD44/All indicates the comparison of mammary stem cells (CD44+) against all differentiated cells (CD10+, CD24+, and MUC1+).

Figure 27A:
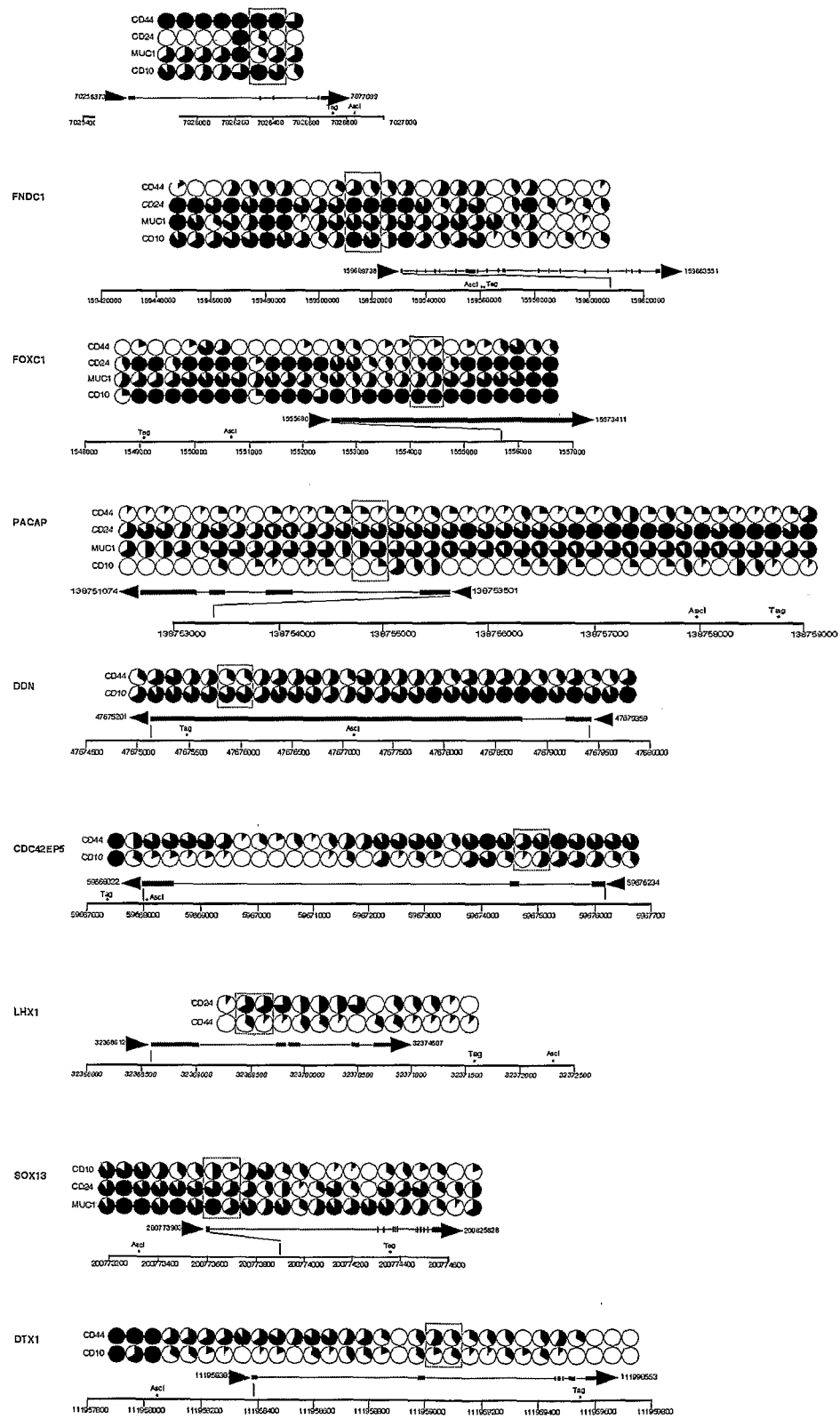

FIG. 27A is a series of diagrammatic representations of the results of a methylation-detecting sequence analysis of segments of the SLC9A3R1 gene region, the FNDC1 gene region, the FOXC1 gene region, the PACAP gene region, the DDN gene region, the CDC42EP5 gene region, the LHX1 gene region, the SOX13 gene region, and the DTX gene region. The circles represent potential methylation sites (CpG) in the analyzed segment of SEQ ID NOs:7, 8, and 11-18. The order of the circles (starting from the left of the rows of circles) is that of the CpG dinucleotides in the analyzed segments of SEQ ID NOs:7, 8, and 11-18 (starting from the 5' end of the analyzed segment nucleotide sequences). The analyses were performed on DNA isolated from CD44+, CD24+, MUC1+, and CD10+ cell populations. Each circle is a pie chart with the amount of shading indicating the frequency (0-100%) at which the relevant potential methylation site was found to be methylated. The top lines under the circles are linear depictions of the relevant gene transcripts and include the exons (shaded boxes) and introns (lines between the shaded boxes) and the bottom line under the circles are linear depictions of the chromosome on which the genes are located. On the chromosome depictions are shown the locations of the MSDK tag sequences that indicated the locations of the relevant AscI recognition sequences, which locations are also shown. The numbering on the bottom lines indicates the base pair (bp) numbers on the chromosomes and the numbering on the top lines indicate the bp numbers, in the chromosomes, of the transcription start sites and termination sites. The transcription initiation sites and the directions of transcription are also shown.

Figure 27B:
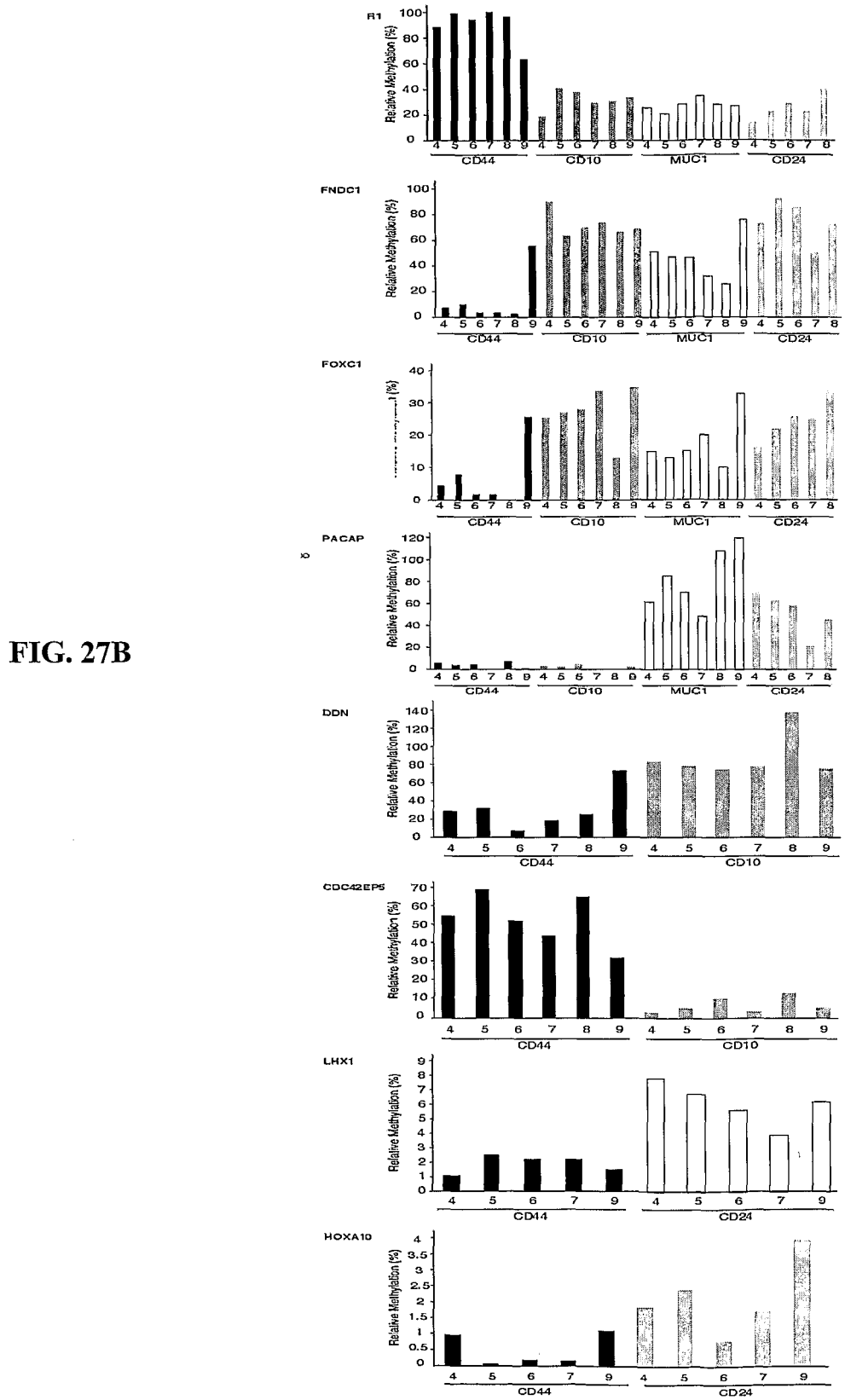

FIG. 27B is a series of bar graphs showing the results of quantitative methylation specific PCR (qMSP) analyses of the SLC9A3R1, FNDC1, FOXC1, PACAP, DDN, CDC42EP5, LHX1, and HOXA10 genes in CD44+, CD10+, MUC1+, and CD24+ cells populations from women of different ages (18-58 years old) and reproductive history. The average Ct value for each gene was normalized against the ACTB value. The data ("Relative expression (%)") are percentages relative to the RPL39 value.

Figure 28:
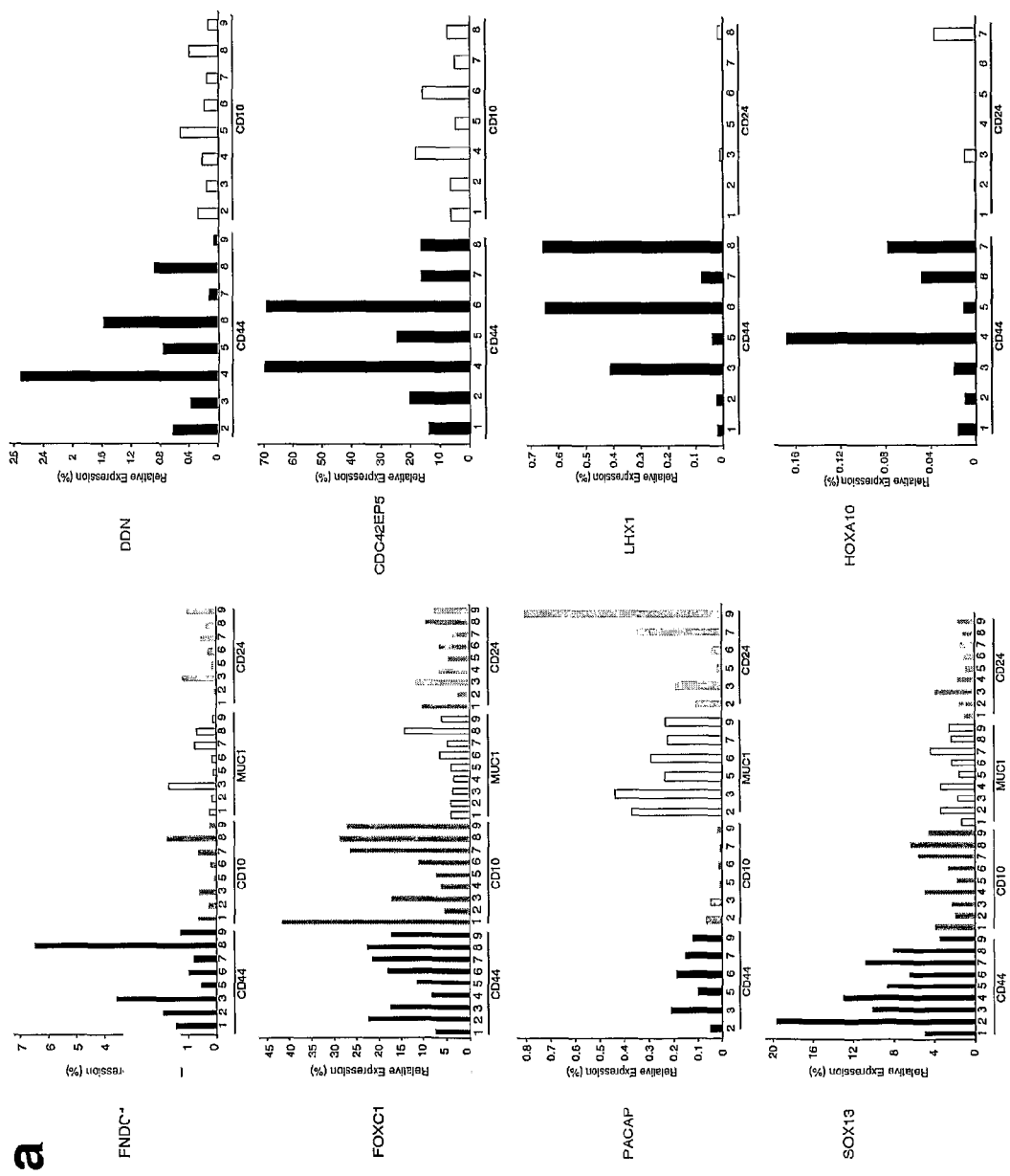

FIG. 28 is a series of bar graphs showing the results of expression analyses of the SLC9A3R1, FNDC1, FOXC1, PACAP, DDN, CDC42EP5, LHX1, and HOXA10 genes in CD44+, CD10+, MUC1+, and CD24+ cells isolated from normal breast tissue. The average Ct value for each gene was normalized against the RPL39 value. The data ("Relative expression (%)") are percentages relative to the RPL39 value.

Figure 29A:
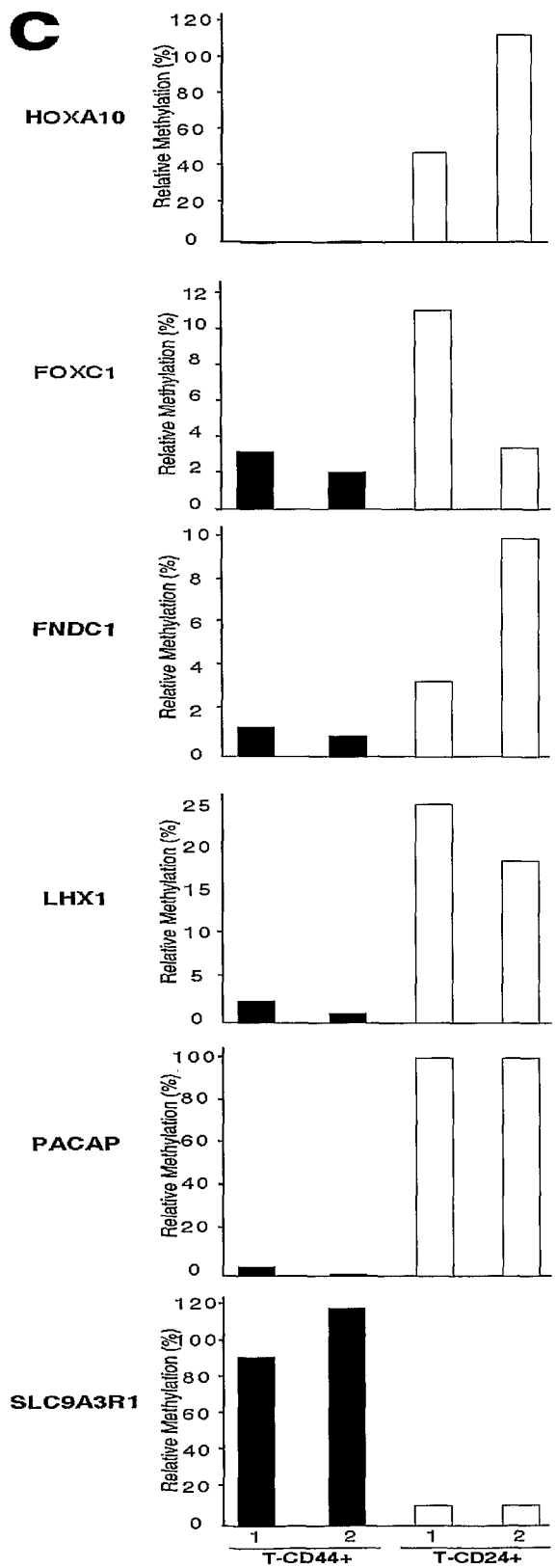
Figure 29B:
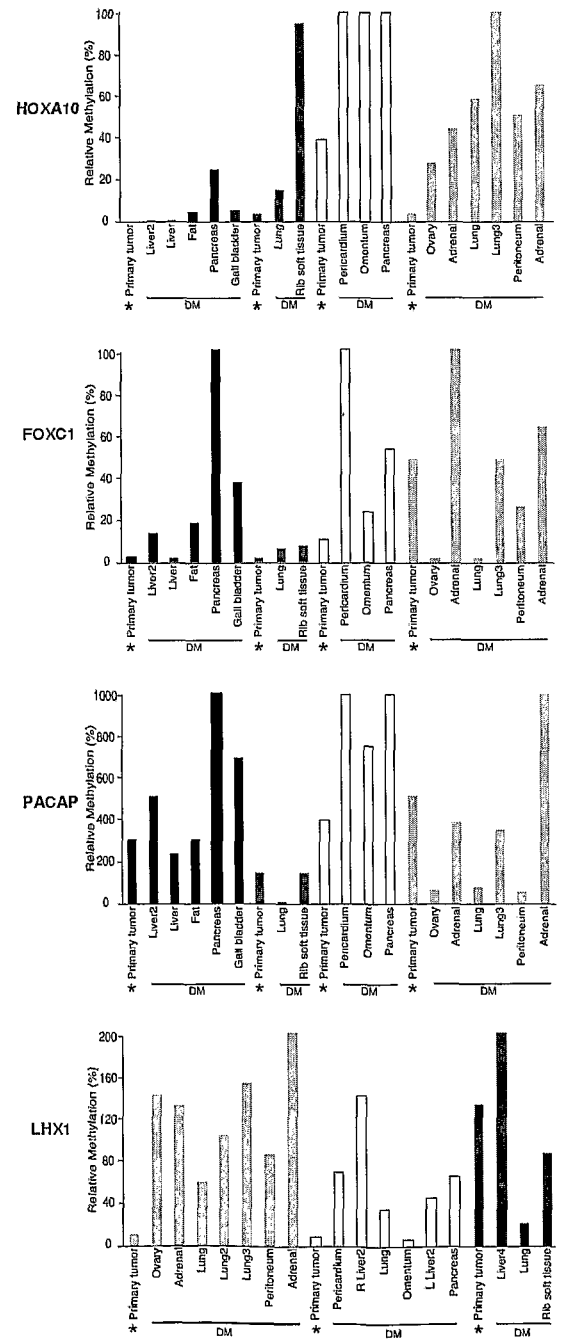

FIGS. 29A-29B are a series of bar graphs depicting the results of quantitative methylation specific PCR (qMSP) analyses of DNA from (A) the SLC9A3R1, FNDC1, FOXC1, PACAP, LHX1, and HOXA10 genes in putative breast cancer stem cells (T-EPCR+) and cells with more differentiated phenotype from the same tumor (T-CD24+), and (B) the HOXA10, FOXC1, PACAP, and LHX1 genes from matched primary tumors (indicated by a star) and distant metastases (DM) collected from different organs. The average Ct value for each gene was normalized against the RPL39 value (see Example 1). The data ("Relative expression (%)") are percentages relative to the RPL39 value.

FIG. 30 is a depiction of the nucleotide sequence (SEQ ID NO:11) of a region of the FNDC1 gene containing the relevant AscI recognition sequence (in bold and underlined) and multiple CpG dinucleotides (shaded). The sequenced segment spans bp −285 to bp −614 (relative to the FNDC1 gene transcription initiation site) and thus the whole sequenced segment is within the promoter region.

FIG. 31 is a depiction of the nucleotide sequence (SEQ ID NO:12) of a region of the FOXC1 gene containing the relevant AscI recognition sequence (in bold and underlined) and multiple CpG dinucleotides (shaded). The sequenced segment spans bp 5250 to bp 4976 (relative to the FOXC1 gene transcription initiation site) and thus the whole sequenced segment is within the promoter region.

FIG. 32 is a depiction of the nucleotide sequence (SEQ ID NO:13) of a region of the PACAP gene containing the relevant AscI recognition sequence (in bold and underlined) and multiple CpG dinucleotides (shaded). The sequenced segment spans bp 4404 to bp 4736 (relative to the PACAP gene transcription initiation site) and thus the whole sequenced segment is within the promoter region.

FIG. 33 is a depiction of the nucleotide sequence (SEQ ID NO:14) of a region of the DDN gene containing the relevant AscI recognition sequence (in bold and underlined) and multiple CpG dinucleotides (shaded). The sequenced segment spans bp 2108 to bp 2290 (relative to the PACAP gene transcription initiation site) and thus the whole sequenced segment is within exon 2.

FIG. 34 is a depiction of the nucleotide sequence (SEQ ID NO:15) of a region of the LHX1 gene containing the relevant AscI recognition sequence (in bold and underlined) and multiple CpG dinucleotides (shaded). The sequenced segment spans bp 3600 to bp 3810 (relative to the LHX1 gene transcription initiation site) and thus the whole sequenced segment is within introns 3-4.

FIG. 35 is a depiction of the nucleotide sequence (SEQ ID NO:16) of a region of the SOX13 gene containing the relevant AscI recognition sequence (in bold and underlined) and multiple CpG dinucleotides (shaded). The sequenced segment spans bp 669 to bp 374 (relative to the SOX13 gene transcription initiation site) and thus the whole sequenced segment is within the promoter area.

FIG. 36 is a depiction of the nucleotide sequence (SEQ ID NO:17) of a region of the DTX gene containing the relevant AscI recognition sequence (in bold and underlined) and multiple CpG dinucleotides (shaded). The sequenced segment spans bp 228 to bp 551 (relative to the DTX gene transcription initiation site) and thus the whole sequenced segment is within the promoter area.

FIG. 37 is a depiction of the nucleotide sequence (SEQ ID NO:18) of a region of the HOXA10 gene containing the relevant AscI recognition sequence (in bold and underlined) and multiple CpG dinucleotides (shaded). The sequenced segment spans bp 4270 to bp 4634 (relative to the HOXA10 gene transcription initiation site) and thus the whole sequenced segment is within the promoter area.

FIG. 38 is a depiction of the nucleotide sequence (SEQ ID NO:1543) of a region of the SLC9A3R1 gene containing the relevant AscI recognition sequence (in bold and underlined) and multiple CpG dinucleotides (shaded). The sequenced segment spans bp 11713 to bp 11978 (relative to the SLC9A3R1 gene transcription initiation site) and thus the whole sequenced segment is within introns 1-2.

FIG. 39 is a depiction of the nucleotide sequence (SEQ ID NO:11544) of a region of the CDC42Ep5 gene containing the relevant AscI recognition sequence (in bold and underlined) and multiple CpG dinucleotides (shaded). The sequenced segment spans bp 7855 to bp 8058 (relative to the CDC42Ep5 gene transcription initiation site) and thus the whole sequenced segment is within exon 3.

DETAILED DESCRIPTION

Various aspects of the invention are described below.

Methylation Specific Digital Karyotyping (MSDK)

MSDK is a method of assessing the relative level of methylation of an entire genome, or part of a genome, of a cell of interest. The cell can be any DNA-containing biological cell in which the DNA is subject to methylation, e.g., prokaryotic cells (e.g., bacteria) or eukaryotic cells (e.g., yeast cells, protozoan cells, invertebrate cells, or vertebrate (e.g., mammalian) cells).

Vertebrate cells can be from any vertebrate species, e.g., reptiles (e.g., snakes, alligators, and lizards), amphibians (e.g., frogs and toads), fish (e.g., salmon, sharks, or trout), birds (e.g., chickens, turkeys, eagles, or ostriches), or mammals. Mammals include, for example, humans, non-human primates (e.g., monkeys, baboons, or chimpanzees), horses, bovine animals (e.g., cows, oxen, or bulls), whales, dolphins, porpoises, pigs, sheep, goats, cats, dogs, rabbits, gerbils, guinea pigs, hamsters, rats, or mice. Vertebrate and mammalian cells can be any nucleated cell of interest, e.g., epithelial cells (e.g., keratinocytes), myoepithelial cells, endothelial cells, fibroblasts, melanocytes, hematological cells (e.g., macrophages, monocytes, granulocytes, T lymphocytes (e.g., CD4+ and CD8+ lymphocytes), B-lymphocytes, natural killer (NK) cells, interdigitating dendritic cells), nerve cells (e.g., neurons, Schwann cells, glial cells, astrocytes, or oligodendrocytes), muscle cells (smooth and striated muscle cells), chondrocytes, osteocytes. Also of interest are stem cells, progenitor cells, and precursor cells of any of the above-listed cells. Moreover the method can be applied to malignant forms of any of cells listed herein.

The cells can be of any tissue or organ, e.g., skin, eye, peripheral nervous system (PNS; e.g., vagal nerve), central nervous system (CNS; e.g., brain or spinal cord), skeletal muscle, heart, arteries, veins, lymphatic vessels, breast, lung, spleen, liver, pancreas, lymph node, bone, cartilage, joints, tendons, ligaments, gastrointestinal tissue (e.g., mouth, esophagus, stomach, small intestine, large intestine (e.g., colon or rectum)), genitourinary system (e.g., kidney, bladder, uterus, vagina, ovary, ureter, urethra, prostate, penis, testis, or scrotum). Cancer cells can be of any of these organs and tissues and include, without limitation, breast cancers (any of the types and grades recited herein), colon cancer, prostate cancer, lung cancer, pancreatic cancer, melanoma.

MSDK can be performed on an entire genome of a cell, e.g., whole DNA extracted from an entire cell or the nucleus of a cell. Alternatively, it can be carried out on part of a cell, e.g., by extracting DNA from mutant cells lacking part of a genome, chromosome microdissection, or subtractive/differential hybridization. The method is performed on double-stranded DNA and, unless otherwise stated, in describing MSDK, the term "DNA" refers to double-stranded DNA.

Method of Making a MSDK Library

In the first step of the MSDK, genomic DNA is exposed to a methylation-sensitive mapping restriction enzyme (MMRE) that cuts the DNA at sites having the recognition sequence for the relevant MMRE. The MMRE can be any MMRE. In eukaryotic cells, methylation generally occurs at C nucleotides in CpG dinucleotide sequences in DNA. The term "CpG" refers to dinucleotide sequences that occur in DNA and consist of a C nucleotide and G nucleotide immediately 3' of the C nucleotide. The "p" in "CpG" denotes the phosphate group that occurs between the C and G nucleoside residues in the CpG dinucleotide sequence.

The MMRE recognition sequence can contain one, two, three, or four C residues that are susceptible to methylation. If one (or more) of the C residues in a MMRE recognition sequence is methylated, the MMRE does not cut the DNA at the relevant MMRE recognition sequence Examples of useful MMRE include, without limitation, AscI, AatII, AciI, AfeI, AgeI, AsisI AvaI, BceAI, BssHI, ClaI, EagI, Hpy99I, MluI, NarI, NotI, SacII, or ZraAI The AscI recognition sequence is GGCGCGCC and thus contains two methylation sites (CpG sequences). If either one or both is methylated, the recognition site is not cut by AscI. There are approximately 5,000 AscI recognition sites per human genome.

Exposure of the genomic DNA to the MMRE results in a plurality of first fragments, the absolute number of which will depend on the relative number of MMRE recognition sites that are methylated. The more that are methylated, the fewer first fragments will result. Most of the first fragments will have at one terminus the MMRE 5' cut sequence (see definition below) and at the other terminus the MMRE 3' cut sequence (see definition below). For each chromosome, two fragments with MMRE cut sequences at only one terminus will be generated; these first fragments are referred to herein as terminal first fragments. One such terminal first fragment contains the 5' terminus of the chromosome at one end and a MMRE 3' cut sequence at the other end and the other terminal fragment contains the 3' terminus of the chromosome at one end and a MMRE 5' cut sequence at the other end.

Figure 1:
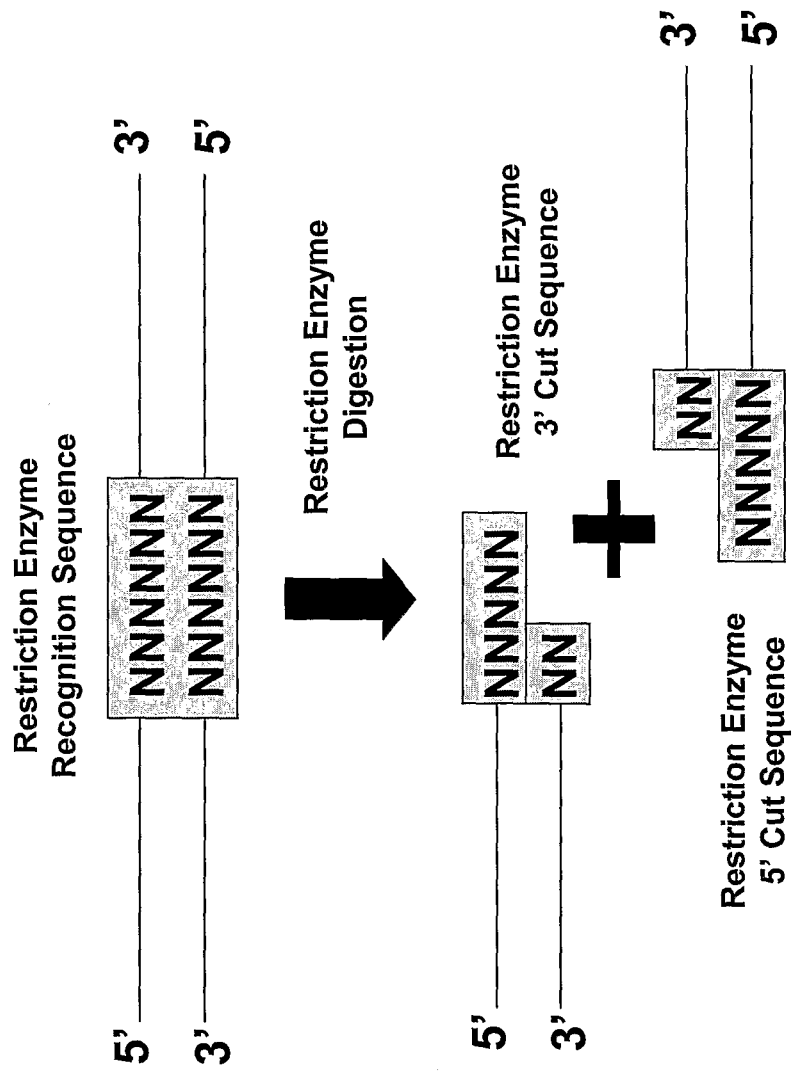
FIG. 1 is a diagrammatic representation of the generation of a restriction enzyme 5' cut sequence and 3' cut sequence by the restriction enzyme cutting DNA at the restriction enzyme's recognition sequence. In the diagram are shown the two strands of a segment of double stranded DNA containing a restriction enzyme recognition sequence in which each of the nucleotides constituting the recognition sequence are shown as an N. The exemplary restriction enzyme recognition sequence in the diagram is a six base pair recognition sequence and cutting by the particular restriction enzyme results in a 3' two nucleotide overhang. The N-containing sequences constituting the restriction enzyme recognition sequence and the restriction enzyme's 3' and 5' cut sequences are boxed and appropriately labeled. Those skilled in the art will appreciate that 5' and 3' termini generated by the multiple restriction enzymes available differ greatly (in nucleotide content, whether cohesive termini are generated, and, if they are, in the nature and number of nucleotides in the overhang). Nevertheless, in the sense that all termini (5' and 3' cut sequences) produced by the action of restriction enzymes that cut at their recognition sequences consist of nucleotides derived from the relevant restriction enzyme recognition sequence, 5' and 3' restriction enzyme cut sequences share qualitative features and differ only in how these nucleotides are distributed between the 5' and 3' cut sequences.

As used herein, a "5' cut sequence" of a restriction enzyme that cuts DNA within the restriction enzyme's recognition sequence is the portion of the restriction enzyme's recognition sequence at the 5' end of a fragment containing the 3' end of the restriction enzyme recognition sequence that is generated by cutting of DNA by the restriction enzyme. As used herein, a "3' cut sequence" of a restriction enzyme that cuts DNA within the restriction enzyme's recognition sequence is the portion of the restriction enzyme's recognition sequence at the 3' end of a fragment containing the 5' end of the restriction enzyme recognition sequence that is generated by cutting of DNA by the restriction enzyme. 5' and 3' cut restriction enzyme cut sequences are illustrated in FIG. 1.

To the termini of the first fragments are conjugated a first member of an affinity pair (see definition in Summary section), e.g., biotin or iminobiotin. This can be achieved by, for example, ligating to the MMRE 5' and 3' cut sequence-containing termini a binding moiety. The binding moiety contains the first member of the affinity pair conjugated (e.g., by a covalent bond or any other stable chemical linkage, e.g., a coordination bond, that can withstand the relatively mild chemical conditions of the MSDK methodology) to either a MMRE 5' cut sequence or a MMRE 3' cut sequence. The majority of the fragments (referred to herein as second fragments) resulting from attachment by this method of the first members of the affinity pair will have first members of an affinity pair bound to both their termini. Second fragments resulting from terminal first fragments will of course have first members of the affinity pair only at one terminus, i.e., the terminus containing the MMRE cut sequence.

The binding moiety can, optionally, also contain a linker (or spacer) nucleotide sequence of any convenient length, e.g., one to 100 base pairs (bp), three to 80 bp, five to 70 bp, seven to 60 bp, nine to 50, or 10 to 40 bp. The linker (or spacer) can be, for example, 30, 31, 32, 33, 34, 35, 26, 37, 38, or 40 bp long. As will be apparent, the linker must not include a fragmenting restriction enzyme (see below) recognition sequence.

Instead of using the above-described binding moiety to attach the first members of an affinity pair to the termini of first fragments, the attachment can be done by any of a variety of chemical means known in the art. In this case, the first member of an affinity pair can optionally contain a functional chemical group that facilitates binding of the first member of the affinity pair to the termini of the first fragments. It will be appreciated that by using this "chemical method", it is possible to attach first members of an affinity pair to both ends of terminal first fragments. Naturally, using the chemical method it is also possible to include the above-described linker (or spacer) nucleotide sequences. Where a functional chemical group is attached to the first member of the affinity pair, the linker (or spacer) nucleotide sequence is located between the first member of the affinity pair and the chemical functional group.

The second fragments are then exposed to fragmenting restriction enzyme (FRE). The FRE can be any restriction enzyme whose recognition sequence occurs relatively frequently in the genomic DNA of interest. Thus, restriction enzymes having four nucleotide recognition sequence are particularly desirable as FRE. In addition, the FRE should not be sensitive to methylation, i.e., its recognition sequence, at least in eukaryotic DNA should not contain a CpG dinucleotide sequence. Preferably, the FRE recognition sequence should occur at least 10 (e.g., at least: 20; 50; 100; 500; 1,000; 2,000; 5,000; 10,000; 25,000; 50,000; 100,000; 200,000; 500,000; $10^6$; or $10^7$) times more frequently in the genome than does the MMRE recognition sequence. Examples of useful FRE whose recognition sequences consist of four nucleotides include, without limitation, AluI, BfaI, CviAII, FatI, HpyCH4V, MseI, NlaIII, or Tsp509I. The recognition sequence for NlaIII is CATG. Exposure of the second fragments to the FRE results in a large number of fragments, the majority of which will have FRE cut sequences at both of their termini and a relatively few with a FRE cut sequence (5' or 3') at one end and the first member of the affinity pair (corresponding to a MMRE cut sequence) at the other end. The latter fragments are referred to herein as third fragments.

The third fragments are then exposed to a solid substrate having bound to it the second member of the affinity pair (e.g., avidin, streptavidin, or a functional fragment of either; see Summary section for examples of other useful second members) corresponding to the first member of the affinity pair in the third fragments. The third fragments bind, via the physical interaction between the first and second members of the affinity pair, to the solid substrate. The solid substrate can be any insoluble substance such as plastic (e.g., plastic microtiter well or petri plate bottoms), metal (e.g., magnetic metallic beads), agarose (e.g., agarose beads), or glass (e.g., glass beads or the bottom of a glass vessel such as a glass beaker, test tube, or flask) to which the third fragments can bind and thus be separated from fragments not containing the first member of the affinity pair.

Fragments not bound to the solid substrate are removed from the mixture and the solid substrate is optionally rinsed or washed free of any non-specifically bound material. The third fragments bound to the solid substrate are referred to as bound third fragments.

The terminus of the bound third fragment not bound to the solid substrate (referred to herein as the free terminus) is then conjugated to a releasing restriction enzyme (RRE) (also referred to herein sometimes as a tagging enzyme) recognition sequence. This can be achieved by, for example, ligating to the free termini (containing a FRE 5' or 3' cut sequence) releasing moieties containing the FRE 5' or 3 cut sequence and, 5' of the cut sequence, the RRE recognition sequence. Restriction enzymes useful as RRE are those that cut DNA at specific distances (depending on the particular type IIs restriction enzyme) from the recognition sequence, e.g., without limitation, the type IIs and type II. An example of a useful RRE is MmeI that has the following non-palindromic recognition sequence: 5'-TCCPuAC, 3'-AGG-PyTG (Pu, purine; Py, pyrimidine) and cuts DNA after the twentieth nucleotide downstream of the TCCPuAc sequence [Boyd et al. (1986) Nucleic Acids Res. 14(13): 5255-5274]. Other useful type IIs restriction enzymes include, without limitation, BsnfI, FokI, and AlwI, and useful type IIB restriction enzymes include, without limitation, BsaXI, CspCI, AloI, PpiI, and others listed in Tengs et al. [(2004) Nucleic Acids Research 32(15):e21(pages 1-9)], the disclosure of which is incorporated herein by reference in its entirety.

Releasing moieties can optionally contain, immediately 5' of the RRE recognition sequence, additional nucleotides as an extending sequence. The extending sequence can be of any convenient length, e.g., one to 100 bp, three to 80 bp, five to 70 bp, seven to 60 bp, nine to 50, or 10 to 40 bp. The extending sequence can be, for example, 20, 21, 22, 23, 24, 25, 26, 27, 28, 29, 30, 31, 32, 33, 34, 35, 26, 37, 38, or 40 bp long.

Conjugating the RRE recognition sequence to the free termini of the bound third fragments results in bound fourth fragments that (a) have RRE recognition sequences at their free termini, and (b) are bound by the first and second members of the affinity pair to the solid substrate. The bound fourth fragments are then exposed to the RRE which cuts the bound fourth fragments at a position that is characteristic of the relevant RRE. In the case of the MmeI RRE, the bound fourth fragment is cut on the downstream side of the twentieth nucleotide after the terminal C residue of the TCCPuAC recognition sequence. The exposure results in the release from the solid substrates of a library of fifth fragments. Each of the fifth fragments contains the RRE recognition sequence (and extending sequence if used) and a plurality of bp of the test genomic DNA, including the FRE recognition sequence closest to an unmethylated MMRE recognition sequence. The absolute number of these bp of the test genomic DNA in the fifth fragments will vary from one RRE to another and is, in the case of MmeI, 20 nucleotides. The sequence of genomic DNA in the fifth fragment (but without the FRE recognition sequence) is referred to herein as a MSDK tag. Since the MmeI and NlaIII recognition sequences overlap by one nucleotide, the tags generated using MmeI as the RRE and NlaIII as the FRE are 17 nucleotides long.

The greater the number of bp between the RRE recognition sequence and the cutting site of the RRE, the longer the MSDK tags will be. The longer the MSDK tags are, the lower the chances of redundancy due to a plurality of occurrences of the tag sequence in the genome of interest will be. In addition, it will be appreciated that the number of bp between FRE recognition sequences and corresponding MMRE recognition sequences in the genomic DNA of interest will optimally be greater than the number of bp between the RRE recognition sequence and the RRE cut site. However problems arising due to this criterion not being met can be obviated by using the binding moiety method of attaching a first member of an affinity pair to first fragment termini and including in the binding moiety a linker (or spacer) nucleotide sequence of appropriate length (see above); the shorter the distance between the any given FRE recognition sequence and a corresponding MMRE recognition sequence in a genome being analyzed, the longer the linker (or spacer) nucleotide sequence would need to be.

Methods of Using a MSDK Tag Library

MSDK libraries generated as described above can be used for a variety of purposes.

The first step in most of such methods would be to at least identify the nucleotide sequences of as many MSDK tags obtained in making a library as possible. There are many ways in which this could be done which will be apparent to those skilled in the art. For example, array technology or the MPSS (massively parallel signature sequencing) method could be exploited for this purpose. Alternatively, the MSDK tag-containing fifth fragments (see above) can be cloned into sequencing vectors (e.g., plasmids) and sequenced using standard sequencing techniques, preferably automated sequencing techniques.

The inventors have used a technique for identifying MSDK tag sequences (see Example 1 below) adapted from the Sequential Analysis of Gene Expression (SAGE) technique [Porter et al. (2001) Cancer Res. 61:5697-5702; Krop et al. (2001) Proc. Natl. Acad. Sci. U.S.A 98:9796-9801; Lal et al. (1999) Cancer Res. 59:5403-5407; and Boon et al. (2002) Proc. Natl. Acad. Sci. U.S.A. 99:11287-11292]. This adapted technique involves:

(a) adding a DNA ligase enzyme to a library of fifth fragments and thereby ligating pairs of fifth fragments having cohesive RRE-derived ends together to form fifth fragment dimers (also referred to herein as "ditags");

(b) increasing the numbers of individual ditags by PCR using primers whose sequences correspond to nucleotide sequences in extender sequences derived from a releasing moiety (see above);

(c) digesting the PCR-amplified ditags with the FRE used to generate the MSDK library and thereby generating digested ditags lacking the RRE site and extender sequences (if used);

(d) concatamerizing (polymerizing) the ditags using a ligase enzyme (e.g., T4 ligase) to create ditag multimers;

(e) cloning the ditag multimers into sequencing vectors and sequencing the inserts (e.g., by automatic sequencing methods); and (f) deducing from the ditag multimer sequences the sequences of individual MSDK tags.

One of skill in the art will naturally know of ways to modify and adapt the above tag identification procedure to his or her particular requirements. For example, one or more of the steps (e.g., step (b), the ditag amplification step or step (c), the step that removes the RRE recognition site and any extender sequence used) could be omitted.

Having obtained the sequences of some or all of the MSDK tags, there are a number of analyses that could be pursued.

Enumeration of MSDK Tags

The numbers of each tag, or a subgroup of tags, in a MSDK library can be computed. Then, for example, optionally having normalized the number of each to the total number of cloned tag sequences obtained, the resulting MSDK profile (consisting of a list of MSDK tags and the abundance (number) of each MSDK tag) can be compared to corresponding MSDK profiles obtained with other cells of interest. In computing the total numbers of individual MSDK tags, where ditags have been amplified by PCR (step (b) above), ditag replicates are deleted from the analysis.

Since the chance of any one ditag combination occurring more than once as a result of step (a) above would be extremely low, replicate ditags would likely be due to the PCR amplification procedure. Ways to estimate the numbers of individual tag sequences include the same methods described above for identifying the tag sequences.

The relative abundance (number) of a given MSDK tag obtained gives an indication of the relative frequency at which the nearest MMRE recognition sequence to the FRE recognition sequence associated with the given tag is unmethylated. The higher the number of the MSDK tag obtained, the more frequently that MMRE recognition sequence is unmethylated. Because, by the nature of the method, any given MMRE recognition sequence is correlated with a MSDK tag associated with the nearest FRE recognition sequence upstream of it and with the nearest FRE recognition sequence downstream of it, if any two MMRE recognition sites occur without an appropriate FRE recognition site between them, it will always be possible to discriminate the methylation status (methylated or not methylated) of both the MMRE recognition sites. On the other hand if three MMRE recognition sites occur without an FRE recognition sequence between the first and third, it might not be possible to discriminate the methylation status of the middle MMRE recognition sequence. However, the chances of this occurring can be reduced to essentially zero by choosing a FRE that has a recognition sequence occurring in the genomic DNA of interest much more frequently than the selected MMRE. Indeed prior to the analysis, since generally the sequence of the genome of interest is known, this potential resolution-impairing eventuality can be tested for in advance and overcome by examining the genomic nucleotide sequences and, if necessary, an alternative MMRE-FRE combination can be selected or a plurality of analyses can be performed using a number of different MMRE-FRE combinations.

MSDK tag profiles composed of all the tag sequences obtained in an MSDK analysis, and preferably (but not necessarily) the relative numbers of all the MSDK tags, can be compared to corresponding profiles obtained with other cell types. Corresponding profiles will of course be those generated using the same MMRE, FRE, and RRE and in at least an overlapping part, if not an identical portion, of the relevant genome. Such comparisons can be used, for example, to identify a test cell of interest. For example, a test cell could be a cell of type x, type y, or type z. The MSDK profile obtained with the test cell can be compared to control corresponding MSDK profiles obtained from control cells of type x, type y, and type z. The test cell will likely be of the same type, or at least most closely related, to the control cell (type x, y, or z) whose MSDK profile the test cell's profile most closely resembles. Alternatively, the MSDK profile of a test cell can be compared to that of a single control cell and, if the test cell's profile is significantly different from that of the control cell's profile, it is likely to be of a different type than the control cell type. Statistical methods for doing the above-described analyses are known to those skilled in the art.

The number of MSDK tag species in any given MSDK tag profile varies greatly depending on how many are available and their relative discriminatory power. Indeed, where a particular MSDK tag can discriminate specifically between two cell types of interest, the MSDK tag profile can contain it alone. Thus MSDK tag profiles can contain as few as one MSDK tag. However, they will generally contain a plurality of different MSDK tags, e.g., at least: 2; 3; 4; 5; 6; 7; 8; 9; 10; 12; 15; 20; 25; 30; 35; 40; 50; 60; 75; 85; 100; 120; 140;

160; 180; 200; 250; 300; 350; 400; 450; 500; 600; 700; 800; 900; a 1,000; 2,000; 5,000; 10,000; or even more tag species.

The range of "cell types" that can be compared in the above analyses is of course enormous. Thus, for example, the MSDK profile of a test bacterium can be compared to control MSDK profiles of bacteria of: various species of the same genus as the test bacterium (if its genus is known but its species is to be defined); various strains of the same species as the test bacterium (if its species is known but its strain is to be defined) or even various isolates of the same strain as the test bacterium but from, for example, various ecological niches (if the strain of the test bacterium, but not its ecological origin, is known). The same principle can be applied to any biological cell and to any level of speciation of a biological cell. Similarly the MSDK profiles of eukaryotic (e.g., mammalian) test cells can be compared to corresponding MSDK profiles of control test cells of various tissues, of various stages of development, and of various lineages. In addition, the MSDK profile of a test vertebrate cell can be compared to one or more control MSDK profiles of cells (of, for example, the same tissue as the test cell) that are normal or malignant in order to determine (diagnose) whether the test cell is a malignant cell. Moreover, the MSDK profile of a cancer test cell can be compared to one or more control MSDK profiles of cancers of a variety of tissues in order to define the tissue origin of the test cell. In addition, the MSDK profile of a test cell can be compared to that or those of (a) control test cell(s) that can be identical to, or similar to or even different from, the test cell but has/have been exposed or subjected to any of large number of experimental or natural influences, e.g., drugs, cytokines, growth factors, hormones, or any other pharmaceutical or biological agents, physical influences (e.g., elevated and/or depressed temperature or pressure), or environmental conditions (e.g., drought or monsoon conditions). It will thus be appreciated that the term "cell type" covers a large variety of cells and that (or those) used or defined in any particular analysis will depend on the nature of analysis being performed. Those skilled in the art will be able to select appropriate control cell types for the analyses of interest.

Examples of MSDK profiles useful as control test profiles are provided herein. Thus, for example, the MSDK profile of a test breast cell (e.g., an epithelial cell, a myoepithelial cell, or a fibroblast) from a human subject could be compared to the MSDK profiles of breast epithelial cells, myoepithelial cells, and fibroblast-enriched stromal cells from both control normal and control breast cancer (e.g., DCIS or invasive breast cancer) subjects in order to establish whether the test breast tissue from which the test breast cell was obtained is cancerous breast tissue. Moreover, the MSDK profile of a test cancer cell can be compared to those of control breast, prostate, colon, lung, and pancreatic cancer cells as part of an analysis to establish the tissue of the test cancer cell. In addition, the MSDK profile of a cell suspected of being either an epithelial or myoepithelial cell can be compared to those of control normal (and/or cancerous, depending on whether the test cell is normal, cancerous, or not yet established to be normal or cancerous) epithelial and myoepithelial cells in order to establish whether the test cell is an epithelial or myoepithelial cell.

Mapping of MMRE Recognition Sequences

Alternatively, or in addition to enumerating MSDK tags, once the tags obtained in by the MSDK analysis have been identified, the locations in the genome of interest corresponding to the tags (referred to herein as "genomic tag sequences) can be established by comparison of the tag sequences to the nucleotide sequence of the genome (or part of the genome) of interest. This can be done manually but is preferably done by computer. The relevant genomic sequence information can be loaded into the computer from a medium (e.g., a computer diskette, a CD ROM, or a DVD) or it can be downloaded from a publicly available internet database.

One method by which the genomic tag sequences can be identified is by first creating a "virtual" tag library using the following information: (a) the nucleotide sequence of the genome (or part of the genome) of interest; (b) the nucleotide sequence of the MMRE recognition sequence; (c) the nucleotide sequence of the FRE recognition sequence; and (d) the number of nucleotides separating the RRE recognition sequence from the RRE cutting site. Optimally, virtual tag sequences that are not unique (i.e. that could arise in a MSDK library from more than one genetic locus) are deleted from the virtual MSDK library. By comparing the sequences of the tags obtained in the test MSDK analysis to the virtual tag library, it is possible to determine the genomic location of MSDK tags of interest, e.g., all the tags obtained by the analysis or one or more of such tags.

Once the genomic location of the genomic tag sequences has been obtained, it is a simple matter to identify genes in which, or close to which, the genomic tag sequences are located. This step can be done manually, but can also be done by a computer. Such genes can be the subject of additional analyses, e.g., those described below.

Methods of Determining Levels of DNA Methylation

The invention features methods of assessing the level of methylation of genomic regions (e.g., genes or subregions of genes) of interest. The methods can be applied to genomic regions identified by the MSDK analyses described above or selected on any other basis, e.g., the observation of differential expression of a gene in two cell types (e.g., a normal cell and a cancer cell of the same tissue as the normal cell) of interest.

The methods are of particular interest in the diagnosis of cancer. In broad terms, it has been claimed that the genomes of cancer cells are hypomethylated relative to corresponding normal cells [Feinberg et al. (1983) Nature 301:89-92]. Moreover, gene hypermethylation is frequently associated with decreased expression of the relevant gene. However, at the individual gene level these generalizations do not apply. Thus, for example, some genes can be hypermethylated in cancer cells in comparison to corresponding normal cells, hypermethylation of some genes is associated with increased expression, and hypomethylation of some genes is associated with decreased expression of the relevant genes. Interestingly, in the examples below, it was observed that hypermethylation of the promoter region of one gene (Cxorf12) was associated with decreased expression of the gene, while hypermethylation of the exons and/or introns of three other genes (PRDM14, HOXD4, and CDC42EP5) was associated with increased expression of the genes.

As used herein, the term "gene" refers to a genomic region starting 10 kb (kilobases) 5' of a transcription initiation site and terminating 2 kb 3' of the polyA signal associated with the coding sequence within the genomic region. Where the polyA signal of another gene is located less than 10 kb 5' of the transcription initiation site of a gene of interest, for the purposes of the instant invention, the gene of interest is considered to start at the first nucleotide immediately after the polyA signal of the other gene. Moreover, where a transcription initiation site of another gene is less than 2 kb 3' prime of the polyA signal of the gene of interest, for the purposes of the instant invention, the gene of interest terminates at the nucleotide immediately before the transcription initiation site of the other gene. From these definitions it will be appreciated that, as used herein, promoter regions and regions 3' of polyA signals of adjacent genes can overlap.

As used herein, the "promoter region" of a gene refers to a genomic region starting 10 kb 5' of a transcription initiation site and terminating at the nucleotide immediately 5' of the transcription initiation site. Where a polyA signal of another gene is located less than 10 kb 5' of the transcription initiation site of a gene of interest, for the purposes of the instant invention, the promoter region of the gene of interest starts at the first nucleotide immediately following the polyA signal of the other gene.

As used herein, the terms "exons" and "introns" refer to amino acid coding and non-coding, respectively, nucleotide sequences occurring between the transcription initiation site and start of the polyA sequence of a gene.

As used herein, a "CpG island" is a sequence of genomic DNA in which the number of CpG dinucleotide sequences is significantly higher than their average frequency in the relevant genome. Generally, CpG islands are not greater than 2,000 (e.g., not greater than: 1,900; 1,800; 1,700; 1,600; 1,500; 1,400; 1,300; 1,200; 1,100; 1,000; 900; 800; 700; 600; 500; 400; 300; 200; 100; 75; 50; 25; or 15) bp long. They will generally contain not less than one CpG sequence to every 100 (e.g., every: 90; 80; 70; 60; 50; 40; 35; 30; 25; 20; 15; 10; or 5) bp in sequence of DNA. CpG islands can be separated by at least 20 (i.e., at least: 20; 35; 50; 60; 80; 100; 150; 200; 250; 300; 350; or 500) bp of genomic DNA.

In the methods of the invention, the degree of methylation of one or more C residues (in CpG sequences) in a gene of a test cell is determined. This degree of methylation can then be compared to that in one or more (e.g., two, three, four, five, six, seven, eight, nine, ten, 11, 12, 15, 18, 20, 25, 30, 35, 40, 50, 75, 100, 200, or more) control cells.

If the level of methylation in the test cell is altered compared to, for example, that of a control cell, the test cell is likely to be different from the control cell. For example, the test cell can be a cell from any of the vertebrate tissues recited herein, the control cell can be a normal of that tissue, and the gene can be any one that is differentially methylated in cells from cancerous versus normal tissue (e.g., any of the genes listed in Tables 2, 5, 7, 8, 10, 12 and 15). If the degree of methylation of the gene in the test cell is different from that in the normal cell, the test cell is likely to be a cancer cell.

Alternatively, the level of methylation in the test cell can be compared to that in two more (see above) control cells. The cell will be the same as, or most closely related to, the control cell in which the degree of methylation is the same as, or most closely resembles, that of the test cell.

The whole of a gene or parts of a gene (e.g., the promoter region, the transcribed regions, the translated region, exons, introns, and/or CpG islands) can be analyzed.

Test and control cells can be the same as those listed above in the section on MSDK. Genes that can analyzed can be any gene differently methylated in two or more cell types of interest. In the methods of the invention any number of genes can be analyzed in order to characterize a test cell of interest. Thus, one, two, three, four, five, six, seven, eight, nine, ten, 11, 12, 13, 14, 15, 16, 17, 18, 19, 20, 22, 25, 28, 30, 35, 40, 45, 50, 60, 70, 80, 80, 100, 200, 500, or even more genes can be analyzed. The genes can be, for example, any of the DNA sequences (e.g., the genes) listed in Tables 2, 5, 7, 8, 10, 12, 15, and 16. The entire genes or one more subregions of the genes (e.g., all or parts of promoter regions, all or parts of transcribed regions, exons, introns, and regions 3' of polyA signals) can be analyzed Specific genes of interest include, for example, the LMX-1A, COL5A, LHX3, TCF7L1, PRDM14, ZCCHC14, HOXD4, SLC9A3R1, CDC42EP5, Cxorf12, LOC389333, SOX13, SLC9A3R1, FNDC1, FOXC1, PACAP, DDN, CDC42EP5, LHX1, and HOXA10 genes.

Methylation levels of one or more of these DNA sequences (e.g., genes) can be used to determine, for example, whether a test epithelial cell from breast tissue is a normal or cancerous epithelial cell (e.g., a DCIS (high, intermediate, or low grade) or invasive breast cancer cell). Particularly useful for such determinations are the PRDM14 and ZCCHC14 genes. For example, with respect to the PRDM14 gene, a gene segment that is or contains all or part of SEQ ID NO:1 (FIG. 6A) can be analyzed in order to discriminate these cell types. Of particular interest for this purpose are nucleotide sequences that include nucleotides: 8-17; 341-392; 371-426; or 391-405 of SEQ ID NO:1. Methylation of the PRDM14 can similarly be used to determine whether a test cell from, for example, pancreas, lung, or prostate is a cancer cell or normal cell. In addition, with respect to the ZCCHC14 gene, a gene segment that is or contains all or part of SEQ ID NO:2 (FIG. 17) can be analyzed in order to discriminate these cell types. Of particular interest for this purpose are nucleotide sequences that include nucleotides: 154-236; 154-279; 154-293; or 154-299 of SEQ ID NO:2. Hypermethylation of these genes, and particularly hypermethylation of their coding regions, would indicate that the relevant test cells are cancer cells.

In addition, methylation levels of one or more of the above-listed genes can be used to determine, for example, whether a test epithelial cell from colon tissue is a normal or cancerous epithelial cell. Particularly useful for such determinations are the LHX3, TCF7L1, and LMX-1A genes. For example, with respect to the LHX3 gene, a gene segment that is or contains all or part of SEQ ID NO:3 (FIG. 6A) can be analyzed in order to discriminate these cell types. Of particular interest for this purpose are nucleotide sequences that include nucleotides: 667-778; 739-788; 918-931; or 885-903 of SEQ ID NO:3. In addition, for example, with respect to the TCF7L1 gene, a gene segment that is or contains all or part of SEQ ID NO:4 (FIG. 8A) can be analyzed in order to discriminate these cell types. Of particular interest for this purpose are nucleotide sequences that include nucleotides: 708-737; 761-780; 807-864; or 914-929 of SEQ ID NO:4. Moreover, for example, with respect to the LMX-1A gene, a gene segment that is or contains all or part of SEQ ID NO:5 (FIG. 7A) can be analyzed in order to discriminate these cell types. Of particular interest for this purpose are nucleotide sequences that include nucleotides: 849-878; 898-940; 948-999; or 1,020-1039 of SEQ ID NO:5. Hypermethylation of these genes would indicate that the test cell is a cancerous colon epithelial cell.

Furthermore, methylation levels of the above-listed genes can be analyzed to determine, for example, whether breast tissue from which a test myoepithelial is obtained is normal or cancerous breast tissue. Particularly useful for such determinations are the HOXD4, SLC9A3R1, and CDC42EP5 genes. For example, with respect to the HOXD4 gene, a gene segment that is or contains all or part of SEQ ID NO:6 (FIG. 18A) can be analyzed in order to discriminate these cell types. Of particular interest for this purpose are nucleotide sequences that include nucleotides: 185-255; 288-313; 312-362; or 328-362 of SEQ ID NO:6. In addition, for example, with respect to the SLC9A3R1 gene, a gene segment that is or contains all or part of SEQ ID NO:7 (FIG.

19A) can be analyzed in order to discriminate these cell types. Of particular interest for this purpose are nucleotide sequences that include nucleotides: 104-126; 104-247; 104-283; or 246-283 of SEQ ID NO:7. Moreover, for example, with respect to the CDC42EP5 gene, a gene segment that is or contains all or part of SEQ ID NO:8 (FIG. 21A) can be analyzed in order to discriminate these cell types. Of particular interest for this purpose are nucleotide sequences that include nucleotides: 181-247; 282-328; 336-359; or 336-390 of SEQ ID NO:8. Hypermethylation of these genes, and particularly their coding regions, would indicate that the test myoepithelial cell is from cancerous breast tissue.

Methylation levels of the above-listed genes can also be analyzed to determine, for example, whether breast tissue from which a test fibroblast is obtained is normal or cancerous breast tissue. Particularly useful for such determinations is the Cxorf12 gene. For example, with respect to the either of these genes, a gene segment that is or contains all or part of SEQ ID NO:9 (FIG. 22A) can be analyzed in order to discriminate these cell types. Of particular interest for this purpose nucleotide sequences that include nucleotides: 120-134; 159-201; 206-247; or 293-313 of SEQ ID NO:9. Hypermethylation of these genes, and particularly their promoter regions, would indicate that the test fibroblast is from cancerous breast tissue.

In addition, methylation levels of the above-listed genes can also be analyzed to determine, for example, whether a test cell is an epithelial cell or a myoepithelial cell. Such assays can be applied to both normal and cancerous cells. Particularly useful for such determinations are the LOC389333 and CDC42EP5 genes. For example, with respect to the LOC389333 gene, a gene segment that is or contains all or part of SEQ ID NO:10 (FIG. 20A) can be analyzed in order to discriminate these cell types. Of particular interest for this purpose are nucleotide sequences that include nucleotides: 306-330; 334-361; 373-407; or 415-484 of SEQ ID NO:10. With respect to the CDC42EP5 gene, examples of gene segments that can be analyzed include those described above for discriminating whether tissue from which a test myoepithelial was obtained was normal or cancerous. Significantly high levels of methylation of these genes would indicate that the test cell was an epithelial rather than a myoepithelial cell.

In addition, methylation levels of the above-listed genes can also be analyzed to determine, for example, whether a test cell is a stem cell, or a differentiated cell derived therefrom, such as an epithelial cell or a myoepithelial cell. Such assays can be applied to both normal and cancerous cells. Particularly useful for such determinations are the SOX13, SLC9A3R1, FNDC1, FOXC1, PACAP, DDN, CDC42EP5, LHX1, and HOXA10 genes. For example, with respect to the FOXC1 gene, a gene segment that is or contains all or part of SEQ ID NO:12 (FIG. 27A) can be analyzed in order to discriminate these cell types. In some cases, significantly high levels of methylation of some of these genes would indicate that the test cell was a stem cell rather than a differentiated cell derived therefrom, (e.g., an epithelial or a myoepithelial cell).

Levels of methylation of C residues of interest can be assessed and expressed in quantitative, semi-quantitative, or qualitative fashions. Thus they can, for example, be measured and expressed as discrete values. Alternatively, they can be assessed and expressed using any of a variety of semi-quantitative/qualitative systems known in the art. Thus, they can be expressed as, for example, (a) one or more of "very high", "high", "average", "moderate", "low", and/or "very low"; (b) one or more of "++++", "+++", "++", "+", "+/−", and/or "−"; (c) methylated or not methylated (i.e., in a digital fashion); (d) ranges such as "0%-10%", "11%-20%", 21%-30%", "31%-40%", etc. (or any convenient range intervals); (e) graphically, e.g., in pie charts.

Methods of measuring the degree of methylation of C residues in the CpG sequences are known in the art. Such methodologies include sequencing of sodium bisulfite-treated DNA and methylation-specific PCR and are described in the Examples below.

Standardizing methylation assays to discriminate between cell types of interest involves experimentation entirely familiar and routine to those in the art. For example, the methylation status of gene Q in a sample cancer cells of interest obtained from a one or more patients and in corresponding normal cells from normal individuals or from the same patients can be assessed. From such experimentation it will be possible to establish a range of "cancer levels" of methylation and a range of "normal levels" of methylation of gene Q. Alternatively, the methylation status of gene Q in cancer cells of each patient can be compared to the methylation status of gene Q in normal cells (corresponding to the cancer cells) obtained from the same patient. In such assays, it is possible that methylation of as few as one cytosine residue could discriminate between cancer and non-cancer cells.

Other methods for quantitating methylation of DNA are known in the art. Such methods are based on: (a) the inability of methylation-sensitive restriction enzymes to cleave sequences that contain one or more methylated CpG sites [Issa et al. (1994) *Nat. Genet.* 7:536-540; Singer-Sam et al. (1990) *Mol. Cell. Biol.* 10:4987-4989; Razin et al. (1991) *Microbiol. Rev.* 55:451-458; Stoger et al. (1993) *Cell* 73:61-71]; and (b) the ability of bisulfite to convert cytosine to uracil and the lack of this ability of bisulfite on methylated cytosine [Frommer et al. (1992) *Proc. Natl. Acad. Sci. USA* 89:1827-1831; Myöhanen et al. (1994) *DNA Sequence* 5:1-8; Herman et al. (1996) *Proc. Natl. Acad. Sci. USA* 93:9821-9826; Gonzalgo et al. (1997) *Nucleic Acids Res.* 25:2529-2531; Sadri et al. (1996) *Nucleic Acids Res.* 24:5058-5059; Xiong et al. (1997) *Nucleic Acids Res.* 25:2532-2534].

Gene Expression Assays

Experiments described in the Examples herein show that in a first cell in which methylation of a gene is altered (increased or decreased) relative to a second cell, expression of the gene in the first cell is also altered relative to the second cell. In addition, previous findings and the data in the Examples indicate that alterations in methylation status, and hence also consequent alterations in expression, of certain genes correlate with phenotypic changes in cells. These findings provide the basis for assays (e.g., diagnostic assays) to discriminate between two or more cell types.

In the methods of the invention, the level of expression of a gene of a test cell determined. This level of expression can then be compared to that in one or more (e.g., two, three, four, five, six, seven, eight, nine, ten, 11, 12, 15, 18, 20, 25, 30, 35, 40, 50, 75, 100, 200, or more) control cells.

If the level of expression in the test cell is altered compared to, for example, that of a control cell, the test cell is likely to be different from the control cell. For example, the test cell can be a cell from any of the vertebrate tissues recited herein, the control cell can be a normal cell of that tissue, and the gene can be one shown to be differentially methylated in cells from cancerous and normal tissue (e.g., any of the genes listed in Tables 2, 5, 7, 8, 10, 12, 15 and 16). If the level of expression of the gene in the test cell is different from that in the normal cell, the test cell is likely to be a cancer cell.

Alternatively, the level of expression in the test cell can be compared to that in two more (see above) control cells. The cell will be the same as, or most closely related to, the control cell in which the level of expression is the same as, or most closely resembles that of the test cell.

Test and control cells can be any of those listed above in the section on MSDK. Genes whose level of expression can be determined can be any gene differently methylated in two more cell types of interest. They can be, for example, any of the genes listed in Tables 2, 5, 7, 8, 10, 12, 15, and 16.

Specific genes of interest include the LMX-14, COL5A, LHX3, TCF7L1, PRDM14, ZCCHC14, HOXD4, SOX13, SLC9A3R1, CDC42EP5, Cxorf12, and LOC389333 genes.

Expression levels of one or more of these genes can be analyzed to determine, for example, whether a test epithelial cell from breast tissue is a normal or cancerous epithelial cell (e.g., a DCIS (high, intermediate, or low grade) or invasive breast cancer cell). Particularly useful for such determinations are the PRDM14 and ZCCHC14 genes. Moreover, expression of the PRDM14 can be used to test whether a test cell from prostate, pancreas, or lung tissue is a cancer cell. Thus, for example, enhanced expression of the PRDM14 gene, or altered expression of the ZCCHC14 gene, in the test breast epithelial cell compared to a control normal breast epithelial cell would be an indication that the test epithelial cell is a cancer cell.

In addition, expression levels of one or more of the above-listed genes can be analyzed to determine, for example, whether a test epithelial cell from colon tissue is a normal or cancerous epithelial cell. Particularly useful for such determinations are the LHX3, TCF7L1, and LMX-1A genes. Altered expression of these genes in the test colon epithelial cell compared to a control normal control epithelial cell would be an indication that the test colon epithelial cell is a cancer cell.

Expression levels of one or more of the above-listed genes in a test myoepithelial cell can be analyzed to determine, for example, whether breast tissue from which the test myoepithelial was obtained is normal or cancerous breast tissue. Particularly useful for such determinations are the HOXD4, SLC9A3R1, and CDC42EP5 genes. Enhanced expression of, for example, the HOXD4 and CSD42EP5 genes, or altered expression of the SLC9A3R1 gene, in the test myoepithelial cell compared to a control myoepithelial from control normal breast tissue, would indicate that the test breast tissue is cancerous breast tissue.

Expression levels of one or more of the above-listed genes in a test fibroblast can also be analyzed to determine, for example, whether breast tissue from which the test fibroblast was obtained is normal or cancerous breast tissue. Particularly useful for such determinations is the Cxorf12 gene. Expression, for example, of this gene at the same or a greater level than in a control fibroblast from control normal breast tissue would indicate that the breast tissue is not cancerous breast tissue.

In addition, expression levels of one or more of the above-listed genes can also be analyzed determine, for example, whether a test cell is an epithelial cell or a myoepithelial cell. Such assays can be applied to both normal and cancerous cells. Particularly useful for such determinations are the LOC3.89333 and CDC42EP5 genes. Expression of these genes in the test cell at level that is the same as or similar to that of a control myoepithelial cell would be an indication that the test cell is a myoepithelial cell. On the other hand, expression of the genes in the test cell at level that is the same as or similar to that of a control epithelial cell would be an indication that the test cell is an epithelial cell.

Levels of expression of genes of interest can be assessed and expressed in quantitative, semi-quantitative, or qualitative fashions. Thus they can, for example, be measured and expressed as discrete values. Alternatively, they can be assessed and expressed using any of a variety of semi-quantitative/qualitative systems known in the art. Thus, they can be expressed as, for example, (a) one or more of "very high", "high", "average", "moderate", "low", and/or "very low"; (b) one or more of "++++", "+++", "++", "+", "+/−", and/or "−"; (c) expressed or not expressed (i.e., in a digital fashion): (d) ranges such as "0%-10%", "11%-20%", 21%-30%", "31%-40%, etc. (or any convenient range intervals); or (e) graphically, e.g., in pie charts.

In the description below, a "gene X" represents any of the genes listed in Tables 2, 5, 7, 8, 10, and 12; mRNA transcribed from gene X is referred to as "mRNA X"; protein encoded by gene X is referred to as "protein X"; and cDNA produced from mRNA X is referred to as "cDNA X". It is understood that, unless otherwise stated, descriptions containing these terms are applicable to any of the genes listed in Tables 2, 5, 7, 8, 10, 12, 15 and 16, mRNAs transcribed from such genes, proteins encoded by such genes, or cDNAs produced from the mRNAs.

In the assays of the invention either: (1) the presence of protein X or mRNA X in cells is tested for or their levels in cells are assessed; or (2) the level of protein X is assessed in a liquid sample such as a body fluid (e.g., urine, saliva, semen, blood, or serum or plasma derived from blood); a lavage such as a breast duct lavage, lung lavage, a gastric lavage, a rectal or colonic lavage, or a vaginal lavage; an aspirate such as a nipple aspirate; or a fluid such as a supernatant from a cell culture. In order to test for the presence, or measure the level, of mRNA X in cells, the cells can be lysed and total RNA can be purified or semi-purified from lysates by any of a variety of methods known in the art. Methods of detecting or measuring levels of particular mRNA transcripts are also familiar to those in the art. Such assays include, without limitation, hybridization assays using detectably labeled mRNA X-specific DNA or RNA probes and quantitative or semi-quantitative RT-PCR methodologies employing appropriate mRNA X and cDNA X-specific oligonucleotide primers. Additional methods for quantitating mRNA in cell lysates include RNA protection assays and serial analysis of gene expression (SAGE). Alternatively, qualitative, quantitative, or semi-quantitative in situ hybridization assays can be carried out using, for example, tissue sections or unlysed cell suspensions, and detectably (e.g., fluorescently or enzyme) labeled DNA or RNA probes.

Methods of detecting or measuring the levels of a protein of interest in cells are known in the art. Many such methods employ antibodies (e.g., polyclonal antibodies or monoclonal antibodies (mAbs)) that bind specifically to the protein. In such assays, the antibody itself or a secondary antibody that binds to it can be detectably labeled. Alternatively, the antibody can be conjugated with biotin, and detectably labeled avidin (a protein that binds to biotin) can be used to detect the presence of the biotinylated antibody. Combinations of these approaches (including "multi-layer" assays) familiar to those in the art can be used to enhance the sensitivity of assays. Some of these assays (e.g., immunohistological methods or fluorescence flow cytometry) can be applied to histological sections or unlysed cell suspensions.

The methods described below for detecting protein X in a liquid sample can also be used to detect protein X in cell lysates.

Methods of detecting protein X in a liquid sample (see above) basically involve contacting a sample of interest with an antibody that binds to protein X and testing for binding of the antibody to a component of the sample. In such assays the antibody need not be detectably labeled and can be used without a second antibody that binds to protein X. For example, by exploiting the phenomenon of surface plasmon resonance, an antibody specific for protein X bound to an appropriate solid substrate is exposed to the sample. Binding of protein X to the antibody on the solid substrate results in a change in the intensity of surface plasmon resonance that can be detected qualitatively or quantitatively by an appropriate instrument, e.g., a Biacore apparatus (Biacore International AB, Rapsgatan, Sweden).

Moreover, assays for detection of protein X in a liquid sample can involve the use, for example, of: (a) a single protein X-specific antibody that is detectably labeled; (b) an unlabeled protein X-specific antibody and a detectably labeled secondary antibody; or (c) a biotinylated protein X-specific antibody and detectably labeled avidin. In addition, as described above for detection of proteins in cells, combinations of these approaches (including "multi-layer" assays) familiar to those in the art can be used to enhance the sensitivity of assays. In these assays, the sample or an (aliquot of the sample) suspected of containing protein X can be immobilized on a solid substrate such as a nylon or nitrocellulose membrane by, for example, "spotting" an aliquot of the liquid sample or by blotting of an electrophoretic gel on which the sample or an aliquot of the sample has been subjected to electrophoretic separation. The presence or amount of protein X on the solid substrate is then assayed using any of the above-described forms of the protein X-specific antibody and, where required, appropriate detectably labeled secondary antibodies or avidin.

The invention also features "sandwich" assays. In these sandwich assays, instead of immobilizing samples on solid substrates by the methods described above, any protein X that may be present in a sample can be immobilized on the solid substrate by, prior to exposing the solid substrate to the sample, conjugating a second ("capture") protein X-specific antibody (polyclonal or mAb) to the solid substrate by any of a variety of methods known in the art. In exposing the sample to the solid substrate with the second protein X-specific antibody bound to it, any protein X in the sample (or sample aliquot) will bind to the second protein X-specific antibody on the solid substrate. The presence or amount of protein X bound to the conjugated second protein X-specific antibody is then assayed using a "detection" protein X-specific antibody by methods essentially the same as those described above using a single protein X-specific antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope to that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles. It is noted that protein X-specific antibodies bound to such beads or particles can also be used for immunoaffinity purification of protein X.

Methods of detecting or for quantifying a detectable label depend on the nature of the label and are known in the art. Appropriate labels include, without limitation, radionuclides (e.g., $^{125}I$, $^{131}I$, $^{35}S$, $^{3}H$, $^{32}P$, $^{33}P$, or $^{14}C$), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, calorimeters, fluorometers, luminometers, and densitometers.

In assays, for example, to diagnose breast cancer, the level of protein X in, for example, serum (or a breast cell) from a patient suspected of having, or at risk of having, breast cancer is compared to the level of protein X in sera (or breast cells) from a control subject (e.g., a subject not having breast cancer) or the mean level of protein X in sera (or breast cells) from a control group of subjects (e.g., subjects not having breast cancer). A significantly higher level, or lower level (depending on whether the gene of interest is expressed at higher or lower level in breast cancer or associated stromal cells), of protein X in the serum (or breast cells) of the patient relative to the mean level in sera (or breast cells) of the control group would indicate that the patient has breast cancer.

Alternatively, if a sample of the subject's serum (or breast cells) that was obtained at a prior date at which the patient clearly did not have breast cancer is available, the level of protein in the test serum (or breast cell) sample can be compared to the level in the prior obtained sample. A higher level, or lower level (depending on whether the gene of interest is expressed at higher or lower level in breast cancer or associated stromal cells) in the test serum (or breast cell) sample would be an indication that the patient has breast cancer.

Moreover, a test expression profile of a gene in a test cell (or tissue) can be compared to control expression profiles of control cells (or tissues) previously established to be of defined category (e.g., DCIS grade, breast cancer stage, or state of differentiation). The category of the test cell (or tissue) will be that of the control cell (or tissue) whose expression profile the test cell's (or tissue's) expression profile most closely resembles. These expression profile comparison assays can be used to compare any of the normal breast tissue with any stage and/or grade of breast cancer recited herein and/or to compare between breast cancer grades and stages. The genes analyzed can be any of those listed in Tables 2, 5, 7, 8, 10, 12, 15, and 16 and the number of genes analyzed can be any number, i.e., one or more. Generally, at least two (e.g., at least: two; three; four; five; six; seven; eight; nine; ten; 11; 12; 13; 14; 15; 17; 18; 20; 23; 25; 30; 35; 40; 45; 50; 60; 70; 80; 90; 100; 120; 150; 200; 250; 300; 350; 400; 450; 500; or more) genes will be analyzed. It is understood that the genes analyzed will include at least one of those listed herein but can also include others not listed herein.

One of skill in the art will appreciate from this description how similar "test level" versus "control level" comparisons can be made between other test and control samples described herein.

It is noted that the patients and control subjects referred to above need not be human patients. They can be for example, non-human primates (e.g., monkeys), horses, sheep, cattle, goats, pigs, dogs, guinea pigs, hamsters, rats, rabbits or mice.

Arrays and Kits and Uses Thereof

The invention features an array that includes a substrate having a plurality of addresses. At least one address of the plurality includes a capture probe that binds specifically to any of the MSDK tags listed in Tables 2, 5, 7, 8, 10, 12, 15, and 16, a nucleic acid X (e.g., a DNA sequence (AscI site) defined by the location of the MSDK tags listed in Tables 2, 5, 7, 8, 10, 12, 15, and 16), or a protein X. The array can have a density of at least, or less than, 10, 20 50, 100, 200, 500, 700, 1,000, 2,000, 5,000 or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

An array can be generated by any of a variety of methods. Appropriate methods include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In one embodiment, at least one address of the plurality includes a nucleic acid capture probe that hybridizes specifically to any of the MSDK tags listed in Tables 2, 5, 7, 8, 10, 12, 15, and 16, e.g., the sense or anti-sense (complement) strand of the tag sequences. Each address of the subset can include a capture probe that hybridizes to a different region of the MSDK tag. Such an array can be useful, for example, for detecting the presence and, optionally, assessing the relative numbers of one or more of the MSDK tags (or the complements thereof) listed in Tables 2, 5, 7, 8, 10, 12, 15, and 16 in a sample, e.g., a MSDK tag library.

In another embodiment, at least one address of the plurality includes a nucleic acid capture probe that hybridizes specifically to a nucleic acid X, e.g., the sense or anti-sense strand. Nucleic acids of interest include, without limitation, all or part of any of the genes identified by the tags listed in Tables 2, 5, 7, 8, 10, 12, 15, and 16, all or part of mRNAs transcribed from such genes, or all or part of cDNA produced from such mRNA. Each address of the subset can include a capture probe that hybridizes to a different region of a nucleic acid. Each address of the subset is unique, overlapping, and complementary to a different variant of gene X (e.g., an allelic variant, or all possible hypothetical variants). The array can be used, for example, to sequence gene X, mRNA X, or cDNA X by hybridization (see, e.g., U.S. Pat. No. 5,695,940) or assess levels of expression of gene X.

In another embodiment, at least one address of the plurality includes a polypeptide capture probe that binds specifically to protein X or fragment thereof. The polypeptide can be a naturally-occurring interaction partner of protein X, e.g., a ligand for protein X where protein X if a receptor or a receptor for protein X where protein X is ligand. Preferably, the polypeptide is an antibody, e.g., an antibody specific for protein X, such as a polyclonal antibody, a monoclonal antibody, or a single-chain antibody.

Antibodies can be polyclonal or monoclonal antibodies; methods for producing both types of antibody are known in the art. The antibodies can be of any class (e.g., IgM, IgG, IgA, IgD, or IgE) and be generated in any of the species recited herein. They are preferably IgG antibodies. Recombinant antibodies, such as chimeric and humanized monoclonal antibodies comprising both human and non-human portions, can also be used in the methods of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225,539; Jones et al. (1986) Nature 321, 552-25; Veroeyan et al. (1988) Science 239, 1534; and Beidler et al. (1988) J. Immunol. 141, 4053-60.

Also useful for the arrays of the invention are antibody fragments and derivatives that contain at least the functional portion of the antigen-binding domain of an antibody. Antibody fragments that contain the binding domain of the molecule can be generated by known techniques. Such fragments include, but are not limited to: F(ab')$_2$ fragments that can be produced by pepsin digestion of antibody molecules; Fab fragments that can be generated by reducing the disulfide bridges of F(ab')$_2$ fragments; and Fab fragments that can be generated by treating antibody molecules with papain and a reducing agent. See, e.g., National Institutes of Health, 1 *Current Protocols In Immunology*, Coligan et al., ed. 2.8, 2.10 (Wiley Interscience, 1991). Antibody fragments also include Fv fragments, i.e., antibody products in which there are few or no constant region amino acid residues. A single chain Fv fragment (scFv) is a single polypeptide chain that includes both the heavy and light chain variable regions of the antibody from which the scFv is derived. Such fragments can be produced, for example, as described in U.S. Pat. No. 4,642,334, which is incorporated herein by reference in its entirety. For a human subject, the antibody can be a "humanized" version of a monoclonal antibody originally generated in a different species.

In another aspect, the invention features a method of analyzing the expression of gene X. The method includes providing an array as described above; contacting the array with a sample and detecting binding of a nucleic acid X or protein X to the array. In one embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of gene X. If a sufficient number of diverse samples is analyzed, clustering (e.g., hierarchical clustering, k-means clustering, Bayesian clustering and the like) can be used to identify other genes which are co-regulated with gene X. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess gene X expression in one or more cell types (see above).

In another embodiment, the array can be used to monitor expression of one or more genes in the array with respect to time. For example, samples obtained from different time points can be probed with the array. Such analysis can identify and/or characterize the development of a gene X-associated disease or disorder (e.g., breast cancer such as invasive breast cancer); and processes, such as a cellular transformation associated with a gene X-associated disease or disorder. The method can also evaluate the treatment and/or progression of a gene X-associated disease or disorder The array is also useful for ascertaining differential expression patterns of one or more genes in normal and abnormal (e.g., malignant) cells. This provides a battery of genes (e.g., including gene X) that could serve as a molecular target for diagnosis or therapeutic intervention.

In another aspect, the invention features a method of analyzing a plurality of probes. The method is useful, e.g., for analyzing gene expression. The method includes: providing a first two dimensional array having a plurality of addresses, each address (of the plurality) being positionally distinguishable from each other address (of the plurality) having a unique capture probe, e.g., wherein the capture probes are from a cell or subject which express gene X or from a cell or subject in which a gene X-mediated response has been elicited, e.g., by contact of the cell with nucleic acid X or protein X, or administration to the cell or subject of a nucleic acid X or protein X; providing a second two dimensional array having a plurality of addresses, each address of the plurality being positionally distinguishable from each other address of the plurality, and each address of the plurality having a unique capture probe, e.g., wherein the capture probes are from a cell or subject which does not express gene X (or does not express as highly as in the case of the cell or subject described above for the first array) or from a cell or subject which in which a gene X-mediated response has not been elicited (or has been elicited to a lesser extent than in the first sample); contacting the first and second arrays with one or more inquiry probes (which are preferably other than a nucleic acid X, protein X, or antibody specific for protein X), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

The invention also features a method of analyzing a plurality of probes or a sample. The method is useful, e.g., for analyzing gene expression. The method includes: providing a first two dimensional array having a plurality of addresses, each address of the plurality being positionally distinguishable from each other address of the plurality having a unique capture probe, contacting the array with a first sample from a cell or subject which express or mis-express gene X or from a cell or subject in which a gene X-mediated response has been elicited, e.g., by contact of the cell with nucleic acid X or protein X, or administration to the cell or subject of nucleic acid X or protein X; providing a second two dimensional array having a plurality of addresses, each address of the plurality being positionally distinguishable from each other address of the plurality, and each address of the plurality having a unique capture probe, and contacting the array with a second sample from a cell or subject which does not express gene X (or does not express as highly as in the case of the as in the case of the cell or subject described for the first array) or from a cell or subject which in which a gene X-mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by a signal generated from a label attached to the nucleic acid, polypeptide, or antibody. The same array can be used for both samples or different arrays can be used. If different arrays are used the same plurality of addresses with capture probes should be present on both arrays.

All the above listed capture probes useful for arrays can also be provided in the form of a kit or article of manufacture, optionally also containing packaging materials. In such kits or articles of manufacture, the capture probes can be provided as preformed arrays, i.e., attached to appropriate substrates as described above. Alternatively they can be provided in unattached form.

The capture probes can be supplied in unattached form in any number. Moreover, each capture probe in a kit or article of manufacture can be provided in a separate vessel (e.g., bottle, vial, or package), all the capture probes can be combined in the same vessel, or a plurality of pools of capture probes can be provided, with each pool being provided in a separate vessel. In the kit or article of manufacture there can optionally be instructions (e.g., on the packing materials or in a package insert) on how to use the arrays or unattached capture probes, e.g., on how to perform any of the methods described herein.

The following examples are intended to illustrate, not limit, the invention.

EXAMPLES

Example 1

Materials and Methods

Tissue Specimens and Primary Cell Cultures

Human breast tumor and fresh, frozen, or formalin fixed, paraffin embedded tumor specimens were obtained from the Brigham and Women's Hospital (Boston, Mass.), Columbia University (New York, N.Y.), University of Cambridge (Cambridge, UK), Duke University (Durham, N.C.), University Hospital Zagreb (Zagreb, Croatia), the National Disease Research Interchange (Philadelphia, Pa.), and the Breast Tumor Bank of the University of Liège (Liège, Belgium). All human tissue was collected without patient identifiers using protocols approved by the Institutional Review Boards of the institutions. In the case of matched tissue samples (i.e., normal and tumor tissue samples obtained from the same individuals), the normal tissue corresponding to the tumor was obtained from the ipsilateral breast several centimeters away from the tumor. Fresh tissue samples were immediately processed for immunomagnetic purification and cell subsets were purified as previously described [Allinen et al. (2004) Cancer Cell 6:17-32 and co-pending U.S. Patent Application Serial No. PCT/US2004/08866, the disclosures of which are incorporated herein by reference in its entirety]. Following the purification procedure, in some cases the purity of each cell population was confirmed by RT-PCR and primary cultures of the different cell types were initiated. Primary stromal fibroblasts were cultured in DMEM medium supplemented with 10% iron fortified bovine calf serum (Hyclone, Logan, Utah) prior to lysis and DNA and RNA isolation. Human embryonic stem cells were cultured on feeder layers using established protocols (for example, see, REF). DNA and RNA were isolated from the other cell-types without prior culturing.

RNA and Genomic DNA Isolation, and cDNA Synthesis

RNA (total and polyA) isolation was performed using a µMACS™ kit (Miltenyi Biotec, Auburn, Calif.) from small numbers of cells, while from large tissue samples, primary cultures and cell lines total RNA was isolated using a guanidium/cesium method [Allinen et al. (2004), supra]. Column flow-through fractions (in the µMACS™ method) and unprecipitated soluble material (guanidium/cesium method) were used for the purification of genomic DNA using SDS/proteinase K digestion followed by phenol-chloroform extraction and isopropanol precipitation. cDNA synthesis was performed using the OMNI-SCRIPT™ kit form Qiagen (Valencia, Calif.) following the manufacturer's instructions.

Generation and Analysis of MSDK (Methylation Specific Digital Karyotyping) Libraries MSDK libraries were generated by a modification of the digital karyotping protocol [Wang et al. (2002) Proc. Natl. Acad. Sci USA 16156-16161]. For each sample, 1-5 µg genomic DNA was sequentially digested with the methylation-sensitive enzyme AscI and the resulting fragments were ligated at their 5' and 3' ends to biotinylated linkers (5'-biotin-TTTGCAGAGGTTCGTAATCGAGT-TGGGTGG-3',5'-phos-CGCGCCACCCAACTCGATTAC-GAACCTCTGC-3'). The biotinylated fragments were then digested with NlaIII as a fragmenting restriction enzyme. Resulting DNA fragments having biotinylated linkers at their termini were immobilized onto streptavidin-conjugated magnetic beads (Dynal, Oslo, Norway).

The remaining steps were essentially the same as those described for LongSAGE with minor modifications [Allinen et al. (2004) supra; Saha et al. (2002) Nat. Biotechnol. 20:508-512]. Briefly, linkers containing the type IIs restriction enzyme MmeI recognition site were ligated to isolated DNA fragments and the bead bound fragments were cut by the MmeI enzyme 21 base pairs away from the restriction enzyme site, resulting in release from the beads into the surrounding solution of tags containing the MmeI recognition site, a linker and 21 base pairs of test genomic DNA. The tags were ligated to form ditags which are formed between single tags containing 5' and 3' MmeI digestion (cut) sites (depending on whether the relevant fragment bound to a bead was derived by from an NlaIII site 5' or 3' of an unmethylated AscI site). The ditags were expanded by PCR, isolated, and ligated to form concatamers, which were cloned into the pZero 1.0 vector (Invitrogen, Carlsbad, Calif.) and sequenced. 21-bp tags were extracted and duplicate ditags (arising due to the PCR expansion step) were removed using SAGE 2002 software. P values were calculated based on pair-wise comparisons between libraries using a Poisson-based algorithm [Cai et al. (2004) Genome Biol. 5:R51; Allinen et al. (2004) supra]. Raw tag counts were used for comparing the libraries and calculating p values, but subsequently tag numbers were normalized in order to control for uneven total tag numbers/library (average total tag number 28,456/library).

In order to determine their chromosomal location, tags that appeared only once in each library were filtered out and matched to a virtual AscI library derived from a human genome sequence. Human genome sequence and mapping information (July 2003, hg16) were downloaded from UCSC Genome Bioinformatics Site. A virtual AscI tag library was constructed based on the genome sequence as follows: predicted AscI sites were located in the genomic sequence, the nearest NlaIII sites in both directions to the AscI sites were identified, and the corresponding virtual MSDK sequence tags were derived. All virtual tags that were not unique in the genome were removed in order to ensure unambiguous mapping of the data. Genes neighboring the AscI sites were also identified in order to determine the effect of methylation on their expression.

Alignment of MSDK, SAGE, and CpG Islands Across the Genome

The frequency of AscI digestion was calculated as percentage of samples (N-EPI-17, I-EPI-7, N-MYOEP-4, D-MYOEP-6, N-STR-17, I-STR-7, N-STR-117, I-STR-17) having raw tag counts of 2 or more at each predicted AscI site. SAGE counts from corresponding samples (N-EPI-1 plus N-EPI-2, I-EPI-7, N-MYOEP-1, D-MYOEP-6, D-MYOEP-7, N-STR-1, N-STRI-17, I-STR-7) were normalized to tags per 200,000. Gene and CpG island position information were downloaded from UCSC Genome Bioinformatics Site (Human genome sequence and mapping information, July 2003, hg16). AscI sites were predicted (as mentioned above) from the genome sequence, and AscI site frequency, SAGE counts, and CpG island positions were drawn together along all chromosomes.

Bisulfite Sequencing, Quantitative Methylation Specific PCR (qMSP), and Quantitative RT-PCR (qRT-PCR)

To determine the location of methylated cytosines, genomic DNA was bisulfite treated, purified, and PCR reactions were performed as previously described [Herman et al. (1996) Proc. Natl. Acad. Sci. USA 93:9821-0826]. PCR products were "blunt-ended", subcloned into pZERO1.0 (Invitrogen), and 4-13 independent colonies were sequenced for each PCR product.

Based on the above sequence analysis qMSP PCR primers were designed for the amplification of methylated or unmethylated DNA. Quantitative MSP and RT-PCR amplifications were performed as follows. Template (2-5 ng bisulfite treated genomic DNA or 1 µl cDNA) and primers were mixed with 2×SYBR Green master mix (ABI, CA) in a 25 µl volume and the reactions were performed in ABI 7500 real time PCR system (50° C., 20 sec; 95° C., 10 min; 95° C., 15 sec, 60° C., 1 min (40 cycles); 95° C., 15 sec; 60° C., 20 sec; 95° C., 15 sec). Triplicates were performed and average Ct values calculated. The Ct (cycle threshold) value is the PCR cycle number at which the reaction reaches a fluorescent intensity above the threshold which is set in the exponential phase of the amplification (based on amplification profile) to allow accurate quantification. In the case of qMSP, methylation of the samples was normalized to methylation independent amplification of the β-actin (ACTB)

gene: % ACTB=100×2$^{(CtACTB-Ctgene)}$. For qRT-PCR expression of the samples was normalized to that of the RPL39 (ribosomal protein L39) gene: % RPL39=10× 2$^{(CtRPL39-Ctgene)}$. Normalizations to the expression of the ribosomal protein L19 (RPL19) and ribosomal protein S13 (RPS13) genes were also performed and gave essentially the same results. Due to the very high abundance of ribosomal protein mRNAs, cDNA was diluted ten-fold for these PCR reactions relative to that of specific genes. The frequency of methylation of the PRDM14 gene in normal and tumor samples was calculated by setting a threshold of methylation as the median+2×standard deviation value of the relative methylation of the normal samples (excluding the one outlier case; see below). Samples above this value (10.66) were defined as methylated.

Example 2

Methylation Specific Digital Karyotyping (MSDK)

Figure 2:
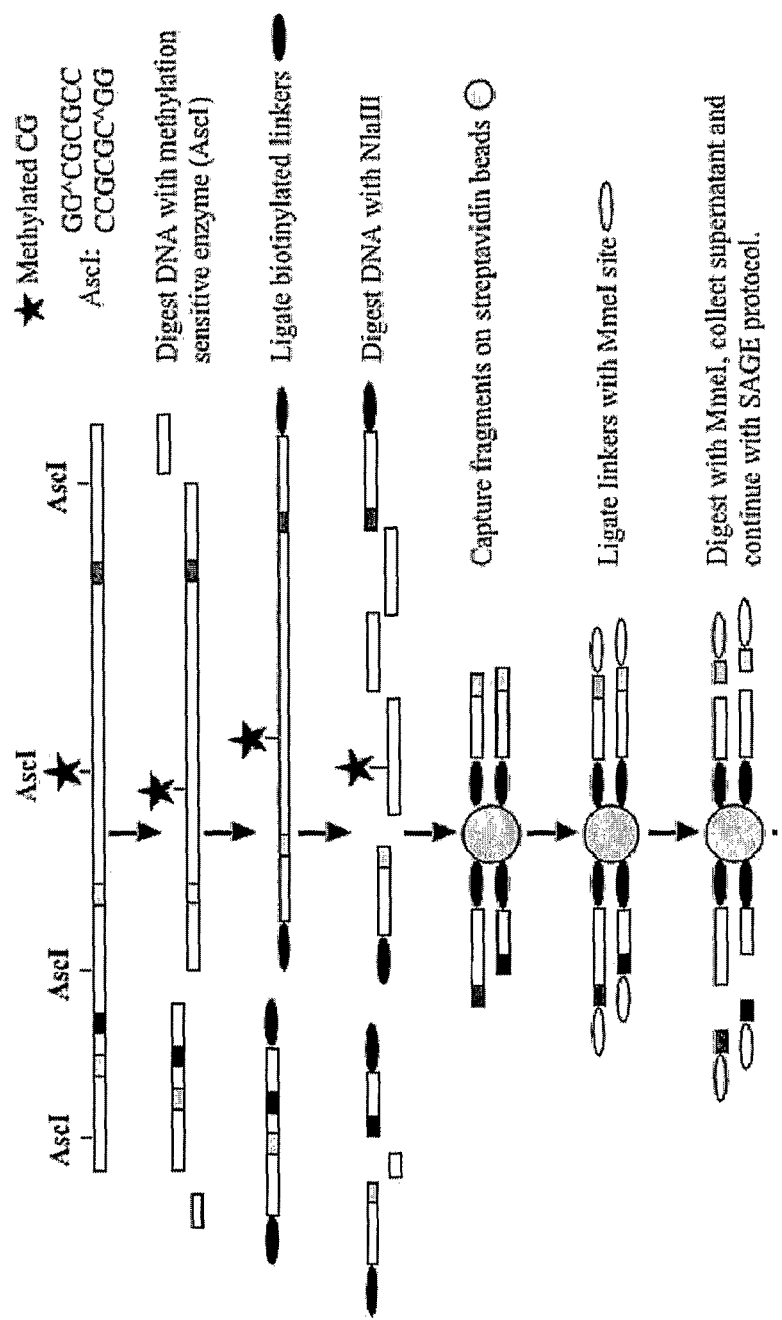
FIG. 2 is a schematic depiction of the MSDK procedure described in Examples 1 and 2.

The MSDK protocol used in the experiments described below is schematically depicted in FIG. 2.

MSDK is a modification of the digital karyotyping (DK) technique recently developed for the analysis of DNA copy number in a quantitative manner on a genome-wide scale [Wang et al. (2002) supra]. DK is based on two concepts: (i) short (e.g., 21 base pair) sequence tags can be derived from specific locations in the human genome; and (ii) these sequence tags can be directly matched to the human genome sequence. The original DK protocol used SacI as a mapping enzyme and NlaIII as a fragmenting enzyme. Using this enzyme combination the tags were obtained from the two (both 5' and 3') NlaIII sites closest to the SacI sites.

In the MSDK method, instead of SacI, a mapping enzyme that is sensitive to DNA methylation was used. AscI was chosen because its recognition sequence (GGCGCGCC) has two CpG (potential methylation) sites, is preferentially found in CpG islands associated with transcribed genes rather than repetitive elements [Dai et al. (2002) Genome Res. 12:1591-1598], and it is a rare cutter enzyme (~5,000 predicted sites/human genome) allowing identification of tags that are highly statistically significantly differentially present in the different libraries at reasonable sequencing depths (20,000-50,000 tags/library). Methylation of either or both methylation sites in an AscI recognition sequence prevents cutting by AscI. The use of AscI and NlaIII as mapping and fragmenting enzymes, respectively, with human genomic DNA, respectively, is expected to result in a total of 7,205 virtual tags (defined as possible tags that can be obtained and uniquely matched to the human genome based on the predicted location of AscI and NlaIII sites). Since AscI will cut only unmethylated DNA, the presence of a tag in the MSDK library indicates that the corresponding AscI site is not methylated, while lack of a virtual tag indicates methylation.

To demonstrate the feasibility of the MSDK method for epigenome profiling, MSDK libraries were generated from genomic DNA isolated from the wild-type HCT116 human colon cancer cell line (HCT WT) and its derivative in which both the DNMT1 and DNMT3b DNA methyltransferase genes have been homozygously deleted (HCT DKO) [Rhee et al. (2002) Nature 416, 552-556]. Due to the deletion of these two DNA methyltransferases, methylation of the genomic DNA in the HCT DKO cells is reduced by greater than 95% relative to the HCT WT cells. Thus, MSDK libraries generated from HCT WT and HCT DKO cells were expected to depict dramatic differences in DNA methylation. 21,278 and 24,775 genomic tags were obtained from the WT and DKO cells, respectively. These tags were matched to a virtual AscI tag library generated as described in Example 1. Unique tags (7,126 from the WT and 7,964 tags from the DKO cells) were compared and 219 were identified as being statistically significantly (p<0.05) differentially present in the two libraries (Table 1). 137 and 82 of these tags were more abundant in the DKO and WT libraries, respectively. Correlating with the overall hypomethylation of the genome of DKO cells, almost all of the 137 tags were at least 10 fold more abundant in the DKO library, while nearly all 82 tags showed only 2-5 fold difference between the two libraries.

TABLE 1

Chromosomal location and analysis of the frequency of MSDK tags in the HCT116 WT and DKO MSDK libraries.

| Chr | Virtual Tag | Observed Tag | WT Variety | WT Copies | DKO Variety | DKO Copies | Tag Variety Ratio DKO/WT | Tag Copy Ratio DKO/WT | Differential Tag (P < 0.05) DKO > WT | Differential Tag (P < 0.05) WT > DKO |
|---|---|---|---|---|---|---|---|---|---|---|
| 1 | 551 | 119 | 73 | 431 | 89 | 538 | 1.219 | 1.248 | 10 | 6 |
| 2 | 473 | 94 | 51 | 383 | 72 | 499 | 1.412 | 1.303 | 10 | 5 |
| 3 | 349 | 83 | 48 | 478 | 59 | 473 | 1.229 | 0.990 | 8 | 5 |
| 4 | 281 | 62 | 33 | 266 | 49 | 265 | 1.485 | 0.996 | 3 | 5 |
| 5 | 334 | 74 | 41 | 437 | 56 | 536 | 1.366 | 1.227 | 10 | 3 |
| 6 | 338 | 65 | 36 | 229 | 51 | 315 | 1.417 | 1.376 | 8 | 4 |
| 7 | 403 | 90 | 60 | 359 | 66 | 344 | 1.100 | 0.958 | 4 | 4 |
| 8 | 334 | 89 | 54 | 460 | 73 | 433 | 1.352 | 0.941 | 3 | 5 |
| 9 | 349 | 86 | 50 | 397 | 67 | 468 | 1.340 | 1.179 | 9 | 5 |
| 10 | 387 | 84 | 43 | 386 | 71 | 468 | 1.651 | 1.212 | 10 | 4 |
| 11 | 379 | 96 | 55 | 408 | 75 | 392 | 1.364 | 0.961 | 6 | 4 |
| 12 | 299 | 72 | 42 | 330 | 52 | 329 | 1.238 | 0.997 | 7 | 4 |
| 13 | 138 | 25 | 12 | 109 | 19 | 105 | 1.583 | 0.963 | 1 | 1 |
| 14 | 228 | 51 | 28 | 234 | 36 | 225 | 1.286 | 0.962 | 4 | 3 |
| 15 | 260 | 52 | 38 | 243 | 37 | 163 | 0.974 | 0.671 | 2 | 4 |
| 16 | 340 | 82 | 43 | 297 | 65 | 347 | 1.512 | 1.168 | 4 | 2 |
| 17 | 400 | 116 | 54 | 401 | 100 | 781 | 1.852 | 1.948 | 16 | 3 |
| 18 | 181 | 39 | 19 | 115 | 29 | 199 | 1.526 | 1.730 | 7 | 0 |
| 19 | 463 | 99 | 59 | 429 | 70 | 391 | 1.186 | 0.911 | 9 | 7 |
| 20 | 236 | 58 | 32 | 213 | 41 | 287 | 1.281 | 1.347 | 4 | 2 |
| 21 | 71 | 11 | 7 | 27 | 6 | 43 | 0.857 | 1.593 | 1 | 0 |
| 22 | 217 | 51 | 31 | 328 | 38 | 260 | 1.226 | 0.793 | 1 | 4 |

TABLE 1-continued

Chromosomal location and analysis of the frequency of MSDK tags in the HCT116 WT and DKO MSDK libraries.

| Chr | Virtual Tag | Observed Tag | WT | | DKO | | Tag Variety Ratio DKO/WT | Tag Copy Ratio DKO/WT | Differential Tag (P < 0.05) | |
|---|---|---|---|---|---|---|---|---|---|---|
| | | | Variety | Copies | Variety | Copies | | | DKO > WT | WT > DKO |
| X | 185 | 22 | 16 | 166 | 18 | 103 | 1.125 | 0.620 | 0 | 2 |
| Y | 9 | 0 | 0 | 0 | 0 | 0 | | | | |
| Matches | 7205 | 1620 | 925 | 7126 | 1239 | 7964 | 1.339 | 1.118 | 137 | 82 |
| No Matches | | 1353 | 799 | 5183 | 816 | 5805 | 1.021 | 1.120 | 29 | 13 |
| Total | 7205 | 2973 | 1724 | 12309 | 2055 | 13769 | 1.192 | 1.119 | 166 | 95 |

Chr, Chromosome.
Virtual tags, the number of MSDK tag species predicted for the indicated chromosome.
Observed Tags, the number of different unique tag species observed in both MSDK libraries for the indicated chromosome.
Variety, the number of different unique tag species for the indicated chromosome and MSDK library.
Copies, the abundance (total number) of all the observed unique tags for the indicated chromosome and MSDK library.
Tag Variety Ratio, the ratio of the numbers of unique tag species for the indicated chromosome detected in the indicated two libraries.
Tag Copy Ratio, the ratio of the abundances (total numbers) of all the unique tags for the indicated chromosomes detected in the indicated two libraries.
Differential Tag (P < 0.05), the number of unique tag species observed for the indicated chromosome that were present in higher abundance in the one indicated MSDK library than in the other indicated MSDK library (P < 0.050).

Single nucleotide polymorphism (SNP) array analysis of the DNA samples used for the generation of MSDK libraries demonstrated that the two cell lines are indistinguishable using this technique and the observed differences in MSDK tag numbers are unlikely to be due to underlying overt DNA copy number alterations. Mapping of the tags to the genome revealed that many of the differentially methylated AscI sites are located in CpG islands and in promoter areas of genes implicated in development and differentiation including numerous homeogenes (Table 2). Consistent with these results, two of these genes, LMX-1A and COL5A, have previously been found to be differentially methylated between HCT116 WT and DKO cells, and are also frequently methylated in primary colorectal carcinomas and colon cancer cell lines [Paz et al. (2003) Hum. Mol. Genet. 12:2209-2210]. Similarly SCGB3A1/HIN-1, a gene frequently methylated in multiple cancer types [Shigematsu et al. (2005) Int. J. Cancer 113:600-604; Krop et al. (2004) Mol. Cancer Res. 2:489-494; Krop et al. (2001) Proc. Natl. Acad. Sci. USA 98:9796-9801] was identified as one of most highly significantly differently present tags (Table 2).

TABLE 2

MSDK tags significantly (p < 0.050) differentially present in HCT116 WT and DKO MSDK libraries and genes associates with the MSDK tags.

| MSDK Tag | SEQ ID NO. | DKO | WT | Ratio DKO/WT | P value | Chr | Gene | Description | Position of AscI site in relation to tr. Start | Distance of AscI site from tr. Start (bp) |
|---|---|---|---|---|---|---|---|---|---|---|
| GTGCCGCCGCGGGCGCC | 19 | 14 | 0 | 14 | 0.0023908 | 1 | KIAA0478 | KIAA0478 gene product | 5' | 308006 |
| GTGCCGCCGCGGGCGCC | 20 | 14 | 0 | 14 | 0.0023908 | 1 | WNT4 | wingless-type MMTV integration site family | 5' | 733 |
| GCACAATGAAAGCATTT | 21 | 0 | 8 | -9 | 0.0375409 | 1 | TCEB3 | elongin A | 3' | 78 |
| GCTGGACACAATGGGTC | 22 | 0 | 15 | -17 | 0.0007148 | 1 | MACF1 | microfilament and actin filament cross-linker | 3' | 35 |
| TGTGAGGGCGAGTGTGA | 23 | 9 | 0 | 9 | 0.020643 | 1 | HIVEP3 | human immunodeficiency virus type I enhancer | 3' | 392630 |
| AGCACCGCTGGAACC | 24 | 2 | 15 | -8 | 0.0024514 | 1 | PTPRF | protein tyrosine phosphatase, receptor type, F | 3' | 727 |
| GCTCACCTACCAGGTG | 25 | 12 | 0 | 12 | 0.0056628 | 1 | Not Found | | | |
| GCCTCTCTGCGCCTGCC | 26 | 15 | 0 | 15 | 0.0015534 | 1 | GFI1 | growth factor independent 1 | 3' | 4842 |
| CCCGGACTTGGCCAGGC | 27 | 47 | 2 | 21 | 2.35 × 10⁻⁸ | 1 | NHLH2 | nescient helix loop helix 2 | 3' | 2971 |
| TTCGGGCCGGGCCGGGA | 28 | 18 | 0 | 18 | 0.0004261 | 1 | LMX1A | LIM homeobox transcription factor 1, alpha | 5' | 752 |
| AGCCCTCGGGTGATGAG | 29 | 14 | 0 | 14 | 0.0023908 | 1 | LMX1A | LIM homeobox transcription factor 1, alpha | 5' | 752 |
| CTTATGTTTACAGCATC | 30 | 4 | 16 | -4 | 0.0103904 | 1 | PAPPA2 | pappalysin 2 isoform 2 | 5' | 255915 |
| CTTATGTTTACAGCATC | 31 | 4 | 16 | -4 | 0.0103904 | 1 | RFWD2 | ring finger and WD repeat domain 2 isoform a | 5' | 21 |
| GTTCTCAAACAGCTTTC | 32 | 2 | 10 | -6 | 0.0365508 | 1 | IPO9 | importin 9 | 5' | 343 |
| TCCAGCAGGGCCTCTG | 33 | 16 | 42 | -3 | 0.000352 | 1 | BTG2 | B-cell translocation gene 2 | 3' | 431 |
| CCCCGACGACGGGCGG | 34 | 28 | 0 | 28 | 5.72 × 10⁻⁶ | 1 | SOX13 | SRY-box 13 | 5' | 571 |
| CCCCGACGACGGGCGG | 34 | 28 | 0 | 28 | 5.72 × 10⁻⁶ | 1 | FLJ40343 | hypothetical protein FLJ40343 | 5' | 31281 |
| GTGAACTTCCAAGATGC | 36 | 14 | 0 | 14 | 0.0023908 | 1 | CNIH3 | cornichon homolog 3 | 5' | 50 |
| ATGCGCCCCCAGCCCC | 37 | 8 | 0 | 8 | 0.0317702 | 1 | MGC13186 | hypothetical protein MGC13186 | 5' | 321138 |
| ATGCGCCCCCAGCCCC | 38 | 8 | 0 | 8 | 0.0317702 | 1 | SIPA1L2 | signal-induced proliferation-associated 1 like | 5' | 114742 |
| GTCCCCGCGCCGCGGCC | 39 | 23 | 0 | 23 | 4.94 × 10⁻⁵ | 1 | UBXD4 | UBX domain containing 4 | 5' | 553390 |
| ATGCGCCGCCGCGGCC | 40 | 23 | 0 | 23 | 4.94 × 10⁻⁵ | 2 | APOB | apolipoprotein B precursor | 5' | 2343039 |
| ATGCGAGGGGCGGTA | 41 | 21 | 43 | -2 | 0.0036483 | 2 | FLJ32954 | hypothetical protein FLJ32954 | 5' | 277913 |
| ATGCGAGGGGCGGTA | 42 | 21 | 43 | -2 | 0.0036483 | 2 | CDC42EP3 | Cdc42 effector protein 3 | 5' | 366 |
| GCAGCATTGCGGCTCCG | 43 | 36 | 0 | 36 | 1.82 × 10⁻⁷ | 2 | SIX2 | sine oculis homeobox homolog 2 | 5' | 160394 |
| TCATTGCATACTGAAGG | 44 | 7 | 19 | -3 | 0.0235641 | 2 | SLC1A4 | solute carrier family 1, member 4 | 5' | 335302 |
| TCATTGCATACTGAAGG | 45 | 7 | 19 | -3 | 0.0235641 | 2 | SERTAD2 | SERTA domain containing 2 | 3' | 245 |
| GCGCTACAACGCGCTCC | 46 | 0 | 9 | -10 | 0.0214975 | 2 | SLC1A4 | solute carrier family 1, member 4 | 5' | 111 |
| GCGCTACAACGCGCTCC | 47 | 0 | 9 | -10 | 0.0214975 | 2 | SERTAD2 | SERTA domain containing 2 | 3' | 335436 |
| CCCCAGCTCGGCGGCGG | 48 | 53 | 0 | 53 | 1.19 × 10⁻¹⁰ | 2 | TCF7L1 | HMG-box transcription factor TCF-3 | 3' | 859 |
| CCTGGCCCTGTTGTGTC | 49 | 8 | 0 | 8 | 0.0317702 | 2 | DUSP2 | dual specificity phosphatase 2 | 5' | 26138 |
| AAGCAGTCTTCTGAGGGG | 50 | 23 | 47 | -2 | 0.0022127 | 2 | CNNM3 | cyclin M3 isoform 1 | 3' | 396 |
| GGAGGGCTGAGTGAGG | 51 | 12 | 0 | 12 | 0.020295 | 2 | FLJ38377 | hypothetical protein FLJ38377 | 5' | 593 |
| AGACCATCCTTGGACCC | 52 | 15 | 0 | 15 | 0.0057312 | 2 | B3GALT1 | UDP-Gal:betaGlcNAc beta | 5' | 524869 |
| GGCGCCAGAGGAAGATC | 53 | 7 | 0 | 7 | 0.0488953 | 2 | SSB | autoantigen La | 5' | 29950 |
| CCCACCGAGGGGAAGA | 54 | 11 | 0 | 11 | 0.0087152 | 2 | SP5 | Sp5 transcription factor | 3' | 1824 |
| TTAATCTGCTTATGAAA | 55 | 0 | 7 | -8 | 0.0172683 | 2 | SP3 | Sp3 transcription factor | 3' | 1637 |
| AAATTCCATAGACAACC | 56 | 11 | 0 | 11 | 0.0087152 | 2 | HOXD4 | homeo box D4 | 3' | 1141 |
| GGTGACAGAGTGCGACT | 57 | 8 | 0 | 8 | 0.0317702 | 3 | Not Found | | | |
| CAGCGACATCTCTGGCT | 58 | 7 | 0 | 7 | 0.0488953 | 3 | DTYMK | deoxythymidylate kinase (thymidylate kinase) | 5' | 2784474 |
| GGAGGCAAACGGGAACC | 59 | 13 | 0 | 13 | 0.0036794 | 3 | IQSEC1 | IQ motif and Sec7 domain 1 | 5' | 315433 |
| GCTCGCCAGGAGGGGC | 60 | 16 | 0 | 16 | 0.0010093 | 3 | RBMS3 | RNA binding motif, single stranded interacting | 5' | 706157 |
| GCTCGCCGAGGAGGGGC | 61 | 16 | 0 | 16 | 0.0010093 | 3 | AZI2 | 5-azacytidine induced 2 isoform a | 5' | 226210 |
| GATCGCTGGGGTTTTGG | 62 | 22 | 0 | 22 | 7.60 × 10⁻⁵ | 3 | DLEC1 | deleted in lung and esophageal cancer 1 isoform | 5' | 9380 |

TABLE 2-continued

MSDK tags significantly (p < 0.050) differentially present in HCT116 WT and DKO MSDK libraries and genes associates with the MSDK tags.

| MSDK Tag | SEQ ID NO. | DKO | WT | Ratio DKO/WT | P value | Chr | Gene | Description | Position of AscI site in relation to tr. Start | Distance of AscI site from tr. Start (bp) |
|---|---|---|---|---|---|---|---|---|---|---|
| GATCGCTGGGGTTTTGG | 63 | 22 | 0 | 22 | 7.60 × 10⁻⁵ | 3 | PLCD1 | phospholipase C, delta 1 | 5' | 200 |
| CTAATCTCTCCATCTGA | 64 | 0 | 8 | −9 | 0.0375409 | 3 | SS18L2 | synovial sarcoma translocation gene on | 5' | 8746 |
| CTATCTCTCCATCTGA | 65 | 0 | 8 | −9 | 0.0375409 | 3 | SEC22L3 | vesicle trafficking protein isoform b | 5' | 129 |
| CGGCGCGTTCCCTGCGG | 66 | 51 | 0 | 51 | 2.82 × 10⁻¹⁰ | 3 | DKFZp313N0621 | hypothetical protein DKFZp313N0621 | 5' | 339665 |
| AACCCCGAAACTGGAAG | 67 | 7 | 0 | 7 | 0.0488953 | 3 | FAM19A4 | family with sequence similarity 19 (chemokine x 010 protein | 5' | 143 |
| GAAGAGTCCCAGCCGGT | 68 | 15 | 40 | −3 | 0.0004426 | 3 | MDS010 | transmembrane protein 39A | 5' | 5211 |
| GAAGAGTCCCAGCCGGT | 69 | 15 | 40 | −3 | 0.0004426 | 3 | TMEM39A | transmembrane protein 39A | 5' | 116 |
| GAGGAGAGAGATGGTCC | 70 | 8 | 0 | 8 | 0.0317702 | 3 | GPR156 | G protein-coupled receptor 156 | 5' | 41213 |
| CCTGCCTCTGGCAGGGG | 71 | 18 | 32 | −2 | 0.042895 | 3 | PLXNA1 | plexin A1 | 5' | 5386 |
| GCCTAGAAGAAGCCGAA | 72 | 25 | 46 | −2 | 0.0076042 | 3 | RAB43 | RAB41 protein | 5' | 577 |
| GGGCGAGTCCGGCAGCC | 73 | 17 | 0 | 17 | 0.0006558 | 3 | CHST2 | carbohydrate (N-acetylglucosamine-6-O) | 3' | 61 |
| CGTGTGAGCTCTCCTGC | 74 | 28 | 47 | −2 | 0.0176231 | 3 | EPHB3 | ephrin receptor EphB3 precursor | 3' | 576 |
| CACTTCCAGCTCTGAG | 75 | 6 | 17 | −3 | 0.0294258 | 3 | FGFR3 | fibroblast growth factor receptor 3 isoform 1 | 5' | 26779 |
| CACATCCAGCCCGGGG | 76 | 16 | 0 | 16 | 0.0037515 | 4 | FLJ33718 | hypothetical protein FLJ33718 | 5' | 30337 |
| CCTGCGCCGGGGAGGC | 77 | 40 | 57 | −2 | 0.0483974 | 4 | ADRA2C | alpha-2C-adrenergic receptor | 3' | 432 |
| TACAATGAAGGGGTCC | 78 | 13 | 0 | 13 | 0.0036794 | 4 | STK32B | serine/threonine kinase 32B | 5' | 28 |
| TACAATGAAGGGGTCAG | 79 | 13 | 0 | 13 | 0.0036794 | 4 | CYTL1 | cytokine-like 1 | 3' | 32301 |
| TTGGTAAGCATTATCTC | 80 | 0 | 7 | −8 | 0.0172683 | 4 | WFS1 | wolframin | 3' | 400 |
| GTCCGTGAATAGAAGG | 81 | 13 | 0 | 13 | 0.0036794 | 4 | Not Found | heterogeneous nuclear ribonucleoprotein D-like | 3' | 741 |
| TTTACATTTAATCTATG | 82 | 0 | 6 | −7 | 0.030837 | 4 | HNRPDL | heterogeneous nuclear ribonucleoprotein D-like | 3' | 1583 |
| TGCGGAGAAGACCCGG | 83 | 3 | 13 | −5 | 0.0196518 | 4 | ELOVL6 | ELOVL family member 6, elongation of long chain | | |
| GGAGGTCTCAGGATCCC | 84 | 10 | 23 | −3 | 0.0264674 | 5 | FLJ20152 | hypothetical protein FLJ20152 | 5' | 108193 |
| AAAGCGATCCAAACACA | 85 | 7 | 0 | 7 | 0.0488953 | 5 | BASP1 | brain abundant, membrane attached signal protein | 5' | 182 |
| ACCCGGGCCGCAGCGGC | 86 | 38 | 2 | 17 | 1.10 × 10⁻⁶ | 5 | EFNA5 | ephrin-A5 | 3' | 1019 |
| CTGGGTTGCGATTAGCT | 87 | 15 | 0 | 15 | 0.0015534 | 5 | PPIC | peptidylprolyl isomerase C | 5' | 62181 |
| ACACATTTATTTTTCAG | 88 | 24 | 0 | 24 | 0.0011958 | 5 | KIAA1961 | KIAA1961 protein isoform 1 | 5' | 146 |
| GTGGGAGTCAAAGAGCT | 89 | 26 | 49 | −2 | 0.004247 | 5 | APXL2 | apical protein 2 | 5' | 4006 |
| TCGCGGGCGCTTGCCC | 90 | 48 | 0 | 48 | 1.03 × 10⁻⁹ | 5 | PITX1 | paired-like homeodomain transcription factor 1 | 3' | 6163 |
| CTGACGCGCTCGCCC | 91 | 10 | 0 | 10 | 0.0488953 | 5 | PACAP | proapoptotic caspase adaptor protein | 5' | 4496 |
| CGTCCCCATCCGGGGC | 92 | 7 | 0 | 7 | 0.013413 | 5 | CPLX2 | complexin 2 | 3' | 1498 |
| TGCCACCCGGAGTGCA | 93 | 9 | 0 | 9 | 0.020643 | 5 | Not Found | | | |
| CTGCCCTTATCCTCGA | 94 | 15 | 0 | 15 | 0.0015534 | 6 | FLT4 | fms-related tyrosine kinase 4 isoform 1 | 3' | 28178 |
| CGCTGACCACCAGGAGG | 95 | 8 | 0 | 8 | 0.0317702 | 6 | FLT4 | fms-related tyrosine kinase 4 isoform 1 | 5' | 24508 |
| GCAGAAAAGCACAAAG | 96 | 11 | 0 | 11 | 0.0087152 | 6 | FLT4 | fms-related tyrosine kinase 4 isoform 1 | 5' | 24508 |
| GTCCTTGTTCCCATAGG | 97 | 19 | 0 | 19 | 0.0002769 | 6 | FOXC1 | forkhead box C1 | 5' | 5056 |
| TCAATGCTCCGGGGG | 98 | 12 | 0 | 12 | 0.0056628 | 6 | TFAP2A | transcription factor Ap-2 alpha | 3' | 4264 |
| GCAGCCGCTTCGGCGCC | 99 | 2 | 14 | −8 | 0.00425 | 6 | EGFL9 | EGF-like-domain, multiple 9 | 3' | 134 |
| AGTCCTGAAGCCAGAAG | 100 | 10 | 0 | 10 | 0.013413 | 6 | VEGF | vascular endothelial growth factor | 5' | 52081 |
| AGCTCTGAAGCCAGAAG | 101 | 10 | 0 | 10 | 0.013413 | 6 | MRPS18A | mitochondrial ribosomal protein S18A | 5' | 30336 |
| CCCTCCGATTCTACTAT | 102 | 0 | 7 | −7 | 0.030837 | 6 | COL12A1 | alpha 1 type XII collagen short isoform | 3' | 394 |
| AAGGAGACCGCACAGGG | 103 | 13 | 0 | 13 | 0.0036794 | 6 | HTR1E | 5-hydroxytryptamine (serotonin) receptor 1E | 5' | 97 |
| AAGGAGACCGCACAGGG | 104 | 13 | 0 | 13 | 0.0036794 | 6 | SYNCRIP | synaptotagmin binding, cytoplasmic RNA | 5' | 1294285 |
| ATTGTCAGATCTGAAT | 105 | 9 | 0 | 9 | 0.020643 | 6 | MAP3K7 | mitogen-activated protein kinase kinase kinase 7 | 5' | 24225 |
| TGGTGATAACTGAACCC | 106 | 15 | 29 | −2 | 0.0333315 | 6 | C6orf66 | hormone-regulated proliferation-associated 20 | 3' | 806 |

TABLE 2-continued

MSDK tags significantly (p < 0.050) differentially present in HCT116 WT and DKO MSDK libraries and genes associates with the MSDK tags.

| MSDK Tag | SEQ ID NO. | DKO | WT | Ratio DKO/WT | P value | Chr | Gene | Description | Position of AscI site in relation to tr. Start | Distance of AscI site from tr. Start (bp) |
|---|---|---|---|---|---|---|---|---|---|---|
| TCCATAGATTGACAAAG | 107 | 27 | 0 | 27 | 8.80 × 10⁻⁶ | 6 | MARCKS | myristoylated alanine-rich protein kinase C | 3' | 3067 |
| TACAAGGCACTATGCTG | 108 | 6 | 16 | −3 | 0.0455421 | 6 | MCMDC1 | minichromosome maintenance protein domain | 3' | 518 |
| GTTATGCCAGAACTTG | 109 | 19 | 2 | 8 | 0.0033039 | 6 | MOXD1 | monooxygenase, DBH-like 1 | 3' | 26536 |
| CAACCCACGGCAGGTG | 110 | 25 | 0 | 25 | 8.07 × 10⁻⁵ | 6 | TAGAP | T-cell activation Rho GTPase-activating protein | 5' | 123822 |
| ATGAGTCCATTTCCTCG | 111 | 8 | 0 | 8 | 0.0317702 | 7 | MGC10911 | hypothetical protein MGC10911 | 5' | 96664 |
| ACCTGAATAAACCCTG | 112 | 0 | 7 | −8 | 0.0172683 | 7 | RAM2 | transcription factor RAM2 | 3' | 259 |
| TATTTGCCAAGTTGTAC | 113 | 0 | 6 | −3 | 0.0294258 | 7 | HOXA11 | homeobox protein A11 | 3' | 622 |
| ACAAAAATGATCGTTCT | 114 | 10 | 24 | −3 | 0.0177309 | 7 | PLEKHA8 | pleckstrin homology domain containing, family A | 3' | 159 |
| GGCTCCGTCTCTGCC | 115 | 10 | 0 | 10 | 0.013413 | 7 | CRHR2 | corticotropin releasing hormone receptor 2 | 3' | 521 |
| GTCCCAGCACGCGGTC | 116 | 13 | 0 | 13 | 0.0036794 | 7 | TBX20 | T-box transcription factor TBX20 | 5' | 607 |
| CCTTGACTGCCTCCATC | 117 | 11 | 0 | 11 | 0.0087152 | 7 | WBSCR17 | Williams Beuren syndrome chromosome region 17 | 5' | 512 |
| TCTGAGTCGCCAGCGTC | 118 | 4 | 18 | −5 | 0.0037714 | 7 | AASS | aminoadipate-semialdehyde synthase | 5' | 171064 |
| GGGGCCTATTCACAGCC | 119 | 23 | 49 | −2 | 0.0010583 | 8 | TNKS | tankyrase, TRF1-interacting ankyrin-related | 5' | 404285 |
| GGGGCCTATTCACAGCC | 120 | 23 | 49 | −2 | 0.0010583 | 8 | PPP1R3B | protein phosphatase 1, regulatory (inhibitor) | 5' | 953 |
| CCAGACCGGCTCGGC | 121 | 5 | 15 | −3 | 0.036438 | 8 | ZDHHC2 | rec | 3' | 683 |
| GTGACGATGGAGGAGCT | 122 | 28 | 54 | −2 | 0.001831 | 8 | DUSP4 | dual specificity phosphatase 4 isoform 1 | 3' | 629 |
| CTCCTCCTTCTTTTGCG | 123 | 3 | 12 | −4 | 0.0325442 | 8 | ADAM9 | a disintegrin and metalloproteinase domain 9 | 3' | 542 |
| GCCAGGGGCAGCAGACGC | 124 | 20 | 0 | 20 | 0.0001799 | 8 | PRDM14 | PR domain containing 14 | 3' | 768 |
| TAACTGTCCTTTCCGTA | 125 | 21 | 0 | 21 | 0.0001169 | 8 | Not Found | | | |
| AAGAGGCAGAAGTGCG | 126 | 37 | 0 | 37 | 1.18 × 10⁻⁷ | 8 | KCNK9 | potassium channel, subfamily K, member 9 | 3' | 360 |
| CTTGCCTCTCATCCTTC | 127 | 24 | 53 | −2 | 0.0003864 | 8 | Sharpin | shank-interacting protein-like 1 | 5' | 328 |
| AAATGAAACTAGTCTTG | 128 | 2 | 11 | −6 | 0.0215511 | 9 | ANKRD15 | ankyrin repeat domain protein 15 | 5' | 171831 |
| TCTGTGTGCTGTGTGCG | 129 | 3 | 14 | −5 | 0.011762 | 9 | SMARCA2 | SWI/SNF-related matrix-associated | 5' | 1580 |
| TAAATAGGCGAGAGGAG | 130 | 13 | 57 | −5 | 2.87 × 10⁻⁸ | 9 | FLJ46321 | FLJ46321 protein | 5' | 299849 |
| TAAATAGGCGAGAGGAG | 131 | 13 | 57 | −5 | 2.87 × 10⁻⁸ | 9 | TLE1 | transducin-like enhancer protein 1 | 3' | 241 |
| GCGGGCGGCGCGGTCC | 132 | 35 | 0 | 35 | 2.79 × 10⁻⁷ | 9 | LHX6 | LIM homeobox protein 6 isoform 1 | 5' | 408 |
| AGGCAGGAGGATGGTCTG | 133 | 13 | 0 | 13 | 0.0133334 | 9 | PRDM12 | PR domain containing 12 | 5' | 5017 |
| GGCGTTAATAGAGAGC | 134 | 7 | 0 | 7 | 0.0488953 | 9 | PRDM12 | PR domain containing 12 | 5' | 5017 |
| AGTTGTTGTTCTTGCA | 135 | 19 | 0 | 19 | 0.0002769 | 9 | PRDM12 | PR domain containing 12 | 3' | 1427 |
| AAGGAGCCTACGTTAAT | 136 | 3 | 12 | −4 | 0.0325442 | 9 | UBADC1 | ubiquitin associated domain containing 1 | 5' | 10 |
| GATAAGAAGGATGAGGA | 137 | 18 | 0 | 18 | 0.0004261 | 9 | BTBD14A | BTB (POZ) domain containing 14A | 5' | 98790 |
| GCCTTGACCCCCCAGGC | 138 | 9 | 0 | 9 | 0.020643 | 9 | BTBD14A | BTB (POZ) domain containing 14A | 5' | 98790 |
| CAGCCAGCTTTCTGCCC | 139 | 38 | 0 | 38 | 7.67 × 10⁻⁸ | 9 | LHX3 | LIM homeobox protein 3 isoform b | 5' | 146 |
| TCCGCCTGTGACTCAAG | 140 | 11 | 0 | 11 | 0.0087152 | 9 | CLIC3 | chloride intracellular channel 3 | 3' | 1683 |
| GTCCTGCTCCTCAAGGG | 141 | 28 | 0 | 28 | 5.72 × 10⁻⁶ | 9 | CLIC3 | chloride intracellular channel 3 | 3' | 1683 |
| GGGGAAGCTTCGAGCGC | 142 | 5 | 16 | −4 | 0.0229995 | 9 | Not Found | | | |
| AAAATAGAGGTTCCTCC | 143 | 10 | 25 | −3 | 0.0117571 | 10 | PRPF18 | PRPF18 pre-mRNA processing factor 18 homolog | 5' | 58621 |
| AAAATAGAGGTTCCTCC | 144 | 10 | 25 | −3 | 0.0117571 | 10 | C10orf30 | chromosome 10 open reading frame 30 | 5' | 25417 |
| AATGAACGACCAGAGCC | 145 | 20 | 37 | −2 | 0.0188826 | 10 | DDX21 | DEAD (Asp-Glu-Ala-Asp) box polypeptide 21 | 3' | 506 |
| AGTTAGTTCCCAACTCA | 146 | 2 | 10 | −6 | 0.0365508 | 10 | MLR2 | ligand-dependent corepressor | 5' | 84 |
| AGTTAGTTCCCAACTCA | 147 | 2 | 10 | −6 | 0.0365508 | 10 | PIK3AP1 | phosphoinositide-3-kinase adaptor protein 1 | 5' | 112373 |
| TGGATTTGGGTTTTCAG | 148 | 10 | 0 | 10 | 0.013413 | 10 | HPSE2 | heparanase 2 | 3' | 2954 |
| GGGACAGGTGGCAGGCC | 149 | 33 | 0 | 33 | 6.62 × 10⁻⁶ | 10 | PAX2 | paired box protein 2 isoform b | 5' | 6126 |
| GAGCTAATCAATAGGCA | 150 | 7 | 0 | 7 | 0.0488953 | 10 | PAX2 | paired box protein 2 isoform b | 5' | 6126 |

TABLE 2-continued

MSDK tags significantly (p < 0.050) differentially present in HCT116 WT and DKO MSDK libraries and genes associates with the MSDK tags.

| MSDK Tag | SEQ ID NO. | DKO | WT | Ratio DKO/WT | P value | Chr | Gene | Description | Position of AscI site in relation to tr. Start | Distance of AscI site from tr. Start (bp) |
|---|---|---|---|---|---|---|---|---|---|---|
| GTTTCCTTATTAATAGA | 151 | 4 | 24 | −7 | 0.0001591 | 10 | TRIM8 | tripartite motif-containing 8 | 5' | 375 |
| CCCCGTGGCGGGAGCGG | 152 | 26 | 0 | 26 | 5.26 × 10⁻⁵ | 10 | NEURL | neuralized-like | 5' | 630 |
| CCCGTGGCGGGAGCGG | 153 | 26 | 0 | 26 | 5.26 × 10⁻⁵ | 10 | FAM26A | family with sequence similarity 26, member A | 5' | 14420 |
| GAGGTAGTGCCCTGTCC | 154 | 13 | 0 | 13 | 0.0036794 | 10 | SH3MD1 | SH3 multiple domains 1 | 3' | 24 |
| TTGTGTGTACATAGGCC | 155 | 8 | 0 | 8 | 0.0317702 | 10 | SORCS1 | SORCS receptor 1 isoform a | 5' | 1301646 |
| GCAGGACGGCGGGGCCA | 156 | 8 | 0 | 8 | 0.0317702 | 10 | LHPP | phospholysine phosphohistidine inorganic | 5' | 14183 |
| GCAGGACGGCGGGGCCA | 157 | 8 | 0 | 8 | 0.0317702 | 10 | OAT | ornithine aminotransferase precursor | 5' | 28768 |
| GGGCCCGCCCAGCCAG | 158 | 11 | 0 | 11 | 0.0087152 | 10 | C10orf137 | erythroid differentiation-related factor 1 | 5' | 556810 |
| GGGCCCGCCCAGCCAG | 159 | 11 | 0 | 11 | 0.0087152 | 10 | CTBP2 | C-terminal binding protein 2 isoform 1 | 5' | 2249 |
| CCTGGAAGGAATTTAGG | 160 | 8 | 0 | 8 | 0.0317702 | 10 | PTPRE | protein tyrosine phosphatase, receptor type, E | 3' | 408 |
| GGAGTTCCATCTCCGAG | 161 | 13 | 0 | 13 | 0.0036794 | 10 | MGMT | O-6-methylguanine-DNA methyltransferase | 5' | 1317729 |
| GGAGTTCCATCTCCGAG | 162 | 13 | 0 | 13 | 0.0036794 | 10 | MKI67 | antigen identified by monoclonal antibody Ki-67 | 5' | 23268 |
| GAAAACTCCAGATAGTG | 163 | 17 | 0 | 17 | 0.0006558 | 11 | ASCL2 | achaete-scute complex homolog-like 2 | 5' | 582 |
| CTTTGAAATAAGCGAAT | 164 | 3 | 13 | −5 | 0.0196518 | 11 | PDE3B | phosphodiesterase 3B, cGMP-inhibited | 3' | 526 |
| GGCAGGAGGATGCGGGG | 165 | 5 | 15 | −3 | 0.036438 | 11 | FJX1 | four jointed box 1 | 3' | 725 |
| TCTAGGACCTCCAGGCC | 166 | 14 | 32 | −3 | 0.0066996 | 11 | SLC39A13 | solute carrier family 39 (zinc transporter) | 5' | 415 |
| TCTAGGACCTCCAGGCC | 167 | 14 | 32 | −3 | 0.0066996 | 11 | SPI1 | spleen focus forming virus (SFFV) proviral | 5' | 29668 |
| CCCTGCCCTTAGTGCTT | 168 | 7 | 0 | 7 | 0.0488953 | 11 | Not Found | | | |
| GCCAACCTGAAGACCCC | 169 | 7 | 0 | 7 | 0.0488953 | 11 | SSSCA1 | Sjogren's syndrome/scleroderma autoantigen 1 | 5' | 12479 |
| GCCAACCTGAAGACCCC | 170 | 7 | 0 | 7 | 0.0488953 | 11 | LTBP3 | latent transforming growth factor beta binding | 5' | 33 |
| GCCCCCTAGGCCCTTTG | 171 | 10 | 0 | 10 | 0.013413 | 11 | FGF19 | fibroblast growth factor 19 precursor | 5' | 44445 |
| CTGCAAAATCTGCTCCT | 172 | 5 | 16 | −4 | 0.0229995 | 11 | Not Found | | | |
| GCTCGTCCAGCTGGGA | 173 | 7 | 0 | 7 | 0.0488953 | 11 | ROBO3 | roundabout, axon guidance receptor, homolog 3 | 5' | 534 |
| GCTCGACCCAGCTGGGA | 174 | 7 | 0 | 7 | 0.0488953 | 11 | FLJ23342 | hypothetical protein FLJ23342 | 5' | 64448 |
| GATTATGAAAGCCCATC | 175 | 14 | 0 | 14 | 0.0023908 | 11 | BARX2 | BarH-like homeobox 2 | 5' | 2434 |
| GATTATGAAAGCCCATC | 176 | 14 | 0 | 14 | 0.0023908 | 11 | RICS | Rho GTPase-activating protein | 5' | 349388 |
| GAACAAACCAGGGATC | 177 | 9 | 0 | 9 | 0.020643 | 12 | KCNA1 | potassium voltage-gated channel, shaker-related | 5' | 1403 |
| TGTGTTCAGAGGGCGGA | 178 | 7 | 0 | 7 | 0.0488953 | 12 | GPR92 | putative G protein-coupled receptor 92 | 5' | 15529 |
| CCTGCCGGTGGAGGGGA | 179 | 13 | 0 | 13 | 0.0036794 | 12 | ST8SIA1 | ST8 alpha-N-acetyl-neuraminide | 3' | 176 |
| GCTGCCCCAAGTGGTCT | 180 | 11 | 0 | 11 | 0.0087152 | 12 | Not Found | | | |
| AGAACGGGAACCGTCCA | 181 | 19 | 0 | 19 | 0.0002769 | 12 | CENTG1 | centaurin, gamma 1 | 3' | 3647 |
| TCTCCGGTGTATGTGCGC | 182 | 6 | 20 | −4 | 0.0074301 | 12 | HMGA2 | high mobility group AT-hook 2 | 3' | 1476 |
| TTTCAGCGGGAGCCGGC | 183 | 10 | 0 | 10 | 0.013413 | 12 | KIAA1853 | KIAA1853 protein | 5' | 64 |
| GAGGCCAGATTTTCTCC | 184 | 40 | 64 | −2 | 0.007793 | 12 | HIP1R | huntingtin interacting protein-1-related | 5' | 170 |
| AAGGCCTGGGAGTTTTCT | 185 | 23 | 38 | −2 | 0.0434041 | 12 | ABCB9 | ATP-binding cassette, sub-family B (MDR/TAP), | 3' | 517 |
| CGAACTTCCCGGTTCCG | 186 | 18 | 0 | 18 | 0.0004261 | 12 | Not Found | | | |
| CAGCGGCCAAAGCTGCC | 187 | 16 | 31 | −2 | 0.0259626 | 12 | RAN | ras-related nuclear protein | 5' | 257 |
| CAGCGGCCAAAGCTGCC | 188 | 16 | 31 | −2 | 0.0259626 | 12 | EPIM | epimorphin isoform 2 | 5' | 32499 |
| CACTGCCTGATGGTGTG | 189 | 23 | 0 | 23 | 0.0001899 | 13 | IL17D | interleukin 17D precursor | 3' | 277 |
| CCACCAGCCTCCCTCGG | 190 | 19 | 36 | −2 | 0.0173058 | 13 | DOCK9 | dedicator of cytokinesis 9 | 5' | 1277 |
| AGTCTGCCAGTAGTTG | 191 | 10 | 26 | −3 | 0.0077231 | 14 | MTHFD1 | methylenetetrahydrofolate dehydrogenase 1 | 5' | 49925 |
| AGTCTGCCAGTAGTTG | 192 | 10 | 26 | −3 | 0.0077231 | 14 | ESR2 | estrogen receptor 2 | 3' | 44089 |
| CCTCTAGGACCAAGCCT | 193 | 12 | 0 | 12 | 0.0056628 | 14 | SLC8A3 | solute carrier family 8 member 3 isoform B | 5' | 270 |
| CTACCTAAGGAGGAGCAG | 194 | 2 | 13 | −7 | 0.0073393 | 14 | MED6 | mediator of RNA polymerase II transcription, | 5' | 41006 |

TABLE 2-continued

MSDK tags significantly (p < 0.050) differentially present in HCT116 WT and DKO MSDK libraries and genes associates with the MSDK tags.

| MSDK Tag | SEQ ID NO. | DKO | WT | Ratio DKO/WT | P value | Chr | Gene | Description | Position of AscI site in relation to tr. Start | Distance of AscI site from tr. Start (bp) |
|---|---|---|---|---|---|---|---|---|---|---|
| GAGTCGCAGTATTTTGG | 195 | 12 | 25 | −2 | 0.045796 | 14 | GTF2A1 | TFIIA alpha, p55 isoform 1 | 3' | 181 |
| CGGCGCAGCTCCAGGTC | 196 | 13 | 0 | 13 | 0.0036794 | 14 | KCNK10 | potassium channel, subfamily K, member 10 | 3' | 3468 |
| GGCCGGTCGCGCCAGTC | 197 | 10 | 0 | 10 | 0.013413 | 14 | EML1 | echinoderm microtubule associated protein like 1 | 5' | 62907 |
| GGGACCCGGAAAGGTGG | 198 | 13 | 0 | 13 | 0.0036794 | 14 | KIAA1446 | brain-enriched guanylate kinase-associated | 5' | 1674 |
| GCTCTGCCCCGTGGCC | 199 | 9 | 23 | −3 | 0.0148748 | 15 | BAHD1 | bromo adjacent homology domain containing 1 | 5' | 138 |
| AGAGCTGAGTCTCACCC | 200 | 8 | 20 | −3 | 0.0285917 | 15 | CDAN1 | codanin 1 | 3' | 359 |
| TCAGGCTTCCCCTTCGG | 201 | 4 | 13 | −4 | 0.0445448 | 15 | PIAS1 | protein inhibitor of activated STAT, 1 | 5' | 190450 |
| CCTGTGGACAGGATACC | 202 | 8 | 0 | 8 | 0.0317702 | 15 | LRRN6A | leucine-rich repeat neuronal 6A | 5' | 140491 |
| TGGGGACTGATGCACCC | 203 | 0 | 12 | −13 | 0.0009509 | 15 | CIB2 | DNA-dependent protein kinase catalytic | 3' | 598 |
| GCAGTAAACCGTGACTT | 204 | 7 | 0 | 7 | 0.0488953 | 15 | ADAMTSL3 | ADAMTS-like 3 | 5' | 114 |
| CGCACTCACACGGACGA | 205 | 7 | 0 | 7 | 0.0488953 | 16 | ZNF206 | zinc finger protein 206 | 3' | 3376 |
| ATCCGGCCAAGCCCTAG | 206 | 10 | 0 | 10 | 0.013413 | 16 | ATF7IP2 | activating transcription factor 7 interacting | 5' | 244550 |
| ATCCGGCCAAGCCCTAG | 207 | 10 | 0 | 10 | 0.013413 | 16 | GRIN2A | N-methyl-D-aspartate receptor subunit 2A | 3' | 809 |
| CGATTCGAAGGGAGGGG | 208 | 27 | 0 | 27 | 3.43 × 10⁻⁵ | 16 | IRX6 | iroquois homeobox protein 6 | 5' | 386305 |
| CCTAACAAGATTGCATA | 209 | 14 | 32 | −3 | 0.0066996 | 16 | DDX19 | DEAD (Asp-Glu-Ala-As) box polypeptide 19 | 3' | 23 |
| CCTAACAAGATTGCATA | 210 | 14 | 32 | −3 | 0.0066996 | 16 | AARS | alanyl-tRNA synthetase | 5' | 9662 |
| TCCCGCGCCAGGCCCC | 211 | 11 | 0 | 11 | 0.0087152 | 16 | ZCCHC14 | zinc finger, CCHC domain containing 14 | 3' | 143 |
| GCAACAGCCTCCGGAGG | 212 | 0 | 8 | −9 | 0.0375409 | 16 | TUBB3 | tubulin, beta, 4 | 3' | 843 |
| CACAGCCAGCCTCCAG | 213 | 36 | 0 | 36 | 1.82 × 10⁻⁷ | 17 | LHX1 | LIM homeobox protein 1 | 3' | 3701 |
| CCTACCTATCCTGGAC | 214 | 14 | 0 | 14 | 0.0023908 | 17 | STAT5A | signal transducer and activator of transcription | 5' | 1085 |
| GCTATGGTTCGGGGGAG | 215 | 42 | 0 | 42 | 1.37 × 10⁻⁸ | 17 | SOST | sclerostin precursor | 3' | 3140 |
| GATGCTCGAACGCAGAG | 216 | 7 | 0 | 7 | 0.0488953 | 17 | SOST | sclerostin precursor | 3' | 3140 |
| GTGAAATTCCGTCTCT | 217 | 23 | 0 | 23 | 4.94 × 10⁻⁵ | 17 | Not Found | | 3' | 8471 |
| GAGGCTGGCACCCAGGC | 218 | 13 | 0 | 13 | 0.0036794 | 17 | C1QL1 | complement component 1, q subcomponent-like 1 | 3' | 13991 |
| CCCCAGAGTGACTAAG | 219 | 10 | 0 | 10 | 0.013413 | 17 | ProSAPiP2 | ProSAPiP2 protein | 3' | 455 |
| TTGAGAACTGCCCCCT | 220 | 3 | 12 | −4 | 0.0325442 | 17 | HOXB9 | homeo box B9 | 5' | 20620 |
| CCCGTTTTTGTGAGTG | 221 | 11 | 23 | −2 | 0.0443851 | 17 | HOXB9 | homeo box B9 | 5' | 20 |
| GGGCGGTGGCAAGGGGC | 222 | 9 | 0 | 9 | 0.020643 | 17 | NXPH3 | neurexophilin 3 | 3' | 43255 |
| CTTAGCCCAGAGAAC | 223 | 18 | 0 | 18 | 0.0004261 | 17 | FLJ20920 | hypothetical protein FLJ20920 | 3' | 527 |
| CATTTCCTGGGCTATTT | 224 | 10 | 0 | 10 | 0.013413 | 17 | MRC2 | mannose receptor, C type 2 | 3' | 206723 |
| GTGACCAGCCTGGAGAG | 225 | 15 | 0 | 15 | 0.0015534 | 17 | SDK2 | sidekick 2 | 5' | 11941 |
| CCCTGCCCTGTCACCC | 226 | 30 | 0 | 30 | 2.41 × 10⁻⁶ | 17 | SLC9A3R1 | solute carrier family 9 (sodium/hydrogen) | 5' | 628261 |
| CTGAATGGGCAAGGAG | 227 | 48 | 0 | 48 | 1.03 × 10⁻⁹ | 17 | ENPP7 | ectonucleotide pyrophosphatase/phosphodiesterase | 5' | 1307 |
| CCTCTTCCCAGACCGAA | 228 | 13 | 0 | 13 | 0.0036794 | 18 | CBX4 | chromobox homolog 4 | 5' | 4600 |
| ACCCGGCACCATCCGGG | 229 | 91 | 0 | 91 | 3.74 × 10⁻¹⁷ | 18 | CBX4 | chromobox homolog 4 | 5' | 66979 |
| GCTGCGGGCACCGGGCG | 230 | 25 | 0 | 25 | 2.08 × 10⁻⁵ | 18 | raptor | raptor | 5' | 1684 |
| GCTCGGTGAGTGTCTCG | 231 | 25 | 0 | 25 | 2.08 × 10⁻⁵ | 18 | NPTX1 | neuronal pentraxin I precursor | 5' | 67 |
| CCTGGTGAGTGTCTCG | 232 | 4 | 22 | −6 | 0.0004645 | 18 | P4HB | prolyl 4-hydroxylase, beta subunit | 5' | 143 |
| TCCCATTCGCCCGG | 233 | 43 | 18 | 2 | 0.0314243 | 18 | EMILIN2 | elastin microfibril interfacer 2 | 3' | 20803 |
| GAAAAGTTGAACTCCTG | 234 | 12 | 0 | 12 | 0.0056628 | 18 | C18orf1 | chromosome 18 open reading frame 1 isoform alpha | | |
| GTGAGGGGAGGTACTG | 235 | 8 | 0 | 8 | 0.0317702 | 18 | IER3IP1 | immediate early response 3 interacting protein | 5' | 70905 |
| TGAAGAAAAGGCCTTTG | 236 | 9 | 0 | 9 | 0.020643 | 18 | ACAA2 | acetyl-coenzyme A acyltransferase 2 | 5' | 380776 |
| GCCCGGGCTGTCCC | 237 | 9 | 0 | 9 | 0.020643 | 18 | GALR1 | galanin receptor 1 | 5' | 146 |
| GCCCGCGGGCTGTCCC | 238 | 9 | 0 | 9 | 0.020643 | 18 | MBP | myelin basic protein | 5' | 232612 |

TABLE 2-continued

MSDK tags significantly (p < 0.050) differentially present in HCT116 WT and DKO MSDK libraries and genes associates with the MSDK tags.

| MSDK Tag | SEQ ID NO. | DKO | WT | Ratio DKO/WT | P value | Chr | Gene | Description | Position of AscI site in relation to tr. Start | Distance of AscI site from tr. Start (bp) |
|---|---|---|---|---|---|---|---|---|---|---|
| TCCTGTCTCATCTGCGA | 239 | 9 | 0 | 9 | 0.020643 | 18 | SALL3 | sal-like 3 | 5' | 463 |
| TCTCGGCGCAAGCAGGC | 240 | 12 | 0 | 12 | 0.0056628 | 18 | SALL3 | sal-like 3 | 3' | 1008 |
| TCCGGAGTTGGGACCTC | 241 | 14 | 0 | 14 | 0.0087469 | 19 | Not Found | | | 51678 |
| GCAAACATCAGGACCAC | 242 | 9 | 0 | 9 | 0.020643 | 19 | KIAA0963 | KIAA0963 | 3' | 18214 |
| AACGGGATCCGCACGGG | 243 | 8 | 0 | 8 | 0.0317702 | 19 | APC2 | adenomatosis polyposis coli 2 | 3' | 2472 |
| GCCTTCCTGTCCCCAA | 244 | 0 | 8 | −9 | 0.0096701 | 19 | KLF16 | BTE-binding protein 4 | 3' | 328 |
| GTGCCAGGAAGCAAGTC | 245 | 10 | 22 | −2 | 0.0390686 | 19 | AP3D1 | adaptor-related protein complex 3, delta 1 | 3' | 13794 |
| AGCCTGCAAAGGGGAGG | 246 | 17 | 34 | −2 | 0.0142228 | 19 | AKAP8L | A kinase (PRKA) anchor protein 8-like | 5' | 13794 |
| GGGTAGAACCTGGGGGA | 247 | 28 | 0 | 28 | 2.23 × 10⁻⁵ | 19 | GTPBP3 | GTP binding protein 3 (mitochondrial) isoform | 3' | 2019 |
| CCCGCTCCTCGGTTCG | 248 | 5 | 16 | −4 | 0.0229995 | 19 | ITPKC | inositol 1,4,5-trisphosphate 3-kinase C | 5' | 273 |
| CCCGCTCCTCGGTTCG | 249 | 5 | 16 | −4 | 0.0229995 | 19 | ADCK4 | aarF domain containing kinase 4 | 5' | 134 |
| CGTGGGAAACCTGATG | 250 | 15 | 31 | −2 | 0.0163452 | 19 | PPP1R13L | CD3-epsilon-associated protein; antisense to protein phosphatase 1, regulatory (inhibitor) | 5' | 1320 |
| CGTGGGAAACCTCGATG | 251 | 15 | 31 | −2 | 0.0163452 | 19 | ASE-1 | CD3-epsilon-associated protein; antisense to calmodulin 3 | 5' | 11721 |
| AGACTAAACCCCGAGG | 252 | 18 | 44 | −3 | 0.0005081 | 19 | CALM3 | | 3' | 129594 |
| CTAGAAGGGGTCGGGGA | 253 | 16 | 0 | 16 | 0.0010093 | 19 | FLJ10781 | hypothetical protein FLJ10781 | 5' | 140 |
| CTAGAAGGGGTCGGGGA | 254 | 16 | 0 | 16 | 0.0010093 | 19 | GRIN2D | N-methyl-D-aspartate receptor subunit 2D | 3' | 48538 |
| TACAGCTGCTGCAGCGC | 255 | 7 | 0 | 7 | 0.0488953 | 19 | GRIN2D | N-methyl-D-aspartate receptor subunit 2D | 3' | 48538 |
| GTTTATTCCAAACACTG | 256 | 7 | 0 | 7 | 0.0488953 | 19 | MYADM | myeloid-associated differentiation marker | 3' | 986 |
| CGGGGTTTCTATGGTAA | 257 | 7 | 19 | −3 | 0.0235641 | 19 | ZNF274 | zinc finger protein 274 isoform b | 3' | 323 |
| CCCAACCAATCTCTACC | 258 | 13 | 0 | 13 | 0.0036794 | 19 | ZNF42 | zinc finger protein 42 isoform 1 | 3' | 10788 |
| CGTAGGGCCGTTCACCC | 259 | 7 | 0 | 7 | 0.0488953 | 19 | Not Found | | 3' | 123 |
| CTCACGACGCCGTGAAG | 260 | 40 | 67 | −2 | 0.0032581 | 20 | SOX12 | SRY (sex determining region Y)-box 12 | 3' | 270 |
| TCAGCCCAGCGGTATCC | 261 | 0 | 9 | −10 | 0.0214975 | 20 | RRBP1 | ribosome binding protein 1 | 3' | 130452 |
| GTTTACCCTCTGTCTCC | 262 | 19 | 0 | 19 | 0.0002769 | 20 | RIN2 | RAB5 interacting protein 2 | 5' | |
| GGGTGCGGAACCCGGCC | 263 | 16 | 0 | 16 | 0.0010093 | 20 | Not Found | | | 56203 |
| CCAGCTTTAGAGTCAGA | 264 | 40 | 0 | 40 | 1.29 × 10⁻⁷ | 20 | Not Found | | | 10805 |
| GGGAATAGGGGGGCGGG | 265 | 14 | 0 | 14 | 0.0087469 | 20 | CDH22 | cadherin 22 precursor | 5' | 82906 |
| ACCCTGAAAGCCTAGCC | 266 | 24 | 0 | 24 | 3.21 × 10⁻⁵ | 21 | ITGB2 | integrin beta chain, beta 2 precursor | 5' | 376 |
| TTCCAAAAGGGGGACAGG | 267 | 3 | 16 | −6 | 0.0041258 | 22 | XBP1 | X-box binding protein 1 | 5' | 24574 |
| CCCACCAGGCACGTGGC | 268 | 21 | 40 | −2 | 0.0105097 | 22 | NPTXR | neuronal pentraxin receptor isoform 1 | 5' | 7284 |
| GCCTCAGCATCCTCCTC | 269 | 18 | 0 | 18 | 0.0004261 | 22 | FLJ27365 | FLJ27365 protein | 5' | 13829 |
| GCCTCAGCATCCTCCTC | 270 | 18 | 0 | 18 | 0.0004261 | 22 | FLJ10945 | hypothetical protein FLJ10945 | 5' | 18029 |
| GCCTGGGGTGTTATGG | 271 | 8 | 22 | −3 | 0.012181 | 22 | FLJ27365 | FLJ27365 protein | 5' | 63440 |
| GCCCTGGGTGTTATGG | 272 | 8 | 22 | −3 | 0.012181 | 22 | FLJ10945 | hypothetical protein FLJ10945 | 5 | 46630 |
| GGCAGGAAGACGGTGGA | 273 | 10 | 22 | −2 | 0.0390686 | 22 | ACR | acrosin precursor | 5' | 1402 |
| GGCAGGAAGACGGTGGA | 274 | 10 | 22 | −2 | 0.0390686 | 22 | ARSA | arylsulfatase A precursor | 5' | 3103 |
| GGGGGCAAGAAAGCAGA | 275 | 8 | 28 | −4 | 0.0007679 | 23 | STAG2 | stromal antigen 2 | 5' | |
| GAAGCAAGAGTTTGGCC | 276 | 19 | 34 | −2 | 0.0335364 | 23 | FLNA | filamin 1 (actin-binding protein-280) | 3' | |

DKO and WT, raw abundance (total numbers) of indicated MSDK observed in DKO and WT libraries.
Ratio DKO/WT, ratio of normalized abundances (total numbers) of the indicated tag in the DKO and WT libraries (a minus sign indicates that the indicated number is the reciprocal of the DKO/WT ratio).
P value, the significance of the difference in the raw abundances of the relevant MSDK tag between the two libraries.
Chr, chromosome in which MSDK tag sequence is located.
Gene, gene with which the indicated MSDK tag was associated.
Description, description of the product of the associated gene.
The positions of the AscI site (recognition sequence) identified by the indicated tag relative to the transcription initiation site (tr. Start) of the gene and the distance of the AscI site (recognition sequence) from the transcription initiation site are indicated.

Figure 3:
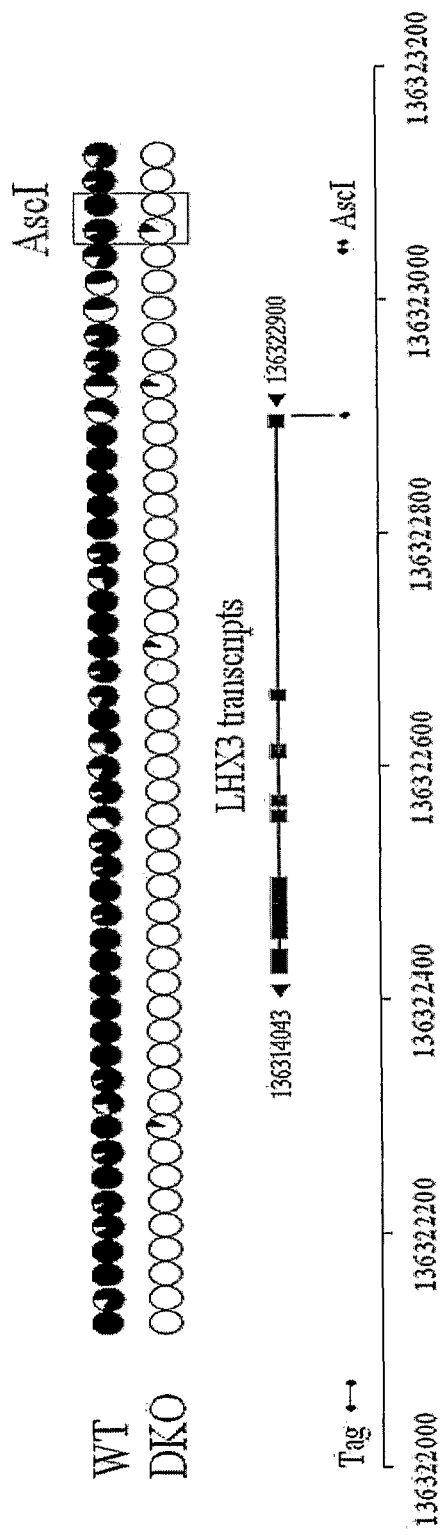
FIGS. 3-5 are diagrammatic representations of the results of a methylation-detecting sequence analysis of segments of the LHX3 gene region (FIG. 3; SEQ ID NO:3), the LMX-1A gene region (FIG. 4; SEQ ID NO:5), and the TCF7L1 gene region (FIG. 5; SEQ ID NO:4) shown in FIGS. 6-8, respectively. The circles represent potential methylation sites (CpG) in the analyzed segment of SEQ ID NOs:3, 5, and 4. The order of circles (starting from the left of the rows of circles) is that of the CpG dinucleotides in the analyzed segments of SEQ ID NOs:3, 5 and 4 (starting from the 5' end of the analyzed segment nucleotide sequences). The analyses were performed on DNA from wild-type HCT116 human colon cancer cells ("WT") and HCT116 cells having both alleles of their DNTM1 and DNMT3b methyltransferase genes "knocked out" ("DKO"). Each circle is pie chart with the amount of shading indicating the frequency (0%-100%) at which the relevant potential methylation site was found to be methylated. The top lines under the circles are linear depictions of the relevant gene transcripts and include the exons (shaded boxes) and introns (lines between the shaded boxes) and the bottom line under the circles are linear depictions of the chromosome on which the genes are located. On the chromosome depictions are shown the locations of the MSDK tag sequences that indicated the locations of the relevant AscI recognition sequences, which locations are also shown. The numbering on the bottom lines indicates the base pair (bp) numbers on the chromosomes and the numbering on the top lines indicate the bp numbers, in the chromosomes, of the transcription start sites and termination sites. The transcription initiation sites and the directions of transcription are also shown.
Figure 4:
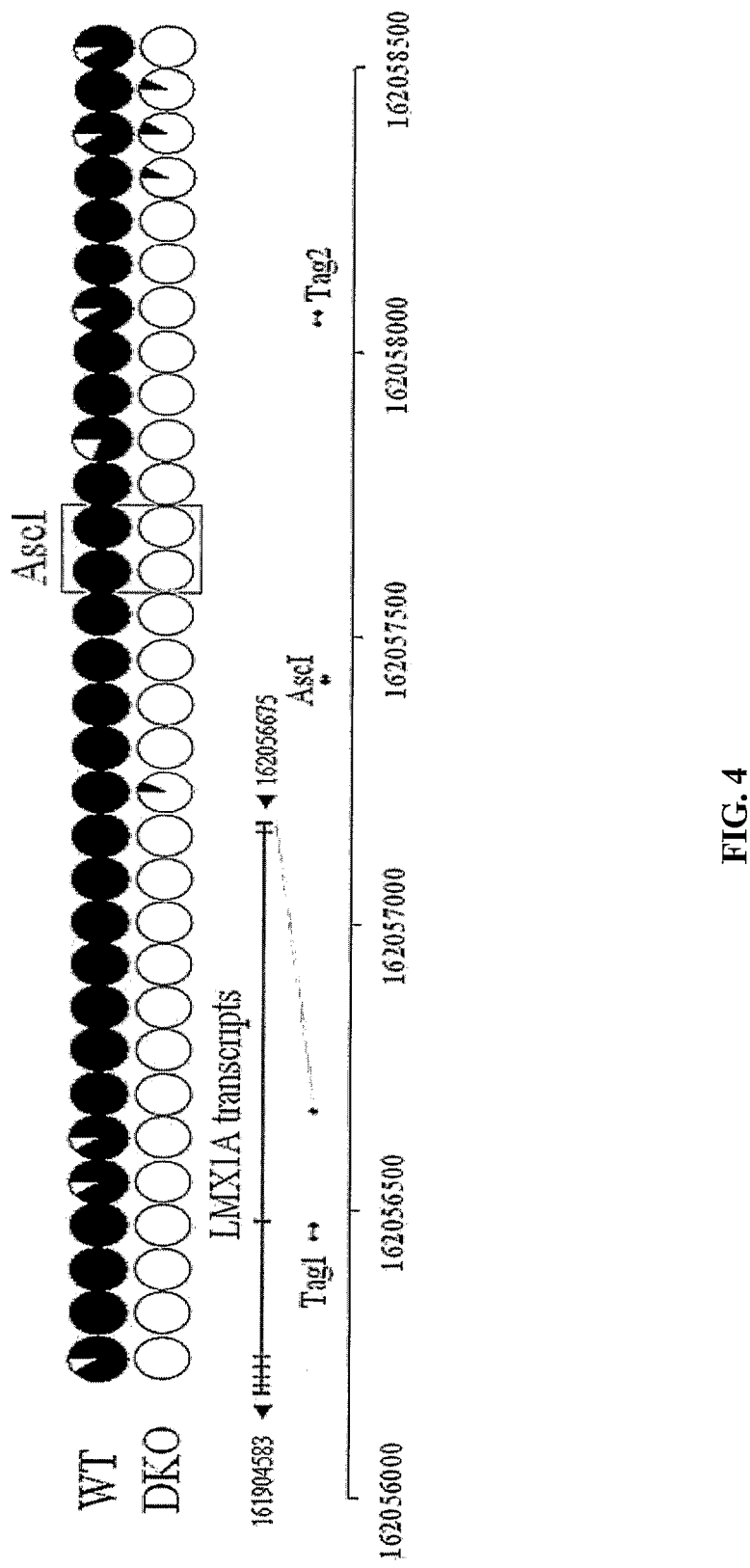
Figure 5:
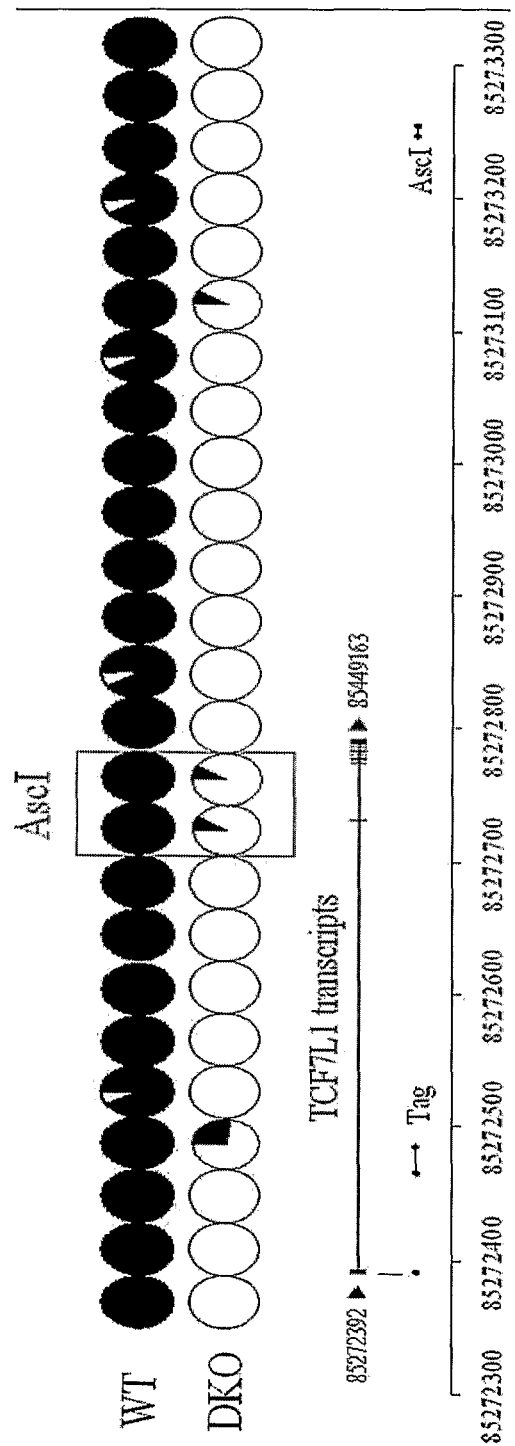
Figure 9:
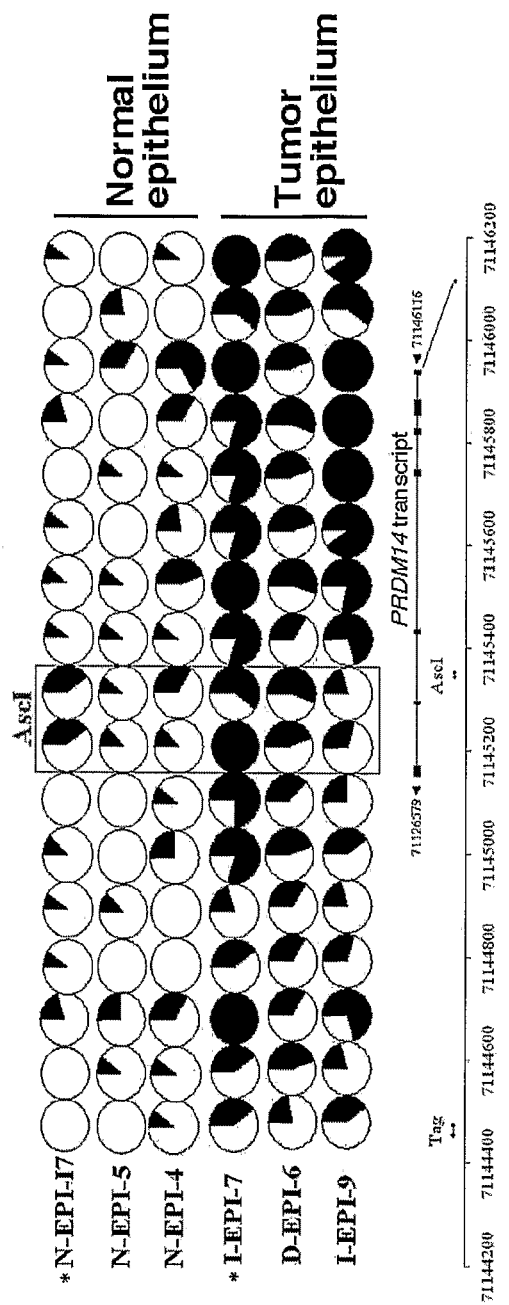
FIGS. 9-15 are diagrammatic representations of the results of a methylation-detecting sequence analysis of the segments of, respectively, the PRDM14 gene region (FIG. 9; SEQ ID NO:1), the ZCCHC14 gene region (FIG. 10; SEQ ID NO:2), the HOXD4 gene region (FIG. 11; SEQ ID NO:6), the SLC9A3R1 gene region (FIG. 12; SEQ ID NO:7), the LOC38933 gene region (FIG. 13; SEQ ID NO:10), the CDC42EP5 gene region (FIG. 14; SEQ ID NO:8), and the Cxorf12 gene region (FIG. 15; SEQ ID NO:9) shown in FIGS. 16A-22A, respectively. The circles represent potential methylation sites (CpG) in the analyzed segments. The order of circles (starting from the left of the rows of circles) is that of the CpG dinucleotides in the analyzed segments (starting from the 5' end of the analyzed segment nucleotide sequences). The analyses were performed on DNA from the indicated cell obtained from the indicated samples (see Table 3). Samples used for the generation of MSDK libraries are marked with an asterisk. Each circle is a pie chart with the amount of shading indicating the frequency (0%-100%) at which the relevant potential methylation site was found to be methylated. The top (bold) lines under the circles are linear depictions of the relevant gene transcripts and include the exons (shaded boxes) and introns (lines between the shaded boxes) and the bottom lines under the circles are linear depictions of the chromosomes on which the genes are located. On the chromosome depictions are shown the locations of the MSDK tag sequences that indicated the location of the relevant AscI recognition sequences, which locations are also shown. The numbering on the bottom lines indicates the bp numbers for the chromosomes and the numbering on the top lines indicate the bp numbers, in the chromosomes, of the transcription start sites and termination sites. The transcription initiation sites and the directions of transcription are also shown.
Figure 10:
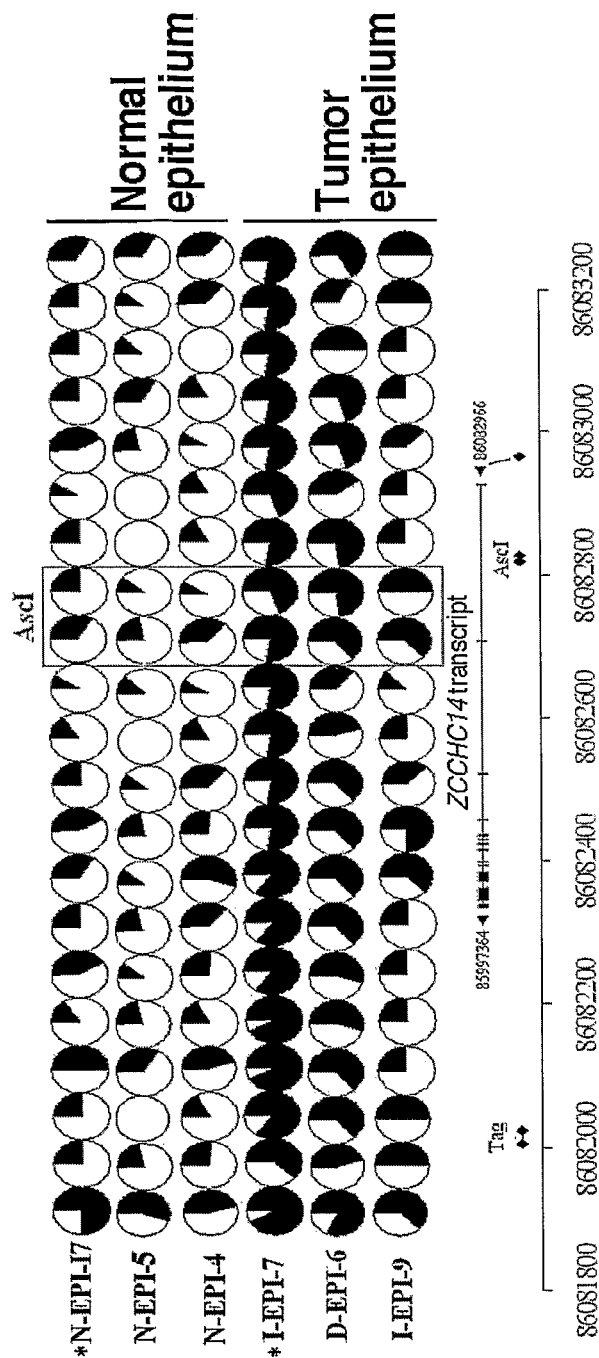
Figure 11:
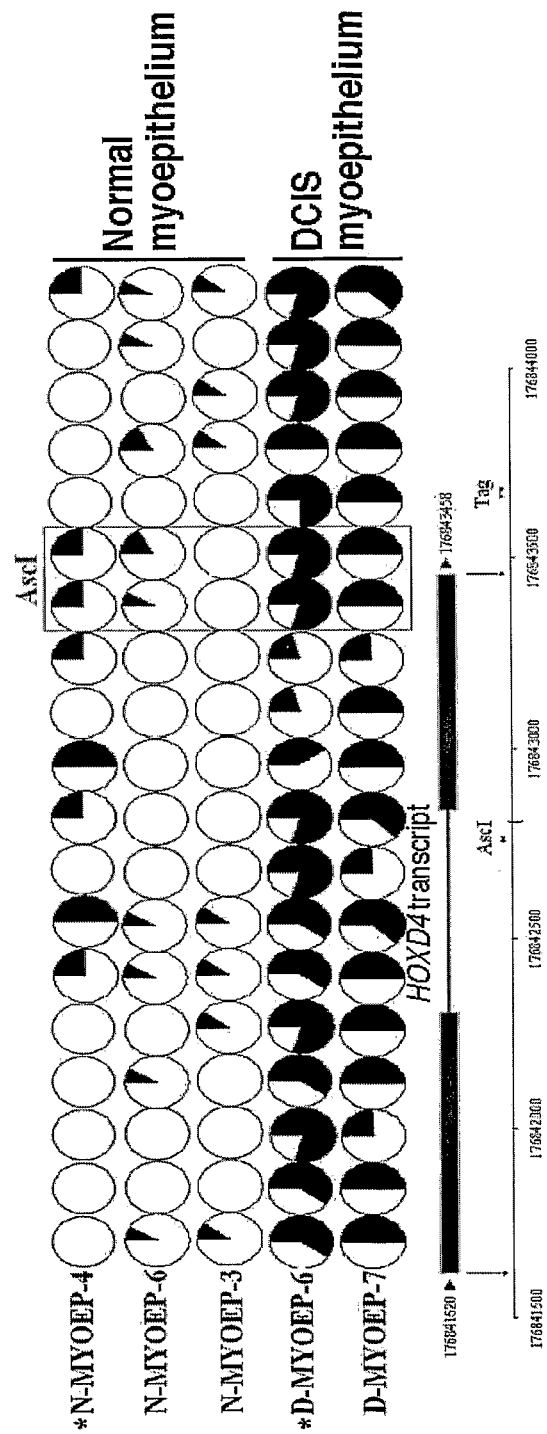
Figure 12:
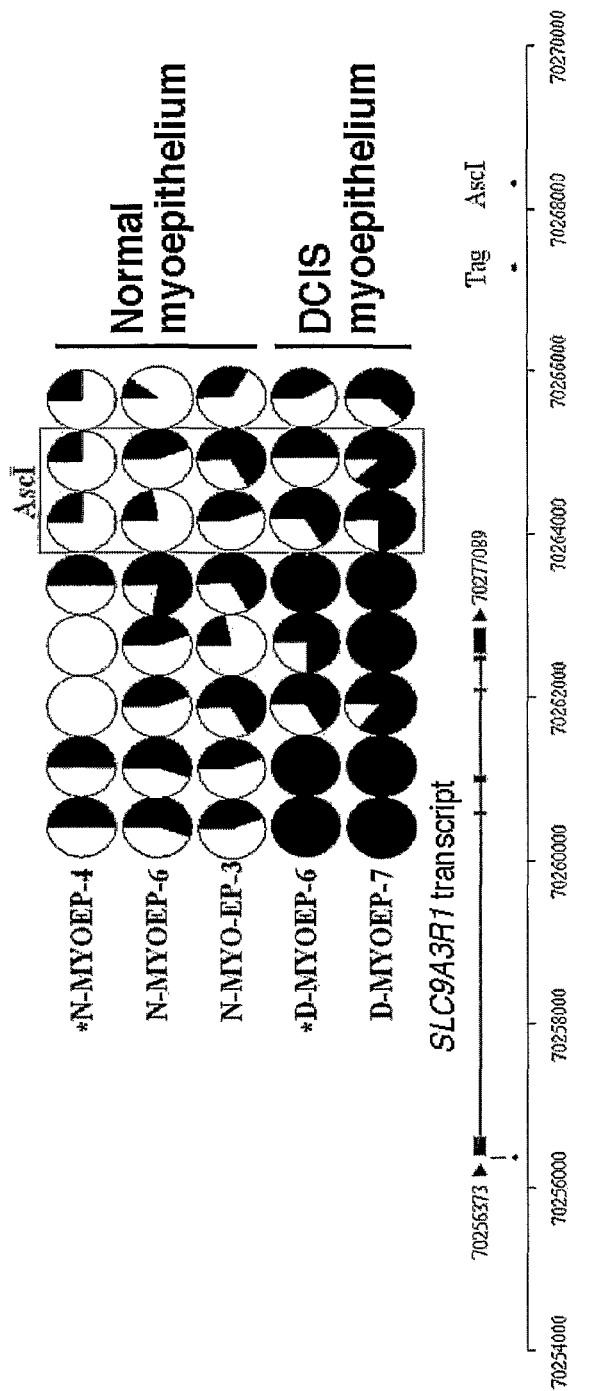
Figure 13:
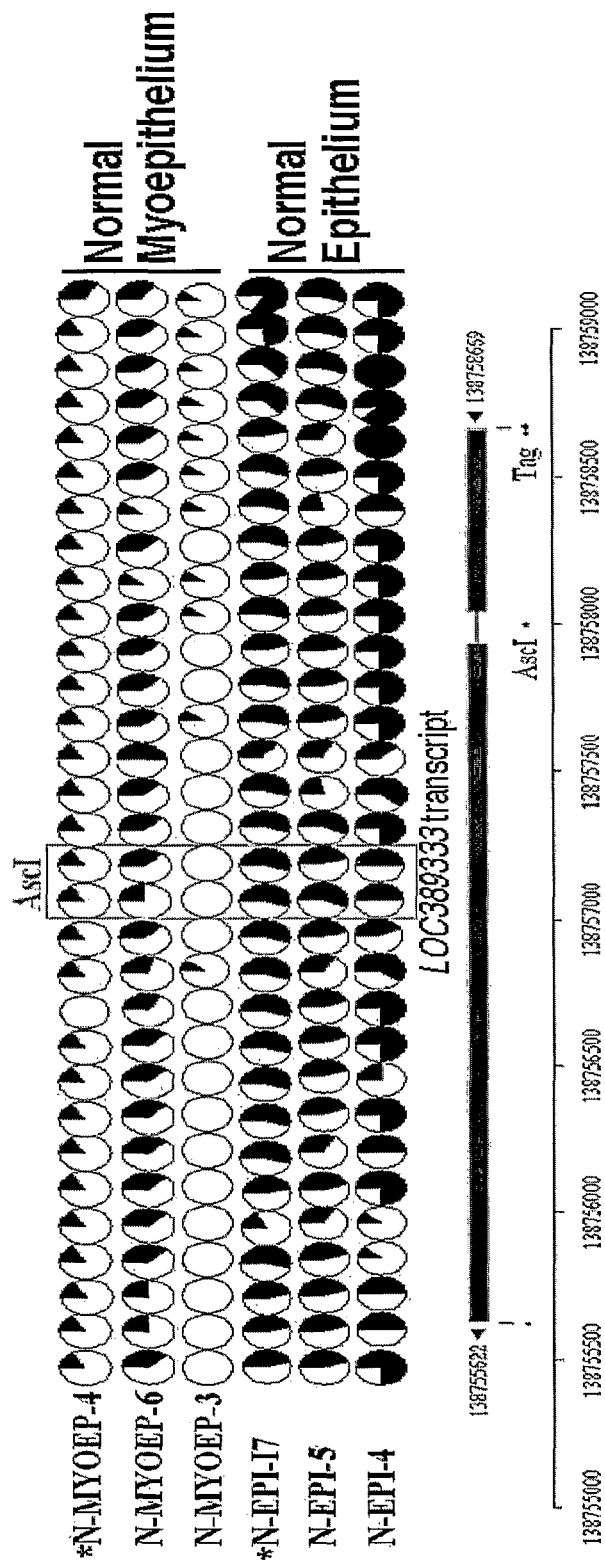
Figure 14:
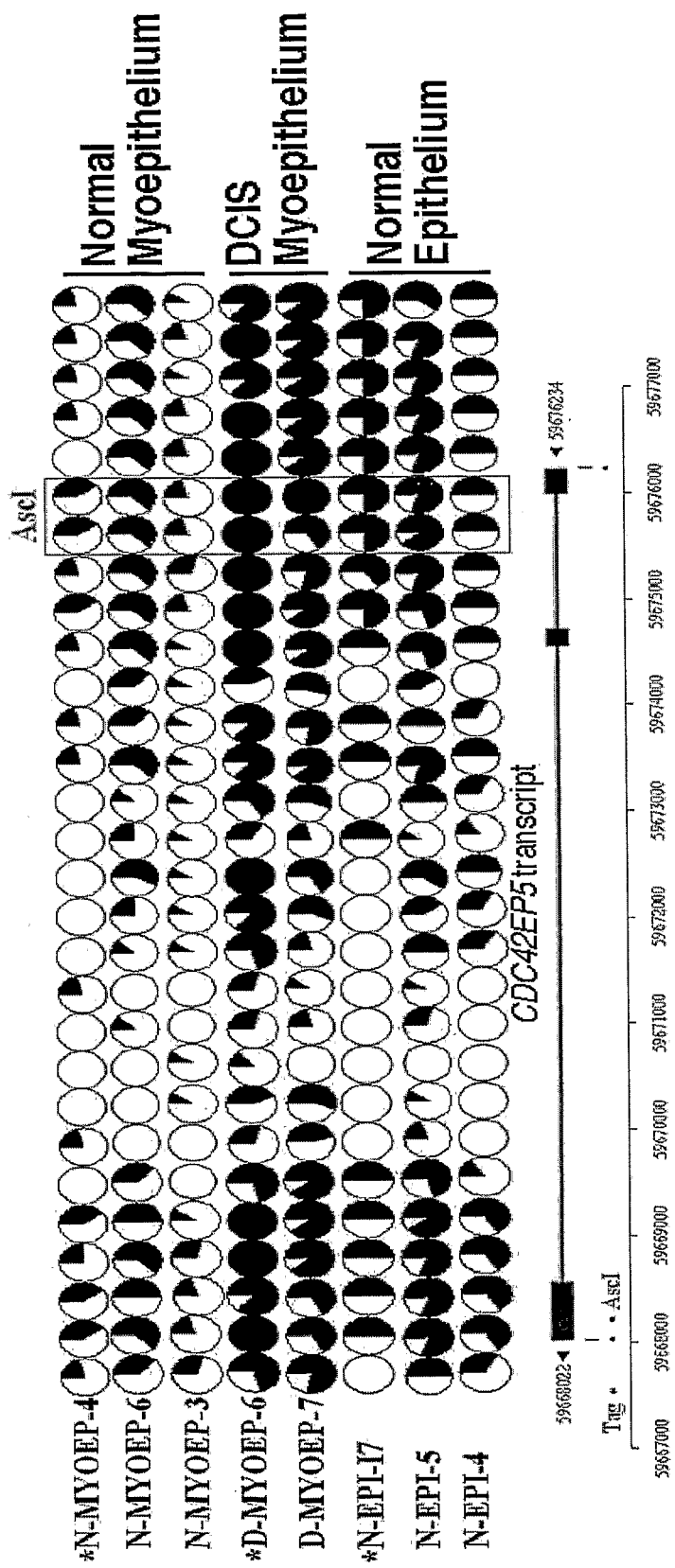
Figure 15:
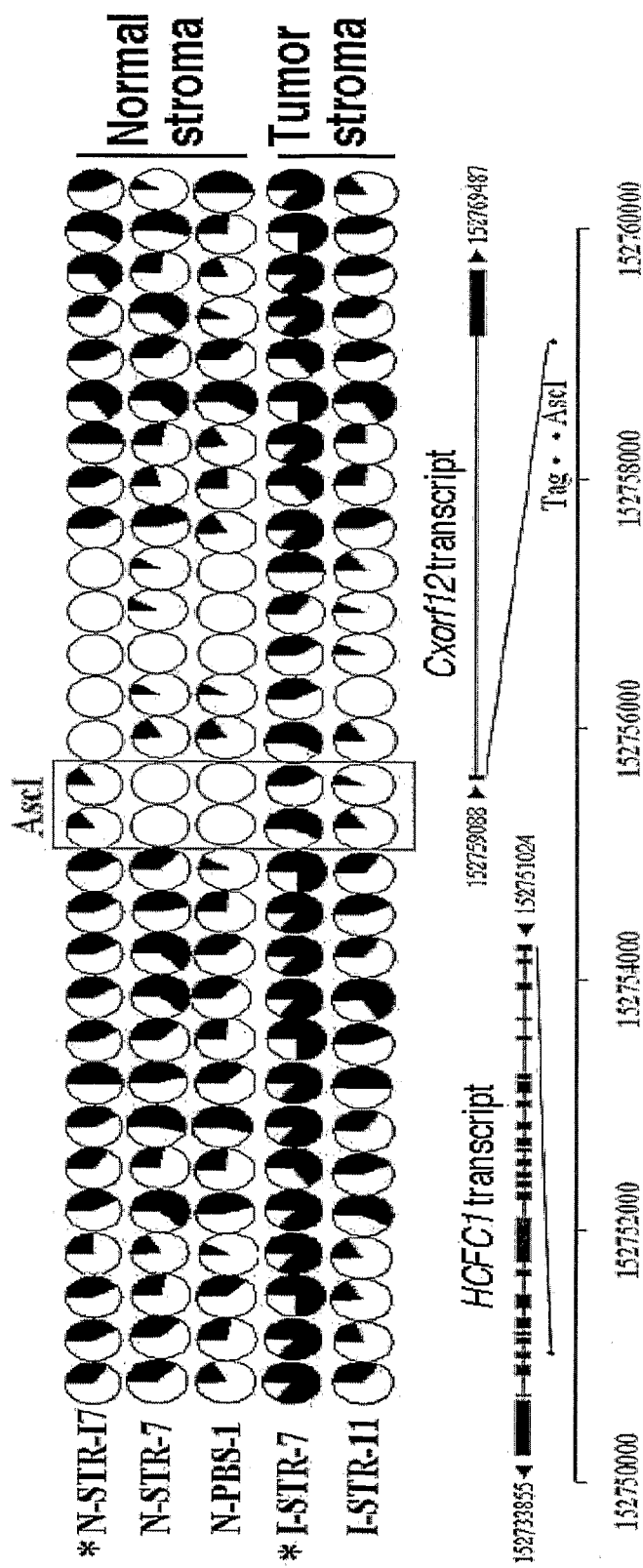
Figure 23A:
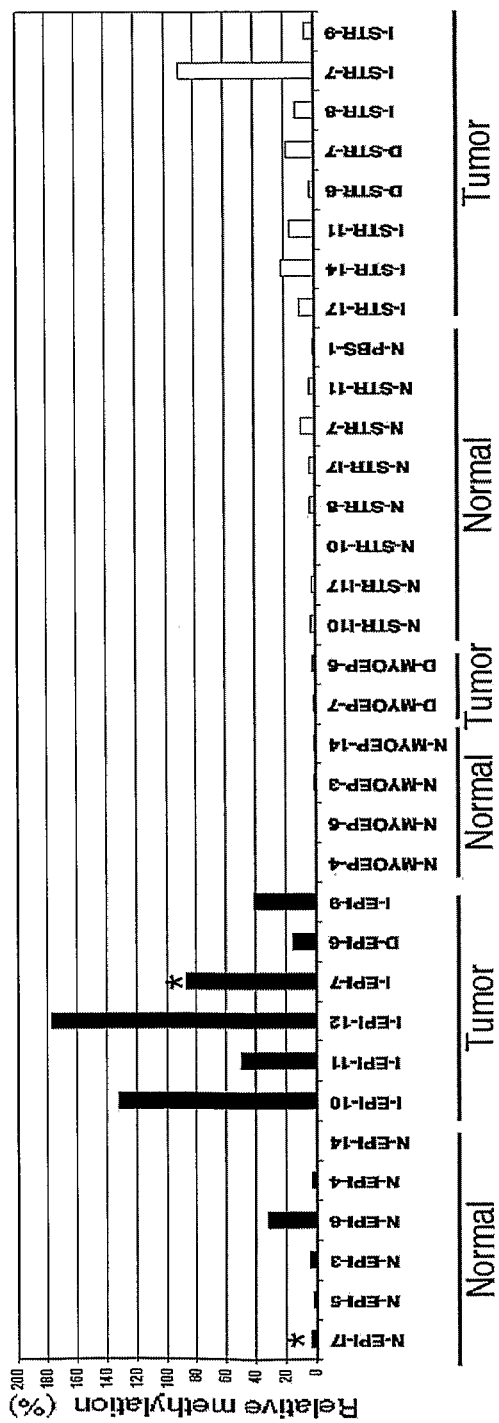
FIGS. 23A-F are a series of bar graphs showing the results of quantitative methylation specific PCR (qMSP) analyses of the PRDM14 (FIG. 23A), HOXD4 (FIG. 23B), SLC9A3R1 (FIG. 23C), CDC42EP5 (FIG. 23D), LOC389333 (FIG. 23E), and Cxorf12 (FIG. 23F) genes in epithelial cells (left set of normal and tumor cell bars), myoepithelial cells (middle set of normal and tumor cell bars), and fibroblast-enriched stromal cells (right set of normal and tumor cells) isolated from the indicated normal breast tissue and breast carcinoma samples. The average Ct value for each gene was normalized against the ACTB value (see Example 1). The data ("Relative methylation (%)") are percentages relative to the ACTB value. Samples used for generation of MSDK libraries are indicated by asterisks. The PRDM14 gene is almost exclusively methylated in tumor epithelial cells and the LOC389333 gene is preferentially methylated in epithelial cells (both tumor and normal) compared to other cell types. The HOXD4, SLC9A3R1, and CDC42EP5 genes, besides being differentially methylated between normal and DCIS and myoepithelial cells, are also methylated in other cell types. The HOXD4 gene is differentially methylated between normal and tumor epithelial cells and frequently methylated in stromal fibroblasts, while the SLC9A3R1 and CDC43EP5 genes are frequently methylated in stromal fibroblasts and occasionally in epithelial cells. The Cxorf12 gene is hypermethylated in tumor fibroblast enriched stromal cells compared to normal cells of the same type and is also methylated in a fraction of epithelial cells.
Figure 23B:
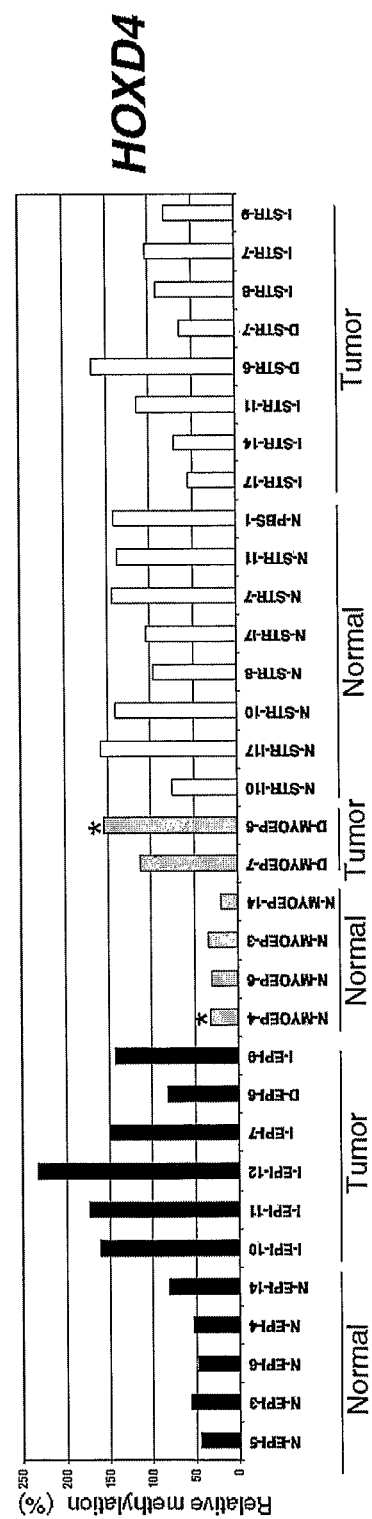
Figure 23C:
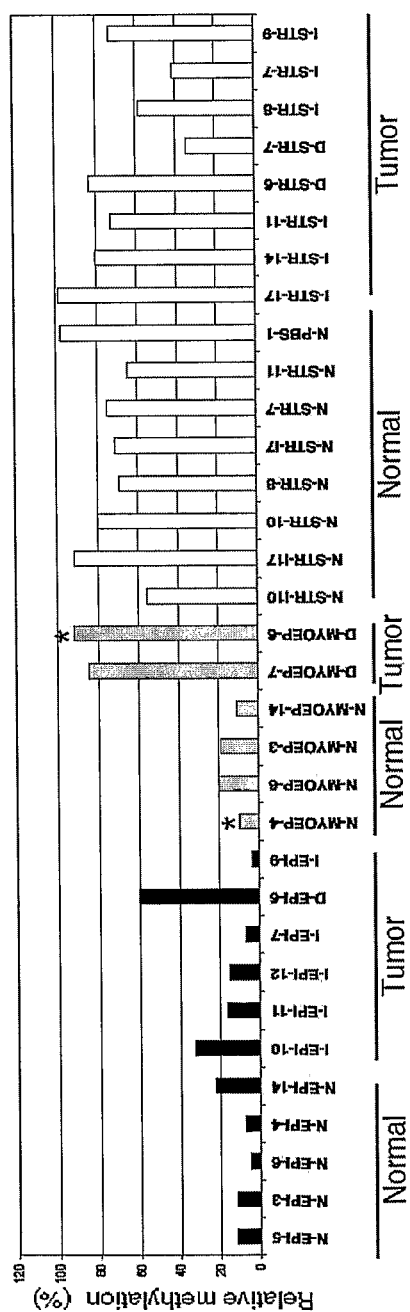
Figure 23D:
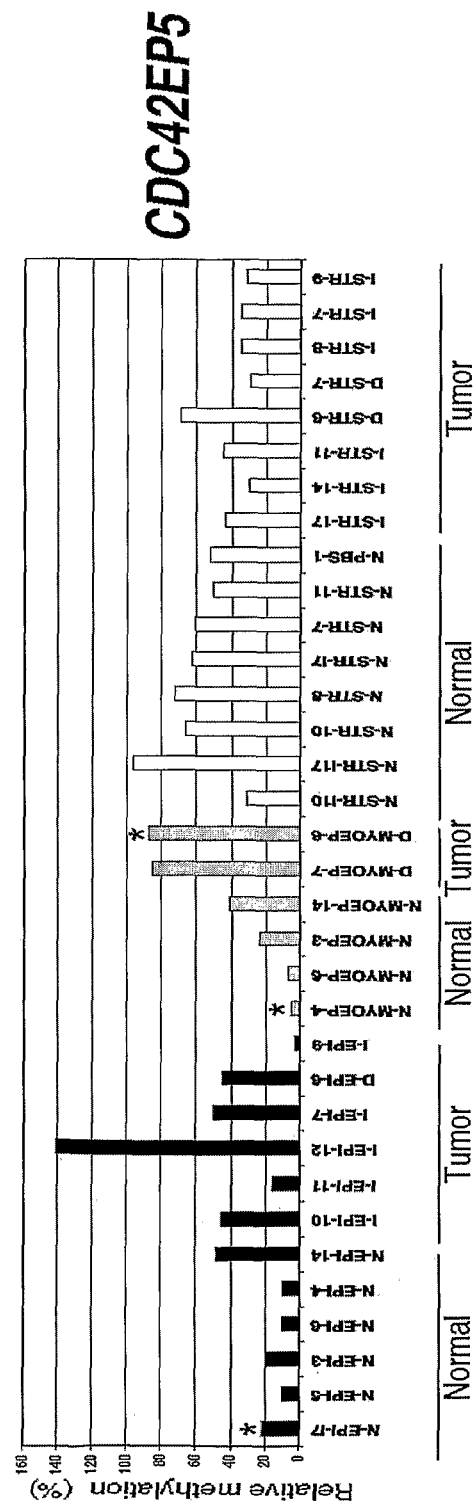
Figure 23E:
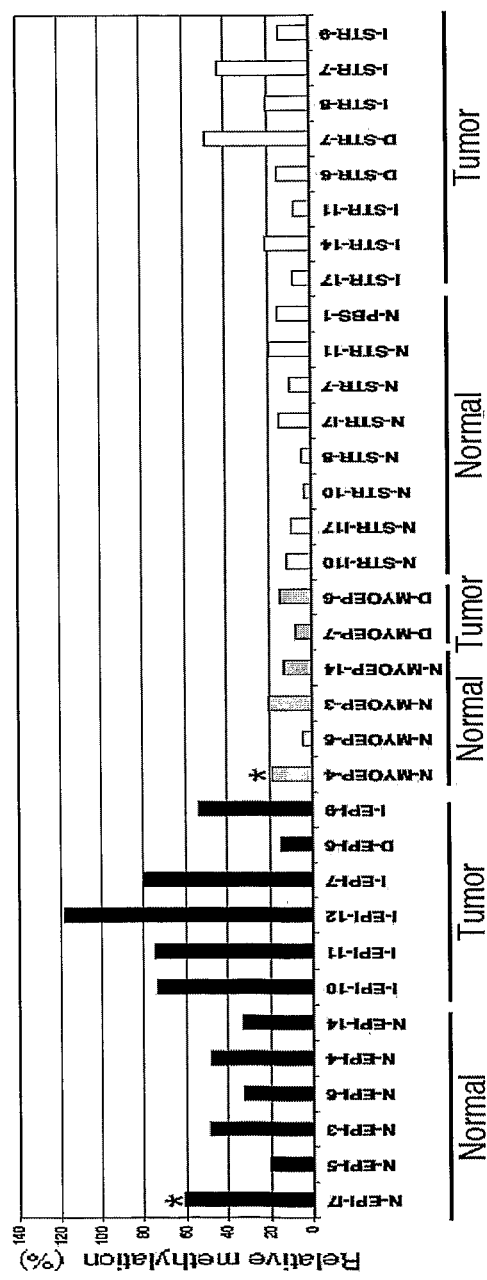
Figure 23F:
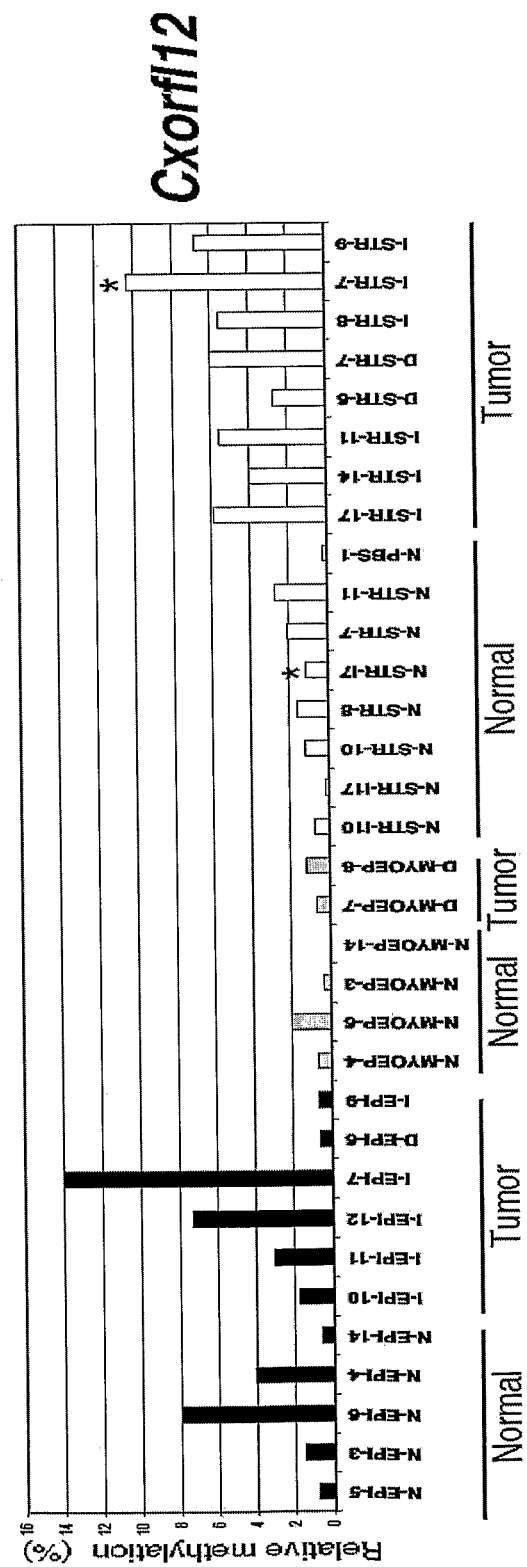

In order to further validate the MSDK technique, three highly differentially present tags were selected from the HCT libraries, the corresponding genomic loci (corresponding to the LHX3, LMX-1A, and TCF7L1 genes) were identified, and sequencing of bisulfite treated genomic DNA (the same as that used for the generation of the MSDK libraries) was performed. In all three cases, the relevant AscI site was completely methylated in the WT and unmethylated in the DKO cells (FIGS. 3-5). In addition, almost all other surrounding CpG showed the same methylation/unmethylation pattern. In FIGS. 6-8 are shown the nucleotide sequences of regions of these three gene segments of which were subjected to the described methylation-detecting sequencing analysis. These results indicated that the MSDK method is suitable for genome-wide analysis of methylation patterns and the identification of differentially methylated sites.

Example 3

Analysis of MSDK Libraries from Cell Populations Isolated from Normal and Cancerous Breast Tissue MSDK libraries were generated from epithelial cells, myoepithelial cells, and fibroblast-enriched stroma isolated from normal breast tissue, in situ (DCIS-ductal carcinoma in situ) breast carcinoma tissue, and invasive breast carcinoma tissue. A detailed description of the samples is in Table 3.

arrays in order to rule out the possibility of overt DNA copy number alterations.

Pair-wise comparisons and statistical analyses of the MSDK libraries revealed that the largest fraction of highly (>10 fold difference) differentially present tags occurred between normal and tumor epithelial cells and the majority of these tags were more abundant in tumor cells (Tables 4 and 5) correlating with the known overall hypomethylation of the cancer genome [Feinberg et al. (1983) Nature 301: 89-92).

TABLE 3

List of breast tissue samples used for methylation analyses.

| Name | Organ | Histology | Cell type | Tumor name | Age | Histology | Grade | LN | ER | PR | Her2 |
|---|---|---|---|---|---|---|---|---|---|---|---|
| D-MYOEP-6 | breast | tumor | myoepithelial | DCIS-6 | 29 | pure extensive DCIS | high | | | | |
| D-EPI-6 | breast | tumor | epithelial | DCIS-6 | 29 | pure extensive DCIS | high | | | | |
| D-MYOEP-7 | breast | tumor | myoepithelial | DCIS-7 | 29 | ext. DCIS adjacent to IDC | intermediate | | pos | low pos | neg |
| N-EPI-I7 | breast | normal | epithelial | | 47 | normal matched to tumor | | | | | |
| I-EPI-7 | breast | tumor | epithelial | IDC-7 | 47 | invasive ductal carcinoma | low | pos | pos | pos | neg |
| N-STR-I7 | breast | normal | stroma | | 47 | normal matched to tumor | | | | | |
| I-STR-7 | breast | tumor | stroma | IDC-7 | 47 | invasive ductal carcinoma | low | pos | pos | pos | neg |
| N-STR-I17 | breast | normal | stroma | | 44 | normal matched to tumor | | | | | |
| I-STR-17 | breast | tumor | stroma | IDC-17 | 44 | invasive ductal carcinoma | intermediate | | | | |
| N-MYOEP-4 | breast | normal | myoepithelial | | 25 | normal reduction | | | | | |
| N-EPI-4 | breast | normal | epithelial | | 25 | normal reduction | | | | | |
| N-MYOEP-6 | breast | normal | myoepithelial | | 19 | normal reduction | | | | | |
| N-MYOEP-3 | breast | normal | myoepithelial | | 24 | normal reduction | | | | | |
| N-STR-7 | breast | normal | stroma | | 26 | normal reduction | | | | | |
| I-STR-11 | breast | tumor | stroma | IDC-11 | 43 | invasive ductal carcinoma | low | pos | pos | pos | neg |
| N-PBS-1 | breast | normal | culture | | 38 | normal reduction | | | | | |
| N-EPI-5 | breast | normal | epithelial | | 58 | normal matched to tumor | high | neg | neg | neg | neg |
| I-EPI-9 | breast | tumor | epithelial | IDC-9 | 45 | invasive ductal carcinoma | intermediate | | pos | pos | neg |
| HCT-WT | colon | tumor | cell line | | | | | | | | |
| HCT-DKO | colon | tumor | cell line | | | | | | | | |

The numbers at the ends of the tissue sample names indicate patients from which the tissue samples were obtained.
Age is the age of the particular patient.
LN indicates whether the carcinoma in the relevant patient had spread to one or more lymph nodes.
ER indicates whether the relevant carcinoma cells expressed the estrogen receptor.
PR indicates whether the relevant carcinoma cells expressed the progesterone receptor.
Her2 indicates whether the relevant carcinoma cells expressed Her2/Neu.
Grade is the histologic grade.

Whenever possible, normal and tumor tissue were derived from the same patient in order to control for possible epigenetic variations due to age, and reproductive and disease status. Fibroblast-enriched stroma were the cells remaining after removal of epithelial cells, myoepithelial cells, leukocytes, and endothelial cells and consist of over 80% fibroblasts. DNA samples were also analyzed with SNP

TABLE 4

Chromosomal location and analysis of the frequency of MSDK tags in the I-EPI-7 and N-EIP-I7 MSDK libraries.

| Chr | Virtual Tags | Observed Tags | I-EPI-7 Variety | I-EPI-7 Copies | N-EPI-I7 Variety | N-EPI-I7 Copies | Tag Variety Ratio I-EPI-7/N-EPI-I7 | Tag Copy Ratio I-EPI-7/N-EPI-I7 | Differential Tag (P < 0.05) I-EPI-7 > N-EPI-I7 | Differential Tag (P < 0.05) N-EPI-I7/I-EPI-7 |
|---|---|---|---|---|---|---|---|---|---|---|
| 1 | 551 | 273 | 265 | 3330 | 98 | 496 | 2.704 | 6.714 | 28 | 5 |
| 2 | 473 | 192 | 183 | 1979 | 62 | 517 | 2.952 | 3.828 | 11 | 4 |
| 3 | 349 | 153 | 142 | 1792 | 58 | 535 | 2.448 | 3.350 | 8 | 2 |
| 4 | 281 | 122 | 118 | 1595 | 42 | 244 | 2.810 | 6.537 | 15 | 0 |
| 5 | 334 | 136 | 126 | 1296 | 55 | 399 | 2.291 | 3.248 | 7 | 3 |
| 6 | 338 | 130 | 120 | 994 | 50 | 245 | 2.400 | 4.057 | 1 | 0 |
| 7 | 403 | 193 | 186 | 1757 | 61 | 340 | 3.049 | 5.168 | 7 | 3 |
| 8 | 334 | 141 | 137 | 1327 | 51 | 300 | 2.686 | 4.423 | 6 | 3 |
| 9 | 349 | 153 | 145 | 1370 | 60 | 405 | 2.417 | 3.383 | 3 | 3 |
| 10 | 387 | 158 | 149 | 1599 | 59 | 378 | 2.525 | 4.230 | 7 | 1 |
| 11 | 379 | 169 | 161 | 1434 | 69 | 327 | 2.333 | 4.385 | 6 | 1 |
| 12 | 299 | 127 | 121 | 1060 | 49 | 331 | 2.469 | 3.202 | 5 | 4 |
| 13 | 138 | 53 | 51 | 474 | 20 | 108 | 2.550 | 4.389 | 1 | 1 |
| 14 | 228 | 96 | 91 | 838 | 28 | 165 | 3.250 | 5.079 | 5 | 0 |
| 15 | 260 | 116 | 108 | 936 | 40 | 158 | 2.700 | 5.924 | 8 | 0 |
| 16 | 340 | 145 | 137 | 1355 | 55 | 279 | 2.491 | 4.857 | 15 | 3 |
| 17 | 400 | 196 | 191 | 1952 | 70 | 496 | 2.729 | 3.935 | 7 | 4 |
| 18 | 181 | 72 | 69 | 527 | 19 | 125 | 3.632 | 4.216 | 1 | 0 |
| 19 | 463 | 173 | 165 | 1711 | 83 | 388 | 1.988 | 4.410 | 8 | 1 |
| 20 | 236 | 95 | 90 | 1009 | 38 | 244 | 2.368 | 4.135 | 4 | 0 |
| 21 | 71 | 24 | 24 | 255 | 8 | 69 | 3.000 | 3.696 | 2 | 0 |
| 22 | 217 | 88 | 85 | 781 | 31 | 205 | 2.742 | 3.810 | 3 | 0 |
| X | 185 | 55 | 53 | 462 | 19 | 116 | 2.789 | 3.983 | 1 | 0 |
| Y | 9 | | | | | | | | | |
| Matches | 7205 | 3060 | 2917 | 29833 | 1125 | 6870 | 2.593 | 4.343 | 159 | 38 |
| No Matches | | 1510 | 820 | 6835 | 930 | 4463 | 0.882 | 1.531 | 13 | 32 |
| Total | 7205 | 4570 | 3737 | 36668 | 2055 | 11333 | 1.818 | 3.236 | 172 | 70 |

The column headings are as indicated for Table 1.

TABLE 5

MSDK tags significantly (p < 0.050) differentially present in N-EPI-I7 and I-EPI-7 MSDK libraries and genes associated with the MSDK tags.

| MSDK Tag | SEQ-ID NO.I7 | I-EPI-7 | N-EPI-I7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| CAACGGAAACAAAAACA | 277 | 4 | 0 | -13 | 0.029464 | 1 | MMP23A | matrix metalloproteinase 23A | 5' | 6922 |
| CAACGGAAACAAAAACA | 278 | 4 | 0 | -13 | 0.029464 | 1 | HSPC182 | HSPC182 protein | 5' | 111089 |
| CCCGCCACGCCGCCCCG | 279 | 0 | 13 | 13 | 0.0158 | 1 | ENO1 | enolase 1 | 3' | 230 |
| CTCCAAAAATCCCTTGA | 280 | 5 | 0 | -16 | 0.046199 | 1 | NBL1 | neuroblastoma, suppression of tumorigenicity 1 | 5' | 158583 |
| CTCCAAAAATCCCTTGA | 281 | 5 | 0 | -16 | 0.046199 | 1 | CAPZB | F-actin capping protein beta subunit | 5' | 64897 |
| GTGCCGCCGCGGGCGCC | 282 | 11 | 61 | 2 | 0.032251 | 1 | KIAA0478 | KIAA0478 gene product | 5' | 308006 |
| GTGCCGCCGCGGGCGCC | 283 | 11 | 61 | 2 | 0.032251 | 1 | WNT4 | wingless-type MMTV integration site family | 5' | 733 |
| CTGCAACTTGGTGCCCC | 284 | 2 | 22 | 3 | 0.027586 | 1 | PRDX1 | peroxiredoxin 1 | 3' | 150 |
| GCCTCTCTGCGCCTGCC | 285 | 18 | 10 | -6 | 0.023961 | 1 | GFI1 | growth factor independent 1 | 3' | 4842 |

TABLE 5-continued

MSDK tags significantly (p < 0.050) differentially present in N-EPI-I7 and I-EPI-7 MSDK libraries and genes associated with the MSDK tags.

| MSDK Tag | SEQ-ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| CTCCGTTTTCTTTTGTT | 286 | 4 | 0 | −13 | 0.029464 | 1 | ALX3 | aristaless-like homeobox 3 | 3' | 1631 |
| AGCGCTTGGCGCTCCCA | 287 | 5 | 54 | 3 | 0.002039 | 1 | NPR1 | natriuretic peptide receptor A/ guanylate cyclase | 3' | 677 |
| TCTGGGGCCGGGTAGCC | 288 | 9 | 216 | 7 | $7.35 \times 10^{-16}$ | 1 | P66beta | transcription repressor p66 beta component of | 5' | 117605 |
| CACCCGCGGGGTGGGG | 289 | 0 | 17 | 17 | 0.028576 | 1 | IL6R | interleukin 6 receptor isoform 2 precursor | 3' | 898 |
| CGTGTGTATCTGGGGGT | 290 | 6 | 51 | 3 | 0.007702 | 1 | MUC1 | mucin 1, transmembrane | 3' | 188528 |
| GCAGCGGCGCTCCGGGC | 291 | 9 | 120 | 4 | $1.75 \times 10^{-7}$ | 1 | MUC1 | mucin 1, transmembrane | 3' | 139119 |
| TGTTCAGAGCCAGCTTG | 292 | 2 | 25 | 4 | 0.01729 | 1 | LMNA | lamin A/C isoform 2 | 3' | 236 |
| CCAGGCTGGCTCACCCT | 293 | 0 | 27 | 27 | 0.003867 | 1 | HAPLN2 | brain link protein-1 | 3' | 4728 |
| CCAGGGCCTGGCACTGC | 294 | 15 | 89 | 2 | 0.003766 | 1 | IGSF9 | immunoglobulin superfamily, member 9 | 5' | 393 |
| TTCGGGCCGGGCCGGGA | 295 | 17 | 90 | 2 | 0.009369 | 1 | LMX1A | LIM homeobox transcription factor 1, alpha | 5' | 752 |
| AGCCCTCGGGTGATGAG | 29 | 7 | 83 | 4 | $4.14 \times 10^{-5}$ | 1 | LMX1A | LIM homeobox transcription factor 1, alpha | 5' | 752 |
| CATTCCAGTTACAGTTG | 297 | 5 | 40 | 2 | 0.027143 | 1 | GPR161 | G protein-coupled receptor 161 | 3' | 198 |
| TCCACAGCGGACGTTCC | 298 | 0 | 32 | 32 | 0.004049 | 1 | TOR3A | torsin family 3, member A | 3' | 100 |
| ACATTGTCCTTTTTGCC | 299 | 2 | 25 | 4 | 0.01729 | 1 | C1orf24 | niban protein | 3' | 292 |
| CCGAGGGGCCTGGCGCC | 300 | 0 | 12 | 12 | 0.026152 | 1 | BTG2 | B-cell translocation gene 2 | 3' | 431 |
| TCCAGGCAGGGCCTCTG | 301 | 8 | 91 | 4 | $2.06 \times 10^{-5}$ | 1 | BTG2 | B-cell translocation gene 2 | 3' | 431 |
| CCCCCGCGACGCGGCGG | 34 | 10 | 4 | −8 | 0.039911 | 1 | SOX13 | SRY-box 13 | 5' | 571 |
| CCCCCGCGACGCGGCGG | 34 | 10 | 4 | −8 | 0.039911 | 1 | FLJ40343 | hypothetical protein FLJ40343 | 5' | 31281 |
| TGGATTTGGTCGTCTCC | 304 | 0 | 25 | 25 | 0.005775 | 1 | PLXNA2 | plexin A2 | 3' | 428 |
| GCCCCCGTGGCGCCCCG | 305 | 8 | 97 | 4 | $6.47 \times 10^{-6}$ | 1 | CENPF | centromere protein F (350/400 kD) | 5' | 51300 |
| GCCCCCGTGGCGCCCCG | 306 | 8 | 97 | 4 | $6.47 \times 10^{-6}$ | 1 | PTPN14 | protein tyrosine phosphatase, non-receptor type | 5' | 589 |
| TCGGTGGTCGCTCGTGG | 307 | 0 | 19 | 19 | 0.019333 | 1 | MGC42493 | hypothetical protein MGC42493 | 5' | 244931 |

TABLE 5-continued

MSDK tags significantly (p < 0.050) differentially present in N-EPI-I7 and I-EPI-7 MSDK libraries and genes associated with the MSDK tags.

| MSDK Tag | SEQ-ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| TCGGTGGTCGCTCGTGG | 308 | 0 | 19 | 19 | 0.019333 | 1 | CDC42BPA | CDC42-binding protein kinase alpha isoform A | 5' | 486 |
| GCTAGGGAAAAACAGGC | 309 | 11 | 59 | 2 | 0.043511 | 1 | MGC42493 | hypothetical protein MGC42493 | 5' | 244931 |
| GCTAGGGAAAAACAGGC | 310 | 11 | 59 | 2 | 0.043511 | 1 | CDC42BPA | CDC42-binding protein kinase alpha isoform A | 5' | 486 |
| GACGCGCTCCCGCGGGC | 311 | 5 | 42 | 3 | 0.01897 | 1 | WNT3A | wingless-type MMTV integration site family | 5' | 59111 |
| GACGCGCTCCCGCGGGC | 312 | 5 | 42 | 3 | 0.01897 | 1 | WNT9A | wingless-type MMTV integration site family | 5' | 41 |
| CAAAGGAGCTGTGGAGC | 313 | 2 | 23 | 4 | 0.026376 | 1 | TAF5L | PCAF associated factor 65 beta | 3' | 192 |
| GAGCGGCCGCCCAGAGC | 314 | 6 | 61 | 3 | 0.001212 | 1 | TAF5L | PCAF associated factor 65 beta | 3' | 192 |
| GCCAATGACAGCGGCGG | 315 | 0 | 17 | 17 | 0.009019 | 1 | EGLN1 | egl nine homolog 1 | 3' | 3449 |
| ATGCGCCCCGCAGCCCC | 316 | 10 | 138 | 4 | $1.24 \times 10^{-8}$ | 1 | MGC13186 | hypothetical protein MGC13186 | 5' | 321138 |
| ATGCGCCCCGCAGCCCC | 317 | 10 | 138 | 4 | $1.24 \times 10^{-8}$ | 1 | SIPA1L2 | signal-induced proliferation-associated 1 like | 5' | 114742 |
| CTGGAACCCCGCACACC | 318 | 0 | 16 | 16 | 0.010329 | 1 | FLJ12606 | hypothetical protein FLJ12606 | 5' | 82 |
| GTCCCCGCGCCGCGGCC | 319 | 28 | 13 | -7 | $3.05 \times 10^{-7}$ | 2 | UBXD4 | UBX domain containing 4 | 5' | 553390 |
| GTCCCCGCGCCGCGGCC | 320 | 28 | 13 | -7 | $3.05 \times 10^{-7}$ | 2 | APOB | apolipoprotein B precursor | 5' | 2343039 |
| AACTTTTAAAGTTTCCC | 321 | 0 | 14 | 14 | 0.017811 | 2 | UBXD4 | UBX domain containing 4 | 5' | 97 |
| AACTTTTAAAGTTTCCC | 322 | 0 | 14 | 14 | 0.017811 | 2 | APOB | apolipoprotein B precursor | 5' | 2896332 |
| GCCACCCAAGCCCGTCG | 323 | 0 | 18 | 18 | 0.006642 | 2 | RAB10 | ras-related GTP-binding protein RAB10 | 5' | 106 |
| GCCACCCAAGCCCGTCG | 324 | 0 | 18 | 18 | 0.006642 | 2 | KIF3C | kinesin family member 3C | 5' | 51464 |
| CCTTTGCTTCCCTTTCC | 325 | 0 | 15 | 15 | 0.013161 | 2 | CRIM1 | cysteine-rich motor neuron 1 | 5' | 100 |
| CCTTTGCTTCCCTTTCC | 326 | 0 | 15 | 15 | 0.013161 | 2 | MYADML | myeloid-associated differentiation marker-like | 5' | 2630025 |
| CACACAAGGCGCCCGCG | 327 | 4 | 37 | 3 | 0.022534 | 2 | SIX2 | sine oculis homeobox homolog 2 | 5' | 160394 |
| TAAGAGTCCAGCAGGCA | 328 | 4 | 0 | -13 | 0.029464 | 2 | RTN4 | reticulon 4 isoform C | 5' | 295 |

TABLE 5-continued

MSDK tags significantly (p < 0.050) differentially present in N-EPI-I7 and I-EPI-7 MSDK libraries and genes associated with the MSDK tags.

| MSDK Tag | SEQ-ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| TCATTGCATACTGAAGG | 329 | 2 | 23 | 4 | 0.026376 | 2 | SLC1A4 | solute carrier family 1, member 4 | 5' | 335302 |
| TCATTGCATACTGAAGG | 330 | 2 | 23 | 4 | 0.026376 | 2 | SERTAD2 | SERTA domain containing 2 | 5' | 245 |
| GCGCTACACGCCGCTCC | 331 | 3 | 35 | 4 | 0.01477 | 2 | SLC1A4 | solute carrier family 1, member 4 | 5' | 111 |
| GCGCTACACGCCGCTCC | 332 | 3 | 35 | 4 | 0.01477 | 2 | SERTAD2 | SERTA domain containing 2 | 5' | 335436 |
| GACGACAGCGCCGCCGC | 333 | 0 | 18 | 18 | 0.006642 | 2 | UXS1 | UDP-glucuronate decarboxylase 1 | 5' | 66 |
| AAATTCCATAGACAACC | 334 | 13 | 7 | -6 | 0.047343 | 2 | HOXD4 | homeo box D4 | 3' | 1141 |
| GGCGTGGGGAGAGGGGG | 335 | 4 | 35 | 3 | 0.032525 | 2 | ZNF533 | zinc finger protein 533 | 5' | 114958 |
| GCTGCAGGCACTGGGTT | 336 | 4 | 0 | -13 | 0.029464 | 2 | ATIC | 5-aminoimidazole-4-carboxamide ribonucleotide | 5' | 203 |
| GCTGCAGGCACTGGGTT | 337 | 4 | 0 | -13 | 0.029464 | 2 | ABCA12 | ATP-binding cassette, sub-family A, member 12 | 5' | 173481 |
| ATGGTGTCGCTGGACAG | 338 | 3 | 37 | 4 | 0.010034 | 2 | ARPC2 | actin related protein 2/3 complex subunit 2 | 5' | 94 |
| ATGGTGTCGCTGGACAG | 339 | 3 | 37 | 4 | 0.010034 | 2 | IL8RA | interleukin 8 receptor alpha | 5' | 50063 |
| GACTTCTGGCAAGGGAG | 340 | 0 | 17 | 17 | 0.028576 | 2 | DOCK10 | dedicator of cytokinesis 10 | 5' | 208215 |
| ACTGCATCCGGCCTCGG | 341 | 16 | 89 | 2 | 0.006496 | 2 | PTMA | prothymosin, alpha (gene sequence 28) | 5' | 93674 |
| CCTAGCATCTCCTCTTG | 342 | 6 | 0 | -19 | 0.016381 | 3 | GRM7 | glutamate receptor, metabotropic 7 isoform b | 5' | 70 |
| GAGGACTGGGGGCTGGG | 343 | 0 | 14 | 14 | 0.017811 | 3 | HRH1 | histamine receptor H1 | 5' | 98409 |
| CTTTGGCCGAGGCCGAG | 344 | 5 | 0 | -16 | 0.010561 | 3 | FGD5 | FYVE, RhoGEF and PH domain containing 5 | 5' | 8578 |
| CGGCGCGTCCCTGCCGG | 345 | 33 | 146 | 1 | 0.005894 | 3 | DKFZp313N0621 | hypothetical protein DKFZp313N0621 | 5' | 339665 |
| GAGAAGCCGCCAGCCGG | 346 | 7 | 49 | 2 | 0.0217 | 3 | PXK | PX domain containing serine/threonine kinase | 3' | 346 |
| CCTGCCTCTGGCAGGGG | 347 | 17 | 82 | 1 | 0.029136 | 3 | PLXNA1 | plexin A1 | 5' | 5386 |
| GTTTCTTCTCAATAGCC | 348 | 0 | 22 | 22 | 0.011411 | 3 | FLJ12057 | hypothetical protein FLJ12057 | 5' | 28432 |
| TCCTTGATGAAATGCGC | 349 | 0 | 14 | 14 | 0.017811 | 3 | SSB4 | SPRY domain-containing SOCS box protein SSB-4 | 5' | 434 |
| GCTGGCGATCTGGGGCT | 350 | 0 | 12 | 12 | 0.026152 | 3 | MGC40579 | hypothetical protein MGC40579 | 3' | 405 |

TABLE 5-continued

MSDK tags significantly (p < 0.050) differentially present in N-EPI-I7 and I-EPI-7 MSDK libraries and genes associated with the MSDK tags.

| MSDK Tag | SEQN-ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| ACCCTTGGAGGAAGGGG | 351 | 0 | 12 | 12 | 0.026152 | 3 | C3orf21 | chromosome 3 open reading frame 21 | 3' | 134 |
| GGGCGGTGGCGGGGACG | 352 | 0 | 14 | 14 | 0.017811 | 4 | RGS12 | regulator of G-protein signalling 12 isoform 2 | 5' | 21007 |
| CCTGCGCCGGGGGAGGC | 353 | 66 | 240 | 1 | 0.011585 | 4 | ADRA2C | alpha-2C-adrenergic receptor | 3' | 432 |
| ATTTAGGGGTCTGTACC | 354 | 0 | 15 | 15 | 0.013161 | 4 | KIAA0232 | KIAA0232 gene product | 5' | 58 |
| GTCCGTGGAATAGAAGG | 355 | 8 | 69 | 3 | 0.001269 | 4 | Not Found | | | |
| GTGGCGCGCTGGCGGGG | 356 | 0 | 13 | 13 | 0.0158 | 4 | RASL1B | RAS-like family 11 member B | 5' | 202915 |
| GTGGCGCGCTGGCGGGG | 357 | 0 | 13 | 13 | 0.0158 | 4 | USP46 | ubiquitin specific protease 46 | 5' | 139 |
| CTGCCCAGTACCTGAGG | 358 | 0 | 18 | 18 | 0.006642 | 4 | SLC4A4 | solute carrier family 4, sodium bicarbonate | 5' | 151833 |
| CCGCGGATCTCGCCGGT | 359 | 2 | 25 | 4 | 0.01729 | 4 | ASAHL | N-acylsphingosine amidohydrolase-like protein | 3' | 67 |
| AGCCACCTGCGCCTGGC | 360 | 14 | 81 | 2 | 0.007548 | 4 | PAQR3 | progestin and adipoQ receptor family member III | 5' | 101 |
| TGCGGAGAAGACCCGGG | 361 | 2 | 24 | 4 | 0.019587 | 4 | ELOVL6 | ELOVL family member 6, elongation of long chain | 3' | 1583 |
| GCTGTCCGCACGCGGCC | 362 | 0 | 15 | 15 | 0.013161 | 4 | SMAD1 | Sma- and Mad-related protein 1 | 5' | 301087 |
| GCTGTCCGCACGCGGCC | 363 | 0 | 15 | 15 | 0.013161 | 4 | HSHIN1 | HIV-1 induced protein HIN-1 isoform 1 | 5' | 5967 |
| TGCACGCACACTCTTCC | 364 | 2 | 29 | 4 | 0.019901 | 4 | LOC152485 | hypothetical protein LOC152485 | 3' | 851 |
| GCGTTTGGGGGTGTCGG | 365 | 0 | 21 | 21 | 0.003436 | 4 | LOC152485 | hypothetical protein LOC152485 | 3' | 851 |
| GTGGGGAGGCTGGGGCG | 366 | 0 | 43 | 43 | 0.00042 | 4 | DCAMKL2 | doublecortin and CaM kinase-like 2 | 5' | 1633428 |
| GTGGGGAGGCTGGGGCG | 367 | 0 | 43 | 43 | 0.00042 | 4 | NR3C2 | nuclear receptor subfamily 3, group C, member 2 | 5' | 3189 |
| CTGCACTAAAATATTCG | 368 | 3 | 29 | 3 | 0.046121 | 4 | MGC45800 | hypothetical protein LOC90768 | 5' | 304606 |
| CTTAGATCTAGCGTTCC | 369 | 6 | 58 | 3 | 0.002127 | 4 | DKFZP564J102 | DKFZP564J102 protein | 5' | 4 |
| CCATATTTGCCCAAGCC | 370 | 0 | 12 | 12 | 0.026152 | 5 | EMB | embigin homolog | 3' | 410 |
| TGACAGGCGTGCGAGCC | 371 | 2 | 43 | 7 | 0.001198 | 5 | MGC33648 | hypothetical protein MGC33648 | 5' | 92617 |
| TGACAGGCGTGCGAGCC | 372 | 2 | 43 | 7 | 0.001198 | 5 | FLJ11795 | hypothetical protein FLJ1795 | 5' | 699674 |

TABLE 5-continued

MSDK tags significantly (p < 0.050) differentially present in N-EPI-I7 and I-EPI-7 MSDK libraries and genes associated with the MSDK tags.

| MSDK Tag | SEQ-ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| CTAGAAAGACAGATTGG | 373 | 0 | 12 | 12 | 0.026152 | 5 | TIGA1 | TIGA1 | 5' | 402673 |
| CTAGAAAGACAGATTGG | 374 | 0 | 12 | 12 | 0.026152 | 5 | C5orf13 | neuronal protein 3.1 | 5' | 594 |
| CTGGGTTGCGATTAGCT | 375 | 23 | 25 | -3 | 0.018417 | 5 | PPIC | peptidylprolyl isomerase C | 5' | 62181 |
| CGTGGCTCGGATTCGGG | 376 | 0 | 13 | 13 | 0.0158 | 5 | ARHGAP26 | GTPase regulator associated with the focal | 3' | 8 |
| CCAGAGGGTCTTAAGTG | 377 | 11 | 71 | 2 | 0.00663 | 5 | NR3C1 | nuclear receptor subfamily 3, group C, member 1 | 3' | 553 |
| CTGCGGGAGCTGCGGCC | 378 | 0 | 17 | 17 | 0.028576 | 5 | SGCD | delta-sarcoglycan isoform 1 | 5' | 597771 |
| TCCGACAAGAAGCCGCC | 379 | 0 | 26 | 26 | 0.004502 | 5 | MSX2 | msh homeo box homolog 2 | 3' | 605 |
| CGTCTCCCATCCCGGGC | 380 | 18 | 17 | -3 | 0.016276 | 5 | CPLX2 | complexin 2 | 3' | 1498 |
| GCAGAAAAAGCACAAAG | 381 | 11 | 4 | -9 | 0.026609 | 5 | FLT4 | fms-related tyrosine kinase 4 isoform 1 | 5' | 24508 |
| GTCAGCGCCGGCCCCAG | 382 | 5 | 44 | 3 | 0.013197 | 6 | EGFL9 | EGF-like-domain, multiple 9 | 3' | 134 |
| ATGAGTCCATTTCCTCG | 383 | 31 | 40 | -3 | 0.029841 | 7 | MGC10911 | hypothetical protein MGC10911 | 5' | 96664 |
| GCGAGGGCCCAGGGGTC | 384 | 12 | 75 | 2 | 0.006269 | 7 | SLC29A4 | solute carrier family 29 (nucleoside | 3' | 67 |
| GGGGGGGAACCGGACCG | 385 | 0 | 18 | 18 | 0.006642 | 7 | ACTB | beta actin | 3' | 865 |
| AACTTGGGGCTGACCGG | 386 | 0 | 30 | 30 | 0.006104 | 7 | AUTS2 | autism susceptibility candidate 2 | 3' | 1095850 |
| CCTTGACTGCCTCCATC | 387 | 5 | 0 | -16 | 0.046199 | 7 | WBSCR17 | Williams Beuren syndrome chromosome region 17 | 5' | 512 |
| CCCAGGCTTGGAATCCC | 388 | 2 | 23 | 4 | 0.026376 | 7 | AP1S1 | adaptor-related protein complex 1, sigma 1 | 5' | 107 |
| TACTTTTAACTGCCTGC | 389 | 0 | 23 | 23 | 0.00317 | 7 | FOXP2 | forkhead box P2 isoform II | 5' | 328728 |
| TACTTTTAACTCCCTGC | 390 | 0 | 23 | 23 | 0.00317 | 7 | PPP1R3A | protein phosphatase 1 glycogen-binding | 5' | 167483 |
| ATTGCATTCTTGAGGGC | 391 | 0 | 12 | 12 | 0.026152 | 7 | SLC4A2 | solute carrier family 4, anion exchanger, member | 3' | 10 |
| GAGCTGGCAAGCCTGGG | 392 | 0 | 14 | 14 | 0.017811 | 7 | ASB10 | ankyrin repeat and SOCS box-containing protein | 3' | 11480 |
| GATGCCACCAGGTTGTG | 393 | 13 | 7 | -6 | 0.047343 | 7 | HTR5A | 5-hydroxytryptamine (serotonin) receptor 5A | 5' | 579 |

TABLE 5-continued

MSDK tags significantly (p < 0.050) differentially present in N-EPI-I7 and
I-EPI-7 MSDK libraries and genes associated with the MSDK tags.

| MSDK Tag | SEQ ID NO. | N-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| GATGCCACCAGGTTGTG | 394 | 13 | 7 | -6 | 0.047343 | 7 | PAXIP1L | PAX transcription activation domain interacting | 5' | 67372 |
| TCCCGCCGCGCGTTGCC | 395 | 0 | 16 | 16 | 0.010329 | 8 | PCM1 | pericentriolar material 1 | 3' | 243 |
| CCCTGTCCTAGTAACGC | 396 | 2 | 36 | 6 | 0.004927 | 8 | DDHD2 | DDHD domain containing 2 | 3' | 541 |
| CGAGGAAGTGACCCTCG | 397 | 0 | 14 | 14 | 0.017811 | 8 | CHD7 | chromodomain helicase DNA binding protein 7 | 5' | 156 |
| GCGGGGGCAGCAGACGC | 398 | 9 | 0 | -29 | 0.002372 | 8 | PRDM14 | PR domain containing 14 | 3' | 768 |
| TAACTGTCCTTTCCGTA | 399 | 23 | 5 | -15 | $6.66 \times 10^{-9}$ | 8 | Not Found | | | |
| TCTGTATTTTCCCGGGG | 400 | 0 | 22 | 22 | 0.011411 | 8 | FAM49B | family with sequence similarity 49, member B | 5' | 528 |
| AAGAGGCAGAACGTGCG | 401 | 34 | 12 | -9 | $2.68 \times 10^{-10}$ | 8 | KCNK9 | potassium channel, subfamily K, member 9 | 3' | 360 |
| GCCTCAGCCCGCACCCG | 402 | 0 | 21 | 21 | 0.015063 | 8 | DGAT1 | diacylglycerol O-acyltransferase 1 | 5' | 84 |
| GACCGGGGCGCAGGGCC | 403 | 0 | 21 | 21 | 0.015063 | 8 | ZNF517 | zinc finger protein 517 | 5' | 130 |
| GACCGGGGCGCAGGGCC | 404 | 0 | 21 | 21 | 0.015063 | 8 | RPL8 | ribosomal protein L8 | 5' | 6362 |
| GTGCGGGCGACGGCAGC | 405 | 12 | 72 | 2 | 0.010135 | 9 | KLF9 | Kruppel-like factor 9 | 3' | 995 |
| GCCCGCCTGAGCAAGGG | 406 | 44 | 23 | -6 | $5.46 \times 10^{-10}$ | 9 | C9orf125 | chromosome 9 open reading frame 125 | 3' | 738 |
| GGTGGAGGCAGGCGGGG | 407 | 0 | 15 | 15 | 0.013161 | 9 | TXN | thioredoxin | 3' | 266 |
| GGCGTTAATAGAGAGGC | 408 | 4 | 0 | -13 | 0.029464 | 9 | PRDM12 | PR domain containing 12 | 5' | 5017 |
| AGGTTGTTGTTCTTGCA | 409 | 20 | 14 | -5 | 0.000803 | 9 | PRDM12 | PR domain containing 12 | 3' | 1427 |
| AGCCGCGGGCAGCCGCC | 410 | 0 | 21 | 21 | 0.015063 | 9 | BARHL1 | BarH-like 1 | 5' | 87 |
| AGCCACCGTACAAGGCC | 411 | 8 | 49 | 2 | 0.039937 | 10 | PFKP | phosphofructokinase, platelet | 3' | 1056 |
| GCGGGCAGCTCGAGGCG | 412 | 0 | 19 | 19 | 0.019333 | 10 | BAMBI | BMP and activin membrane-bound inhibitor | 3' | 203 |
| GCGGCCGCGGGCAGGGG | 413 | 0 | 20 | 20 | 0.01441 | 10 | TRIM8 | tripartite motif-containing 8 | 5' | 375 |
| CCCCGTGGCGGGAGCGG | 414 | 22 | 119 | 2 | 0.001632 | 10 | NEURL | neuralized-like | 5' | 630 |
| CCCCGTGGCGGGAGCGG | 415 | 22 | 119 | 2 | 0.001632 | 10 | FAM26A | family with sequence similarity 26, member A | 5' | 14420 |
| GCCTGGCTCTCCTTCGC | 416 | 0 | 15 | 15 | 0.013161 | 10 | KIAA1598 | KIAA1598 | 3' | 509 |

TABLE 5-continued

MSDK tags significantly (p < 0.050) differentially present in N-EPI-I7 and I-EPI-7 MSDK libraries and genes associated with the MSDK tags.

| MSDK Tag | SEQN- ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| AAAAGTAAACAGGTATT | 417 | 4 | 0 | −13 | 0.029464 | 10 | PLEKHA1 | pleckstrin homology domain containing, family A | 5' | 162 |
| CCGCGCTGAGGGGGGGC | 418 | 0 | 17 | 17 | 0.028576 | 10 | CTBP2 | C-terminal binding protein 2 isoform 1 | 3' | 1219 |
| TCAGAGGCTGATGGGGC | 419 | 6 | 52 | 3 | 0.006425 | 10 | MGMT | O-6-methylguanine-DNA methyltransferase | 5' | 1340765 |
| TCAGAGGCTGATGGGGC | 420 | 6 | 52 | 3 | 0.006425 | 10 | MKI67 | antigen identified by monoclonal antibody Ki-67 | 5' | 232 |
| CGGAGCCGCCCCAGGGG | 421 | 0 | 28 | 28 | 0.009196 | 11 | RNH | ribonuclease/angiogenin inhibitor | 3' | 381 |
| ATGCCACCCCAGGTTGC | 422 | 0 | 21 | 21 | 0.015063 | 11 | OSBPL5 | oxysterol-binding protein-like protein 5 isoform | 3' | 397 |
| GCGCTGCCCTATATTGG | 423 | 11 | 75 | 2 | 0.00341 | 11 | FLJ11336 | hypothetical protein FLJ11336 | 3' | 375 |
| TCGTCCTGGGTGGAGGG | 424 | 2 | 22 | 3 | 0.027586 | 11 | C11ORF4 | chromosome 11 hypothetical protein ORF4 | 5' | 458 |
| TCGTCCTGGGTGGAGGG | 425 | 2 | 22 | 3 | 0.027586 | 11 | BAD | BCL2-antagonist of cell death protein | 5' | 708 |
| GCCTCTGCAGCCAGGTG | 426 | 6 | 0 | −19 | 0.005543 | 11 | DRAP1 | DR1-associated protein 1 | 3' | 368 |
| CCACAGACCAGTGGGTG | 427 | 6 | 42 | 2 | 0.037507 | 11 | TPCN2 | two pore segment channel 2 | 3' | 305 |
| CCCCGGCAGGCGGCGGC | 428 | 17 | 89 | 2 | 0.010843 | 11 | ROBO3 | roundabout, axon guidance receptor, homolog 3 | 5' | 64774 |
| CCCCGGCAGGCGGCGGC | 429 | 17 | 89 | 2 | 0.010843 | 11 | FLJ23342 | hypothetical protein FLJ23342 | 5' | 208 |
| GAACAAACCCAGGGATC | 430 | 18 | 11 | −5 | 0.000558 | 12 | KCNA1 | potassium voltage-gated channel, shaker-related | 5' | 1403 |
| TCGGAGTCCCCGTCTCC | 431 | 5 | 56 | 3 | 0.001392 | 12 | ANKRD33 | ankyrin repeat domain 33 | 5' | 73619 |
| AGAACGGGAACCGTCCA | 432 | 29 | 15 | −6 | $6.88 \times 10^{-7}$ | 12 | CENTG1 | centaurin, gamma 1 | 3' | 3647 |
| GCCTGGACGGCCTCGGG | 433 | 2 | 23 | 4 | 0.026376 | 12 | CSRP2 | cysteine and glycine-rich protein 2 | 3' | 185 |
| GTGCGGCGCGGCTCAGC | 434 | 0 | 18 | 18 | 0.022346 | 12 | DIP13B | DIP13 beta | 3' | 6 |
| TTGCAAAGAACGGAGCC | 435 | 0 | 12 | 12 | 0.026152 | 12 | CUTL2 | cut-like 2 | 3' | 265 |
| TTTCAGCGGGAGCCGCC | 436 | 24 | 19 | −4 | 0.000698 | 12 | KIAA1853 | KIAA1853 protein | 5' | 64 |
| CGAACTTCCCGGTTCCG | 437 | 43 | 19 | −7 | $4.00 \times 10^{-11}$ | 12 | Not Found | | | |
| CAGCGGCCAAAGCTGCC | 438 | 32 | 129 | 1 | 0.03085 | 12 | RAN | ras-related nuclear protein | 5' | 257 |

TABLE 5-continued

MSDK tags significantly (p < 0.050) differentially present in N-EPI-I7 and I-EPI-7 MSDK libraries and genes associated with the MSDK tags.

| MSDK Tag | SEQN-ID NO. | I-EPI-I7 | N-EPI-I7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| CAGCGGCCAAAGCTGCC | 439 | 32 | 129 | 1 | 0.03085 | 12 | EPIM | epimorphin isoform 2 | 5' | 32499 |
| GTAGGTGGCGGCGAGCG | 440 | 0 | 22 | 22 | 0.011411 | 13 | USP12 | ubiquitin-specific protease 12-like 1 | 3' | 653 |
| CTGTACATCGGGGCGGC | 441 | 6 | 0 | -19 | 0.016381 | 13 | SOX1 | SRY (sex determining region Y)-box 1 | 5' | 425 |
| GCTGCTGCCCCCAGCCC | 442 | 0 | 19 | 19 | 0.005254 | 14 | KIAA0323 | KIAA0323 | 3' | 158 |
| CGCAGTTCGGAAGGACC | 443 | 0 | 12 | 12 | 0.026152 | 14 | MTHFD1 | methylenetetrahydrofolate dehydrogenase 1 | 5' | 559 |
| CGCAGTTCGGAAGGACC | 444 | 0 | 12 | 12 | 0.026152 | 14 | ESR2 | estrogen receptor 2 | 5' | 93455 |
| CTGAGGCTGCGCCCGCC | 445 | 0 | 12 | 12 | 0.026152 | 14 | GPR68 | G protein-coupled receptor 68 | 5' | 164030 |
| GGGCGGTGCCGCCAGTC | 446 | 3 | 49 | 5 | 0.000941 | 14 | EML1 | echinoderm microtubule associated protein like 1 | 5' | 62907 |
| GCCCCACGCCCCCTGGC | 447 | 9 | 65 | 2 | 0.00516 | 14 | C14orf153 | chromosome 14 open reading frame 153 | 5' | 681 |
| GCCCCACGCCCCCTGGC | 448 | 9 | 65 | 2 | 0.00516 | 14 | BAG5 | BCL2-associated athanogene 5 | 5' | 19 |
| CTCGTGCGAGTCGCGCG | 449 | 0 | 17 | 17 | 0.028576 | 15 | NDNL2 | necdin-like 2 | 5' | 405209 |
| GCCCCGGCCGCCGCGCC | 450 | 4 | 38 | 3 | 0.018724 | 15 | Not Found | | | |
| AGAGCTGAGTCTCACCC | 451 | 5 | 45 | 3 | 0.01099 | 15 | CDAN1 | codanin 1 | 3' | 359 |
| GAGCCTCTTATGGCTCG | 452 | 0 | 12 | 12 | 0.026152 | 15 | RORA | RAR-related orphan receptor A isoform c | 3' | 205 |
| TCAGGCTTCCCCTTCGG | 453 | 15 | 81 | 2 | 0.012835 | 15 | PIAS1 | protein inhibitor of activated STAT, 1 | 5' | 190450 |
| GCCGGGCCCCGCCCTGC | 454 | 0 | 21 | 21 | 0.015063 | 15 | C15orf17 | chromosome 15 open reading frame 17 | 5' | 295 |
| CCTTGAGAGCAGAGAGC | 455 | 6 | 41 | 2 | 0.044419 | 15 | LRRN6A | leucine-rich repeat neuronal 6A | 3' | 43 |
| CTAAGTGGGCAGCACTG | 456 | 0 | 19 | 19 | 0.005254 | 15 | ARNT2 | aryl-hydrocarbon receptor nuclear translocator | 3' | 128 |
| GGCCGGGCTGGCACCGG | 457 | 0 | 19 | 19 | 0.005254 | 16 | TMEM8 | transmembrane protein 8 (five membrane-spanning | 3' | 496 |
| GGTGCAGCTCTGAGGCG | 458 | 0 | 44 | 44 | 0.000342 | 16 | RHOT2 | ras homolog gene family, member T2 | 5' | 119 |
| GAGTGCCCGGCTCGCCC | 459 | 0 | 18 | 18 | 0.022346 | 16 | C1QTNF8 | C1q and tumor necrosis factor related protein 8 | 3' | 5691 |
| CCCGCGGGAGAGACCGG | 460 | 5 | 48 | 3 | 0.006311 | 16 | E4F1 | p120E4F | 5' | 8954 |
| CCCGCGGGAGAGACCGG | 461 | 5 | 48 | 3 | 0.006311 | 16 | MGC21830 | hypothetical protein MGC21830 | 5' | 3623 |

TABLE 5-continued

MSDK tags significantly (p < 0.050) differentially present in N-EPI-I7 and I-EPI-7 MSDK libraries and genes associated with the MSDK tags.

| MSDK Tag | SEQN-ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| CGCAGTGTCCTAGTGCC | 462 | 0 | 24 | 24 | 0.002455 | 16 | CGI-14 | CGI-14 protein | 5' | 89 |
| GAGCTCAGAGCTCCTCC | 463 | 0 | 20 | 20 | 0.00615 | 16 | CGI-14 | CGI-14 protein | 5' | 89 |
| CCTTCCTGCGAACCCCT | 464 | 0 | 13 | 13 | 0.0158 | 16 | MMP25 | matrix metallo-proteinase 25 | 3' | 11905 |
| CGGGCCGGGTCGGCCTC | 465 | 0 | 41 | 41 | 0.000635 | 16 | NUDT16L1 | nudix-type motif 16-like 1 | 5' | 110 |
| GTGGCGCTCGGGGTGCG | 466 | 0 | 13 | 13 | 0.0158 | 16 | PPL | periplakin | 5' | 283 |
| CCGGGTCCGCGGGCGAG | 467 | 14 | 123 | 3 | $5.66 \times 10^{-6}$ | 16 | USP7 | ubiquitin specific protease 7 (herpes | 3' | 725 |
| ATCCGGCCAAGCCCTAG | 468 | 8 | 62 | 2 | 0.004442 | 16 | ATF7IP2 | activating transcription factor 7 interacting | 5' | 244550 |
| ATCCGGCCAAGCCCTAG | 469 | 8 | 62 | 2 | 0.004442 | 16 | GRIN2A | N-methyl-D-aspartate receptor subunit 2A | 5' | 809 |
| GTTAAAAACTTCCAGCC | 470 | 0 | 12 | 12 | 0.026152 | 16 | DNAH3 | dynein, axonemal, heavy polypeptide 3 | 3' | 895 |
| GGGTAGGCACAGCCGTC | 471 | 4 | 61 | 5 | 0.000219 | 16 | TBX6 | T-box 6 isoform 1 | 5' | 85 |
| TGCGCGCGTCGGTGGCG | 472 | 4 | 45 | 3 | 0.004991 | 16 | LOC51333 | mesenchymal stem cell protein DSC43 | 3' | 9832 |
| CGGTGCCCGGGAGGCCC | 473 | 4 | 0 | −13 | 0.029464 | 16 | CHD9 | chromodomain helicase DNA binding protein 9 | 5' | 2004600 |
| CGGTGCCCGGGAGGCCC | 474 | 4 | 0 | −13 | 0.029464 | 16 | SALL1 | sal-like 1 | 5' | 654 |
| GTGCAGTCTCGGCCCGG | 475 | 2 | 43 | 7 | 0.001198 | 16 | FBXL8 | F-box and leucine-rich repeat protein 8 | 3' | 3905 |
| TCCCGCGCCCAGGCCCC | 476 | 9 | 0 | −29 | 0.002372 | 16 | ZCCHC14 | zinc finger, CCHC domain containing 14 | 3' | 143 |
| GCAGCCCCTTGGTGGAG | 477 | 21 | 8 | −8 | $2.32 \times 10^{-6}$ | 16 | TUBB3 | tubulin, beta, 4 | 3' | 843 |
| CCGTGTTGTCCTGGCCG | 478 | 3 | 40 | 4 | 0.00559 | 17 | MNT | MAX binding protein | 3' | 228 |
| CCACACCTCTCTCCAGG | 479 | 0 | 18 | 18 | 0.006642 | 17 | SENP3 | SUMO1/sentrin/SMT3 specific protease 3 | 5' | 326 |
| GGCAACCACTCAGGACG | 480 | 2 | 51 | 8 | 0.000235 | 17 | HCMOGT-1 | sperm antigen HCMOGT-1 | 3' | 69709 |
| CACAGCCAGCCTCCCAG | 213 | 23 | 9 | −8 | $8.64 \times 10^{-7}$ | 17 | LHX1 | LIM homeobox protein 1 | 3' | 3701 |
| CCAAGGAACCTGAAAAC | 482 | 0 | 14 | 14 | 0.017811 | 17 | ACLY | ATP citrate lyase isoform 1 | 3' | 446 |
| GCCCAAAAGGAGAATGA | 483 | 6 | 0 | −19 | 0.016381 | 17 | PHOSPHO1 | phosphatase, orphan 1 | 3' | 5786 |
| CACGCCACCACCCACCC | 484 | 0 | 16 | 16 | 0.010329 | 17 | NXPH3 | neurexophilin 3 | 5' | 318 |
| GAAACCCCTCTGAGCCC | 485 | 0 | 17 | 17 | 0.028576 | 17 | ABC1 | amplified in breast cancer 1 | 3' | 235 |

TABLE 5-continued

MSDK tags significantly (p < 0.050) differentially present in N-EPI-I7 and I-EPI-7 MSDK libraries and genes associated with the MSDK tags.

| MSDK Tag | SEQ-ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| GTGACCAGCCTGGAGAG | 486 | 15 | 14 | −3 | 0.030075 | 17 | SDK2 | sidekick 2 | 5' | 206723 |
| CTGAATGGGGCAAGGAG | 487 | 48 | 40 | −4 | $1.40 \times 10^{-6}$ | 17 | ENPP7 | ectonucleotide pyrophosphatase/ phosphodiesterase | 5' | 628261 |
| CCCCAGGCCGGGTGTCC | 303 | 9 | 58 | 2 | 0.016753 | 17 | CBX8 | chromobox homolog 8 | 5' | 16730 |
| CCCCGACCCCAGGCGGG | 489 | 0 | 19 | 19 | 0.005254 | 18 | RNF152 | ring finger protein 152 | 5' | 1155 |
| TAAACTCTTTTCCTGTT | 490 | 0 | 12 | 12 | 0.026152 | 19 | PIAS4 | protein inhibitor of activated STAT, 4 | 5' | 17748 |
| TAAACTCTTTTCCTGTT | 491 | 0 | 12 | 12 | 0.026152 | 19 | EEF2 | eukaryotic translation elongation factor 2 | 5' | 4554 |
| ACCCTCGCGTGGGCCCC | 492 | 16 | 98 | 2 | 0.001595 | 19 | ZNF136 | zinc finger protein 136 (clone pHZ-20) | 5' | 89 |
| ACCCTCGCGTGGGCCCC | 493 | 16 | 98 | 2 | 0.001595 | 19 | ZNF625 | zinc finger protein 625 | 5' | 6300 |
| TCCGGGGCCCCGCCCCC | 494 | 0 | 13 | 13 | 0.0158 | 19 | KLF1 | Kruppel-like factor 1 (erythroid) | 3' | 1241 |
| CGCCCCGGTGCCCAACG | 495 | 16 | 75 | 1 | 0.048103 | 19 | PKN1 | protein kinase N1 isoform 2 | 5' | 13821 |
| CGCCCCGGTGCCCAACG | 496 | 16 | 75 | 1 | 0.048103 | 19 | DDX39 | DEAD (Asp-Glu-Ala-Asp) box polypeptide 39 | 5' | 173 |
| AGCCTGCAAAGGGGAGG | 497 | 18 | 83 | 1 | 0.039473 | 19 | AKAP8L | A kinase (PRKA) anchor protein 8-like | 5' | 13794 |
| TCCCTGTCCCTGCAATC | 498 | 5 | 0 | −16 | 0.046199 | 19 | SPTBN4 | spectrin, beta, non-erythrocytic 4 | 3' | 52746 |
| CCCGCTCCTTCGGTTCG | 499 | 14 | 73 | 2 | 0.025146 | 19 | ITPKC | inositol 1,4,5-trisphosphate 3-kinase C | 5' | 273 |
| CCCGCTCCTTCGGTTCG | 500 | 14 | 73 | 2 | 0.025146 | 19 | ADCK4 | aarF domain containing kinase 4 | 5' | 134 |
| TTGGGTTCGCTCAGCGG | 501 | 6 | 52 | 3 | 0.006425 | 19 | ASE-1 | CD3-epsilon-associated protein; antisense to | 5' | 1320 |
| TTGGGTTCGCTCAGCGG | 502 | 6 | 52 | 3 | 0.006425 | 19 | PPP1R13L | protein phosphatase 1, regulatory (inhibitor) | 5' | 11721 |
| GCTGCGGCCGGCCGGGG | 503 | 0 | 20 | 20 | 0.01441 | 19 | UBE2S | ubiquitin carrier protein | 5' | 478 |
| GACAGACCCGGTCCCTG | 504 | 0 | 12 | 12 | 0.026152 | 20 | RRBP1 | ribosome binding protein 1 | 3' | 270 |
| CGCTCCCACGTCCGGGA | 505 | 3 | 35 | 4 | 0.01477 | 20 | SNTA1 | acidic alpha 1 syntrophin | 3' | 288 |
| CTTTCAAACTGGACCCG | 506 | 3 | 30 | 3 | 0.038252 | 20 | Not Found | | | |
| GGGGATTCTACCCTGGG | 507 | 20 | 100 | 2 | 0.009572 | 20 | ARFGEF2 | ADP-ribosylation factor guanine | 5' | 93944 |

TABLE 5-continued

MSDK tags significantly (p < 0.050) differentially present in N-EPI-I7 and I-EPI-7 MSDK libraries and genes associated with the MSDK tags.

| MSDK Tag | SEQ ID NO. | I-EPI-I7 | I-EPI-7 | Ratio I-EPI-7/N-EPI-I7 | P value | Chr | Gene | Description | Position of AscI site in relation to tr. Start | Distance of AscI site from tr. Start (bp) |
|---|---|---|---|---|---|---|---|---|---|---|
| GGGGATTCTACCCTGGG | 508 | 20 | 100 | 2 | 0.009572 | 20 | PREX1 | PREX1 protein | 5' | 62 |
| TGTCACAGACTCCCAGC | 509 | 5 | 39 | 2 | 0.032404 | 21 | USP25 | ubiquitin specific protease 25 | 5' | 664846 |
| TGTCACAGACTCCCAGC | 510 | 5 | 39 | 2 | 0.032404 | 21 | NRIP1 | receptor interacting protein 140 | 5' | 96802 |
| TGGGCTGCTGTCGGGGG | 511 | 0 | 14 | 14 | 0.017811 | 21 | CLIC6 | chloride intracellular channel 6 | 3' | 868 |
| CGCGCGCAGCGGGCGCC | 512 | 0 | 13 | 13 | 0.0158 | 22 | EIF3S7 | eukaryotic translation initiation factor 3 | 5' | 51 |
| GCCCTGGGGTGTTATGG | 513 | 0 | 22 | 22 | 0.011411 | 22 | FLJ27365 | FLJ27365 protein | 5' | 13829 |
| GCCCTGGGGTGTTATGG | 514 | 0 | 22 | 22 | 0.011411 | 22 | FLJ10945 | hypothetical protein FLJ10945 | 5' | 18029 |
| CCCCTTCTCAGCTCCGG | 515 | 0 | 12 | 12 | 0.026152 | 22 | TUBGCP6 | tubulin, gamma complex associated protein 6 | 5' | 73 |
| ATTTACACGGGGCTCAC | 516 | 0 | 13 | 13 | 0.0158 | 23 | STAG2 | stromal antigen 2 | 5' | 1402 |

The column headings are as in Table 2 except that the MSDK libraries compared are the N-EPI-I7 and I-EPI-7 libraries (see Table 3 for details of the tissues from which these libraries were made).

Although statistically significant differences were observed, a more similar pattern was observed in the comparison of normal and tumor fibroblast-enriched stroma (Tables 6-8).

TABLE 6

Chromosomal location and analysis of the frequency of MSDK tags in the I-STR-I7 and I-STR-7 MSDK libraries.

| Chr | Virtual Tags | Observed Tags | N-STR-I7 Variety | N-STR-I7 Copies | I-STR-7 Variety | I-STR-7 Copies | Tag Variety Ratio I-STR-7/N-STR-I7 | Tag Copy Ratio I-STR-7/N-STR-I7 | Differential Tag (P < 0.05) I-STR-7 > N-STR-I7 | Differential Tag (P < 0.05) N-STR-I7 > I-STR-7 |
|---|---|---|---|---|---|---|---|---|---|---|
| 1 | 551 | 197 | 55 | 315 | 190 | 1877 | 3.455 | 5.959 | 43 | 0 |
| 2 | 473 | 140 | 47 | 325 | 134 | 1576 | 2.851 | 4.849 | 31 | 0 |
| 3 | 349 | 124 | 38 | 309 | 120 | 1437 | 3.158 | 4.650 | 24 | 0 |
| 4 | 281 | 89 | 28 | 126 | 85 | 788 | 3.036 | 6.254 | 21 | 0 |
| 5 | 334 | 104 | 45 | 274 | 98 | 1170 | 2.178 | 4.270 | 19 | 0 |
| 6 | 338 | 99 | 31 | 138 | 95 | 825 | 3.065 | 5.978 | 16 | 0 |
| 7 | 403 | 134 | 43 | 162 | 131 | 1094 | 3.047 | 6.753 | 28 | 1 |
| 8 | 334 | 111 | 30 | 131 | 107 | 928 | 3.567 | 7.084 | 24 | 0 |
| 9 | 349 | 127 | 36 | 277 | 124 | 1125 | 3.444 | 4.061 | 27 | 0 |
| 10 | 387 | 126 | 39 | 202 | 121 | 1009 | 3.103 | 4.995 | 23 | 0 |
| 11 | 379 | 121 | 40 | 204 | 116 | 870 | 2.900 | 4.265 | 15 | 0 |
| 12 | 299 | 106 | 33 | 179 | 102 | 856 | 3.091 | 4.782 | 17 | 1 |
| 13 | 138 | 43 | 18 | 87 | 39 | 414 | 2.167 | 4.759 | 5 | 0 |
| 14 | 228 | 67 | 24 | 129 | 65 | 585 | 2.708 | 4.535 | 10 | 0 |
| 15 | 260 | 80 | 22 | 102 | 77 | 552 | 3.500 | 5.412 | 11 | 0 |
| 16 | 340 | 113 | 40 | 189 | 104 | 802 | 2.600 | 4.243 | 15 | 1 |
| 17 | 400 | 160 | 50 | 385 | 152 | 1550 | 3.040 | 4.026 | 27 | 0 |
| 18 | 181 | 54 | 18 | 101 | 49 | 417 | 2.722 | 4.129 | 6 | 0 |
| 19 | 463 | 148 | 44 | 193 | 141 | 1053 | 3.205 | 5.456 | 24 | 1 |
| 20 | 236 | 71 | 18 | 132 | 69 | 771 | 3.833 | 5.841 | 19 | 0 |
| 21 | 71 | 21 | 9 | 35 | 20 | 187 | 2.222 | 5.343 | 4 | 0 |
| 22 | 217 | 68 | 20 | 165 | 67 | 630 | 3.350 | 3.818 | 7 | 0 |

TABLE 6-continued

Chromosomal location and analysis of the frequency of MSDK tags in the I-STR-I7 and I-STR-7 MSDK libraries.

| Chr | Virtual Tags | Observed Tags | N-STR-I7 Variety | N-STR-I7 Copies | I-STR-7 Variety | I-STR-7 Copies | Tag Variety Ratio I-STR-7/N-STR-I7 | Tag Copy Ratio I-STR-7/N-STR-I7 | Differential Tag (P ≤ 0.05) I-STR-7 > N-STR-I7 | Differential Tag (P ≤ 0.05) N-STR-I7 > I-STR-7 |
|---|---|---|---|---|---|---|---|---|---|---|
| X | 185 | 51 | 19 | 75 | 47 | 408 | 2.474 | 5.440 | 12 | 1 |
| Y | 9 | | | | | | | | | |
| Matches | 7205 | 2354 | 747 | 4235 | 2253 | 20924 | 3.016 | 4.941 | 428 | 5 |
| No Matches | | 3343 | 2771 | 14479 | 796 | 7166 | 0.287 | 0.495 | 62 | 397 |
| Total | 7205 | 5697 | 3518 | 18714 | 3049 | 28090 | 0.867 | 1.501 | 490 | 402 |

The column headings are as indicated for Table 1.

TABLE 7

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| AGTCCCCAGGGCTGGCA | 517 | 9 | 30 | 2 | 0.03582 | 1 | HES5 | hairy and enhancer of split 5 | 5' | 16528 |
| ATTAACCTTTGAAGCCC | 518 | 0 | 17 | 17 | 0.00238 | 1 | SHREW1 | transmembrane protein SHREW1 | 3' | 687 |
| GGGCTGCCTCGCCGGGC | 519 | 11 | 34 | 2 | 0.03524 | 1 | ESPN | espin | 5' | 5344 |
| GGGCTGCCTCGCCGGGC | 520 | 11 | 34 | 2 | 0.03524 | 1 | RP1-120G22.10 | brain acyl-CoA hydrolase isoform hBACHa/X | 5' | 25682 |
| GAAATGCTAAGGGGTTG | 521 | 4 | 37 | 6 | $7.3 \times 10^{-5}$ | 1 | PIK3CD | phosphoinositide-3-kinase, catalytic, delta | 5' | 39 |
| TAAATTCCACTGAAAAT | 522 | 0 | 7 | 7 | 0.01683 | 1 | PAX7 | paired box gene 7 isoform 1 | 3' | 9827 |
| GTGCCGCCGCGGGCGCC | 523 | 4 | 31 | 5 | 0.00032 | 1 | KIAA0478 | KIAA0478 gene product | 5' | 308006 |
| GTGCCGCCGCGGGCGCC | 524 | 4 | 31 | 5 | 0.00032 | 1 | WNT4 | wingless-type MMTV integration site family, | 5' | 733 |
| AAAATGTTCTCAAACCC | 525 | 0 | 11 | 11 | 0.00359 | 1 | ARID1A | AT rich interactive domain 1A (SWI- like) | 5' | 75135 |
| AGCACCCGCCTGGAACC | 526 | 6 | 21 | 2 | 0.03859 | 1 | PTPRF | protein tyrosine phosphatase, receptor type, F | 3' | 727 |
| GCTCACCTACCCAGGTG | 527 | 3 | 44 | 10 | $2 \times 10^{-6}$ | 1 | Not Found | | | |
| GCAGGTAGACCAGGCCT | 528 | 2 | 15 | 5 | 0.01234 | 1 | GLIS1 | GLIS family zinc finger 1 | 5' | 4943 |
| CAGCTTTTGAAATCAGG | 529 | 8 | 34 | 3 | 0.00589 | 1 | KIAA1579 | hypothetical protein FLJ10770 | 5' | 196 |
| GCCTCTCTGCGCCTGCC | 530 | 8 | 28 | 2 | 0.03562 | 1 | GFI1 | growth factor independent 1 | 3' | 4842 |
| CGCAGAATCCCGGAGGC | 531 | 0 | 8 | 8 | 0.01239 | 1 | EVI5 | ecotropic viral integration site 5 | 3' | 7704 |
| CCCGGACTTGGCCAGGC | 532 | 34 | 120 | 2 | $1 \times 10^{-6}$ | 1 | NHLH2 | nescient helix loop helix 2 | 3' | 2971 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| AGCGCTTGGCGCTCCCA | 533 | 3 | 18 | 4 | 0.00867 | 1 | NPR1 | natriuretic peptide receptor A/guanylate cyclase | 3' | 677 |
| GCCCAACCCCGGGGAGT | 534 | 3 | 21 | 5 | 0.0037 | 1 | P66beta | transcription repressor p66 beta component of | 5' | 117605 |
| TCTGGGGCCGGGTAGCC | 535 | 15 | 54 | 2 | 0.00125 | 1 | P66beta | transcription repressor p66 beta component of | 5' | 117605 |
| CGTGTGTATCTGGGGGT | 536 | 3 | 17 | 4 | 0.01446 | 1 | MUC1 | mucin 1, transmembrane | 3' | 188528 |
| GCAGCGGCGCTCCGGGC | 537 | 4 | 54 | 9 | 0 | 1 | MUC1 | mucin 1, transmembrane | 3' | 139119 |
| GATCCTCGCCCGCGCCT | 538 | 0 | 20 | 20 | 0.00085 | 1 | EFNA4 | ephrin A4 isoform a | 3' | 365 |
| CCGGTTTCCCAGCGCCC | 539 | 0 | 9 | 9 | 0.00623 | 1 | MUC1 | mucin 1, transmembrane | 3' | 111426 |
| CTGCTCGGGGACCCCC | 540 | 0 | 9 | 9 | 0.00623 | 1 | MTX1 | metaxin 1 isoform 1 | 3' | 304 |
| GGCGCCGCCATCTTGCC | 541 | 0 | 9 | 9 | 0.00623 | 1 | MTX1 | metaxin 1 isoform 1 | 3' | 304 |
| CCAGGGCCTGGCACTGC | 542 | 13 | 101 | 5 | 0 | 1 | IGSF9 | immunoglobulin superfamily, member 9 | 5' | 393 |
| TTCGGGCCGGGCCGGGA | 543 | 21 | 68 | 2 | 0.00073 | 1 | LMX1A | LIM homeobox transcription factor 1, alpha | 5' | 752 |
| AGCCCTCGGGTGATGAG | 29 | 13 | 56 | 3 | 0.00019 | 1 | LMX1A | LIM homeobox transcription factor 1, alpha | 5' | 752 |
| GAGGGGGGCAAAACTAC | 545 | 0 | 12 | 12 | 0.00296 | 1 | SCYL3 | SCY1-like 3 isoform 1 | 3' | 561 |
| CTTATGTTTACAGCATC | 546 | 2 | 15 | 5 | 0.01234 | 1 | PAPPA2 | pappalysin 2 isoform 2 | 5' | 255915 |
| CTTATGTTTACAGCATC | 547 | 2 | 15 | 5 | 0.01234 | 1 | RFWD2 | ring finger and WD repeat domain 2 isoform a | 5' | 21 |
| TATTTGGTGCTGCCACA | 548 | 0 | 7 | 7 | 0.01683 | 1 | LHX4 | LIM homeobox protein 4 | 3' | 5084 |
| TCTCCTTGCTCGCTCCG | 549 | 0 | 13 | 13 | 0.00244 | 1 | XPR1 | xenotropic and polytropic retrovirus receptor | 5' | 128896 |
| TCTCCTTGCTCGCTCCG | 550 | 0 | 13 | 13 | 0.00244 | 1 | ACBD6 | acyl-Coenzyme A binding domain containing 6 | 5' | 797 |
| GTTCTCAAACAGCTTTC | 551 | 0 | 16 | 16 | 0.0031 | 1 | IPO9 | importin 9 | 3' | 343 |
| TCCAGGCAGGGCCTCTG | 552 | 11 | 54 | 3 | $8.4 \times 10^{-5}$ | 1 | BTG2 | B-cell translocation gene 2 | 3' | 431 |
| TCAGATAGTTCTCCAGC | 553 | 0 | 8 | 8 | 0.01239 | 1 | NFASC | neurofascin isoform 4 | 5' | 19 |
| TCAGATAGTTCTCCAGC | 554 | 0 | 8 | 8 | 0.01239 | 1 | LRRN5 | leucine rich repeat neuronal 5 precursor | 5' | 143165 |
| ACGTTTTTAACTACACA | 555 | 0 | 20 | 20 | 0.00024 | 1 | ELK4 | ELK4 protein isoform a | 3' | 621 |
| CTGTCCAACTCCCAGGG | 556 | 0 | 16 | 16 | 0.00081 | 1 | MAPKAPK2 | mitogen-activated protein kinase-activated | 3' | 1117 |
| TGGATTTGGTCGTCTCC | 557 | 0 | 8 | 8 | 0.01239 | 1 | PLXNA2 | plexin A2 | 3' | 428 |
| GCCCCGTGGCGCCCCG | 558 | 16 | 57 | 2 | 0.00095 | 1 | CENPF | centromere protein F (350/400 kD) | 5' | 51300 |
| GCCCCGTGGCGCCCCG | 559 | 16 | 57 | 2 | 0.00095 | 1 | PTPN14 | protein tyrosine phosphatase, non-receptor type | 5' | 589 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| CCACACCAGGATTCGAG | 560 | 0 | 7 | 7 | 0.01683 | 1 | HSPC163 | HSPC163 protein | 3' | 375 |
| GTGAACTTCCAAGATGC | 561 | 7 | 26 | 2 | 0.01495 | 1 | CNIH3 | comichon homolog 3 | 3' | 50 |
| GCTAGGGAAAAACAGGC | 562 | 2 | 32 | 11 | $5.5 \times 10^{-5}$ | 1 | MGC42493 | hypothetical protein MGC42493 | 5' | 244931 |
| GCTAGGGAAAAACAGGC | 563 | 2 | 32 | 11 | $5.5 \times 10^{-5}$ | 1 | CDC42BPA | CDC42-binding protein kinase alpha isoform A | 5' | 486 |
| GACGCGCTCCCGCGGGC | 564 | 0 | 16 | 16 | 0.00081 | 1 | WNT3A | wingless-type MMTV integration site family | 5' | 59111 |
| GACGCGCTCCCGCGGGC | 565 | 0 | 16 | 16 | 0.00081 | 1 | WNT9A | wingless-type MMTV integration site family | 5' | 41 |
| GAGCGGCCGCCCAGAGC | 566 | 7 | 39 | 4 | 0.00054 | 1 | TAF5L | PCAF associated factor 65 beta | 3' | 192 |
| ATGCGCCCCGCAGCCCC | 567 | 16 | 76 | 3 | $3 \times 10^{-6}$ | 1 | MGC13186 | hypothetical protein MGC13186 | 5' | 321138 |
| ATGCGCCCCGCAGCCCC | 568 | 16 | 76 | 3 | $3 \times 10^{-6}$ | 1 | SIPA1L2 | signal-induced proliferation-associated 1 like | 5' | 114742 |
| CTCTCACCCGAGGAGCG | 569 | 0 | 10 | 10 | 0.00467 | 2 | OACT2 | O-acyltransferase (membrane bound) domain | 3' | 47 |
| GTTCCTGCTCTCCACGA | 570 | 3 | 19 | 4 | 0.00645 | 2 | KLF11 | Kruppel-like factor 11 | 3' | 387 |
| GTCCCCGCGCCGCGGCC | 571 | 29 | 67 | 2 | 0.03072 | 2 | UBXD4 | UBX domain containing 4 | 5' | 553390 |
| GTCCCCGCGCCGCGGCC | 572 | 29 | 67 | 2 | 0.03072 | 2 | APOB | apolipoprotein B precursor | 5' | 2343039 |
| CTTTTGTCCCTTTTGTC | 573 | 0 | 23 | 23 | 0.00028 | 2 | ADCY3 | adenylate cyclase 3 | 5' | 619 |
| GCCACCCAAGCCCGTCG | 574 | 0 | 9 | 9 | 0.00623 | 2 | RAB10 | ras-related GTP-binding protein RAB10 | 5' | 106 |
| GCCACCCAAGCCCGTCG | 575 | 0 | 9 | 9 | 0.00623 | 2 | KIF3C | kinesin family member 3C | 5' | 51464 |
| ACCTTAGGCCCTTCTCT | 576 | 0 | 11 | 11 | 0.00359 | 2 | FOSL2 | FOS-like antigen 2 | 5' | 2425 |
| ATGCGAGGGGCGCGGTA | 577 | 18 | 80 | 3 | $3 \times 10^{-6}$ | 2 | FLJ32954 | hypothetical protein FLJ32954 | 5' | 277913 |
| ATGCGAGGGGCGCGGTA | 578 | 18 | 80 | 3 | $3 \times 10^{-6}$ | 2 | CDC42EP3 | Cdc42 effector protein 3 | 5' | 366 |
| GATTCTGTCTATGCTTC | 579 | 2 | 21 | 7 | 0.00133 | 2 | THUMPD2 | THUMP domain containing 2 | 5' | 16 |
| GCAGCATTGCGGCTCCG | 580 | 19 | 157 | 6 | 0 | 2 | SIX2 | sine oculis homeobox homolog 2 | 5' | 160394 |
| CACACAAGGCGCCCGCG | 581 | 6 | 29 | 3 | 0.00299 | 2 | SIX2 | sine oculis homeobox homolog 2 | 5' | 160394 |
| TCATTGCATACTGAAGG | 582 | 2 | 18 | 6 | 0.00391 | 2 | SLC1A4 | solute carrier family 1, member 4 | 5' | 335302 |
| TCATTGCATACTGAAGG | 583 | 2 | 18 | 6 | 0.00391 | 2 | SERTAD2 | SERTA domain containing 2 | 5' | 245 |
| CTGGAGCTCAGCACTGA | 584 | 0 | 12 | 12 | 0.00296 | 2 | Not Found | | | |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| TTCACCCCCACCCACTC | 585 | 0 | 15 | 15 | 0.00413 | 2 | Not Found | | | |
| CCCCAGCTCGGCGGCGG | 586 | 63 | 195 | 2 | 0 | 2 | TCF7L1 | HMG-box transcription factor TCF-3 | 3' | 859 |
| AGGGCAATCCAGCCCTC | 587 | 0 | 13 | 13 | 0.00923 | 2 | LOC51315 | hypothetical protein LOC51315 | 3' | 197 |
| AAGCAGTCTTCGAGGGG | 588 | 7 | 61 | 6 | 0 | 2 | CNNM3 | cyclin M3 isoform 1 | 5' | 396 |
| CGGTGGGGTAGGCGGTC | 589 | 0 | 13 | 13 | 0.00923 | 2 | SEMA4C | semaphorin 4C | 3' | 336 |
| AGAGTGACGTGCTGTGG | 590 | 0 | 12 | 12 | 0.00296 | 2 | MERTK | c-mer proto-oncogene tyrosine kinase | 3' | 281 |
| CACCAAACCTAGAAGGC | 591 | 4 | 24 | 4 | 0.00251 | 2 | GLI2 | GLI-Kruppel family member GLI2 isoform alpha | 5' | 56228 |
| CACCAAACCTAGAAGGC | 591 | 4 | 24 | 4 | 0.00251 | 2 | FLJ14816 | hypothetical protein FLJ14816 | 5' | 269933 |
| TCCCCATTTCACCAAGG | 593 | 0 | 7 | 7 | 0.01683 | 2 | PTPN18 | protein tyrosine phosphatase, non-receptor type | 3' | 187 |
| GGCGAGGGGCCTCTGG | 594 | 2 | 13 | 4 | 0.02369 | 2 | FLJ38377 | hypothetical protein FLJ38377 | 3' | 593 |
| AGACCATCCTTGGACCC | 595 | 3 | 41 | 9 | $6 \times 10^{-6}$ | 2 | B3GALT1 | UDP-Gal: betaGlcNAc beta | 5' | 524869 |
| GGCGCCAGAGGAAGATC | 596 | 8 | 30 | 2 | 0.01991 | 2 | SSB | autoantigen La | 5' | 29950 |
| TGTAAGGCGGCGGGAG | 597 | 18 | 55 | 2 | 0.00496 | 2 | SP3 | Sp3 transcription factor | 3' | 1637 |
| AAATTCCATAGACAACC | 598 | 0 | 14 | 14 | 0.00122 | 2 | HOXD4 | homeo box D4 | 3' | 1141 |
| ATGGTGTCGCTGGACAG | 599 | 0 | 14 | 14 | 0.00122 | 2 | ARPC2 | actin related protein 2/3 complex subunit 2 | 5' | 94 |
| ATGGTGTCGCTGGACAG | 600 | 0 | 14 | 14 | 0.00122 | 2 | IL8RA | interleukin 8 receptor alpha | 5' | 50063 |
| TCACATTTCAGTTTGGG | 601 | 4 | 24 | 4 | 0.00251 | 2 | COL4A4 | alpha 4 type IV collagen precursor | 3' | 339 |
| ACTGCATCCGGCCTCGG | 602 | 10 | 48 | 3 | 0.00028 | 2 | PTMA | prothymosin, alpha (gene sequence 28) | 5' | 93674 |
| CACCCGCGGTGCCGGGC | 603 | 13 | 40 | 2 | 0.02012 | 2 | PTMA | prothymosin, alpha (gene sequence 28) | 3' | 2352 |
| GGGTCTTCATCTGATCC | 604 | 6 | 25 | 3 | 0.01087 | 2 | FLJ43879 | FLJ43879 protein | 5' | 109293 |
| GGGTGGGGGTGCAGGC | 605 | 0 | 17 | 17 | 0.00068 | 2 | FLJ22671 | hypothetical protein FLJ22671 | 5' | 144084 |
| CAGCCGACTCTCTGGCT | 606 | 0 | 35 | 35 | $1 \times 10^{-6}$ | 3 | DTYMK | deoxythymidylate kinase (thymidylate kinase) | 5' | 2784474 |
| CCTAGCATCTCCTCTTG | 607 | 0 | 7 | 7 | 0.01683 | 3 | GRM7 | glutamate receptor, metabotropic 7 isoform b | 5' | 70 |
| CTATACTGGCTCGTCCT | 608 | 0 | 13 | 13 | 0.00244 | 3 | SLC6A11 | solute carrier family 6 (neurotransmitter | 5' | 108592 |
| CTATACTGGCTCGTCCT | 609 | 0 | 13 | 13 | 0.00244 | 3 | ATP2B2 | plasma membrane calcium ATPase 2 isoform b | 5' | 257778 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| GAGGACTGGGGGCTGGG | 610 | 0 | 10 | 10 | 0.03148 | 3 | HRH1 | histamine receptor H1 | 5' | 98409 |
| GGAGGCAAACGGGAACC | 611 | 5 | 19 | 3 | 0.03849 | 3 | IQSEC1 | IQ motif and Sec7 domain 1 | 5' | 315433 |
| CCCGACGGGCGGCGCGG | 612 | 0 | 7 | 7 | 0.01683 | 3 | DLEC1 | deleted in lung and eso-phageal cancer 1 isoform | 5' | 9380 |
| CCCGACGGGCGGCGCGG | 613 | 0 | 7 | 7 | 0.01683 | 3 | PLCD1 | phospholipase C, delta 1 | 5' | 200 |
| GATCGCTGGGGTTTTGG | 614 | 5 | 38 | 5 | 0.00013 | 3 | DLEC1 | deleted in lung and eso-phageal cancer 1 isoform | 5' | 9380 |
| GATCGCTGGGGTTTTGG | 615 | 5 | 38 | 5 | 0.00013 | 3 | PLCD1 | phospholipase C, delta 1 | 5' | 200 |
| CGGCGCGTCCCTGCCGG | 616 | 61 | 140 | 2 | 0.00079 | 3 | DKFZp313N0621 | hypothetical protein DKFZp313N0621 | 5' | 339665 |
| CCACTTCCCCATTGGTC | 617 | 37 | 132 | 2 | 0 | 3 | ARMET | arginine-rich, mutated in early stage tumors | 5' | 633 |
| CACACCCCGCCCCAGC | 618 | 24 | 74 | 2 | 0.00071 | 3 | ACTR8 | actin-related protein 8 | 3' | 338 |
| AACCCCGAAACTGGAAG | 619 | 2 | 19 | 6 | 0.00296 | 3 | FAM19A4 | family with sequence similarity 19 (chemokine) | 5' | 143 |
| GAAGAGTCCCAGCCGGT | 620 | 0 | 52 | 52 | 0 | 3 | MDS010 | x 010 protein | 5' | 5211 |
| GAAGAGTCCCAGCCGGT | 621 | 0 | 52 | 52 | 0 | 3 | TMEM39A | tranamembrane protein 39A | 5' | 116 |
| CAACCCCAACCGCGTTC | 622 | 7 | 56 | 5 | $1 \times 10^{-6}$ | 3 | MUC13 | mucin 13, epithelial transmembrane | 5' | 120784 |
| CCTGCCTCTGGCAGGGG | 623 | 16 | 100 | 4 | 0 | 3 | PLXNA1 | plexin A1 | 5' | 5386 |
| GCGTTGGGCACCCCTGC | 624 | 0 | 7 | 7 | 0.01683 | 3 | Not Found | | | |
| GCCTAGAAGAAGCCGAA | 625 | 8 | 50 | 4 | $2.9 \times 10^{-5}$ | 3 | RAB43 | RAB41 protein | 5' | 577 |
| GGGCCGAGTCCGGCAGC | 626 | 6 | 32 | 4 | 0.00258 | 3 | CHST2 | carbohydrate (N-acetylglucosamine-6-O) | 3' | 61 |
| GAAAGGGCAGTCCCGCC | 627 | 0 | 18 | 18 | 0.00185 | 3 | ZIC1 | zinc finger protein of the cerebellum 1 | 5' | 155 |
| GAAAGGGCAGTCCCGCC | 628 | 0 | 18 | 18 | 0.00185 | 3 | ZIC4 | zinc finger protein of the cerebellum 4 | 5' | 2618 |
| CTCGGTGGCGGGACCGG | 629 | 8 | 26 | 2 | 0.02912 | 3 | SCHIP1 | schwannomin interacting protein 1 | 3' | 490368 |
| GCCGGGCCGGTGACTCC | 630 | 2 | 41 | 14 | $2 \times 10^{-6}$ | 3 | FLJ22595 | hypothetical protein FLJ22595 | 5' | 111198 |
| GCCGGGCCGGTGACTCC | 631 | 2 | 41 | 14 | $2 \times 10^{-6}$ | 3 | KPNA4 | karyopherin alpha 4 | 5' | 372 |
| CCCAGAGACTTTATCCT | 632 | 0 | 9 | 9 | 0.00623 | 3 | FNDC3B | fibronectin type III domain containing 3B | 5' | 856 |
| CCCAGAGACTTTATCCT | 633 | 0 | 9 | 9 | 0.00623 | 3 | PLD1 | phospholipase D1, phophatidylcholine-specific | 5' | 301657 |
| CGTGTGAGCTCTCCTGC | 634 | 15 | 105 | 5 | 0 | 3 | EPHB3 | ephrin receptor EphB3 precursor | 3' | 576 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| TCTCAACACGCTAGGCA | 635 | 3 | 22 | 5 | 0.00215 | 3 | Not Found | | | |
| GGTACCTGCATCCTCTC | 636 | 0 | 10 | 10 | 0.03148 | 3 | HES1 | hairy and enhancer of split 1 | 5' | 1004 |
| GGAAGCGCCCTGCCCTC | 637 | 0 | 18 | 18 | 0.00035 | 4 | Not Found | | | |
| CACTTCCCAGCTCTGAG | 638 | 2 | 17 | 6 | 0.0052 | 4 | FGFR3 | fibroblast growth factor receptor 3 isoform 1 | 5' | 26779 |
| CACCTCTGCCGTGCTGC | 639 | 0 | 45 | 45 | 0 | 4 | RNF4 | ring finger protein 4 | 5' | 176 |
| CACCTCTGCCGTGCTGC | 640 | 0 | 45 | 45 | 0 | 4 | ZFYVE28 | zinc finger, FYVE domain containing 28 | 5' | 50261 |
| GGGCGGTGGCGGGGACG | 641 | 0 | 12 | 12 | 0.00296 | 4 | RGS12 | regulator of G-protein signalling 12 isoform 2 | 5' | 21007 |
| GCTCTGGGCGCCCTTTC | 642 | 7 | 52 | 5 | $6 \times 10^{-6}$ | 4 | RGS12 | regulator of G-protein signalling 12 isoform 2 | 5' | 21007 |
| CCTGCGCCGGGGAGGC | 643 | 39 | 119 | 2 | $1.1 \times 10^{-5}$ | 4 | ADRA2C | alpha-2C-adrenergic receptor | 3' | 432 |
| TACAATGAAGGGGTCAG | 644 | 4 | 22 | 4 | 0.00554 | 4 | STK32B | serine/threonine kinase 32B | 5' | 28 |
| TACAATGAAGGGGTCAG | 645 | 4 | 22 | 4 | 0.00554 | 4 | CYTL1 | cytokine-like 1 | 5' | 32301 |
| GCATTGATTGCTGTCCC | 646 | 0 | 9 | 9 | 0.00623 | 4 | MAIN2B2 | mannosidase, alpha, class 2B, member 2 | 5' | 11294 |
| GCATTGATTGCTGTCCC | 647 | 0 | 9 | 9 | 0.00623 | 4 | PPP2R2C | gamma isoform of regulatory subunit B55, protein | 5' | 91597 |
| GTCCGTGGAATAGAAGG | 648 | 0 | 18 | 18 | 0.00185 | 4 | Not Found | | | |
| ACGCCGGCGCCGCTCGC | 649 | 0 | 7 | 7 | 0.01683 | 4 | FLJ13197 | hypothetical protein FLJ13197 | 3' | 1219 |
| AAAGCACAGGCTCTCCC | 650 | 2 | 14 | 5 | 0.0165 | 4 | SLC4A4 | solute carrier family 4, sodium bicarbonate | 5' | 151833 |
| CCGCGGATCTCGCCGGT | 651 | 5 | 24 | 3 | 0.00765 | 4 | ASAHL | N-acylsphingosine amidohydrolase-like protein | 3' | 67 |
| AGCCACCTGCGCCTGGC | 652 | 12 | 52 | 3 | 0.00033 | 4 | PAQR3 | progestin and adipoQ receptor family member III | 5' | 101 |
| CAAGGGTTCACATATGC | 653 | 0 | 8 | 8 | 0.01239 | 4 | WDFY3 | WD repeat and FYVE domain containing 3 isoform | 3' | 249 |
| CGCTTCGGGGTGCATCT | 654 | 0 | 12 | 12 | 0.00296 | 4 | PDHA2 | pyruvate dehydrogenase (lipoamide) alpha 2 | 5' | 290397 |
| CGCTTCGGGGTGCATCT | 655 | 0 | 12 | 12 | 0.00296 | 4 | UNC5C | unc5C | 5' | 683 |
| CCGGGCAGCCTCAGAGG | 656 | 2 | 15 | 5 | 0.01234 | 4 | FABP2 | intestinal fatty acid binding protein 2 | 5' | 132509 |
| GCTGTCCGCACGCGGCC | 657 | 0 | 10 | 10 | 0.03148 | 4 | SMAD1 | Sma- and Mad-related protein 1 | 5' | 301087 |
| GCTGTCCGCACGCGGCC | 658 | 0 | 10 | 10 | 0.03148 | 4 | HSHIN1 | HIV-1 induced protein HIN-1 isoform 1 | 5' | 5967 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| TGCACGCACACTCTTCC | 659 | 3 | 15 | 3 | 0.0273 | 4 | LOC152485 | hypothetical protein LOC152485 | 3' | 851 |
| GTGGGGAGGCTGGGGCG | 660 | 3 | 20 | 4 | 0.00474 | 4 | DCAMKL2 | doublecortin and CaM kinase-like 2 | 5' | 1633428 |
| GTGGGGAGGCTGGGGCG | 661 | 3 | 20 | 4 | 0.00474 | 4 | NR3C2 | nuclear receptor sub-family 3, group C, member 2 | 5' | 3189 |
| TTTTTCATCTTCCCCCC | 662 | 2 | 20 | 7 | 0.0023 | 4 | GLRB | glycine receptor, beta | 5' | 64 |
| TTTTTCATCTTCCCCCC | 663 | 2 | 20 | 7 | 0.0023 | 4 | PDGFC | platelet-derived growth factor C precursor | 5' | 104727 |
| CTTAGATCTAGCGTTCC | 664 | 3 | 28 | 6 | 0.00034 | 4 | DKFZP564J102 | DKFZP564J102 protein | 5' | 4 |
| TAACGCTCCCGGGCCTC | 665 | 4 | 27 | 4 | 0.00113 | 5 | Not Found | | | |
| TCTGCACGCCGGGGTCT | 666 | 7 | 24 | 2 | 0.02576 | 5 | POLS | polymerase (DNA directed) sigma | 5' | 23056 |
| GGAGGTCTCAGGATCCC | 667 | 7 | 24 | 2 | 0.02576 | 5 | FLJ20152 | hypothetical protein FLJ20152 | 5' | 108193 |
| CCCACTTTCAAAGGGGG | 668 | 40 | 97 | 2 | 0.00318 | 5 | FST | follistatin isoform FST344 precursor | 5' | 517 |
| CCCACTTTCAAAGGGGG | 669 | 40 | 97 | 2 | 0.00318 | 5 | MOCS2 | molybdopterin sypthase large subunit MOCS2B | 5' | 370479 |
| ACCCGGGCCGCAGCGGC | 670 | 20 | 95 | 3 | 0 | 5 | EFNA5 | ephrin-A5 | 3' | 1019 |
| CTGGGTTGCGATTAGCT | 671 | 0 | 19 | 19 | 0.00146 | 5 | PPIC | peptidylprolyl isomerase C | 5' | 62181 |
| ACACATTTATTTTTCAG | 672 | 0 | 14 | 14 | 0.00122 | 5 | KIAA1961 | KIAA1961 protein isoform 1 | 3' | 146 |
| GTGGGAGTCAAAGAGCT | 673 | 10 | 55 | 4 | $2.8 \times 10^{-5}$ | 5 | APXL2 | apical protein 2 | 5' | 4006 |
| CCGCTGGTGCACTCCGG | 674 | 13 | 37 | 2 | 0.04341 | 5 | TCF7 | transcription factor 7 (T-cell specific | 3' | 252 |
| GTTTCTTCCCGCCCATC | 675 | 0 | 25 | 25 | 0.00012 | 5 | PHF15 | PHD finger protein 15 | 3' | 1577 |
| TCGCCGGGCGCTTGCCC | 90 | 16 | 76 | 3 | $3 \times 10^{-6}$ | 5 | PITX1 | paired-like homeodomain transcription factor 1 | 3' | 6163 |
| CTGACCGCGCTCGCCCC | 91 | 8 | 28 | 2 | 0.03562 | 5 | PACAP | proapoptotic caspase adaptor protein | 5' | 4496 |
| CCAGAGGGTCTTAAGTG | 678 | 6 | 33 | 4 | 0.00184 | 5 | NR3C1 | nuclear receptor sub-family 3, group C, member 1 | 3' | 553 |
| ACCCACCAACACACGCC | 679 | 4 | 21 | 3 | 0.00732 | 5 | RANBP17 | RAN binding protein 17 | 3' | 402 |
| CGTCTCCCATCCCGGGC | 680 | 0 | 24 | 24 | 0.00007 | 5 | CPLX2 | complexin 2 | 3' | 1498 |
| GCAGCAGCCTGTAATCC | 681 | 0 | 11 | 11 | 0.00359 | 5 | ZNF346 | zinc finger rotein 346 | 3' | 167 |
| GCCTGGCTTCCCCCCAG | 682 | 21 | 135 | 4 | 0 | 5 | PRR7 | proline rich 7 (synaptic) | 3' | 7903 |
| CGCCAGAGCTCTTTGTG | 683 | 10 | 38 | 3 | 0.00645 | 5 | HNRPH1 | heterogeneous nuclear ribonucleoprotein H1 | 3' | 442 |
| GTTTCACGTCTCTGAGT | 684 | 0 | 8 | 8 | 0.01239 | 5 | BTNL9 | butyrophilin-like 9 | 3' | 12750 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| CTTTAGGTCGCAGGACA | 685 | 0 | 14 | 14 | 0.00122 | 6 | FOXF2 | forkhead box F2 | 5' | 6373 |
| TCAATGCTCCGGCGGGG | 686 | 4 | 65 | 11 | 0 | 6 | TFAP2A | transcription factor AP-2 alpha | 5' | 4264 |
| GGTCTCCGAAGCGAGCG | 687 | 9 | 47 | 3 | 0.00018 | 6 | MDGA1 | MAM domain containing | 3' | 934 |
| GTGAAAGCATACCGTCA | 688 | 0 | 8 | 8 | 0.01239 | 6 | TFEB | transcription factor EB | 3' | 726 |
| GCTCTCACACAATAGGA | 689 | 0 | 8 | 8 | 0.01239 | 6 | DSCR1L1 | Down syndrome critical region gene 1-like 1 | 5' | 165679 |
| AAGGAGACCGCACAGGG | 690 | 7 | 45 | 4 | $6.9 \times 10^{-5}$ | 6 | HTR1E | 5-hydroxytryptamine (serotonin) receptor 1E | 5' | 97 |
| AAGGAGACCGCACAGGG | 691 | 7 | 45 | 4 | $6.9 \times 10^{-5}$ | 6 | SYNCRIP | synaptotagmin binding, cytoplasmic RNA | 5' | 1294285 |
| GTTGGAAATGGTGCGAA | 692 | 0 | 10 | 10 | 0.00467 | 6 | MAP3K7 | mitogen-activated protein kinase kinase kinase 7 | 5' | 24225 |
| ATTGTCAGATCTGGAAT | 693 | 2 | 12 | 4 | 0.03293 | 6 | MAP3K7 | mitogen-activated protein kinase kinase kinase 7 | 5' | 24225 |
| TCCATAGATTGACAAAG | 694 | 2 | 20 | 7 | 0.0023 | 6 | MARCKS | myristoylated alanine-rich protein kinase C | 3' | 3067 |
| TACAAGGCACTATGCTG | 695 | 0 | 20 | 20 | 0.00085 | 6 | MCMDC1 | minichromosome maintenance protein domain | 3' | 518 |
| GAGAACGGCTCGGGCGC | 696 | 4 | 42 | 7 | $1.1 \times 10^{-5}$ | 6 | IBRDC1 | IBR domain containing 1 | 5' | 21103 |
| GTTATGGCCAGAACTTG | 697 | 3 | 47 | 10 | $1 \times 10^{-6}$ | 6 | MOXD1 | monooxygenase, DBH-like 1 | 5' | 26536 |
| AACTTGAGAGCGATTTC | 698 | 0 | 13 | 13 | 0.00244 | 6 | RAB32 | RAB32, member RAS oncogene family | 3' | 160 |
| GCAGTGTTCTGCTTGGC | 699 | 2 | 23 | 8 | 0.00081 | 6 | SYNJ2 | synaptojanin 2 | 5' | 124 |
| CAACCCACGGGCAGGTG | 110 | 13 | 60 | 3 | $5.3 \times 10^{-5}$ | 6 | TAGAP | T-cell activation Rho GTPase-activating protein | 5' | 123822 |
| GGCAGACAGGCCCTATC | 701 | 0 | 7 | 7 | 0.01683 | 6 | FGFR1OP | FGFR1 oncogene partner isoform a | 3' | 316 |
| GCAAACGTCTAGTTATC | 702 | 0 | 20 | 20 | 0.00024 | 7 | LOC90637 | hypothetical protein LOC90637 | 5' | 49 |
| ATGAGTCCATTTCCTCG | 703 | 8 | 67 | 6 | 0 | 7 | MGC10911 | hypothetical protein MGC10911 | 5' | 96664 |
| GGGGGGGAACCGGACCG | 704 | 0 | 18 | 18 | 0.00185 | 7 | ACTB | beta actin | 3' | 865 |
| GGGGGTCTTTCCCCCTC | 705 | 0 | 13 | 13 | 0.00244 | 7 | FSCN1 | fascin 1 | 3' | 1392 |
| CATTTCCTCGGGTGTGA | 706 | 2 | 16 | 5 | 0.00705 | 7 | MPP6 | membrane protein, palmitoylated 6 | 3' | 216 |
| TATTTGCCAAGTTGTAC | 113 | 0 | 8 | 8 | 0.01239 | 7 | HOXA11 | homeobox protein A11 | 3' | 622 |
| ACAAAAATGATCGTTCT | 708 | 3 | 20 | 4 | 0.00474 | 7 | PLEKHA8 | pleckstrin homology domain containing, family A | 3' | 159 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| TCCGCCCTGCCCCGGGC | 709 | 0 | 17 | 17 | 0.00068 | 7 | ZNRF2 | zinc finger/RING finger 2 | 3' | 94 |
| GGCTCTCCGTCTCTGCC | 710 | 3 | 18 | 4 | 0.00867 | 7 | CRHR2 | corticotropin releasing hormone receptor 2 | 3' | 521 |
| GAACGTGCGTTTGCTTT | 711 | 0 | 9 | 9 | 0.00623 | 7 | Not Found | | | |
| GTCCCCAGCACGCGGTC | 712 | 5 | 33 | 4 | 0.00079 | 7 | TBX20 | T-box transcription factor TBX20 | 5' | 607 |
| TGCCCTGGGCTGCCCGC | 713 | 4 | 17 | 3 | 0.03271 | 7 | TBX20 | T-box transcription factor TBX20 | 5' | 4120 |
| TGGCAAACCCATTCTTG | 714 | 5 | 80 | 11 | 0 | 7 | MRPS24 | mitochondrial ribosomal protein S24 | 3' | 159 |
| GCCAGACTCCTGACTTG | 715 | 5 | 50 | 7 | $2 \times 10^{-6}$ | 7 | POLD2 | polymerase (DNA directed), delta 2, regulatory | 3' | 11 |
| AACTTGGGGCTGACCGG | 716 | 2 | 13 | 4 | 0.02369 | 7 | AUTS2 | autism susceptibility candidate 2 | 3' | 1095850 |
| CCCAGTCTAGCCAAGGT | 717 | 0 | 12 | 12 | 0.01257 | 7 | Not Found | | | |
| CCCCGCCGCGCTGATTG | 718 | 0 | 8 | 8 | 0.01239 | 7 | GTF2I | general transcription factor II, i isoform 1 | 3' | 1037 |
| CCTTCCGCCCGAGCGTC | 719 | 0 | 7 | 7 | 0.01683 | 7 | POR | P450 (cytochrome) oxidoreductase | 5' | 39477 |
| TAATCTCCCTAAATACC | 720 | 0 | 14 | 14 | 0.00718 | 7 | Not Found | | | |
| CACTAGACGTGCCTGAG | 721 | 0 | 11 | 11 | 0.01852 | 7 | DLX5 | distal-less homeo box 5 | 3' | 3450 |
| TTTGGAGGAGTGGAGTT | 722 | 4 | 28 | 5 | 0.00064 | 7 | MYLC2PL | myosin light chain 2, precursor | 5' | 185120 |
| GGCGGCGGCCACTTCTG | 723 | 0 | 12 | 12 | 0.01257 | 7 | SRPK2 | SFRS protein kinase 2 isoform a | 3' | 120 |
| TCTGAGTCGCCAGCGTC | 724 | 3 | 31 | 7 | 0.00013 | 7 | AASS | aminoadipate-semialdehyde synthase | 5' | 171064 |
| AGTATCAAAACGGCAGC | 725 | 2 | 17 | 6 | 0.0052 | 7 | | Not Found | | |
| CCGCGGCGCGCTCTCCC | 726 | 0 | 11 | 11 | 0.01852 | 7 | CUL1 | cullin 1 | 5' | 351 |
| TTATTTTTACAGCAAAC | 727 | 0 | 10 | 10 | 0.00467 | 7 | Not Found | | | |
| GAGCTGGCAAGCCTGGG | 728 | 0 | 8 | 8 | 0.01239 | 7 | ASB10 | ankyrin repeat and SOCS box-containing protein | 3' | 11480 |
| GATGCCACCAGGTTGTG | 729 | 4 | 28 | 5 | 0.00064 | 7 | HTR5A | 5-hydroxytryptamine (serotonin) receptor 5A | 5' | 579 |
| GATGCCACCAGGTTGTG | 730 | 4 | 28 | 5 | 0.00064 | 7 | PAXIP1L | PAX transcription activation domain interacting | 5' | 67372 |
| CGGACCACGCGTCCCTG | 731 | 5 | 0 | -8 | 0.02613 | 7 | C7orf3 | chromosome 7 open reading frame 3 | 5' | 154 |
| CGGACCACGCGTCCCTG | 732 | 5 | 0 | -8 | 0.02613 | 7 | C7orf2 | limb region 1 protein | 5' | 56421 |
| GGGGCCTATTCACAGCC | 733 | 13 | 61 | 3 | $3.8 \times 10^{-5}$ | 8 | TNKS | tankyrase, TRF1-interacting ankyrin-related | 5' | 404285 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| GGGGCCTATTCACAGCC | 734 | 13 | 61 | 3 | $3.8 \times 10^{-5}$ | 8 | PPP1R3B | protein phosphatase 1, regulatory (inhibitor) | 5' | 953 |
| CCAGACGCCGGCTCGGC | 735 | 6 | 39 | 4 | 0.00023 | 8 | ZDHHC2 | rec | 3' | 683 |
| GCTTTTCAACCGTAGCG | 736 | 0 | 8 | 8 | 0.01239 | 8 | KCTD9 | potassium channel tetramerisation domain | 3' | 587 |
| GTGACGATGGAGGAGCT | 737 | 0 | 33 | 33 | 0.00001 | 8 | DUSP4 | dual specificity phosphatase 4 isoform 1 | 3' | 629 |
| CACACACACACCCGGGC | 738 | 2 | 14 | 5 | 0.0165 | 8 | GPR124 | G protein-coupled receptor 124 | 3' | 114 |
| CCTCCTGTTCCTCTGCC | 739 | 3 | 36 | 8 | $3.7 \times 10^{-5}$ | 8 | RAB11FIP1 | Rab coupling protein isoform 3 | 3' | 230 |
| CCCTGTCCTAGTAACGC | 740 | 0 | 12 | 12 | 0.01257 | 8 | DDHD2 | DDHD domain containing 2 | 3' | 541 |
| CTCCTCCTTCTTTTGCG | 741 | 4 | 37 | 6 | $7.3 \times 10^{-5}$ | 8 | ADAM9 | a disintegrin and metalloproteinase domain 9 | 3' | 542 |
| CTTCAATTTGGTGAGGG | 742 | 2 | 12 | 4 | 0.03293 | 8 | MYST3 | MYST histone acetyltransferase (monocytic) | 3' | 462 |
| CGAGGAAGTGACCCTCG | 743 | 0 | 7 | 7 | 0.01683 | 8 | CHD7 | chromodomain helicase DNA binding protein 7 | 5' | 156 |
| GCGGGGGCAGCAGACGC | 744 | 5 | 21 | 3 | 0.01878 | 8 | PRDM14 | PR domain containing 14 | 3' | 768 |
| CACCAGTCTTCGCCCGC | 745 | 0 | 7 | 7 | 0.01683 | 8 | RDH10 | retinol dehydrogenase 10 | 5' | 204 |
| CACCAGTCTTCGCCCGC | 746 | 0 | 7 | 7 | 0.01683 | 8 | RPL7 | ribosomal protein L7 | 5' | 1264 |
| TAACTGTCCTTTCCGTA | 747 | 4 | 19 | 3 | 0.01426 | 8 | Not Found | | | |
| TGCCATTCTGGAGAGCT | 748 | 0 | 15 | 15 | 0.00413 | 8 | LOC157567 | hypothetical protein LOC157567 | 5' | 57 |
| TAATTCGAGCACTTTGA | 749 | 0 | 13 | 13 | 0.00244 | 8 | FLJ20366 | hypothetical protein FLJ203666 | 5' | 1280 |
| AATAGGTAACTCACAAA | 750 | 0 | 28 | 28 | $6.6 \times 10^{-5}$ | 8 | FLJ14129 | hypothetical protein FLJ14129 | 5' | 237 |
| AAGTTGGCCACCTCGGG | 751 | 0 | 11 | 11 | 0.00359 | 8 | SCRIB | scribble isoform b | 3' | 194 |
| ACTGCCTTGCCCCCTCC | 752 | 0 | 18 | 18 | 0.00185 | 8 | PLEC1 | plectin 1 isoform 1 | 5' | 1296 |
| CTTGCCTCTCATCCTTC | 753 | 12 | 91 | 5 | 0 | 8 | Sharpin | shank-interacting protein-like 1 | 3' | 328 |
| GGGGTAACTCTTGAGTC | 754 | 0 | 7 | 7 | 0.01683 | 8 | Sharpin | shank-interacting protein-like 1 | 3' | 328 |
| GCCTCAGCCCGCACCCG | 755 | 0 | 8 | 8 | 0.01239 | 8 | DGAT1 | diacylglycerol O-acyltransferase 1 | 5' | 84 |
| GGCACGGGAGCTGCTCC | 756 | 3 | 42 | 9 | $4 \times 10^{-6}$ | 8 | ADCK5 | aarF domain containing kinase 5 | 3' | 748 |
| GCGCCAACCCGGGCTGC | 757 | 4 | 29 | 5 | 0.00051 | 8 | CPSF1 | cleavage and polyadenylation specific factor 1 | 5' | 318 |
| GCACCTCAGGCGGCAGT | 758 | 2 | 12 | 4 | 0.03293 | 8 | KIFC2 | kinesin family member C2 | 5' | 153 |
| GCACCTCAGGCGGCAGT | 759 | 2 | 12 | 4 | 0.03293 | 8 | CYHR1 | cysteine and histidine rich 1 | 5' | 735 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| GACCTACTGGATTGCTC | 760 | 0 | 20 | 20 | 0.00085 | 9 | ANKRD15 | ankyrin repeat domain protein 15 | 5' | 171831 |
| AAATGAAACTAGTCTTG | 761 | 0 | 17 | 17 | 0.00238 | 9 | ANKRD15 | ankyrin repeat domain protein 15 | 5' | 171831 |
| TCTGTGTGCTGTGTGCG | 762 | 3 | 17 | 4 | 0.01446 | 9 | SMARCA2 | SWI/SNF-related matrix-associated | 3' | 1580 |
| CACAGCAGCCCGTCAGG | 763 | 0 | 9 | 9 | 0.00623 | 9 | TYRP1 | tyrosinase-related protein 1 | 5' | 2080245 |
| CACAGCAGCCCGTCAGG | 764 | 0 | 9 | 9 | 0.00623 | 9 | PTPRD | protein tyrosine phosphatase, receptor type, D | 5' | 1594466 |
| AGGGGGCTGCTCCGGAG | 765 | 7 | 27 | 3 | 0.0099 | 9 | MOBKL2B | MOB1, Mps One Binder kinase activator-like 2B | 3' | 1418 |
| GGGATACACACAGGGGA | 766 | 2 | 12 | 4 | 0.03293 | 9 | PAX5 | paired box 5 | 3' | 48156 |
| GTGCGGGCGACGGCAGC | 767 | 3 | 34 | 8 | $7.8 \times 10^{-5}$ | 9 | KLF9 | Kruppel-like factor 9 | 3' | 995 |
| GGGTGCCGCGGCCACGA | 768 | 6 | 24 | 3 | 0.01444 | 9 | GNAQ | guanine nucleotide binding protein (G protein) | 3' | 302 |
| TAAATAGGCGAGAGGAG | 769 | 6 | 34 | 4 | 0.00131 | 9 | FLJ46321 | FLJ46321 protein | 5' | 299849 |
| TAAATAGGCGAGAGGAG | 770 | 6 | 34 | 4 | 0.00131 | 9 | TLE1 | transducin-like enhancer protein 1 | 5' | 241 |
| ATCGAGTGCGACGCCTG | 771 | 0 | 15 | 15 | 0.00099 | 9 | PHF2 | PHD finger protein 2 isoform b | 3' | 686 |
| CCGCTTGCCCCGAAACC | 772 | 0 | 10 | 10 | 0.03148 | 9 | PTPN3 | protein tyrosine phosphatase, non-receptor type | 5' | 316517 |
| TCTTCTATTGCCTGATT | 773 | 0 | 10 | 10 | 0.00467 | 9 | SUSD1 | sushi domain containing 1 | 3' | 17 |
| AAGTCAGTGCGCAAACG | 774 | 0 | 8 | 8 | 0.01239 | 9 | STOM | stomatin isoform a | 5' | 128954 |
| GCGGGCGGCGCGGTCCC | 775 | 44 | 121 | 2 | $6.9 \times 10^{-5}$ | 9 | LHX6 | LIM homeobox protein 6 isoform 1 | 3' | 408 |
| ATTTGTGCAGCTACCGT | 776 | 0 | 9 | 9 | 0.00623 | 9 | Not Found | | | |
| AGGCAGGAGATGGTCTG | 777 | 4 | 21 | 3 | 0.00732 | 9 | PRDM12 | PR domain containing 12 | 5' | 5017 |
| GGCGTTAATAGAGAGGC | 778 | 0 | 13 | 13 | 0.00244 | 9 | PRDM12 | PR domain containing 12 | 5' | 5017 |
| AGGTTGTTGTTCTTGCA | 779 | 5 | 29 | 4 | 0.00133 | 9 | PRDM12 | PR domain containing 12 | 3' | 1427 |
| AGCCCTGGGCTCTCTCT | 780 | 0 | 7 | 7 | 0.01683 | 9 | C9orf67 | chromosome 9 open reading frame 67 | 5' | 11874 |
| AGCCCTGGGCTCTCTCT | 781 | 0 | 7 | 7 | 0.01683 | 9 | C9orf59 | chromosome 9 open reading frame 59 | 5' | 1343 |
| CTCCTTTTGAGCCCCTG | 782 | 0 | 8 | 8 | 0.01239 | 9 | C9orf67 | chromosome 9 open reading frame 67 | 5' | 11874 |
| CTCCTTTTGAGCCCCTG | 783 | 0 | 8 | 8 | 0.01239 | 9 | C9orf59 | chromosome 9 open reading frame 59 | 5' | 1343 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| CTCCCAGTACAGGAGCC | 784 | 12 | 45 | 2 | 0.00281 | 9 | RAPGEF1 | guanine nucleotide-releasing factor 2 isoform a | 5' | 2333 |
| TACGCGGGTGGGGGAGA | 785 | 8 | 31 | 3 | 0.01478 | 9 | ADAMTS13 | a disintegrin-like and metalloprotease | 3' | 6658 |
| CAGGGCCCTGGGTGCTG | 786 | 0 | 8 | 8 | 0.01239 | 9 | OLFM1 | olfactomedin related ER localized protein | 3' | 74 |
| AAGGAGCCTACGTTAAT | 787 | 0 | 10 | 10 | 0.00467 | 9 | UBADC1 | ubiquitin associated domain containing 1 | 3' | 10 |
| GAGGACAGCCGGCTCGT | 788 | 0 | 7 | 7 | 0.01683 | 9 | LHX3 | LIM homeobox protein 3 isoform b | 3' | 4193 |
| CAGCCAGCTTTCTGCCC | 139 | 16 | 91 | 4 | 0 | 9 | LHX3 | LIM homeobox protein 3 isoform b | 5' | 146 |
| TTTTCCCGAGGCCAGAG | 790 | 11 | 33 | 2 | 0.04578 | 9 | EGFL7 | EGF-like-domain, multiple 7 | 3' | 2912 |
| AAGAGCAAATAAGAGGC | 791 | 0 | 7 | 7 | 0.01683 | 10 | KIAA0934 | KIAA0934 | 3' | 138 |
| AGCCACCGTACAAGGCC | 792 | 12 | 40 | 2 | 0.01181 | 10 | PFKP | phosphofructokinase, platelet | 3' | 1056 |
| CCCCAGGCCTCGGCCAG | 793 | 0 | 7 | 7 | 0.01683 | 10 | ANKRD16 | ankyrin repeat domain 16 isoform a | 5' | 375 |
| CTCAGAGGAGGGGCAGA | 794 | 0 | 11 | 11 | 0.00359 | 10 | ANKRD16 | ankyrin repeat domain 16 isoform a | 5' | 375 |
| AAAATAGAGGTTCCTCC | 795 | 0 | 30 | 30 | $2.8 \times 10^{-5}$ | 10 | PRPF18 | PRP18 pre-mRNA processing factor 18 homolog | 5' | 58621 |
| AAAATAGAGGTTCCTCC | 796 | 0 | 30 | 30 | $2.8 \times 10^{-5}$ | 10 | C10orf30 | chromosome 10 open reading frame 30 | 5' | 25417 |
| ACCTCGAAGCCGCCAAG | 797 | 0 | 7 | 7 | 0.01683 | 10 | ZNF32 | zinc finger protein 32 | 5' | 101 |
| AATGAACGACCAGACCC | 798 | 10 | 56 | 4 | 0.00002 | 10 | DDX21 | DEAD (Asp-Glu-Ala-Asp) box polypeptide 21 | 3' | 506 |
| GGTCGCTCCTCGTTGGG | 799 | 0 | 10 | 10 | 0.00467 | 10 | C10orf13 | hypothetical protein MGC39320 | 3' | 771 |
| GAGTTTCTTTAGTAAAG | 800 | 0 | 10 | 10 | 0.00467 | 10 | GPR120 | G protein-coupled receptor 120 | 3' | 255 |
| AGTTAGTTCCCAACTCA | 801 | 0 | 10 | 10 | 0.00467 | 10 | MLR2 | ligand-dependent corepressor | 5' | 84 |
| AGTTAGTTCCCAACTCA | 802 | 0 | 10 | 10 | 0.00467 | 10 | PIK3AP1 | phosphoinositide-3-kinase adaptor protein 1 | 5' | 112373 |
| GGGACAGGTGGCAGGCC | 803 | 19 | 64 | 2 | 0.00074 | 10 | PAX2 | paired box protein 2 isoform b | 5' | 6126 |
| GAGCTAATCAATAGGCA | 804 | 0 | 10 | 10 | 0.00467 | 10 | PAX2 | paired box protein 2 isoform b | 5' | 6126 |
| TGGGAAAGGTCTTGTGG | 805 | 10 | 36 | 2 | 0.01161 | 10 | LZTS2 | leucine zipper, putative tumor suppressor 2 | 3' | 2691 |
| GCGGCCGCGGGCAGGGG | 806 | 0 | 7 | 7 | 0.01683 | 10 | TRIM8 | tripartite motif-containing 8 | 5' | 375 |
| CTGCCCGCAGGTGGCGC | 807 | 9 | 42 | 3 | 0.00094 | 10 | CNNM2 | cyclin M2 isoform 1 | 3' | 212 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| GAGGTAGTGCCCTGTCC | 808 | 3 | 16 | 4 | 0.01997 | 10 | SH3MD1 | SH3 multiple domains 1 | 3' | 24 |
| TTGTGTGTACATAGGGC | 809 | 0 | 11 | 11 | 0.00359 | 10 | SORCS1 | SORCS receptor 1 isoform a | 5' | 1301646 |
| GCTCATTGCGTCCCGCT | 810 | 8 | 33 | 3 | 0.00804 | 10 | KIAA1598 | KIAA1598 | 3' | 509 |
| AGCAGCAGCCCCATCCC | 811 | 12 | 42 | 2 | 0.00672 | 10 | EMX2 | empty spiracles homolog 2 | 5' | 166361 |
| AGCAGCAGCCCCATCCC | 811 | 12 | 42 | 2 | 0.00672 | 10 | PDZK8 | PDZ domain containing 8 | 5' | 657 |
| GGGCCCCGCCCAGCCAG | 813 | 0 | 18 | 18 | 0.00185 | 10 | C10orf137 | erythroid differentiation-related factor 1 | 5' | 556810 |
| GGGCCCCGCCCAGCCAG | 814 | 0 | 18 | 18 | 0.00185 | 10 | CTBP2 | C-terminal binding protein 2 isoform 1 | 5' | 2249 |
| TGCGCTTGGCAGCCGGG | 815 | 0 | 8 | 8 | 0.01239 | 10 | ADAM12 | a disintegrin and metalloprotease domain 12 | 3' | 464 |
| TCAGAGGCTGATGGGGC | 816 | 7 | 31 | 3 | 0.00755 | 10 | MGMT | O-6-methylguanine-DNA methyltransferase | 5' | 1340765 |
| TCAGAGGCTGATGGGGC | 817 | 7 | 31 | 3 | 0.00755 | 10 | MK167 | antigen identified by monoclonal antibody Ki-67 | 5' | 232 |
| TGGAGGCAGGTGCACAG | 818 | 0 | 12 | 12 | 0.01257 | 10 | CYP2E1 | cytochrome P450, family 2, subfamily E | 3' | 826 |
| CAGCCGAAGTGGCGCTC | 819 | 0 | 13 | 13 | 0.00244 | 11 | NALP6 | NACHT, leucine rich repeat and PYD containing 6 | 3' | 1950 |
| GCCTGGCACTGGGTCCA | 820 | 0 | 12 | 12 | 0.01257 | 11 | C11orf13 | HRAS1-related cluster-1 | 5' | 374 |
| GCCTGGCACTGGGTCCA | 821 | 0 | 12 | 12 | 0.01257 | 11 | MGC35138 | hypothetical protein MGC35138 | 5' | 297 |
| GAAAACTCCAGATAGTG | 822 | 6 | 21 | 2 | 0.03859 | 11 | ASCL2 | achaete-scute complex homolog-like 2 | 3' | 582 |
| CTTTGAAATAAGCGAAT | 823 | 0 | 7 | 7 | 0.01683 | 11 | PDE3B | phosphodiesterase 3B, cGMP-inhibited | 3' | 526 |
| GCGCTGCCCTATATTGG | 824 | 3 | 22 | 5 | 0.00215 | 11 | FLJ11336 | hypothetical protein FLJ11336 | 3' | 375 |
| TCTAGGACCTCCAGGCC | 825 | 12 | 69 | 4 | $1 \times 10^{-6}$ | 11 | SLC39A13 | solute carrier family 39 (zinc transporter) | 5' | 415 |
| TCTAGGACCTCCAGGCC | 826 | 12 | 69 | 4 | $1 \times 10^{-6}$ | 11 | SPI1 | spleen focus forming virus (SFFV) proviral | 5' | 29668 |
| CCCTGCCCTTAGTGCTT | 827 | 0 | 10 | 10 | 0.03148 | 11 | Not Found | | | |
| CTCTGGGCTGTGAGGAC | 828 | 0 | 12 | 12 | 0.00296 | 11 | C11ORF4 | chromosome 11 hypothetical protein ORF4 | 5' | 458 |
| CTCTGGGCTGTGAGGAC | 829 | 0 | 12 | 12 | 0.00296 | 11 | BAD | BCL2-antagonist of cell death protein | 5' | 708 |
| CGCCCCTTCCCTGCGCC | 830 | 0 | 15 | 15 | 0.00413 | 11 | FBXL11 | F-box and leucine-rich repeat protein 11 | 5' | 454 |
| CCACAGACCAGTGGGTG | 831 | 0 | 14 | 14 | 0.00718 | 11 | TPCN2 | two pore segment channel 2 | 3' | 305 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| GCCCTGCATACAACCCT | 832 | 6 | 26 | 3 | 0.00682 | 11 | Not Found | | | |
| GCTCAGAGGCGCTGGAA | 833 | 3 | 21 | 5 | 0.0037 | 11 | ZBTB16 | zinc finger and BTB domain containing 16 | 3' | 913 |
| CCCCGGCAGGCGGCGGC | 834 | 8 | 35 | 3 | 0.0043 | 11 | ROBO3 | roundabout, axon guidance receptor, homolog 3 | 5' | 64774 |
| CCCCGGCAGGCGGCGGC | 835 | 8 | 35 | 3 | 0.0043 | 11 | FLJ23342 | hypothetical protein FLJ23342 | 5' | 208 |
| GATTATGAAAGCCCATC | 836 | 0 | 17 | 17 | 0.00068 | 11 | BARX2 | BarH-like homeobox 2 | 5' | 2434 |
| GATTATGAAAGCCCATC | 837 | 0 | 17 | 17 | 0.00068 | 11 | RICS | Rho GTPase-activating protein | 5' | 349388 |
| CGACATATCAGGGATCA | 838 | 0 | 8 | 8 | 0.01239 | 11 | APLP2 | amyloid beta (A4) precursor-like protein 2 | 5' | 589 |
| CTCCAGCCCTGTGTCCT | 839 | 0 | 13 | 13 | 0.00923 | 12 | M160 | scavenger receptor cysteine-rich type 1 protein | 3' | 3750 |
| CCTGCCGGTGGAGGGCA | 840 | 12 | 44 | 2 | 0.00377 | 12 | ST8SIA1 | ST8 alpha-N-acetyl-neuraminide | 5' | 176 |
| CCACGTCTTAGCACTCT | 841 | 2 | 19 | 6 | 0.00296 | 12 | DDX11 | DEAD H (Asp-Glu-Ala-Asp/His) box polypeptide 11 | 5' | 277542 |
| CCACGTCTTAGCACTCT | 842 | 2 | 19 | 6 | 0.00296 | 12 | C1QDC1 | C1q domain containing 1 isoform 2 | 5' | 41819 |
| GCTGCCCCAAGTGGTCT | 180 | 4 | 33 | 5 | 0.00031 | 12 | Not Found | | | |
| GCGGCCTCAGGTGAGCG | 844 | 2 | 13 | 4 | 0.02369 | 12 | EIF4B | eukaryotic translation initiation factor 4B | 3' | 587 |
| TCCCCACCCCTGGTACC | 845 | 0 | 7 | 7 | 0.01683 | 12 | LOC56901 | NADH ubiquinone oxidoreductase MLRQ subunit | 5' | 1764 |
| TCTCCGTGTATGTGCGC | 846 | 3 | 20 | 4 | 0.00474 | 12 | HMGA2 | high mobility group AT-hook 2 | 3' | 1476 |
| TTGACAGGCAGACAAGT | 847 | 0 | 9 | 9 | 0.00623 | 12 | ATP2B1 | plasma membrane calcium ATPase 1 isoform 1b | 5' | 52908 |
| CCTTCCTCCCCACGCAG | 848 | 2 | 16 | 5 | 0.00705 | 12 | NFYB | nuclear transcription factor Y, beta | 5' | 197 |
| TTGCAAAGAACGGAGCC | 849 | 0 | 9 | 9 | 0.00623 | 12 | CUTL2 | cut-like 2 | 3' | 265 |
| TCAAGTGTGAGGGGAAG | 850 | 2 | 22 | 7 | 0.00104 | 12 | PBP | proslatic binding protein | 5' | 32016 |
| TCAAGTGTGAGGGGAAG | 851 | 2 | 22 | 7 | 0.00104 | 12 | FLJ20674 | hypothetical protein FLJ20674 | 5' | 104 |
| ACAAAGTACCGTGGTTC | 852 | 0 | 16 | 16 | 0.0031 | 12 | TSP-NY | testis-specific protein TSP-NY isoform a | 3' | 81 |
| GAGGCCAGATTTTCTCC | 853 | 2 | 46 | 15 | 0 | 12 | HIP1R | huntingtin interacting protein-1-related | 5' | 170 |
| AAGGCTGGGAGTTTTCT | 854 | 4 | 22 | 4 | 0.00554 | 12 | ABCB9 | ATP-binding cassette, sub-family B (MDR/TAP) | 3' | 517 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| GGGCGGCCGGCGGGGGC | 855 | 10 | 0 | -15 | 0.00558 | 12 | Not Found | | | |
| CGAACTTCCCGGTTCCG | 856 | 21 | 96 | 3 | 0 | 12 | Not Found | | | |
| CAGCGGCCAAAGCTGCC | 857 | 16 | 69 | 3 | 2.5 × 10⁻⁵ | 12 | RAN | ras-related nuclear protein | 5' | 257 |
| CAGCGGCCAAAGCTGCC | 858 | 16 | 69 | 3 | 2.5 × 10⁻⁵ | 12 | EPIM | epimorphin isoform 2 | 5' | 32499 |
| CGCAGGCTACCAGTGCA | 859 | 2 | 12 | 4 | 0.03293 | 12 | PUS1 | pseudouridylate synthase 1 | 5' | 740 |
| CACTGCCTGATGGTGTG | 860 | 18 | 107 | 4 | 0 | 13 | IL17D | interleukin 17D precursor | 3' | 277 |
| AAGGTCTCTACCGCGCC | 861 | 0 | 13 | 13 | 0.00244 | 13 | WDFY2 | WD repeat- and FYVE domain-containing protein 2 | 5' | 130880 |
| AAGGTCTCTACCGCGCC | 862 | 0 | 13 | 13 | 0.00244 | 13 | DDX26 | DEAD/H (Asp-Glu-Ala-Asp/His) box polypeptide 26 | 5' | 629 |
| TTTGCTACGTGTACATC | 863 | 0 | 14 | 14 | 0.00122 | 13 | RANBP5 | RAN binding protein 5 | 3' | 23155 |
| CCACCAGCCTCCCTCGG | 864 | 8 | 79 | 7 | 0 | 13 | DOCK9 | dedicator of cytokinesis 9 | 5' | 1277 |
| CAGTGGCCTCCATCTGG | 865 | 7 | 26 | 2 | 0.01495 | 13 | KDELC1 | KDEL (Lys-Asp-Glu-Leu) containing 1 | 3' | 141 |
| GGTTCGAAGGGCAGCGG | 866 | 4 | 46 | 8 | 3 × 10⁻⁶ | 14 | PPM1A | protein phosphatase 1A isoform 1 | 3' | 733 |
| AGCTCTGCCAGTAGTTG | 867 | 5 | 32 | 4 | 0.00112 | 14 | MTHFD1 | methylenetetrahydro-folate dehydrogenase 1 | 5' | 49925 |
| AGCTCTGCCAGTAGTTG | 868 | 5 | 32 | 4 | 0.00112 | 14 | ESR2 | estrogen receptor 2 | 5' | 44089 |
| TGCCCAGCCCTCAGCAC | 869 | 0 | 11 | 11 | 0.00359 | 14 | SFRS5 | splicing factor, arginine/serine-rich 5 | 5' | 40145 |
| CCTCTAGGACCAAGCCT | 870 | 2 | 24 | 8 | 0.00064 | 14 | SLC8A3 | solute carrier family 8 member 3 isoform B | 3' | 270 |
| GAGTCGCAGTATTTTGG | 871 | 6 | 31 | 3 | 0.0036 | 14 | GTF2A1 | TFIIA alpha, p55 isoform 1 | 3' | 181 |
| CGGCGCAGCTCCAGGTC | 872 | 21 | 55 | 2 | 0.01977 | 14 | KCNK10 | potassium channel, subfamily K, member 10 | 3' | 3468 |
| GCCTTCAGGTTGCGGGT | 873 | 0 | 16 | 16 | 0.00081 | 14 | BCL11B | B-cell CLL/lymphoma 11B isoform2 | 3' | 25026 |
| GCCCCACGCCCCCTGGC | 874 | 8 | 50 | 4 | 2.9 × 10⁻⁵ | 14 | C14orf153 | chromosome 14 open reading frame 153 | 5' | 681 |
| GCCCCACGCCCCCTGGC | 875 | 8 | 50 | 4 | 2.9 × 10⁻⁵ | 14 | BAG5 | BCL2-associated athanogene 5 | 5' | 19 |
| GAGGCCAGCCTGAGGGC | 876 | 0 | 7 | 7 | 0.01683 | 14 | C14orf151 | chromosome 14 open reading frame 151 | 5' | 39104 |
| GAGGCCAGCCTGAGGGC | 877 | 0 | 7 | 7 | 0.01683 | 14 | FLJ42486 | FLJ42486 protein | 5' | 45756 |
| TTCCAGTGGCAAGTTGA | 878 | 12 | 43 | 2 | 0.00504 | 14 | CDCA4 | cell division cycle associated 4 | 3' | 550 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| TCGAGCCGCGCGGTCGT | 879 | 0 | 8 | 8 | 0.01239 | 15 | KLF13 | Kruppel-like factor 13 | 3' | 1607 |
| GCTCTGCCCCCGTGGCC | 880 | 6 | 58 | 6 | 0 | 15 | BAHD1 | bromo adjacent homology domain containing 1 | 5' | 138 |
| GCAGAGGCTGAGCGGCC | 881 | 0 | 8 | 8 | 0.01239 | 15 | C15orf21 | D-PCa-2 protein isoform c | 3' | 11782 |
| GCCGCCCCCGACCGAA | 882 | 0 | 8 | 8 | 0.01239 | 15 | ONECUT1 | one cut domain, family member 1 | 3' | 4340 |
| TTTCTCCTGATGGAGTC | 883 | 0 | 12 | 12 | 0.00296 | 15 | DAPK2 | death-associated protein kinase 2 | 5' | 207 |
| TCAGGCTTCCCCTTCGG | 884 | 7 | 27 | 3 | 0.0099 | 15 | PIAS1 | protein inhibitor of activated STAT, 1 | 5' | 190450 |
| GCCCCAACCGGTCCTTC | 885 | 9 | 29 | 2 | 0.04715 | 15 | PKM2 | pyruvate kinase 3 isoform 1 | 3' | 300 |
| GACCCCACAAGGGCTTG | 886 | 3 | 41 | 9 | $6 \times 10^{-6}$ | 15 | LOC92912 | hypothetical protein LOC92912 | 5' | 119 |
| CCTTGAGAGCAGAGAGC | 887 | 4 | 31 | 5 | 0.00032 | 15 | LRRN6A | leucine-rich repeat neuronal 6A | 3' | 43 |
| TGGGGACTGATGCACCC | 888 | 6 | 30 | 3 | 0.00501 | 15 | CIB2 | DNA-dependent protein kinase catalytic | 3' | 598 |
| CACGTGAGGGGTGGTA | 889 | 4 | 32 | 5 | 0.00045 | 15 | BLP2 | BBP-like protein 2 isoform a | 5' | 22 |
| CCCGCGGGAGAGACCGG | 890 | 3 | 28 | 6 | 0.00034 | 16 | E4F1 | p120E4F | 5' | 8954 |
| CCCGCGGGAGAGACCGG | 891 | 3 | 28 | 6 | 0.00034 | 16 | MGC21830 | hypothetical protein MGC21830 | 5' | 3623 |
| CCGGGTCCGCGGGCGAG | 892 | 13 | 40 | 2 | 0.02012 | 16 | USP7 | ubiquitin specific protease 7 (herpes | 3' | 725 |
| ATCCGGCCAAGCCCTAG | 893 | 6 | 37 | 4 | 0.00047 | 16 | ATF7IP2 | activating transcription factor 7 interacting | 5' | 244550 |
| ATCCGGCCAAGCCCTAG | 894 | 6 | 37 | 4 | 0.00047 | 16 | GRIN2A | N-methyl-D-aspartate receptor subunit 2A | 5' | 809 |
| TTCCTACCCCTACACC | 895 | 2 | 20 | 7 | 0.0023 | 16 | TXNDC11 | thioredoxin domain containing 11 | 3' | 238 |
| GAGGGAGCTTGACATTC | 896 | 5 | 40 | 5 | $6.5 \times 10^{-5}$ | 16 | LOC146174 | hypothetical protein LOC146174 | 3' | 214 |
| GCCTATAGGGTCCTGGG | 897 | 2 | 12 | 4 | 0.03293 | 16 | HS3ST2 | heparan sulfate D-glucosaminyl | 3' | 227 |
| GGGTAGGCACAGCCGTC | 898 | 3 | 27 | 6 | 0.00044 | 16 | TBX6 | T-box 6 isoform 1 | 5' | 85 |
| TGCGCGCGTCGGTGGCG | 899 | 6 | 22 | 2 | 0.02566 | 16 | LOC51333 | mesenchymal stem cell protein DSC43 | 3' | 9832 |
| AACTATCCAGGGACCTG | 900 | 2 | 14 | 5 | 0.0165 | 16 | FLJ38101 | hypothetical protein FLJ38101 | 5' | 167223 |
| AACTATCCAGGGACCTG | 901 | 2 | 14 | 5 | 0.0165 | 16 | ZNF423 | zinc finger protein 423 | 5' | 31051 |
| GTTGGGGAAGGCACCGC | 902 | 6 | 34 | 4 | 0.00131 | 16 | FLJ38101 | hypothetical protein FLJ38101 | 5' | 167223 |
| GTTGGGGAAGGCACCGC | 903 | 6 | 34 | 4 | 0.00131 | 16 | ZNF423 | zinc finger rotein 423 | 5' | 31051 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| ACAATAGCGCGATCGAG | 904 | 3 | 20 | 4 | 0.00474 | 16 | IRX5 | iroquois homeobox protein 5 | 5' | 455 |
| ACAATAGCGCGATCGAG | 904 | 3 | 20 | 4 | 0.00474 | 16 | IRX3 | iroquois homeobox protein 3 | 5' | 644277 |
| GGGCGCGCCGCGCCGCG | 906 | 7 | 0 | −11 | 0.00579 | 16 | IRX5 | iroquois homeobox protein 5 | 5' | 455 |
| GGGCGCGCCGCGCCGCG | 907 | 7 | 0 | −11 | 0.00579 | 16 | IRX3 | iroquois homeobox protein 3 | 5' | 644277 |
| CGATTCGAAGGGAGGGG | 908 | 0 | 41 | 41 | $1 \times 10^{-6}$ | 16 | IRX6 | iroquois homeobox protein 6 | 5' | 386305 |
| GTGCAGTCTCGGCCCGG | 909 | 6 | 35 | 4 | 0.00093 | 16 | FBXL8 | F-box and leucine-rich repeat protein 8 | 3' | 3905 |
| GGGATCCTCTTGCAAAG | 910 | 4 | 21 | 3 | 0.00732 | 16 | DNCL2B | dynein, cytoplasmic, light polypeptide 2B | 5' | 939218 |
| GGGATCCTCTTGCAAAG | 911 | 4 | 21 | 3 | 0.00732 | 16 | MAF | v-maf musculoaponeurotic fibrosarcoma oncogene | 5' | 1024 |
| AGCCACCACACCCTTCC | 912 | 8 | 32 | 3 | 0.01092 | 16 | EFCBP2 | neuronal calcium-binding protein 2 | 3' | 36 |
| AACACCCTCAGCCAGCC | 913 | 0 | 9 | 9 | 0.00623 | 17 | MNT | MAX binding protein | 3' | 8124 |
| CCGTGTTGTCCTGCCCG | 914 | 4 | 28 | 5 | 0.00064 | 17 | MNT | MAX binding protein | 3' | 228 |
| CAAAGCCACACAGTTTA | 915 | 0 | 8 | 8 | 0.01239 | 17 | MGC2941 | hypothetical protein MGC2941 | 3' | 1256 |
| GCGGAGCCCAGTCCCGA | 916 | 0 | 17 | 17 | 0.00238 | 17 | MGC2941 | hypothetical protein MGC2941 | 3' | 1256 |
| CCACACCTCTCTCCAGG | 917 | 0 | 16 | 16 | 0.00081 | 17 | SENP3 | SUMO1/sentrin/SMT3 specific protease 3 | 5' | 326 |
| TGGGAGTCACGTCCTCA | 918 | 0 | 13 | 13 | 0.00244 | 17 | FLJ20014 | hypothetical protein FLJ20014 | 3' | 948 |
| CGCTTTTGACACATTGG | 919 | 9 | 42 | 3 | 0.00094 | 17 | NDEL1 | nudE nuclear distribution gene E homolog like 1 | 3' | 550 |
| GCTGCCGCCGGCGCAGC | 920 | 3 | 26 | 6 | 0.00077 | 17 | GLP2R | glucagon-like peptide 2 receptor precursor | 5' | 181348 |
| CTGGTCTGCGGCCTCCG | 921 | 0 | 20 | 20 | 0.00024 | 17 | LOC116236 | hypothetical protein LOC116236 | 3' | 155 |
| GCCGCGCACAGGCCGGT | 922 | 3 | 28 | 6 | 0.00034 | 17 | NF1 | neurofibromin | 3' | 603 |
| CACCAGAAACCTCGGGG | 923 | 4 | 23 | 4 | 0.00427 | 17 | DUSP14 | dual specificity phosphatase 14 | 5' | 198 |
| CCAAGGAACCTGAAAAC | 924 | 0 | 9 | 9 | 0.00623 | 17 | ACLY | ATP citrate lyase isoform 1 | 3' | 446 |
| CCTACCTATCCCTGGAC | 925 | 7 | 49 | 5 | $1.7 \times 10^{-5}$ | 17 | STAT5A | signal transducer and activator of transcription | 3' | 1085 |
| GCTATGGGTCGGGGGAG | 215 | 49 | 140 | 2 | $6 \times 10^{-6}$ | 17 | SOST | sclerostin precursor | 3' | 3140 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| GATGCTCGAACGCAGAG | 927 | 0 | 10 | 10 | 0.00467 | 17 | SOST | sclerostin precursor | 3' | 3140 |
| GAGGCTGGCACCCAGGC | 928 | 0 | 22 | 22 | 0.00016 | 17 | C1QL1 | complement component 1, q subcomponent-like 1 | 3' | 8471 |
| AACACGCTGGCTCTTGC | 929 | 0 | 12 | 12 | 0.00296 | 17 | CRHR1 | corticotropin releasing hormone receptor 1 | 3' | 1129 |
| GAGCTGATCACCATTCT | 930 | 0 | 9 | 9 | 0.00623 | 17 | KPNB1 | karyopherin beta 1 | 3' | 758 |
| TGTGTCTGCGTAGAAAT | 931 | 0 | 7 | 7 | 0.01683 | 17 | HOXB9 | homeo box B9 | 3' | 455 |
| GTCCTGCGGGGCGAGAG | 932 | 3 | 22 | 5 | 0.00215 | 17 | NME2 | nucleoside-diphosphate kinase 2 | 5' | 163 |
| CATTTCCTGGGCTATTT | 933 | 0 | 7 | 7 | 0.01683 | 17 | MRC2 | mannose receptor, C type 2 | 3' | 527 |
| CCCCTGCCCTGTCACCC | 226 | 0 | 48 | 48 | 0 | 17 | SLC9A3R1 | solute carrier family 9 (sodium/hydrogen | 3' | 11941 |
| CTGCCCGGCAGCCAGCC | 935 | 0 | 7 | 7 | 0.01683 | 17 | CBX2 | chromobox homolog 2 isoform 2 | 5' | 361 |
| TTGACTCGCCGCTTCCC | 936 | 0 | 8 | 8 | 0.01239 | 17 | CBX8 | chromobox homolog 8 | 5' | 620 |
| CCCCAGGCCGGGTGTCC | 303 | 10 | 65 | 4 | $1 \times 10^{-6}$ | 17 | CBX8 | chromobox homolog 8 | 5' | 16730 |
| CCTCTTCCCAGACCGAA | 938 | 0 | 18 | 18 | 0.00185 | 17 | CBX4 | chromobox homolog 4 | 5' | 1307 |
| ACCCGCACCATCCCGGG | 229 | 88 | 201 | 2 | $4.1 \times 10^{-5}$ | 17 | CBX4 | chromobox homolog 4 | 5' | 4600 |
| TCCCTCATTCGCCCCGG | 940 | 18 | 79 | 3 | $4 \times 10^{-6}$ | 18 | EMILIN2 | elastin microfibtil interfacer 2 | 3' | 143 |
| CACACGCACGGGAGCGC | 941 | 0 | 8 | 8 | 0.01239 | 18 | ZFP161 | zinc finger protein 161 homolog | 5' | 2780 |
| TGAAGAAAAGGCCTTTG | 942 | 0 | 7 | 7 | 0.01683 | 18 | ACAA2 | acetyl-coenzyme A acyltransferase 2 | 5' | 380776 |
| GAACTATCTTCTACCAA | 943 | 2 | 21 | 7 | 0.00133 | 18 | RNF152 | ring finger protein 152 | 5' | 1155 |
| CGCATAAGGGGTGTGGC | 944 | 0 | 7 | 7 | 0.01683 | 18 | FBXO15 | F-box protein 15 | 3' | 23 |
| GAGAATAAATTACTGGG | 945 | 0 | 7 | 7 | 0.01683 | 18 | ZNF236 | zinc finger protein 236 | 5' | 1649 |
| TCCGGAGTTGGGACCTC | 946 | 2 | 22 | 7 | 0.00104 | 19 | Not Found | | | |
| CTCCGGCTTCAGTGGCC | 947 | 3 | 20 | 4 | 0.00474 | 19 | C19orf24 | chromosome 19 open reading frame 24 | 3' | 156 |
| AACGGGATCCGCACGGG | 948 | 3 | 21 | 5 | 0.0037 | 19 | APC2 | adenomatosis polyposis coli 2 | 3' | 18214 |
| GCCATCTCTTCGGGCGC | 949 | 6 | 0 | −9 | 0.00911 | 19 | KLF16 | BTE-binding protein 4 | 3' | 2472 |
| ACAGTAGCGCCCCCTCT | 950 | 0 | 13 | 13 | 0.00244 | 19 | MGC17791 | hypothetical protein MGC17791 | 5' | 57795 |
| ACAGTAGCGCCCCCTCT | 951 | 0 | 13 | 13 | 0.00244 | 19 | SEMA6B | semaphorin 6B isoform 1 precursor | 5' | 23231 |
| CTCCGAGGCGGCCACCC | 952 | 0 | 9 | 9 | 0.00623 | 19 | ARHGEF18 | Rho-specific guanine nucleotide exchange factor | 5' | 106295 |
| CTCCGAGGCGGCCACCC | 953 | 0 | 9 | 9 | 0.00623 | 19 | INSR | insulin receptor | 5' | 559 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| CCCTCTGCAAGCACCAC | 954 | 0 | 9 | 9 | 0.00623 | 19 | FLJ23420 | hypothetical protein FLJ23420 | 5' | 19155 |
| ATCGTAGCTCGCTGCAG | 955 | 0 | 10 | 10 | 0.03148 | 19 | FLJ23420 | hypothetical protein FLJ23420 | 5' | 75 |
| AAGGACGGGAGGGAGAA | 956 | 0 | 8 | 8 | 0.01239 | 19 | LASS4 | LAG1 longevity assurance homolog 4 | 5' | 60310 |
| AAGGACGGGAGGGAGAA | 957 | 0 | 8 | 8 | 0.01239 | 19 | FBN3 | fibrillin 3 precursor | 5' | 1561 |
| CAGACTTTAGTTTTGAA | 958 | 0 | 11 | 11 | 0.01852 | 19 | UBL5 | ubiquitin-like 5 | 5' | 197 |
| CAGACTTTAGTTTTGAA | 959 | 0 | 11 | 11 | 0.01852 | 19 | FBXL12 | F-box and leucine-rich repeat protein 12 | 5' | 8685 |
| GTCGTTCAGGGGCGTCT | 960 | 0 | 14 | 14 | 0.00122 | 19 | LOC90580 | hypothetical protein BC011833 | 3' | 349 |
| GCTCCAGCGATGATTGT | 961 | 0 | 11 | 11 | 0.01852 | 19 | ELAVL3 | ELAV-like protein 3 isoform 1 | 3' | 923 |
| ACCCTCGCGTGGGCCCC | 962 | 13 | 42 | 2 | 0.01177 | 19 | ZNF136 | zinc finger protein 136 (clone pHZ-20) | 5' | 89 |
| ACCCTCGCGTGGGCCCC | 963 | 13 | 42 | 2 | 0.01177 | 19 | ZNF625 | zinc finger protein 625 | 5' | 6300 |
| CCTCCCGCCCGGCCCGG | 964 | 2 | 13 | 4 | 0.02369 | 19 | SAMD1 | sterile alpha motif domain containing 1 | 5' | 889 |
| AGCCTGCAAAGGGGAGG | 965 | 0 | 50 | 50 | 0 | 19 | AKAP8L | A kinase (PRKA) anchor protein 8-like | 5' | 13794 |
| CAGAGGGAATAACCAGT | 966 | 0 | 12 | 12 | 0.01257 | 19 | KIAA1533 | KIAA1533 | 3' | 119 |
| ACCTCAAGCACGCGGTC | 967 | 0 | 8 | 8 | 0.01239 | 19 | KIAA1533 | KIAA1533 | 3' | 576 |
| TGATTGTGTGTGAGGCT | 968 | 0 | 16 | 16 | 0.0031 | 19 | Not Found | | | |
| ACGAGCACACTGAAAAG | 969 | 6 | 44 | 5 | 0.00004 | 19 | AKT2 | v-akt murine thymoma viral oncogene homolog 2 | 3' | 451 |
| TTGGGTTCGCTCAGCGG | 970 | 6 | 30 | 3 | 0.00501 | 19 | ASE-1 | CD3-epsilon-associated protein; antisense to | 5' | 1320 |
| TTGGGTTCGCTCAGCGG | 971 | 6 | 30 | 3 | 0.00501 | 19 | PPP1R13L | protein phosphatase 1, regulatory (inhibitor) | 5' | 11721 |
| CGTGGGAAACCTCGATG | 972 | 0 | 23 | 23 | $8.5 \times 10^{-5}$ | 19 | ASE-1 | CD3-epsilon-associated protein; antisense to | 5' | 1320 |
| CGTGGGAAACCTCGATG | 973 | 0 | 23 | 23 | $8.5 \times 10^{-5}$ | 19 | PPP1R13L | protein phosphatase 1, regulatory (inhibitor) | 5' | 11721 |
| AGACTAAACCCCCGAGG | 974 | 7 | 64 | 6 | 0 | 19 | ASE-1 | CD3-epsilon-associated protein; antisense to | 3' | 824 |
| CTGGTGGGAAGGTGGC | 975 | 2 | 20 | 7 | 0.0023 | 19 | SIX5 | sine oculis homeobox homolog 5 | 3' | 1102 |
| TACAGCTGCTGCAGCGC | 976 | 2 | 12 | 4 | 0.03293 | 19 | GRIN2D | N-methyl-D-aspartate receptor subunit 2D | 3' | 48538 |
| GTTTATTCCAAACACTG | 977 | 0 | 10 | 10 | 0.00467 | 19 | GRIN2D | N-methyl-D-aspartate receptor subunit 2D | 3' | 48538 |
| CTCACGACGCCGTGAAG | 978 | 33 | 96 | 2 | 0.00021 | 20 | SOX12 | SRY (sex determining region Y)-box 12 | 3' | 123 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| TCAGCCCAGCGGTATCC | 979 | 2 | 21 | 7 | 0.00133 | 20 | RRBP1 | ribosome binding protein 1 | 3' | 270 |
| GTTTACCCTCTGTCTCC | 980 | 7 | 56 | 5 | $1 \times 10^{-6}$ | 20 | RIN2 | RAB5 interacting protein 2 | 5' | 130452 |
| GAAAAGACTGCCCTCTG | 981 | 0 | 7 | 7 | 0.01683 | 20 | ZNF336 | zinc finger protein 336 | 5' | 2846 |
| GACAACGCGGGGAAGGA | 982 | 0 | 10 | 10 | 0.00467 | 20 | NAPB | N-ethylmaleimide-sensitive factor attachment | 3' | 859 |
| GCAAGGGCAGAGAAAG | 983 | 0 | 8 | 8 | 0.01239 | 20 | PDRG1 | p53 and DNA damage-regulated protein | 3' | 23 |
| GCTGAGAGCTGCGGGTG | 984 | 0 | 11 | 11 | 0.00359 | 20 | TSPYL3 | TSPY-like 3 | 3' | 38 |
| AGCAACTTTCCTGGGTC | 985 | 6 | 32 | 4 | 0.00258 | 20 | PLAGL2 | pleinmorphic adenoma gene-like 2 | 3' | 179 |
| CGCTCCCACGTCCGGGA | 986 | 0 | 16 | 16 | 0.00081 | 20 | SNTA1 | acidic alpha 1 syntrophin | 3' | 288 |
| CTTTCAAACTGGACCCG | 987 | 0 | 28 | 28 | $6.6 \times 10^{-5}$ | 20 | Not Found | | | |
| CGCGCAGCTCGCTGAGG | 988 | 2 | 21 | 7 | 0.00133 | 20 | Not Found | | | |
| GGATAGGGGTGGCCGGG | 989 | 0 | 24 | 24 | 0.00015 | 20 | MATN4 | matrilin 4 isoform 1 precursor | 3' | 11782 |
| CGCAACCCTGGCGACGC | 990 | 0 | 13 | 13 | 0.00244 | 20 | CDH22 | cadherin 22 precursor | 5' | 56203 |
| GGGAATAGGGGGGCGGG | 991 | 15 | 73 | 3 | $3 \times 10^{-6}$ | 20 | CDH22 | cadherin 22 precursor | 5' | 56203 |
| GGGGATTCTACCCTGGG | 992 | 10 | 54 | 4 | $3.9 \times 10^{-5}$ | 20 | ARFGEF2 | ADP-ribosylation factor guanine | 5' | 93944 |
| GGGGATTCTACCCTGGG | 993 | 10 | 54 | 4 | $3.9 \times 10^{-5}$ | 20 | PREX1 | PREX1 protein | 5' | 62 |
| CCTGCGCCGCCGCCCGG | 994 | 8 | 29 | 2 | 0.0267 | 20 | CEBPB | CCAAT/enhancer binding protein beta | 3' | 446 |
| ATCCCCGAGCTGCTGGA | 995 | 7 | 30 | 3 | 0.01035 | 20 | TMEPAI | transmembrane prostate androgen-induced protein | 3' | 277 |
| TCCAGAGGCCCGAGCTC | 996 | 8 | 26 | 2 | 0.02912 | 20 | PPP1R3D | protein phosphatase 1, regulatory subunit 3D | 3' | 627 |
| AAGCGGGGAGGCTGAGG | 997 | 0 | 19 | 19 | 0.00029 | 20 | OSBPL2 | oxysterol-binding protein-like protein 2 isoform | 3' | 254 |
| TGTCACAGACTCCCAGC | 998 | 8 | 38 | 3 | 0.00165 | 21 | USP25 | ubiquitin specific protease 25 | 5' | 664846 |
| TGTCACAGACTCCCAGC | 999 | 8 | 38 | 3 | 0.00165 | 21 | NRIP1 | receptor interacting protein 140 | 5' | 96802 |
| GAAATGTGGCCAGTGCA | 1000 | 0 | 7 | 7 | 0.01683 | 21 | SIM2 | single-minded homolog 2 long isoform | 3' | 48171 |
| AGTCCTTGCTGGGGTCC | 1001 | 0 | 18 | 18 | 0.00185 | 21 | PKNOX1 | PBX/knotted 1 homeobox 1 isoform 1 | 3' | 384 |
| ACCCTGAAAGCCTAGCC | 266 | 8 | 59 | 5 | $1 \times 10^{-6}$ | 21 | ITGB2 | integrin beta chain, beta 2 precursor | 5' | 10805 |

TABLE 7-continued

MSDK tags significantly (p <0.050) differentially present in N-STR-I7 and I-STR-7 MSDK libraries and genes associated with the MSDK tags.

| MSDK Tag | SEQ ID NO. | N-STR-I7 | I-STR-7 | Ratio I-STR-7/N-STR-I7 | P value | Chr | Gene | Description | Position of AscI site in relation to tr. Start | Distance of AscI site from tr. Start (bp) |
|---|---|---|---|---|---|---|---|---|---|---|
| AATGGAACTGACCACTG | 1003 | 9 | 36 | 3 | 0.00621 | 22 | TUBA8 | tubulin, alpha 8 | 5' | 44 |
| GGGGGCCTGCAGGGTGG | 1004 | 34 | 105 | 2 | $3.3 \times 10^{-5}$ | 22 | ARVCF | armadillo repeat protein | 3' | 720 |
| CCCACCAGGCACGTGGC | 1005 | 19 | 50 | 2 | 0.02718 | 22 | NPTXR | neuronal pentraxin receptor isoform 1 | 5' | 376 |
| GTGGCCGTGGACCCTGA | 1006 | 5 | 23 | 3 | 0.00997 | 22 | ATF4 | activating transcription factor 4 | 5' | 850 |
| GCCTCAGCATCCTCCTC | 1007 | 2 | 30 | 10 | $8.6 \times 10^{-5}$ | 22 | FLJ27365 | FLJ27365 protein | 5' | 24574 |
| GCCTCAGCATCCTCCTC | 1008 | 2 | 30 | 10 | $8.6 \times 10^{-5}$ | 22 | FLJ10945 | hypothetical protein FLJ10945 | 5' | 7284 |
| GCCCTGGGGTGTTATGG | 1009 | 2 | 26 | 9 | 0.00029 | 22 | FLJ27365 | FLJ27365 protein | 5' | 13829 |
| GCCCTGGGGTGTTATGG | 1010 | 2 | 26 | 9 | 0.00029 | 22 | FLJ10945 | hypothetical protein FLJ10945 | 5' | 18029 |
| AAGAGCCAGGCCACGGG | 1011 | 2 | 14 | 5 | 0.0165 | 22 | FLJ41993 | FLJ41993 protein | 5' | 2751 |
| GTTTCGAAATGAGCTCC | 1012 | 0 | 12 | 12 | 0.00296 | 23 | GPM6B | glycoprotein M6B isoform 1 | 3' | 267 |
| GAGATGCGCCTACGCCC | 1013 | 11 | 65 | 4 | $2 \times 10^{-6}$ | 23 | NHS | Nance-Horan syndrome protein | 3' | 274 |
| TAGTTCACTATCGCTTC | 1014 | 4 | 19 | 3 | 0.01426 | 23 | SH3KBP1 | SH3-domain kinase binding protein 1 | 3' | 346 |
| GGTCTCCTGAGGACCAG | 1015 | 4 | 19 | 3 | 0.01426 | 23 | Not Found | | | |
| ACTCATCCCTGAAGAGT | 1016 | 0 | 10 | 10 | 0.00467 | 23 | DDX3X | DEAD/H (Asp-Glu-Ala-Asp/His) box polypeptide 3 | 5' | 246 |
| CCTCAGATCAGGATGGG | 1017 | 2 | 20 | 7 | 0.0023 | 23 | NYX | nyctalopin | 5' | 4793 |
| GTCTGGTCGATGTTGCG | 1018 | 4 | 25 | 4 | 0.00186 | 23 | MID2 | midline 2 isoform 1 | 5' | 50400 |
| GTCTGGTCGATGTTGCG | 1019 | 4 | 25 | 4 | 0.00186 | 23 | DS1PI | delta sleep inducing peptide, immunorcactor | 5' | 42 |
| TAGTACTTTCAGGTAGG | 1020 | 0 | 9 | 9 | 0.00623 | 23 | UBE2A | ubiquitin-conjugating enzyme E2A isoform 2 | 3' | 285 |
| ATTTACACGGGGCTCAC | 1021 | 0 | 10 | 10 | 0.03148 | 23 | STAG2 | stromal antigen 2 | 5' | 1402 |
| GGGGCGAAGAAAGCAGA | 1022 | 3 | 26 | 6 | 0.00077 | 23 | STAG2 | stromal antigen 2 | 5' | 1402 |
| ATCCTGTCCCTGGCCTC | 1023 | 0 | 9 | 9 | 0.00623 | 23 | SLC6A8 | solute carrier family 6 (neurotransmitter | 3' | 89 |
| GCGGCAGCGGCGCCGGC | 1024 | 11 | 0 | -17 | 0.00314 | 23 | CXorf12 | chromosome X open reading frame 12 | 5' | 745 |
| GCGGCAGCGGCGCCGGC | 1025 | 11 | 0 | -17 | 0.00314 | 23 | HCFC1 | host cell factor C1 (VP16-accessory protein) | 5' | 7318 |
| GAAGCAAGAGTTTGGCC | 1026 | 2 | 62 | 21 | 0 | 23 | FLNA | filamin 1 (actin-binding protein-280) | 3' | 3103 |

The column headings are as in Table 2 except that the MSDK libraries compared are the N-STR-I7 and I-STR-7 MSDK libraries (See Table 3 for details of the tissues from which these libraries were made).

TABLE 8

MSDK tags significantly (p <0.050) differentially present in N-STR-117 and I-STR-17 MSDK libraries and genes associated with the MSDK tags.

| MSDK Tag | SEQ ID NO. | N-STR-I17 | I-STR-I17 | Ratio I-STR-I7/N-STR-I17 | P value | Chr | Gene | Description | Position of AscI site in relation to tr. Start | Distance of AscI site from tr. Start (bp) |
|---|---|---|---|---|---|---|---|---|---|---|
| AAGCTGCTGCGGCGGGC | 1027 | 5 | 0 | -7 | 0.0254984 | 1 | B3GALT6 | UDP-Gal: betaGal beta 1,3-galactosyltransferase | 3' | 335 |
| GCGCGGGAAGGGGTGGA | 1028 | 0 | 8 | 8 | 0.0316311 | 1 | SPEN | spen homolog, trans-regulator | 5' | 11971 |
| GTGGTCTTCAGAGGTAG | 1029 | 0 | 8 | 8 | 0.0316311 | 1 | TAL1 | T-cell acute lymphocytic leukemia 1 | 5' | 2571 |
| TCCGAACTTCCGGACCC | 1030 | 2 | 15 | 5 | 0.0037833 | 1 | Not Found | | | |
| GCCCAACCCCGGGGAGT | 1031 | 0 | 6 | 6 | 0.0179052 | 1 | P66beta | transcription repressor p66 beta component of | 5' | 117605 |
| TCTGGGGCCGGGTAGCC | 1032 | 28 | 53 | 1 | 0.0231777 | 1 | P66beta | transcription repressor p66 beta component of | 5' | 117605 |
| GCAGCGGCGCTCCGGGC | 1033 | 20 | 48 | 2 | 0.0034829 | 1 | MUC1 | mucin 1, transmembrane | 3' | 139119 |
| CTCTCACCCGAGGAGCG | 1034 | 0 | 9 | 9 | 0.0203814 | 2 | OACT2 | O-acyltransferase (membrane bound) domain | 3' | 47 |
| GCAGCATTGCGGCTCCG | 1035 | 25 | 58 | 2 | 0.0016016 | 2 | SIX2 | sine oculis homeobox homolog 2 | 5' | 160394 |
| TCATTGCATACTGAAGG | 1036 | 0 | 5 | 5 | 0.0308794 | 2 | SLC1A4 | solute carrier family 1, member 4 | 5' | 335302 |
| TCATTGCATACTGAAGG | 1037 | 0 | 5 | 5 | 0.0308794 | 2 | SERTAD2 | SERTA domain containing 2 | 5' | 245 |
| CCCCAGCTCGGCGGCGG | 1038 | 20 | 53 | 2 | 0.0006521 | 2 | TCF7L1 | HMG-box transcription factor TCF-3 | 3' | 859 |
| AAGCAGTCTTCGAGGGG | 1039 | 0 | 8 | 8 | 0.0072167 | 2 | CNNM3 | cyclin M3 isoform 1 | 5' | 396 |
| CCCCCACCCCCAGCCC | 1040 | 4 | 17 | 3 | 0.0100324 | 2 | TLK1 | tousled-like kinase 1 | 5' | 221 |
| TGTAAGGCGGCGGGGAG | 1041 | 3 | 15 | 4 | 0.0093236 | 2 | SP3 | Sp3 transcription factor | 3' | 1637 |
| ACTGCATCCGGCCTCGG | 1042 | 25 | 9 | -4 | 0.0116348 | 2 | PTMA | prothymosin, alpha (gene sequence 28) | 5' | 93674 |
| GGAGGCAAACGGGAACC | 1043 | 0 | 8 | 8 | 0.0316311 | 3 | IQSEC1 | IQ motif and Sec7 domain 1 | 5' | 315433 |
| CGGCGCGTCCCTGCCGG | 1044 | 21 | 44 | 2 | 0.0186262 | 3 | DKFZp313N0621 | hypothetical protein DKFZp313N0621 | 5' | 339665 |
| CCACTTCCCCATTGGTC | 1045 | 35 | 68 | 1 | 0.0057244 | 3 | ARMET | arginine-rich, mutated in early stage tumors | 5' | 633 |
| CCTGCCTCTGGCAGGGG | 1046 | 9 | 31 | 3 | 0.0025605 | 3 | PLXNA1 | plexin A1 | 5' | 5386 |
| CTCGGTGGCGGGACCGG | 1047 | 7 | 20 | 2 | 0.0253353 | 3 | SCHIP1 | schwannomin interacting protein 1 | 3' | 490368 |
| CGTGTGAGCTCTCCTGC | 1048 | 17 | 40 | 2 | 0.0105223 | 3 | EPHB3 | ephrin receptor EphB3 precursor | 3' | 576 |
| CCTGCGCCGGGGGAGGC | 1049 | 37 | 94 | 2 | 0.0000051 | 4 | ADRA2C | alpha-2C-adrenergic receptor | 3' | 432 |
| AAAGCACAGGCTCTCCC | 1050 | 0 | 5 | 5 | 0.0308794 | 4 | SLC4A4 | solute carrier family 4, sodium bicarbonate | 5' | 151833 |

TABLE 8-continued

MSDK tags significantly (p <0.050) differentially present in N-STR-117 and I-STR-17 MSDK libraries and genes associated with the MSDK tags.

| MSDK Tag | SEQ ID NO. | N-STR-I17 | I-STR-17 | Ratio I-STR-I7/ N-STR-I17 | P value | Chr | Gene | Description | Position of AscI site in relation to tr. Start | Distance of AscI site from tr. Start (bp) |
|---|---|---|---|---|---|---|---|---|---|---|
| TGCGGAGAAGACCCGGG | 1051 | 0 | 11 | 11 | 0.0056118 | 4 | ELOVL6 | ELOVL family member 6, elongation of long chain | 3' | 1583 |
| GGAGGTCTCAGGATCCC | 1052 | 0 | 14 | 14 | 0.0007408 | 5 | FLJ20152 | hypothetical protein FLJ20152 | 5' | 108193 |
| GCAGGCTGCAGGTTCCG | 1053 | 2 | 11 | 4 | 0.0248947 | 5 | RAI14 | retinoic acid induced 14 | 5' | 411295 |
| GCAGGCTGCAGGTTCCG | 1054 | 2 | 11 | 4 | 0.0248947 | 5 | C1QTNF3 | C1q and tumor necrosis factor related protein 3 | 5' | 201285 |
| CCCACTTTCAAAGGGGG | 1055 | 0 | 13 | 13 | 0.0008961 | 5 | FST | follistatin isoform FST344 precursor | 5' | 517 |
| CCCACTTTCAAAGGGGG | 1056 | 0 | 13 | 13 | 0.0008961 | 5 | MOCS2 | molybdopterin synthase large subunit MOCS2B | 5' | 370479 |
| CCGCTGGTGCACTCCGG | 1057 | 2 | 13 | 5 | 0.0080417 | 5 | TCF7 | transcription factor 7 (T-cell specific | 3' | 252 |
| CGTCTCCCATCCCGGGC | 1058 | 13 | 43 | 2 | 0.0003622 | 5 | CPLX2 | complexin 2 | 3' | 1498 |
| GCTGCGGCCCTCCGGGG | 1059 | 2 | 10 | 4 | 0.0363689 | 6 | ITPR3 | inositol 1,4,5-triphos-phate receptor, type 3 | 5' | 179 |
| GCTGCGGCCCTCCGGGG | 1060 | 2 | 10 | 4 | 0.0363689 | 6 | FLJ43752 | FLJ43752 protein | 5' | 28049 |
| GGTCTCCGAAGCGAGCG | 1061 | 0 | 6 | 6 | 0.0179052 | 6 | MDGA1 | MAM domain containing | 3' | 934 |
| GCAGCCGCTTCGGCGCC | 1062 | 16 | 36 | 2 | 0.023022 | 6 | EGFL9 | EGF-like-domain, multiple 9 | 3' | 134 |
| TCCATAGATTGACAAAG | 1063 | 12 | 3 | -5 | 0.0358865 | 6 | MARCKS | myristoylated alanine-rich protein kinase C | 3' | 3067 |
| GCGAGGGCCCAGGGGTC | 1064 | 15 | 48 | 2 | 0.0001996 | 7 | SLC29A4 | solute carrier family 29 (nucleoside | 3' | 67 |
| GTCCCCAGCACGCGGTC | 1065 | 2 | 15 | 5 | 0.0037833 | 7 | TBX20 | T-box transcription factor TBX20 | 5' | 607 |
| AACTTGGGGCTGACCGG | 1066 | 7 | 29 | 3 | 0.0007208 | 7 | AUTS2 | autism susceptibility candidate 2 | 3' | 1095850 |
| GGACGCGCTGAGTGGTG | 1067 | 0 | 6 | 6 | 0.0179052 | 7 | KIAA1862 | KIAA1862 protein | 5' | 148 |
| GGACGCGCTGAGTGGTG | 1068 | 0 | 6 | 6 | 0.0179052 | 7 | FLJ12700 | hypothetical protein FLJ12700 | 5' | 90181 |
| TAATTCGAGCACTTTGA | 1069 | 0 | 5 | 5 | 0.0308794 | 8 | FLJ20366 | hypothetical protein FLJ20366 | 5' | 1280 |
| AAGAGGCAGAACGTGCG | 1070 | 37 | 70 | 1 | 0.006975 | 8 | KCNK9 | potassium channel, subfamily K, member 9 | 3' | 360 |
| AGAGGAGCAGGAAGCGA | 1071 | 0 | 6 | 6 | 0.0179052 | 9 | PAX5 | paired box 5 | 3' | 48156 |
| TAAATAGGCGAGAGGAG | 1072 | 6 | 18 | 2 | 0.0274955 | 9 | FLJ46321 | FLJ46321 protein | 5' | 299849 |
| TAAATAGGCGAGAGGAG | 1073 | 6 | 18 | 2 | 0.0274955 | 9 | TLE1 | transducin-like en-hancer protein 1 | 5' | 241 |
| ATCGAGTGCGACGCCTG | 1074 | 4 | 14 | 3 | 0.0337426 | 9 | PHF2 | PHD finger protein 2 isoform b | 3' | 686 |

TABLE 8-continued

MSDK tags significantly (p <0.050) differentially present in N-STR-117 and I-STR-17 MSDK libraries and genes associated with the MSDK tags.

| MSDK Tag | SEQ ID NO. | N-STR-I17 | I-STR-17 | Ratio I-STR-I7/N-STR-I17 | P value | Chr | Gene | Description | Position of AscI site in relation to tr. Start | Distance of AscI site from tr. Start (bp) |
|---|---|---|---|---|---|---|---|---|---|---|
| GGCGTTAATAGAGAGGC | 1075 | 0 | 5 | 5 | 0.0308794 | 9 | PRDM12 | PR domain containing 12 | 5' | 5017 |
| CTCCCAGTACAGGAGCC | 1076 | 0 | 12 | 12 | 0.0036439 | 9 | RAPGEF1 | guanine nucleotide-releasing factor 2 isoform a | 5' | 2333 |
| GAGGACAGCCGGCTCGT | 1077 | 6 | 0 | -8 | 0.0154516 | 9 | LHX3 | LIM homeobox protein 3 isoform b | 3' | 4193 |
| CAGCCAGCTTTCTGCCC | 139 | 7 | 22 | 2 | 0.0114719 | 9 | LHX3 | LIM homeobox protein 3 isoform b | 5' | 146 |
| AGCCACCGTACAAGGCC | 1079 | 0 | 11 | 11 | 0.0056118 | 10 | PFKP | phosphofructokinase, platelet | 3' | 1056 |
| TGACGGCAAAAGCCGCC | 1080 | 0 | 8 | 8 | 0.0316311 | 10 | EGR2 | early growth response 2 protein | 3' | 1010 |
| TGGGAAAGGTCTTGTGG | 1081 | 0 | 20 | 20 | 0.0000356 | 10 | LZTS2 | leucine zipper, putative tumor suppressor 2 | 3' | 2691 |
| CCCCGTGGCGGGAGCGG | 1082 | 15 | 38 | 2 | 0.0074135 | 10 | NEURL | neuralized-like | 5' | 630 |
| CCCCGTGGCGGGAGCGG | 1083 | 15 | 38 | 2 | 0.0074135 | 10 | FAM26A | family with sequence similarity 26, member A | 5' | 14420 |
| TTGTGTGTACATAGGCC | 1084 | 0 | 8 | 8 | 0.0316311 | 10 | SORCS1 | SORCS receptor 1 isoform a | 5' | 1301646 |
| CGGAGCCGCCCCAGGGG | 1085 | 5 | 0 | -7 | 0.0254984 | 11 | RNH | ribonuclease/angiogenin inhibitor | 3' | 381 |
| TCTAGGACCTCCAGGCC | 1086 | 11 | 32 | 2 | 0.0064141 | 11 | SLC39A13 | solute carrier family 39 (zinc transporter) | 5' | 415 |
| TCTAGGACCTCCAGGCC | 1087 | 11 | 32 | 2 | 0.0064141 | 11 | SPI1 | spleen focus forming virus (SFFV) proviral | 5' | 29668 |
| GAGGCCTCTGAGGAGCG | 1088 | 0 | 9 | 9 | 0.0203814 | 11 | OVOL1 | OVO-like 1 binding protein | 5' | 452 |
| GAGGCCTCTGAGGAGCG | 1089 | 0 | 9 | 9 | 0.0203814 | 11 | DKFZp761E198 | hypothetical protein DKFZp761E198 | 5' | 6534 |
| CGCCCCTTCCGTGCGCC | 1090 | 0 | 7 | 7 | 0.0100816 | 11 | FBXL11 | F-box and leucine-rich repeat protein 11 | 5' | 454 |
| TCGGAGTCCCCGTCTCC | 1091 | 0 | 5 | 5 | 0.0308794 | 12 | ANKRD33 | ankyrin repeat domain 33 | 5' | 73619 |
| GCCTGGACGGCCTCGGG | 1092 | 5 | 21 | 3 | 0.003569 | 12 | CSRP2 | cysteine and glycine-rich protein 2 | 3' | 185 |
| ACTGTCTCCGCGAAGAG | 1093 | 4 | 16 | 3 | 0.0139338 | 12 | CSRP2 | cysteine and glycine-rich protein 2 | 3' | 185 |
| CGAACTTCCCGGTTCCG | 1094 | 14 | 46 | 2 | 0.0002219 | 12 | Not Found | | | |
| CAGCGGCCAAAGCTGCC | 1095 | 9 | 29 | 2 | 0.0029267 | 12 | RAN | ras-related nuclear protein | 5' | 257 |
| CAGCGGCCAAAGCTGCC | 1096 | 9 | 29 | 2 | 0.0029267 | 12 | EPIM | epimorphin isoform 2 | 5' | 32499 |
| TTTGCTACGTGTACATC | 1097 | 0 | 6 | 6 | 0.0179052 | 13 | RANBP5 | RAN binding protein 5 | 3' | 23155 |
| GCGGACGAGGCCCCGCG | 1098 | 0 | 5 | 5 | 0.0308794 | 13 | CUL4A | cullin 4A isoform 2 | 3' | 322 |

TABLE 8-continued

MSDK tags significantly (p <0.050) differentially present in N-STR-117 and I-STR-17 MSDK libraries and genes associated with the MSDK tags.

| MSDK Tag | SEQ ID NO. | N-STR-I17 | I-STR-17 | Ratio I-STR-I7/ N-STR-I17 | P value | Chr | Gene | Description | Position of AscI site in relation to tr. Start | Distance of AscI site from tr. Start (bp) |
|---|---|---|---|---|---|---|---|---|---|---|
| CCCCCAAGACACATCAA | 1099 | 0 | 10 | 10 | 0.0018237 | 14 | C14orf87 | chromosome 14 open reading frame 87 | 5' | 18535 |
| CCCCCAAGACACATCAA | 1100 | 0 | 10 | 10 | 0.0018237 | 14 | C14orf49 | chromosome 14 open reading frame 49 | 5' | 40614 |
| GGCCGGTGCCGCCAGTC | 1101 | 6 | 18 | 2 | 0.0274955 | 14 | EML1 | echinoderm microtubule associated protein like 1 | 5' | 62907 |
| GAGGCCAGCCTGAGGGC | 1102 | 0 | 5 | 5 | 0.0308794 | 14 | C14orf151 | chromosome 14 open reading frame 151 | 5' | 39104 |
| GAGGCCAGCCTGAGGGC | 1103 | 0 | 5 | 5 | 0.0308794 | 14 | FLJ42486 | FLJ42486 protein | 5' | 45756 |
| ACACCTGTGTCACCTGG | 1104 | 0 | 10 | 10 | 0.013797 | 15 | OCA2 | P protein | 3' | 2135 |
| GCTCTGCCCCGTGGCC | 1105 | 0 | 6 | 6 | 0.0179052 | 15 | BAHD1 | bromo adjacent homology domain containing 1 | 5' | 138 |
| CCCACCCCCACACCCCC | 1106 | 0 | 9 | 9 | 0.0203814 | 16 | CPNE2 | copine II | 5' | 179 |
| GCAGCCCCTTGGTGGAG | 1107 | 3 | 12 | 3 | 0.0408401 | 16 | TUBB3 | tubulin, beta, 4 | 3' | 843 |
| CCGTGTTGTCCTGCCCG | 1108 | 0 | 11 | 11 | 0.0013551 | 17 | MNT | MAx binding protein | 3' | 228 |
| AAGGTGAAGAAGGGCGG | 1109 | 6 | 18 | 2 | 0.0274955 | 17 | UNC119 | unc119 (Celegans) homolog isoform a | 3' | 355 |
| GCCGCGCACAGGCCGGT | 1110 | 12 | 26 | 2 | 0.0499764 | 17 | NF1 | neurofibromin | 3' | 603 |
| CCTACCTATCCCTGGAC | 1111 | 5 | 21 | 3 | 0.003569 | 17 | STAT5A | signal transducer and activator of transcription | 3' | 1085 |
| GCCTGACCCTTTTCTGC | 1112 | 0 | 8 | 8 | 0.0316311 | 17 | CBX2 | chromobox homolog 2 isoform 2 | 5' | 361 |
| ACCCGCACCATCCCGGG | 229 | 15 | 41 | 2 | 0.0026364 | 17 | CBX4 | chromobox homolog 4 | 5' | 4600 |
| CGCTATATTGGACCGCA | 1114 | 0 | 8 | 8 | 0.0316311 | 18 | KCTD1 | potassium channel tetramerisation domain | 3' | 90452 |
| GCCCGCGGGGCTGTCCC | 1115 | 0 | 6 | 6 | 0.0179052 | 18 | GALR1 | galanin receptor 1 | 5' | 146 |
| GCCCGCGGGGCTGTCCC | 1116 | 0 | 6 | 6 | 0.0179052 | 18 | MBP | myelin basic protein | 5' | 232612 |
| TCTCGGCGCAAGCAGGC | 1117 | 0 | 7 | 7 | 0.0100816 | 18 | SALL3 | sal-like 3 | 3' | 1008 |
| GCGGGTCGGGCCGGGGC | 1118 | 0 | 6 | 6 | 0.0179052 | 18 | NFATC1 | nuclear factor of activated T-cells, cytosolic | 3' | 4015 |
| CTAGAAGGGGTCGGGGA | 1119 | 17 | 36 | 2 | 0.0356297 | 19 | CALM3 | calmodulin 3 | 5' | 129594 |
| CTAGAAGGGGTCGGGGA | 1120 | 17 | 36 | 2 | 0.0356297 | 19 | FLJ10781 | hypothetical protein FLJ10781 | 5' | 140 |
| GCGGCCGCTCGGCAGCC | 1121 | 0 | 9 | 9 | 0.0055033 | 19 | GLTSCR1 | glioma tumor suppressor candidate region gene 1 | 5' | 70312 |
| GCGGCCGCTCGGCAGCC | 1122 | 0 | 9 | 9 | 0.0055033 | 19 | ZNF541 | zinc finger protein 541 | 5' | 63752 |
| GCTGCGGCCGGCCGGGG | 1123 | 5 | 16 | 2 | 0.0283658 | 19 | UBE2S | ubiquitin carrier protein | 5' | 478 |

TABLE 8-continued

MSDK tags significantly (p <0.050) differentially present in N-STR-117 and I-STR-17 MSDK libraries and genes associated with the MSDK tags.

| MSDK Tag | SEQ ID NO. | N-STR-I17 | I-STR-17 | Ratio I-STR-I7/N-STR-I17 | P value | Chr | Gene | Description | Position of AscI site in relation to tr. Start | Distance of AscI site from tr. Start (bp) |
|---|---|---|---|---|---|---|---|---|---|---|
| TCAGCCCAGCGGTATCC | 1124 | 2 | 11 | 4 | 0.0248947 | 20 | RRBP1 | ribosome binding protein 1 | 3' | 270 |
| GGGGATTCTACCCTGGG | 1125 | 3 | 26 | 6 | 0.0001076 | 20 | ARFGEF2 | ADP-ribosylation factor guanine | 5' | 93944 |
| GGGGATTGTACCCTGGG | 1126 | 3 | 26 | 6 | 0.0001076 | 20 | PREX1 | PREX1 protein | 5' | 62 |
| CCTGCGCCGCCGCCCGG | 1127 | 7 | 32 | 3 | 0.0002443 | 20 | CEBPB | CCAAT/enhancer binding protein beta | 3' | 446 |
| CTGGCCGCCGTGCTGGC | 1128 | 0 | 9 | 9 | 0.0203814 | 20 | TAF4 | TBP-associated factor 4 | 3' | 243 |
| ACCCTGAAAGCCTAGCC | 266 | 4 | 16 | 3 | 0.0139338 | 21 | ITGB2 | integrin beta chain, beta 2 precursor | 5' | 10805 |
| CTGGACAGAGCCCTCGG | 1130 | 0 | 10 | 10 | 0.013797 | 22 | TCF20 | transcription factor 20 isoform 2 | 5' | 128618 |
| CTGCCTGCGGAGGCACA | 1131 | 0 | 5 | 5 | 0.0308794 | 22 | CELSR1 | cadherin EGF LAG seven-pass G-type receptor 1 | 5' | 39397 |
| AAGAGCCAGGCCACGGG | 1132 | 4 | 16 | 3 | 0.0139338 | 22 | FLJ41993 | FLJ41993 protein | 5' | 2751 |
| GCGGCCGAGGCGACAGC | 1133 | 0 | 5 | 5 | 0.0308794 | 22 | CHKB | choline/ethanolamine kinase isoform b | 3' | 293 |
| CGGGGTGCCGAGCCCCG | 1134 | 0 | 6 | 6 | 0.0179052 | 22 | ACR | acrosin precursor | 5' | 63440 |
| CGGGGTGCCGAGCCCCG | 1135 | 0 | 6 | 6 | 0.0179052 | 22 | ARSA | arylsulfatase A precursor | 5' | 46630 |
| TGCAAGATACGCGGGGC | 1136 | 0 | 6 | 6 | 0.0 17905223 | | AMMECR1 | AMMECR1 protein | 3' | 72 |

The column headings are as in Table 2 except that the MSDK libraries compared are the N-STR-I17 and I-STR-17 MSDK libraries (See Table 3 for details of the tissues from which the libraries were made).

The comparison of myoepithelial cells isolated from normal breast tissue to those isolated from in situ carcinoma (DCIS) revealed some dramatic differences and indicated relative hypermethylation of the DCIS myoepithelial cells (Tables 9 and 10).

TABLE 9

Chromosomal location and analysis of the frequency of MSDK tags in the N-MYOEP-4 and D-MYOEP-6 MSDK libraries.

| Chr | Virtual Tag | Observed Tag | N-MYOEP-4 Variety | N-MYOEP-4 Copies | D-MYOEP-6 Variety | D-MYOEP-6 Copies | Tag Variety Ratio N-MYOEP-4/D-MYOEP-6 | Tag Copy Ratio N-MYOEP-4/D-MYOEP-6 | Differential Tag (P < 0.05) N-MYOEP-4 > D-MYOEP-6 | Differential Tag (P < 0.05) N-MYOEP-4 < D-MYOEP-6 |
|---|---|---|---|---|---|---|---|---|---|---|
| 1 | 551 | 164 | 131 | 833 | 96 | 529 | 1.365 | 1.575 | 4 | 1 |
| 2 | 473 | 122 | 97 | 874 | 72 | 524 | 1.347 | 1.668 | 4 | 0 |
| 3 | 349 | 96 | 81 | 812 | 62 | 529 | 1.306 | 1.535 | 2 | 0 |
| 4 | 281 | 88 | 66 | 464 | 50 | 313 | 1.320 | 1.482 | 3 | 1 |
| 5 | 334 | 100 | 81 | 644 | 59 | 362 | 1.373 | 1.779 | 6 | 0 |
| 6 | 338 | 88 | 72 | 391 | 49 | 252 | 1.469 | 1.552 | 2 | 1 |
| 7 | 403 | 122 | 99 | 651 | 80 | 435 | 1.238 | 1.497 | 2 | 3 |
| 8 | 334 | 96 | 80 | 513 | 53 | 302 | 1.509 | 1.699 | 2 | 0 |
| 9 | 349 | 103 | 90 | 743 | 60 | 507 | 1.500 | 1.465 | 3 | 1 |
| 10 | 387 | 116 | 104 | 573 | 58 | 361 | 1.793 | 1.587 | 2 | 2 |
| 11 | 379 | 119 | 96 | 514 | 70 | 330 | 1.371 | 1.558 | 2 | 0 |

TABLE 9-continued

Chromosomal location and analysis of the frequency of MSDK tags
in the N-MYOEP-4 and D-MYOEP-6 MSDK libraries.

| Chr | Virtual Tag | Observed Tag | N-MYOEP-4 Variety | N-MYOEP-4 Copies | D-MYOEP-6 Variety | D-MYOEP-6 Copies | Tag Variety Ratio N-MYOEP-4/ D-MYOEP-6 | Tag Copy Ratio N-MYOEP-4/ D-MYOEP-6 | Differential Tag (P < 0.05) N-MYOEP-4 > D-MYOEP-6 | Differential Tag (P < 0.05) N-MYOEP-4 < D-MYOEP-6 |
|---|---|---|---|---|---|---|---|---|---|---|
| 12 | 299 | 98 | 75 | 514 | 63 | 393 | 1.190 | 1.308 | 1 | 1 |
| 13 | 138 | 44 | 36 | 208 | 23 | 133 | 1.565 | 1.564 | 4 | 1 |
| 14 | 228 | 69 | 55 | 300 | 35 | 198 | 1.571 | 1.515 | 1 | 1 |
| 15 | 260 | 90 | 71 | 350 | 49 | 227 | 1.449 | 1.542 | 1 | 1 |
| 16 | 340 | 104 | 83 | 506 | 55 | 255 | 1.509 | 1.984 | 4 | 0 |
| 17 | 400 | 134 | 99 | 764 | 83 | 589 | 1.193 | 1.297 | 4 | 3 |
| 18 | 181 | 44 | 37 | 268 | 26 | 173 | 1.423 | 1.549 | 1 | 1 |
| 19 | 463 | 128 | 99 | 609 | 79 | 443 | 1.253 | 1.375 | 3 | 1 |
| 20 | 236 | 75 | 63 | 392 | 43 | 246 | 1.465 | 1.593 | 3 | 0 |
| 21 | 71 | 20 | 13 | 103 | 12 | 69 | 1.083 | 1.493 | 0 | 1 |
| 22 | 217 | 54 | 42 | 291 | 34 | 213 | 1.235 | 1.366 | 1 | 0 |
| X | 185 | 43 | 36 | 201 | 26 | 177 | 1.385 | 1.136 | 0 | 2 |
| Y | | 9 | | | | | | | | |
| Matches | 7205 | 2117 | 1706 | 11518 | 1237 | 7560 | 1.379 | 1.524 | 55 | 21 |
| No Matches | | 1571 | 793 | 5412 | 1010 | 5831 | 0.785 | 0.928 | 19 | 22 |
| Total | 7205 | 3688 | 2499 | 16930 | 2247 | 13391 | 1.112 | 1.264 | 74 | 43 |

The column headings are as indicated for Table 1.

TABLE 10

MSDK tags significantly differentially (p < 0.050) present in N-MYOEP-4 and D-MYOEP-6 MSDK libraries and genes associated with the MSDK tags.

| MSDK Tag | SEQ ID NO. | N-MYOEP-4 | D-MYOEP-6 | Ratio N/D | P value | Chr | Gene | Description | Position of AscI site in relation to tr. Start | Distance of AscI site from tr. Start (bp) |
|---|---|---|---|---|---|---|---|---|---|---|
| ATTAACCTTTGAAGCCC | 1137 | 17 | 3 | 4 | 0.009539 | 1 | SHREW1 | transmembrane protein SHREW1 | 3' | 687 |
| GCCTCTCTGCGCCTGCC | 1138 | 32 | 12 | 2 | 0.04196 | 1 | GFI1 | growth factor independent 1 | 3' | 4842 |
| CGCAAAAGCGGGCAGCC | 1139 | 9 | 0 | 9 | 0.008683 | 1 | DHX9 | DEAH (Asp-Glu-Ala-His) box polypeptide 9 isoform | 5' | 139 |
| CGCAAGAGGCGCAGGCA | 1140 | 0 | 5 | -6 | 0.029059 | 1 | WNT3A | wingless-type MMTV integration site family | 5' | 59111 |
| CGCAAGAGGCGCAGGCA | 1141 | 0 | 5 | -6 | 0.029059 | 1 | WNT9A | wingless-type MMTV integration site family | 5' | 41 |
| GAGCGGCCGCCCAGAGC | 1142 | 21 | 4 | 4 | 0.004625 | 1 | TAF5L | PCAF associated factor 65 beta | 3' | 192 |
| CCCCAGCTCGGCGGCGG | 1143 | 144 | 83 | 1 | 0.014399 | 2 | TCF7L1 | HMG-box transcription factor TCF-3 | 3' | 859 |
| AGAGTGACGTGCTGTGG | 1144 | 7 | 0 | 7 | 0.014679 | 2 | MERTK | c-mer proto-oncogene tyrosine kinase | 3' | 281 |
| AAATTCCATAGACAACC | 1145 | 16 | 0 | 16 | 0.000509 | 2 | HOXD4 | homeo box D4 | 3' | 1141 |
| TGTATTGCTTCTTCCCT | 1146 | 9 | 0 | 9 | 0.008683 | 2 | ITM2C | integral membrane protein 2C isoform 1 | 5' | 36609 |
| GGGCCGAGTCCGGCAGC | 1147 | 26 | 5 | 4 | 0.001331 | 3 | CHST2 | carbohydrate (N-acetylglucosamine-6-O) | 3' | 61 |
| CTCGGTGGCGGGACCGG | 1148 | 23 | 4 | 5 | 0.002085 | 3 | SCHIP1 | schwannomin interacting protein 1 | 3' | 490368 |

TABLE 10-continued

MSDK tags significantly differentially (p < 0.050) present in N-MYOEP-4 and D-MYOEP-6 MSDK libraries and genes associated with the MSDK tags.

| MSDK Tag | SEQ ID NO. | N-MYOEP-4 | D-MYOEP-6 | Ratio N/D | P value | Chr | Gene | Description | Position of AscI site in relation to tr. Start | Distance of AscI site from tr. Start (bp) |
|---|---|---|---|---|---|---|---|---|---|---|
| GCGGCGCCCTCTGCTGG | 1149 | 6 | 0 | 6 | 0.022859 | 4 | FLJ37478 | hypothetical protein FLJ37478 | 5' | 50272 |
| GCGGCGCCCTCTGCTGG | 1150 | 6 | 0 | 6 | 0.022859 | 4 | WHSC2 | Wolf-Hirschhorn syndrome candidate 2 protein | 5' | 565 |
| TGGCCCCCGCTGCCCGC | 1151 | 6 | 0 | 6 | 0.022859 | 4 | FLJ37478 | hypothetical protein FLJ37478 | 5' | 74 |
| TGGCCCCCGCTGCCCGC | 1152 | 6 | 0 | 6 | 0.022859 | 4 | WHSC2 | Wolf-Hirschhorn syndrome candidate 2 protein | 5' | 50763 |
| AGCCACCTGCGCCTGGC | 1153 | 7 | 17 | -3 | 0.04018 | 4 | PAQR3 | progestin and adipoQ receptor family member III | 5' | 101 |
| CTTAGATCTAGCGTTCC | 1154 | 21 | 7 | 2 | 0.03636 | 4 | DKFZP564J102 | DKFZP564J102 protein | 5' | 4 |
| GGAGGTCTGAGGATGCC | 1155 | 13 | 0 | 13 | 0.006039 | 5 | FLJ20152 | hypothetical protein FLJ20152 | 5' | 108193 |
| TGACAGGCGTGCGAGCC | 1156 | 28 | 7 | 3 | 0.003434 | 5 | MGC33648 | hypothetical protein MGC33648 | 5' | 92617 |
| TGACAGGCGTGCGAGCC | 1157 | 28 | 7 | 3 | 0.003434 | 5 | FLJ11795 | hypothetical protein FLJ11795 | 5' | 699674 |
| CCTACGGCTACGGCCCC | 1158 | 6 | 0 | 6 | 0.022859 | 5 | FOXD1 | forkhead box D1 | 3' | 1974 |
| CCACTACTTAAGTTTAC | 1159 | 6 | 0 | 6 | 0.022859 | 5 | UNQ9217 | AASA9217 | 3' | 335 |
| CTGGGTTGCGATTAGCT | 1160 | 23 | 6 | 3 | 0.009778 | 5 | PPIC | peptidylprolyl isomerase C | 5' | 62181 |
| GTTTCTTCCCGCCCATC | 1161 | 26 | 6 | 3 | 0.003292 | 5 | PHF15 | PHD finger protein 15 | 3' | 1577 |
| TGGTTTACCTTGGCATA | 252 | 11 | 0 | 11 | 0.002278 | 6 | FOXF2 | forkhead box F2 | 5' | 6373 |
| CAACCCACGGGCAGGTG | 110 | 0 | 6 | -8 | 0.01482 | 6 | TAGAP | T-cell activation Rho GTPase-activating protein | 5' | 123822 |
| AAACAGGCGTGCGGGAG | 1164 | 7 | 0 | 7 | 0.014679 | 6 | T | transcription factor T | 3' | 1509 |
| ACAAAAATGATCGTTCT | 1165 | 3 | 12 | -5 | 0.022893 | 7 | PLEKHA8 | pleckstrin homology domain containing, family A | 3' | 159 |
| GTCCCCAGCACGCGGTC | 1166 | 21 | 5 | 3 | 0.009372 | 7 | TBX20 | T-box transcription factor TBX20 | 5' | 607 |
| CACTAGACCTGCCTGAG | 1167 | 18 | 5 | 3 | 0.028555 | 7 | DLX5 | distal-less homeo box 5 | 3' | 3450 |
| TCTGGGGGCAAATACGT | 1168 | 0 | 7 | -9 | 0.030903 | 7 | CAV1 | caveolin 1 | 3' | 1501 |
| AGTATCAAAACGGCAGC | 1169 | 0 | 6 | -8 | 0.01482 | 7 | Not Found | | | |
| CGAGGAAGTGACCCTCG | 1170 | 6 | 0 | 6 | 0.022859 | 8 | CHD7 | chromodomain helicase DNA binding protein 7 | 5' | 156 |
| CGGCTTCCCAGGCCCAC | 1171 | 19 | 4 | 4 | 0.008734 | 8 | FLJ43860 | FLJ43860 protein | 5' | 11074 |
| CAGCGCTACGCGCGGGG | 1172 | 6 | 0 | 6 | 0.022859 | 9 | EPB41L4B | erythrocyte membrane protein band 4.1 like 4B | 3' | 1346 |

TABLE 10-continued

MSDK tags significantly differentially (p < 0.050) present in N-MYOEP-4 and D-MYOEP-6 MSDK libraries and genes associated with the MSDK tags.

| MSDK Tag | SEQ ID NO. | N-MYOEP-4 | D-MYOEP-6 | Ratio N/D | P value | Chr | Gene | Description | Position of AscI site in relation to tr. Start | Distance of AscI site from tr. Start (bp) |
|---|---|---|---|---|---|---|---|---|---|---|
| GTGGGGGGCGACCTGTC | 1173 | 21 | 4 | 4 | 0.004625 | 9 | RGS3 | regulator of G-protein signalling 3 isoform 6 | 3' | 1569 |
| TACGCGGGTGGGGGAGA | 1174 | 3 | 14 | -6 | 0.007269 | 9 | ADAMTS13 | a disintegrin-like and metalloprotease | 3' | 6658 |
| AGCCCCCCATTGAAAAG | 1175 | 6 | 0 | 6 | 0.022859 | 9 | OLFM1 | olfactomedin related ER localized protein | 3' | 13681 |
| AAGAGCAAATAAGAGGC | 1176 | 0 | 9 | -11 | 0.013226 | 10 | KI1AA0934 | KIAA0934 | 3' | 138 |
| CTTTTTTTTTCTTTTAA | 1177 | 0 | 7 | -9 | 0.006886 | 10 | MLLT10 | myeloid/lymphoid or mixed-lineage leukemia | 5' | 6870 |
| CTTTTTTTTTCTTTTAA | 1178 | 0 | 7 | -9 | 0.006886 | 10 | FLJ45187 | FLJ45187 protein | 5' | 1620 |
| GAAGCGCTGACGCTGTG | 1179 | 10 | 0 | 10 | 0.021759 | 10 | GRID1 | glutamate receptor, ionotropic, delta 1 | 3' | 1043 |
| GTTACGCGCCTGCCTCC | 1180 | 7 | 0 | 7 | 0.014679 | 10 | GPR123 | G protein-coupled receptor 123 | 3' | 17484 |
| CCAGCCCGGGCCCGGGG | 1181 | 6 | 0 | 6 | 0.022859 | 11 | FDX1 | ferredoxin 1 precursor | 5' | 133525 |
| CCAGCCCGGGCCCGGGG | 1182 | 6 | 0 | 6 | 0.022859 | 11 | RDX | radixin | 5' | 16634 |
| GCTCAGAGGCGCTGGAA | 1183 | 18 | 5 | 3 | 0.028555 | 11 | ZBTB16 | zinc finger and BTB domain containing 16 | 3' | 913 |
| CCACGTCTTAGCACTCT | 1184 | 9 | 0 | 9 | 0.008683 | 12 | DDXI1 | DEAD/H (Asp-Glu-Ala-Asp/His) box polypeptide 11 | 5' | 277542 |
| CCACGTCTTAGCACTCT | 1185 | 9 | 0 | 9 | 0.008683 | 12 | C1QDC1 | C1q domain containing 1 isoform 2 | 5' | 41819 |
| AAGGCTGGGAGTTTTCT | 1186 | 6 | 20 | -4 | 0.005935 | 12 | ABCB9 | ATP-binding cassette, sub-family B (MDR/TAP) | 3' | 517 |
| CAGCATTGTTTTCACCA | 1187 | 0 | 7 | -9 | 0.030903 | 13 | SGCG | gamma sarcoglycan | 5' | 20979 |
| GGCTTCGGCCCAGGGTG | 1188 | 8 | 0 | 8 | 0.011061 | 13 | PABPC3 | poly(A) binding protein, cytoplasmic 3 | 5' | 77913 |
| GGCTTCGGCCCAGGGTG | 1189 | 8 | 0 | 8 | 0.011061 | 13 | CENPJ | centromere protein J | 5' | 95344 |
| CATTCCTTGCGTGGCTC | 1190 | 7 | 0 | 7 | 0.014679 | 13 | CDX2 | caudal type homeo box transcription factor 2 | 3' | 1338 |
| GTGACCCCGCCCCTCC | 1191 | 6 | 0 | 6 | 0.022859 | 13 | FOXO1A | forkhead box O1A | 3' | 37 |
| TTTGCTACGTGTACATC | 1192 | 7 | 0 | 7 | 0.014679 | 13 | RANBP5 | RAN binding protein 5 | 3' | 23155 |
| GCCACGAGCCCTAGCGG | 1193 | 0 | 6 | -8 | 0.01482 | 14 | FLJ10357 | hypothetical protein FLJ10357 | 5' | 22 |
| GCCCCACGCCCCCTGGC | 1194 | 29 | 8 | 3 | 0.004647 | 14 | C14orf153 | chromosome 14 open reading frame 153 | 5' | 681 |
| GCCCCACGCCCCCTGGC | 1195 | 29 | 8 | 3 | 0.004647 | 14 | BAG5 | BCL2-associated athanogene 5 | 5' | 19 |
| AGAGCTGAGTCTCACCC | 1196 | 5 | 14 | -4 | 0.042959 | 15 | CDAN1 | codanin 1 | 3' | 359 |
| GAGCTGCCTGCTTCCCC | 1197 | 13 | 3 | 3 | 0.037287 | 15 | SIN3A | transcription co-repressor Sin3A | 5' | 2969 |
| CAGGACGACTCAAAGGC | 1198 | 6 | 0 | 6 | 0.022859 | 16 | ATP6V0C | ATPase, H' transporting, lysosomal, V0 subunit | 5' | 17685 |

TABLE 10-continued

MSDK tags significantly differentially (p < 0.050) present in N-MYOEP-4 and D-MYOEP-6 MSDK libraries and genes associated with the MSDK tags.

| MSDK Tag | SEQ ID NO. | N-MYOEP-4 | D-MYOEP-6 | Ratio N/D | P value | Chr | Gene | Description | Position of AscI site in relation to tr. Start | Distance of AscI site from tr. Start (bp) |
|---|---|---|---|---|---|---|---|---|---|---|
| CGATTCGAACCCAGGGG | 1199 | 42 | 13 | 3 | 0.003577 | 16 | IRX6 | iroquois homeobox protein 6 | 5' | 386305 |
| GTGCAGTCTCGGCCCGG | 1200 | 33 | 2 | 13 | 0.00001 | 16 | FBXL8 | F-box and leucine-rich repeat protein 8 | 3' | 3905 |
| TTTGCTTAGAGCCCAGC | 1201 | 6 | 0 | 6 | 0.022859 | 16 | SLC7A6 | solute carrier family 7 (cationic amino acid) | 3' | 74 |
| CCTACCTATCCCTGGAC | 1202 | 21 | 5 | 3 | 0.009372 | 17 | STAT5A | signal transducer and activator of transcription | 3' | 1085 |
| GCTATGGGTCGGGGGAG | 215 | 0 | 29 | -37 | 0 | 17 | SOST | sclerostin recursor | 3' | 3140 |
| CTGACGGGCACCGAGCC | 1204 | 6 | 0 | 6 | 0.022859 | 17 | TBX21 | T-box 21 | 3' | 715 |
| CCCCGTTTTTGTGAGTG | 221 | 10 | 24 | -3 | 0.0135 | 17 | HOXB9 | homeo box B9 | 5' | 20620 |
| GCCCAAAAGGAGAATGA | 1206 | 5 | 16 | -4 | 0.01586 | 17 | PHOSPHO1 | phosphatase, orphan 1 | 3' | 5786 |
| GCCCGGCGGGCCTCCGG | 1207 | 6 | 0 | 6 | 0.022859 | 17 | CD300A | leukocyte membrane antigen | 5' | 12316 |
| CCCCTGCCCTGTCACCC | 226 | 28 | 0 | 28 | 0.000028 | 17 | SLC9AR1 | solute carrier family 9 (sodium/hydrogen) | 3' | 11941 |
| GAAAAGTTGAACTCCTG | 1209 | 0 | 6 | -8 | 0.01482 | 18 | C18orf1 | chromosome 18 open reading frame 1 isoform alpha | 3' | 20803 |
| GTGGAGGGAGGTACTG | 1210 | 12 | 0 | 12 | 0.008257 | 18 | IER3IP1 | immediate early response 3 interacting protein | 5' | 70905 |
| CGTGCGCCCGGGCTGGC | 1211 | 7 | 0 | 7 | 0.014679 | 19 | UHRF1 | ubiquitin-like, containing PHD and RING finger | 5' | 1499 |
| CGTGCGCCCGGGCTGGC | 1212 | 7 | 0 | 7 | 0.014679 | 19 | M6PRBP1 | mannose 6 phosphate receptor binding protein 1 | 5' | 41638 |
| ATCGTAGCTCGCTGCAG | 1213 | 0 | 5 | -6 | 0.029059 | 19 | FLJ23420 | hypothetical protein FLJ23420 | 5' | 75 |
| CACGAAGCCGCCGGGCC | 1214 | 6 | 0 | 6 | 0.022859 | 19 | KLF2 | Kruppel-like factor | 3' | 540 |
| TTCGGCCCCATCCCTCG | 313 | 22 | 0 | 22 | 0.000068 | 19 | CDC42EP5 | CDC42 effector protein 5 | 3' | 8020 |
| GACAGACCCGGTCCCTG | 1216 | 6 | 0 | 6 | 0.022859 | 20 | RRBP1 | ribosome binding protein 1 | 3' | 270 |
| TCCAGAGGCCCGAGCTC | 1217 | 24 | 8 | 2 | 0.024137 | 20 | PPP1R3D | protein phosphatase 1, regulatory subunit 3D | 3' | 627 |
| CTTCGACTCCGGAGGCC | 1218 | 7 | 0 | 7 | 0.014679 | 20 | CDH4 | cadherin 4, type 1 preproprotein | 5' | 490627 |
| CAATCACGAATTTGTTA | 1219 | 0 | 5 | -6 | 0.029059 | 21 | HMGN1 | high-mobility group nucleosome binding domain 1 | 3' | 131 |
| CACCGGGCGCAGTAGCG | 1220 | 27 | 9 | 2 | 0.016802 | 22 | Not Found | | | |
| GGTCTCCTGAGGACCAG | 1221 | 0 | 8 | -10 | 0.021437 | 23 | Not Found | | | |

TABLE 10-continued

MSDK tags significantly differentially (p < 0.050) present in N-MYOEP-4 and D-MYOEP-6 MSDK libraries and genes associated with the MSDK tags.

| MSDK Tag | SEQ ID NO. | N-MYOEP-4 | D-MYOEP-6 | Ratio N/D | P value | Chr | Gene | Description | Position of AscI site in relation to tr. Start | Distance of AscI site from tr. Start (bp) |
|---|---|---|---|---|---|---|---|---|---|---|
| CTCGCATAAAGGCCACC | 1222 | 0 | 7 | -9 | 0.0068862 | 3 | LAMP2 | lysosomal-associated membrane protein 2 | 5' | 16644 |

The column headings are as in Table 2 except that the MSDK libraries are the N-MYOBP-4 and D-MYOEP-6 MSDK libraries (see Table 3 for details of the tissues from which the libraries were made).

Besides identifying epigenetic differences between normal and tumor tissue, cell type-specific differences in methylation patterns were seen by comparing MSDK libraries generated from normal epithelial and normal myoepithelial cells (Tables 11 and 12). Epithelial and myoepithelial cells are thought to originate from a common bi-potential progenitor cell [Bocker et al. (2002) Lab. Invest. 82:737-746]. The methylation differences observed between these two cell types raise the possibility of their different clonal origin or epigenetic reprogramming of the cells during lineage specific differentiation. Indeed, during embryonic development, epigenetic changes are known to occur in a cell lineage specific manner and play a role in differentiation [Kremenskoy et al. (2003) Biochem. Biophys. Res. Commun. 311:884-890].

TABLE 11

Chromosomal location analysis of the frequency of MSDK tags in the N-MYOEP-4 and N-EPI-I7 MSDK libraries.

| Chr | Virtual Tags | Observed Tags | N-MYOEP-4 | | N-EPI-I7 | | Tag Variety Ratio N-MYOEP-4/N-EPI-I7 | Tag Copy Ratio N-MYOEP-4/N-EPI I7 | Differential Tag (P < 0.05) | |
|---|---|---|---|---|---|---|---|---|---|---|
| | | | Variety | Copies | Variety | Copies | | | N-MYOEP-4 > N-EPI-I7 | N-MYOEP-4 < N-EPI-I7 |
| 1 | 551 | 163 | 131 | 833 | 98 | 496 | 1.337 | 1.679 | 4 | 2 |
| 2 | 473 | 112 | 97 | 874 | 62 | 517 | 1.565 | 1.691 | 6 | 1 |
| 3 | 349 | 101 | 81 | 812 | 58 | 535 | 1.397 | 1.518 | 2 | 1 |
| 4 | 281 | 80 | 66 | 464 | 42 | 244 | 1.571 | 1.902 | 1 | 2 |
| 5 | 334 | 99 | 81 | 644 | 55 | 399 | 1.473 | 1.614 | 4 | 4 |
| 6 | 338 | 89 | 72 | 391 | 50 | 245 | 1.440 | 1.596 | 1 | 1 |
| 7 | 403 | 116 | 99 | 651 | 61 | 340 | 1.623 | 1.915 | 5 | 2 |
| 8 | 334 | 97 | 80 | 513 | 51 | 300 | 1.569 | 1.710 | 1 | 2 |
| 9 | 349 | 106 | 90 | 743 | 60 | 405 | 1.500 | 1.835 | 8 | 0 |
| 10 | 387 | 121 | 104 | 573 | 59 | 378 | 1.763 | 1.516 | 2 | 4 |
| 11 | 379 | 113 | 96 | 514 | 69 | 327 | 1.391 | 1.572 | 1 | 4 |
| 12 | 299 | 93 | 75 | 514 | 49 | 331 | 1.531 | 1.553 | 1 | 0 |
| 13 | 138 | 38 | 36 | 208 | 20 | 108 | 1.800 | 1.926 | 1 | 1 |
| 14 | 228 | 63 | 55 | 300 | 28 | 165 | 1.964 | 1.818 | 1 | 0 |
| 15 | 260 | 84 | 71 | 350 | 40 | 158 | 1.775 | 2.215 | 1 | 0 |
| 16 | 340 | 103 | 83 | 506 | 55 | 279 | 1.509 | 1.814 | 1 | 1 |
| 17 | 400 | 124 | 99 | 764 | 70 | 496 | 1.414 | 1.540 | 4 | 2 |
| 18 | 181 | 42 | 37 | 268 | 19 | 125 | 1.947 | 2.144 | 3 | 1 |
| 19 | 463 | 130 | 99 | 609 | 83 | 388 | 1.193 | 1.570 | 4 | 2 |
| 20 | 236 | 75 | 63 | 392 | 38 | 244 | 1.658 | 1.607 | 2 | 0 |
| 21 | 71 | 14 | 13 | 103 | 8 | 69 | 1.625 | 1.493 | 0 | 0 |
| 22 | 217 | 49 | 42 | 291 | 31 | 205 | 1.355 | 1.420 | 0 | 1 |
| X | 185 | 39 | 36 | 201 | 19 | 116 | 1.895 | 1.733 | 0 | 1 |
| Y | 9 | | | | | | | | | |
| Matches | 7205 | 2051 | 1706 | 11518 | 1125 | 6870 | 1.516 | 1.677 | 53 | 32 |
| No Matches | | 1532 | 793 | 5412 | 930 | 4463 | 0.853 | 1.213 | 34 | 29 |
| Total | 7205 | 3583 | 2499 | 16930 | 2055 | 11333 | 1.216 | 1.494 | 87 | 61 |

The column headings are as indicated for Table 1.

TABLE 12

MSDK tags significantly (p < 0.050) differentially present in N-MYOEP4 and N-EPI-I7 MSDK libraries and genes associated with the MSDK tags.

| MSDK Tag | SEQ ID NO. | N-MYOEP-4 | N-EPI-I7 | Ratio N-MYOEP-4/N-EPI-I7 | P value | Chr | Gene | Description | Position of AscI site in relation to tr. Start | Distance of AscI site from tr. Start (bp) |
|---|---|---|---|---|---|---|---|---|---|---|
| AGCACCCGCCTGGAACC | 223 | 3 | 13 | −6 | 0.008872 | 1 | PTPRF | protein tyrosine phosphatase, receptor type, F | 3' | 727 |
| TCCGAACTTCCGGACCC | 224 | 10 | 0 | 10 | 0.004784 | 1 | Not Found | | | |
| TCTGGGGCCGGGTAGCC | 225 | 36 | 9 | 3 | 0.007572 | 1 | P66beta | transcription repressor p66 beta component of | 5' | 117605 |
| GCAGCGGCGCTCCGGGC | 226 | 38 | 9 | 3 | 0.004154 | 1 | MUC1 | mucin 1, transmembrane | 3' | 139119 |
| AGCCCTCGGGTGATGAG | 29 | 27 | 7 | 3 | 0.012636 | 1 | LMX1A | LIM homeobox transcription factor 1, alpha | 5' | 752 |
| ACGTTTTTAACTACACA | 228 | 0 | 11 | −16 | 0.003192 | 1 | ELK4 | ELK4 protein isoform a | 3' | 621 |
| GCCACCCAAGCCCGTCG | 229 | 11 | 0 | 11 | 0.003665 | 2 | RAB10 | ras-related GTP-binding protein RAB10 | 5' | 106 |
| GCCACCCAAGCCCGTCG | 230 | 11 | 0 | 11 | 0.003665 | 2 | KIF3C | kinesin family member 3C | 5' | 51464 |
| GCAGCATTGCGGCTCCG | 231 | 102 | 42 | 2 | 0.00343 | 2 | SIX2 | sine oculis homeobox homolog 2 | 5' | 160394 |
| CACACAAGGCGCCCGCG | 232 | 17 | 4 | 3 | 0.039281 | 2 | SIX2 | sine oculis homeobox homolog 2 | 5' | 160394 |
| CTGGAGCTCAGCACTGA | 233 | 10 | 0 | 10 | 0.032551 | 2 | Not Found | | | |
| CCCCAGCTCGGCGGCGG | 234 | 144 | 76 | 1 | 0.038423 | 2 | TCF7L1 | HMG-box transcription factor TCF-3 | 3' | 859 |
| CGTGGCCGGTCAGTGCC | 235 | 7 | 0 | 7 | 0.016949 | 2 | ARHGEF4 | Rho guanine nucleotide exchange factor 4 isoform | 3' | 123018 |
| GGCGCCAGAGGAAGATC | 236 | 6 | 16 | −4 | 0.021688 | 2 | SSB | autoantigen La | 5' | 29950 |
| CGGCGGGGCAGCCGACG | 237 | 19 | 4 | 3 | 0.018727 | 3 | CCR4 | chemokine (C-C motif) receptor 4 | 5' | 133333 |
| CGGCGCGTCCCTGCCGG | 238 | 75 | 33 | 2 | 0.031796 | 3 | DKFZp313N0621 | hypothetical protein DKFZp313N0621 | 5' | 339665 |
| CACACCCCGCCCCCAGC | 239 | 0 | 39 | −58 | 0 | 3 | ACTR8 | actin-related protein 8 | 3' | 338 |
| TGCGGCGCGGGCGGCC | 240 | 11 | 0 | 11 | 0.018565 | 4 | ZFYVE28 | zinc finger, FYVE domain containing 28 | 3' | 107 |
| GTCCGTGGAATAGAAGG | 241 | 0 | 8 | −12 | 0.002774 | 4 | Not Found | | | |
| TTTCTTTTATGCAGTTC | 242 | 0 | 8 | −12 | 0.002774 | 4 | CAMK2D | calcium/calmodulin-dependent protein kinase II | 5' | 26 |

TABLE 12-continued

MSDK tags significantly (p < 0.050) differentially present in N-MYOEP4 and N-EPI-I7 MSDK libraries and genes associated with the MSDK tags.

| MSDK Tag | SEQ ID NO. | N-MYOEP-4 | N-EPI-I7 | Ratio N-MYOEP-4/N-EPI-I7 | P value | Chr | Gene | Description | Position of AscI site in relation to tr. Start | Distance of AscI site from tr. Start (bp) |
|---|---|---|---|---|---|---|---|---|---|---|
| ATTTAGTTCTTGTTTTG | 243 | 0 | 5 | -7 | 0.026319 | 5 | NPR3 | natriuretic peptide receptor C/guanylate cyclase | 5' | 304 |
| TGACAGGCGTGCGAGCC | 244 | 28 | 2 | 9 | 0.000182 | 5 | MGC33648 | hypothetical protein MGC33648 | 5' | 92617 |
| TGACAGGCGTGCGAGCC | 245 | 28 | 2 | 9 | 0.000182 | 5 | FLJ11795 | hypothetical protein FLJ11795 | 5' | 699674 |
| ACCCGGGCCGCAGCGGC | 246 | 3 | 13 | -6 | 0.008872 | 5 | EFNA5 | ephrin-A5 | 3' | 1019 |
| CGGCCGCTCAGCAACTT | 247 | 0 | 8 | -12 | 0.015444 | 5 | KCNN2 | small conductance calcium-activated potassium | 3' | 832 |
| ACACATTTATTTTTCAG | 248 | 5 | 15 | -4 | 0.01736 | 5 | KIAA1961 | KIAA1961 protein isoform 1 | 3' | 146 |
| TCTCTTGGGGAGATGGG | 249 | 7 | 0 | 7 | 0.016949 | 5 | PACAP | proapoptotic caspase adaptor protein | 5' | 4496 |
| CTGACCGCGCTCGCCCC | 91 | 26 | 0 | 26 | 0.000147 | 5 | PACAP | proapoptotic caspase adaptor protein | 5' | 4496 |
| TCCGACAAGAAGCCGCC | 251 | 14 | 0 | 14 | 0.007231 | 5 | MSX2 | msh homeo box homolog 2 | 3' | 605 |
| TGGTTTACCTTGGCATA | 252 | 11 | 0 | 11 | 0.003665 | 6 | FOXF2 | forkhead box F2 | 5' | 6373 |
| AAGGAGACCGCACAGGG | 253 | 3 | 10 | -5 | 0.042045 | 6 | HTR1E | 5-hydroxytrypta-mine (serotonin) receptor 1E | 5' | 97 |
| AAGGAGACCGCACAGGG | 254 | 3 | 10 | -5 | 0.042045 | 6 | SYNCRIP | synaptotagmin binding, cytoplasmic RNA | 5' | 1294285 |
| GGGGGGGAACCGGACCG | 255 | 15 | 0 | 15 | 0.000992 | 7 | ACTB | beta actin | 3' | 865 |
| GTGCGGCCGCCGCGGCC | 256 | 15 | 3 | 3 | 0.029313 | 7 | C7orf26 | chromosome 7 open reading frame 26 | 5' | 362 |
| AACTTGGGGCTGACCGG | 257 | 19 | 0 | 19 | 0.001464 | 7 | AUTS2 | autism susceptibility candidate 2 | 3' | 1095850 |
| CCTTGACTGCCTCCATC | 258 | 22 | 5 | 3 | 0.014564 | 7 | WBSCR17 | Williams Beuren syndrome chromosome region 17 | 5' | 512 |
| TAAAATAAACTCAGGAC | 259 | 0 | 7 | -10 | 0.030545 | 7 | SEMA3C | semaphorin 3C | 3' | 214 |
| CACTAGACCTGCCTGAG | 260 | 18 | 3 | 4 | 0.009065 | 7 | DLX5 | distal-less homeo box 5 | 3' | 3450 |
| AGTATCAAAACGGCAGC | 261 | 0 | 5 | -7 | 0.026319 | 7 | Not Found | | | |

TABLE 12-continued

MSDK tags significantly (p < 0.050) differentially present in N-MYOEP4 and N-EPI-I7 MSDK libraries and genes associated with the MSDK tags.

| MSDK Tag | SEQ ID NO. | N-MYOEP-4 | N-EPI-I7 | Ratio N-MYOEP-4/N-EPI-I7 | P value | Chr | Gene | Description | Position of AscI site in relation to tr. Start | Distance of AscI site from tr. Start (bp) |
|---|---|---|---|---|---|---|---|---|---|---|
| GGGGCCTATTCACAGCC | 262 | 0 | 8 | −12 | 0.015444 | 8 | TNKS | tankyrase, TRF1-interacting ankyrin-related | 5' | 404285 |
| GGGGCCTATTCACAGCC | 263 | 0 | 8 | −12 | 0.015444 | 8 | PPP1R3B | protein phosphatase 1, regulatory (inhibitor | 5' | 953 |
| CCCATCCCCCACCCGGA | 264 | 0 | 5 | −7 | 0.026319 | 8 | LOXL2 | lysyl oxidase-like 2 | 3' | 403 |
| AAGTTGGCCAGCTCGGG | 265 | 7 | 0 | 7 | 0.016949 | 8 | SCRIB | scribble isoform b | 3' | 194 |
| TCTGTGTGCTGTGTGCG | 266 | 14 | 2 | 5 | 0.017367 | 9 | SMARCA2 | SWI/SNF-related matrix-associated | 3' | 1580 |
| ATCGAGTGCGACGCCTG | 267 | 10 | 0 | 10 | 0.032551 | 9 | PHF2 | PHD finger protein 2 isoform b | 3' | 686 |
| GGTGGAGGCAGGCGGGG | 268 | 7 | 0 | 7 | 0.016949 | 9 | TXN | thioredoxin | 3' | 266 |
| GTGGGGGGCGACCTGTC | 269 | 21 | 3 | 5 | 0.003859 | 9 | RGS3 | regulator of G-protein signalling 3 isoform 6 | 3' | 1569 |
| GCCTTCGACCCCCAGGC | 270 | 16 | 3 | 4 | 0.020923 | 9 | BTBD14A | BTB (POZ) domain containing 14A | 5' | 98790 |
| CAGCCAGCTTTCTGCCC | 139 | 66 | 28 | 2 | 0.034004 | 9 | LHX3 | LIM homeobox protein 3 isoform b | 5' | 146 |
| GGGGAAGCTTCGAGCGC | | 20 | 4 | 3 | 0.013339 | 9 | Not Found | | | |
| AGGCAACAGGCAGGAAG | 273 | 7 | 0 | 7 | 0.016949 | 9 | CACNA1B | calcium channel, voltage-dependent, L type | 3' | 86 |
| AAAATAGAGGTTCCTCC | 274 | 4 | 34 | −13 | 0 | 10 | PRPF18 | PRP18 pre-mRNA processing factor 18 homolog | 5' | 58621 |
| AAAATAGAGGTTCCTCC | 275 | 4 | 34 | −13 | 0 | 10 | C10orf30 | chromosome 10 open reading frame 30 | 5' | 25417 |
| AATGAACGACCAGACCC | 276 | 15 | 35 | −3 | 0.000614 | 10 | DDX21 | DEAD (Asp-Glu-Ala-Asp) box polypeptide 21 | 3' | 506 |
| CAACTGGCCCCAACTAG | 277 | 8 | 0 | 8 | 0.012577 | 10 | CDH23 | cadherin related 23 isoform 2 precursor | 3' | 159 |
| AGTTAGTTCCCAACTCA | 278 | 0 | 5 | −7 | 0.026319 | 10 | MLR2 | ligand-dependent corepressor | 5' | 84 |
| AGTTAGTTCCCAACTCA | 279 | 0 | 5 | −7 | 0.026319 | 10 | PIK3AP1 | phosphoinositide-3-kinase adaptor protein 1 | 5' | 112373 |

TABLE 12-continued

MSDK tags significantly (p < 0.050) differentially present in N-MYOEP4 and N-EPI-I7 MSDK libraries and genes associated with the MSDK tags.

| MSDK Tag | SEQ ID NO. | N-MYOEP-4 | N-EPI-I7 | Ratio N-MYOEP-4/N-EPI-I7 | P value | Chr | Gene | Description | Position of AscI site in relation to tr. Start | Distance of AscI site from tr. Start (bp) |
|---|---|---|---|---|---|---|---|---|---|---|
| CCGCGCTGAGGGGGGGC | 280 | 11 | 0 | 11 | 0.018565 | 10 | CTBP2 | C-terminal binding protein 2 isoform 1 | 3' | 1219 |
| GGGCCCCGCCCAGCCAG | 281 | 0 | 14 | −21 | 0.000103 | 10 | C10orf137 | erythroid differentiation-related factor 1 | 5' | 556810 |
| GGGCCCCGCCCAGCCAG | 282 | 0 | 14 | −21 | 0.000103 | 10 | CTBP2 | C-terminal binding protein 2 isoform 1 | 5' | 2249 |
| TCTAGGACCTCCAGGCC | 283 | 30 | 53 | −3 | 0.000667 | 11 | SLC39A13 | solute carrier family 39 (zinc transporter) | 5' | 415 |
| TCTAGGACCTCCAGGCC | 284 | 30 | 53 | −3 | 0.000667 | 11 | SPI1 | spleen focus forming virus (SFFV) proviral | 5' | 29668 |
| TCCAGCCCACCTGACAG | 285 | 0 | 7 | −10 | 0.030545 | 11 | FLJ22794 | FLJ22794 protein | 5' | 1744 |
| GAGCAGCCAGGGCCGGA | 286 | 14 | 0 | 14 | 0.007231 | 11 | FBXL11 | F-box and leucine-rich repeat protein 11 | 5' | 454 |
| AGCCACGCACCCAGACT | 287 | 0 | 5 | −7 | 0.026319 | 11 | PIG8 | translokin | 3' | 649 |
| AGGGAAGCAGAAAGGCC | 288 | 0 | 5 | −7 | 0.026319 | 11 | MGC39545 | hypothetical protein LOC403312 | 3' | 1123 |
| GCCGCCACTGCCTCAGG | 289 | 23 | 5 | 3 | 0.010564 | 12 | DTX1 | deltex homolog 1 | 5' | 312 |
| GTAGGTGGCGGCGAGCG | 290 | 18 | 0 | 18 | 0.001868 | 13 | USP12 | ubiquitin-specific protease 12-like 1 | 3' | 653 |
| GATATCAAGGTCGCAGA | 291 | 2 | 8 | −6 | 0.049231 | 13 | GTF3A | general transcription factor IIIA | 3' | 126 |
| GGCCGGTGCCGCCAGTC | 292 | 18 | 3 | 4 | 0.009065 | 14 | EML1 | echinoderm microtubule associated protein like 1 | 5' | 62907 |
| GCCCCGGCCGCCGCGCC | 293 | 20 | 4 | 3 | 0.013339 | 15 | Not Found | | | |
| GTGCAGTCTCGGCCCGG | 294 | 33 | 2 | 11 | 0.000043 | 16 | FBXL8 | F-box and leucine-rich repeat protein 8 | 3' | 3905 |
| GGGATCCTCTTGCAAAG | 295 | 5 | 14 | −4 | 0.029708 | 16 | DNCL2B | dynein, cytoplasmic, light polypeptide 2B | 5' | 939218 |
| GGGATCCTCTTGCAAAG | 296 | 5 | 14 | −4 | 0.029708 | 16 | MAF | v-maf musculoaponeurotic fibrosarcoma oncogene | 5' | 1024 |
| CCGTGTTGTCCTGCCCG | 297 | 21 | 3 | 5 | 0.003859 | 17 | MNT | MAX binding protein | 3' | 228 |
| CCACACCTCTCTCCAGG | 298 | 11 | 0 | 11 | 0.003665 | 17 | SENP3 | SUMO1/sentrin/SMT3 specific protease 3 | 5' | 326 |

TABLE 12-continued

MSDK tags significantly (p < 0.050) differentially present in N-MYOEP4 and N-EPI-I7 MSDK libraries and genes associated with the MSDK tags.

| MSDK Tag | SEQ ID NO. | N-MYOEP-4 | N-EPI-I7 | Ratio N-MYOEP-4/N-EPI-I7 | P value | Chr | Gene | Description | Position of AscI site in relation to tr. Start | Distance of AscI site from tr. Start (bp) |
|---|---|---|---|---|---|---|---|---|---|---|
| GGCAACCACTCAGGACG | 299 | 17 | 2 | 6 | 0.0053 | 17 | HCMOGT-1 | sperm antigen HCMOGT-1 | 3' | 69709 |
| GCTATGGGTCGGGGGAG | 215 | 0 | 45 | -67 | 0 | 17 | SOST | sclerostin precursor | 3' | 3140 |
| GCCGCTGCGGCTGCAGC | 301 | 0 | 5 | -7 | 0.02631 | 17 | MGC29814 | hypothetical protein MGC29814 | 5' | 24968 |
| GCCGCTGCGGCTGCAGC | 302 | 0 | 5 | -7 | 0.02631 | 17 | RNF157 | ring finger protein 157 | 5' | 89 |
| CCCCAGGCCGGGTGTCC | 303 | 33 | 9 | 2 | 0.01811 | 17 | CBX8 | chromobox homolog 8 | 5' | 16730 |
| GCGGGCGCGGCTCTGGG | 304 | 11 | 0 | 11 | 0.003665 | 18 | TUBB6 | tubulin, beta 6 | 5' | 689 |
| CGAGGGATCTAGGTAGC | 305 | 0 | 5 | -7 | 0.02631 | 18 | FHOD3 | formin homology 2 domain containing 3 | 5' | 30 |
| GTGGAGGGGAGGTACTG | 306 | 12 | 0 | 12 | 0.01257 | 18 | IER3IP1 | immediate early response 3 interacting protein | 5' | 70905 |
| TGCTTTTCTGCCCCACT | 307 | 7 | 0 | 7 | 0.01694 | 18 | KIAA0427 | KIAA0427 | 5' | 530689 |
| TGCTTTTCTGCCCCACT | 308 | 7 | 0 | 7 | 0.01694 | 18 | SMAD2 | Sma- and Mad-related protein 2 | 5' | 77514 |
| GATTTGTTGCAGGGTCT | 309 | 14 | 0 | 14 | 0.007231 | 19 | AMH | anti-Mullerian hormone | 3' | 2281 |
| GGCCCCGCCCACAGCCC | 310 | 7 | 0 | 7 | 0.01694 | 19 | ZNF560 | zinc finger protein 560 | 5' | 18 |
| TAGGTTCTATGCTCAGT | 311 | 0 | 5 | -7 | 0.02631 | 19 | AKAP8L | A kinase (PRKA) anchor protein 8-like | 5' | 13794 |
| GTTTATTCCAAACACTG | 312 | 3 | 10 | -5 | 0.04204 | 19 | GRIN2D | N-methyl-D-aspartate receptor subunit 2D | 3' | 48538 |
| TTCGGCCCCATCCCTCG | 313 | 22 | 0 | 22 | 0.000508 | 19 | CDC42EP5 | CDC42 effector protein 5 | 3' | 8020 |
| GCTGCGGCCGGCCGGGG | 314 | 11 | 0 | 11 | 0.018565 | 19 | UBE2S | ubiquitin carrier protein | 5' | 478 |
| CGCTCCACGTCCGGGA | 315 | 15 | 3 | 3 | 0.02931 | 20 | SNTA1 | acidic alpha 1 syntrophin | 3' | 288 |
| CTTTCAAACTGGACCCG | 316 | 16 | 3 | 4 | 0.02092 | 20 | Not Found | | | |
| TTCCAAAAGGGGCAGG | 317 | 2 | 9 | -7 | 0.02771 | 22 | XBP1 | X-box binding protein 1 | 5' | 82906 |
| TAGTACTTTCAGGTAGG | 318 | 2 | 8 | -6 | 0.04923 | 23 | UBE2A | ubiquitin-conjugating enzyme E2A isoform 2 | 3' | 285 |

The column headings are as in Table 2 except that the MSDK libraries compared are the N-MYOEP-4 and N-EPI-I7 MSDK libraries (see Table 3 for details of the tissues from which these libraries were made).

In addition to pair-wise comparison of MSDK libraries, genome-wide analyses of methylation and gene expression patterns were performed by combining MSDK and SAGE (Serial Analysis of Gene Expression) data for each breast cell type. The AscI cutting frequencies were determined and SAGE tag counts were superimposed (details in Example 1). They were then mapped to the human genome together with all predicted CpG islands and AscI sites. Based on the combined as well as cell-type-specific MSDK and SAGE analysis, it was determined that highly expressed genes are preferentially located in gene dense areas [Caron et al. (2001) Science 291:1289-1292] and that these areas correlate with the locations of the most frequently cut (thus unmethylated) AscI sites. Interestingly, while the ratio of the observed and predicted MSDK tags averaged for all cells tested was nearly equal for most chromosomes, chromosomes X and 17 had a lower and a higher observed/expected tag ratio, respectively, in all samples suggesting overall hyper- and hypo-methylation in these specific chromosomes (Tables 1, 2, and 4-12).

Example 4

Confirmation of MSDK Results by Sequencing Studies

To confirm the MSDK results, several highly differentially methylated genes from each pair-wise comparison were selected and their methylation was analyzed by performing sequence analysis of bisulfite treated genomic DNA from the same sample that was used for MSDK and also from additional samples obtained from independent patients. These genes included PRDM14 and ZCCHC14 (hypermethylated in tumor epithelial cells), HOXD4 and SLC9A3R1 (hypermethylated in DCIS myoepithelial cells) and LOC389333 (more methylated in myoepithelial than in epithelial cells), CDC42EP5 (hypermethylated in DCIS myoepithelial cells and also different between normal epithelial and myoepithelial cells), and Cxorf12 (hypermethylated in tumor stroma compared to normal) (FIGS. 9-15). Interestingly PRDM14 and HOXD4 were also differentially methylated between HCT 116 WT and DKO cells (unmethylated in DKO) suggesting their potential involvement in multiple tumor types or location in a chromosomal area prone to epigenetic modifications. In all these cases bisulfite sequence analysis confirmed the MSDK results although the absolute frequency of methylation was somewhat variable among samples.

In FIGS. 16A-22B are shown the nucleotide sequences of the gene regions that were subjected to the above methylation-detecting sequencing analysis.

Example 5

Determination of Frequency and Consistency of Methylation Difference by Quantitative Methylation Specific PCR (qMSP)

To determine how frequently and consistently methylation differences in these selected genes occur, a quantitative methylation specific PCR (qMSP) assay was developed for some of the genes and their methylation status in a larger set of samples and in multiple cell types was analyzed. This assay depends on the relative ability of two sets of PCR primers targeting segments of DNA that include at least one CpG sequence to anneal to bisulfite treated DNA and cause the amplification of the sequence that the primers span. One set of primers is designed to anneal to the target sequences efficiently and cause the relatively rapid amplification if the target sequences in the DNA are not methylated and the other pair of primers is designed to act similarly if the target sequences in the DNA are methylated.

Figure 24:
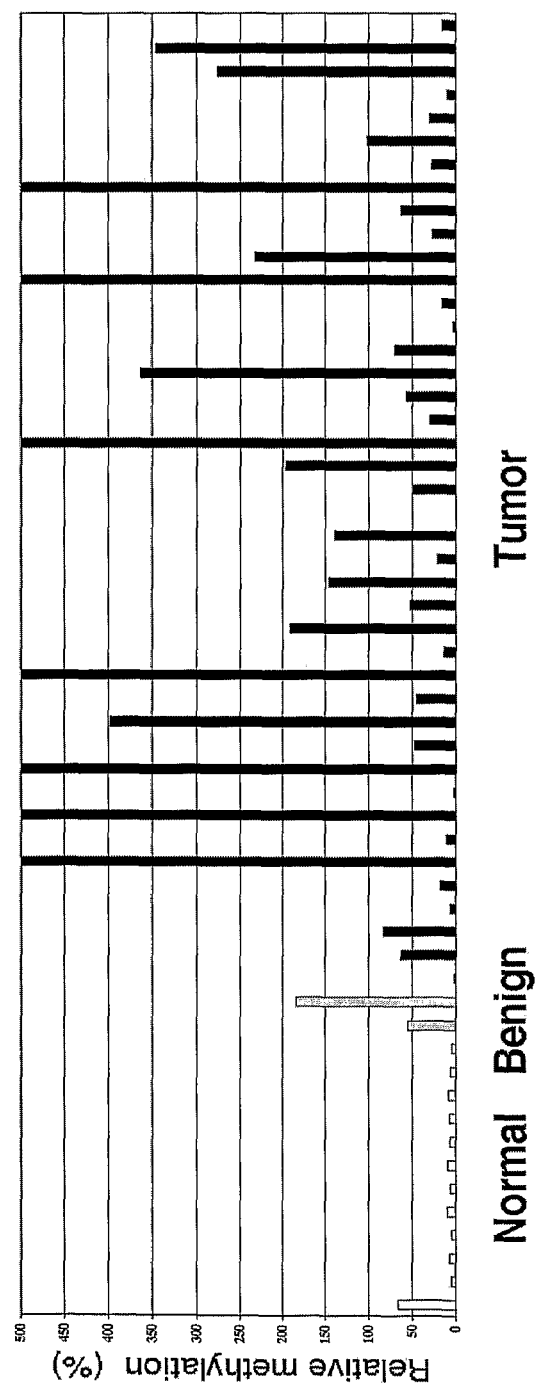
FIG. 24 is a bar graph showing the results of qMSP analyses of the PRDM14 gene in a panel of normal breast tissues, benign breast tumors (fibroadenomas, papillomas, and fibrocystic disease), and breast carcinomas. The data were computed as described for FIG. 23. 500% was set as the upper limit of relative methylation although a few samples showed a difference above this threshold.
Figure 25A:
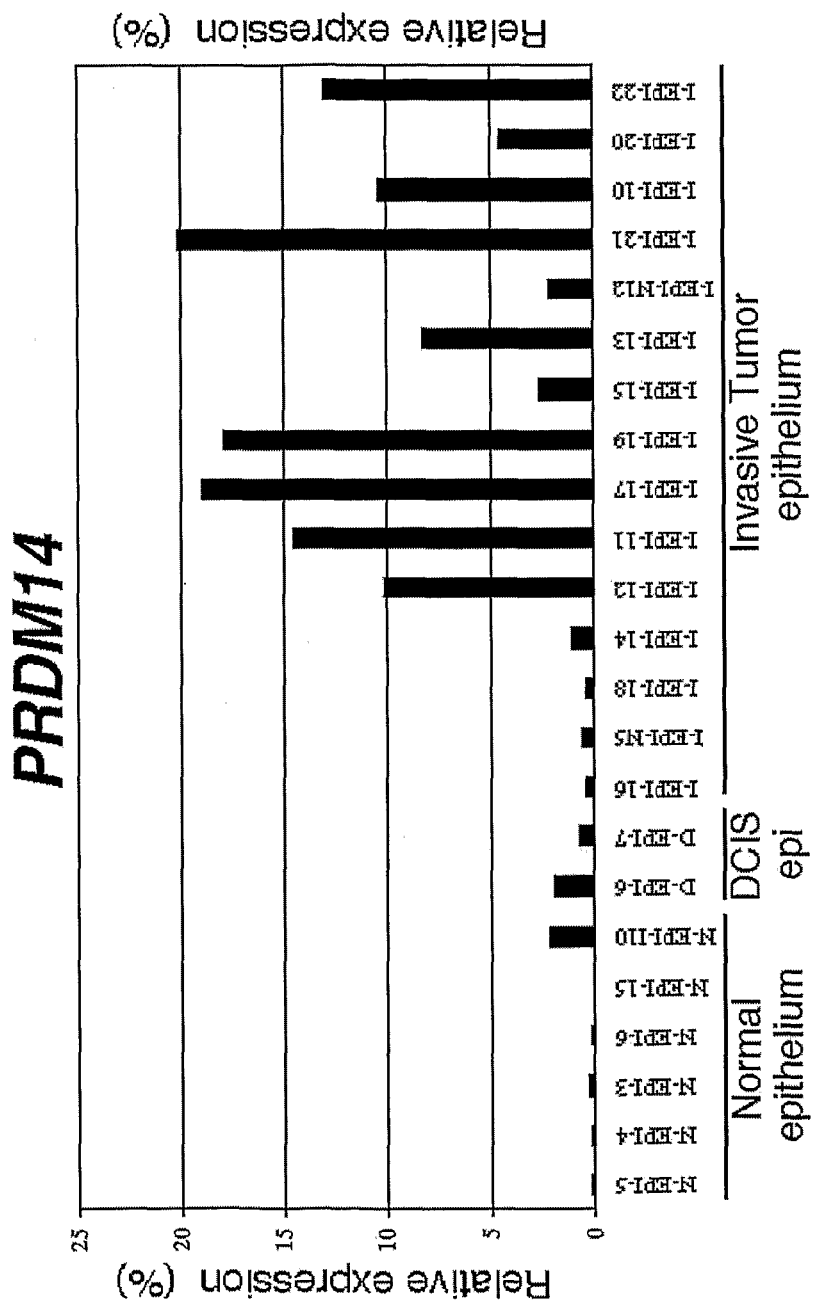
FIGS. 25A-D are a series of bar graphs showing the results of expression analyses of the PRDM14 (FIG. 25A), Cxorf12 (FIG. 25B), CDC42EP5 (FIG. 25C), and HOXD4 (FIG. 25D) genes in normal breast and breast carcinoma (tumor) epithelial cells, fibroblast-enriched stromal cells (stroma), and myoepithelial cells and in invasive breast carcinoma cell myofibroblasts. The average Ct value for each gene was normalized against the RPL39 value (see Example 1). The data ("Relative expression (%)") are percentages relative to the RPL39 value. Using RPL19 and RPS13 values for normalization gave essentially the same results. The PRDM14 gene was relatively overexpressed in invasive breast carcinoma epithelial cells. The Corf12 gene was expressed at a relatively higher level in normal than in tumor fibroblast-enriched stromal cells. The CDC42EP5 and HOXD4 genes showed higher expression in DCIS myoepithelial cells and invasive breast carcinoma myofibroblasts compared to normal myoepithelial cells and also, in the case of the CDC42EP5 gene, to normal epithelial cells.
Figure 25B:
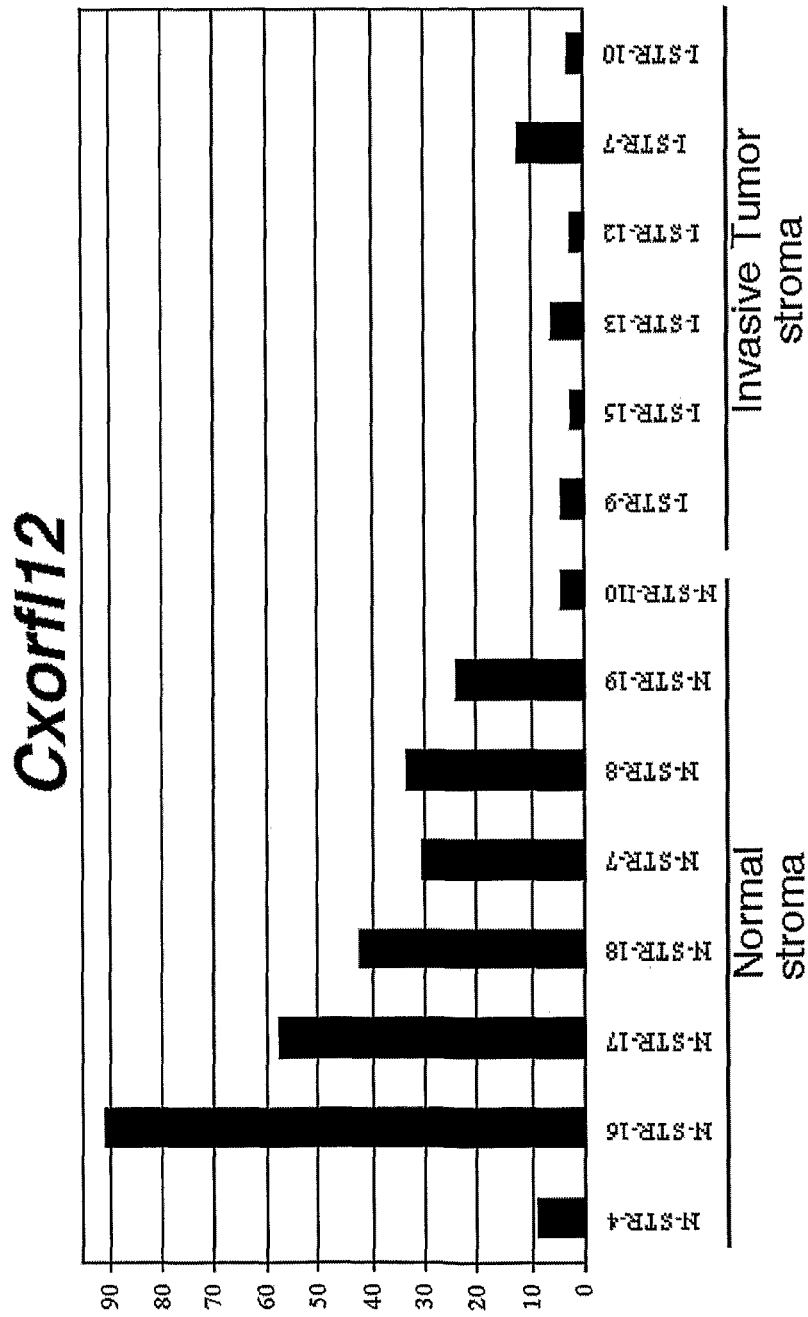
Figure 25C:
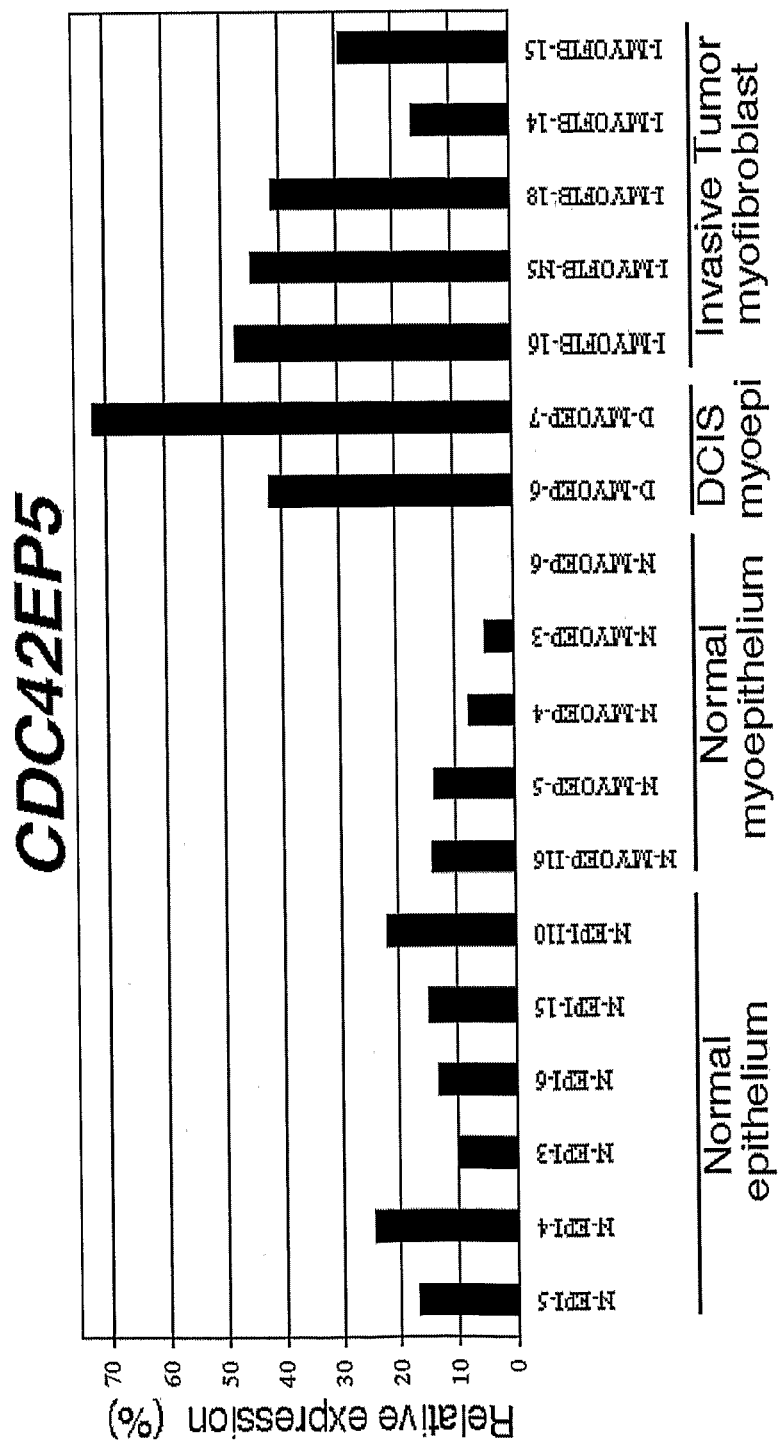
Figure 25D:
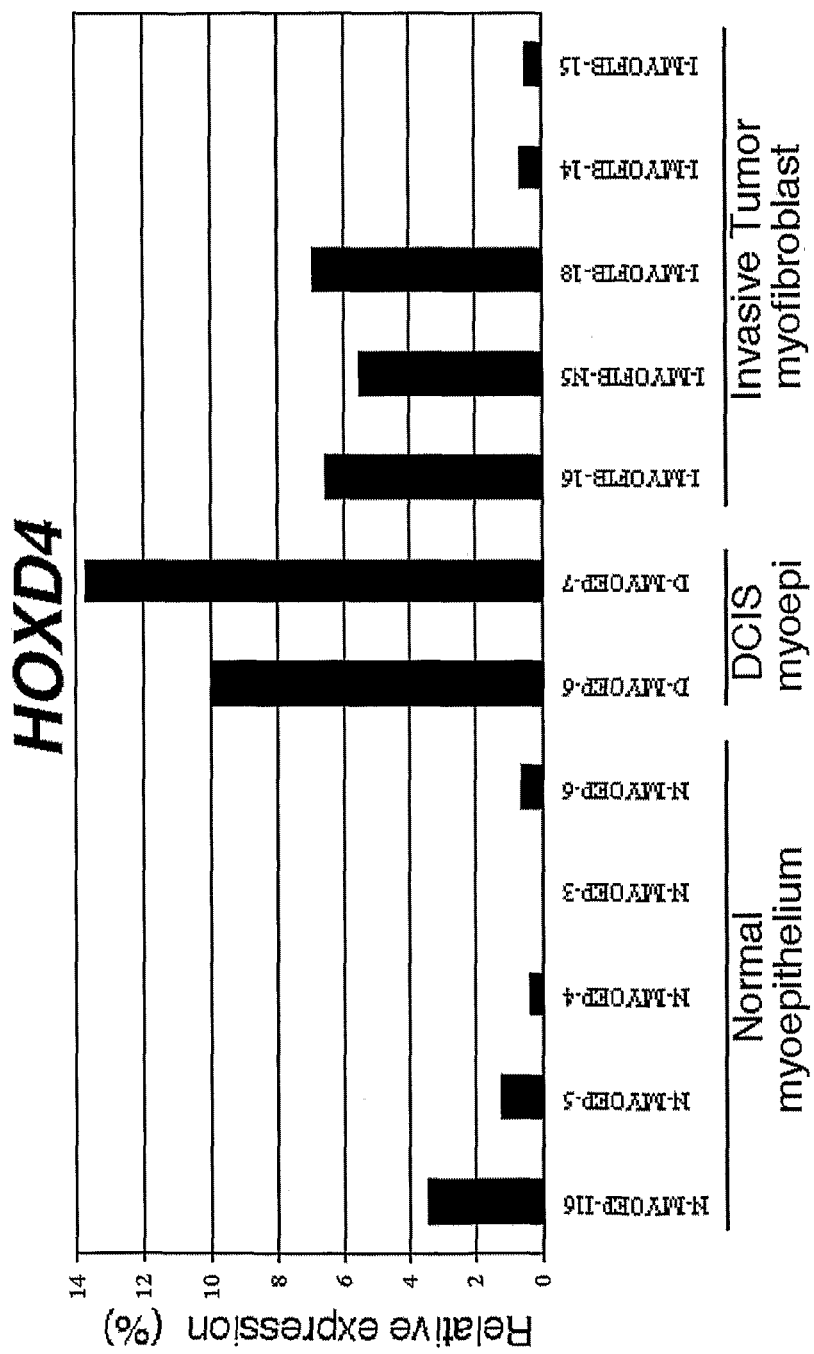

This analysis not only confirmed the original MSDK data and the bisulfite sequencing results, but also revealed the methylation status of each gene in all three cell types both in normal and tumor tissue (FIGS. 23A-F). The frequency of PRDM14 methylation was further analyzed in a panel of normal breast tissue (purified organoids), benign breast tumors (fibroadenomas, fibrocystic dysplasias, and papillomas), and breast carcinomas (FIG. 24). The majority of breast carcinomas demonstrated high methylation of PRDM14, while only one out of 10 normal breast tissue samples, and a few benign tumors had low level methylation. Based on these data, PRDM14 is a candidate biomarker for breast cancer diagnosis since it is methylated in 90% of invasive tumors and only 10% of normal breast tissue.

In addition, a MSP analysis of genomic DNA from a variety of pancreatic, prostate, lung, and breast cancer samples indicated that the PRDM14 gene is hypermethylated in a wide range of cancers (Table 13). Bisulfite treated DNA from the various cancer and normal tissues was amplified with: (a) a pair of PCR primers that effectively anneals only to methylated target sequences and causes the production of a detectable PCR product; and (b) and pair of primers that effectively only anneals to unmethylated target sequences and causes the production of a detectable PCR product.

TABLE 13

Methylation of the PRDM14 gene in pancreatic, prostatic, lung, and breast cancer.

| | | U | WM | M | Total | U % | M % (M + WM) |
|---|---|---|---|---|---|---|---|
| Pancreas | N | 7 | 1 | 1 | 9 | 77.8 | 22.2 |
| | N in CA | 2 | 0 | 0 | 2 | 100.0 | 0.0 |
| | CA | 1 | 1 | 5 | 7 | 14.3 | 85.7 |
| Prostate | N | 6 | 0 | 0 | 6 | 100.0 | 0.0 |
| | N in CA | 2 | 0 | 2 | 4 | 50.0 | 50.0 |
| | CA | 2 | 1 | 2 | 5 | 40.0 | 60.0 |
| | Xenograft | 0 | 0 | 7 | 7 | 0.0 | 100.0 |
| Lung | N | 4 | 0 | 0 | 4 | 100.0 | 0.0 |
| | N in CA | 6 | 0 | 6 | 12 | 50.0 | 50.0 |
| | CA | 14 | 3 | 87 | 104 | 13.5 | 86.5 |
| | Cell lines | 0 | 0 | 4 | 4 | 0.0 | 100.0 |
| Breast | N | 2 | 1 | 0 | 3 | 66.7 | 33.3 |
| | N in CA | 0 | 1 | 0 | 1 | 0.0 | 100.0 |
| | CA | 40 | 7 | 91 | 138 | 29.0 | 71.0 |

N, normal tissue from a healthy person (not a cancer patient).
N in CA, normal tissue adjacent to cancer tissue.
CA, cancer tissue.
Xenograft, cancer tissue grown in nude mice.
U, PCR product was detectable (on electrophoretic gels) only in PCR with unmethylated target-specific PCR primers.
WM (weakly methylated), PCR product was detectable (on electrophoetic gels) in PCR with both methylated and unmethylated target-specific PCR primers, but the methylated primer specific PCR was weak compared to the other sample.
The numbers in the M, WM, M, and Total columns are the numbers of different samples tested.

Example 6

Analysis of Gene Expression by Quantitative RT-PCR (qRT-PCR)

To further characterize the effect of methylation changes on gene expression, the expression of selected genes in cells purified from normal breast tissue, and in situ and invasive breast carcinomas was analyzed by RT-PCR (FIGS. 25A-D). Of the four genes analyzed both for methylation and gene expression, only one (Cxorf12) had the differentially methylated sites localized in the predicted promoter area, while in the other three genes (PRDM14, HOXD4, and CDC42EP5) the differentially methylated AscI and surrounding CpG sites were located in an intron or distal exon. Consistent with these findings, the relative expression of Cxorf12 was positively correlated with methylation, while that of the other three genes was inversely correlated methylation. Thus, in all cases there was a strong correlation between differential methylation of the genes and their differential expression, but only methylation in the promoter area was associated with down-regulation of expression; in other regions it correlated with higher mRNA levels. These results are consistent with prior reports indicating that methylation in non-core (i.e., outside of the promoter) regions do not negatively affect transcription [Ushijima (2005) Nat. Rev. Cancer 5:223-231] and in some cases (e.g. H19/IGF2, an imprinted gene) DNA methylation in an intron leads to increased gene expression [Feinberg et al. (2004) Nat. Rev. Cancer 4:143-153; Bell et al. (2000) Nature 405, 482-485]. The imprinting of IGF2 is dependent on CTCF binding to an enhancer-blocking element within the H19 gene, the methylation of which inhibits CTCF binding and leads to loss of imprinting (LOI) [Feiber et al. (2004) supra; Bell et al. (2000) supra]. Interestingly, the differentially methylated regions identified in the PRDM14 and CDC42EP5 genes (see above) appear to have a CTCF binding site [Bell et al. (2000) supra]. Thus, some of the genes identified herein are potentially subject to imprinting and the results presented above indicate possible loss of imprinting in a cell type and tumor stage specific manner.

In summary, a novel sequence-based method (Methylation Specific Digital Karyotyping; MSDK) for the analysis of the genome-wide methylation profiles is provided. MSDK analysis of three cell types (epithelial and myoepithelial cells and stromal fibroblasts) from normal breast tissue and in situ and invasive breast carcinomas revealed that distinct epigenetic changes occur in all three cell types during breast tumorigenesis. Alterations in stromal and myoepithelial cells thus likely play a role in the establishment of the abnormal tumor microenvironment and contribute to tumor progression.

A number of embodiments of the invention have been described. Nevertheless, it will be understood that various modifications may be made without departing from the spirit and scope of the invention. Accordingly, other embodiments are within the scope of the following claims.

Example 7

Figures 26A, 26B:
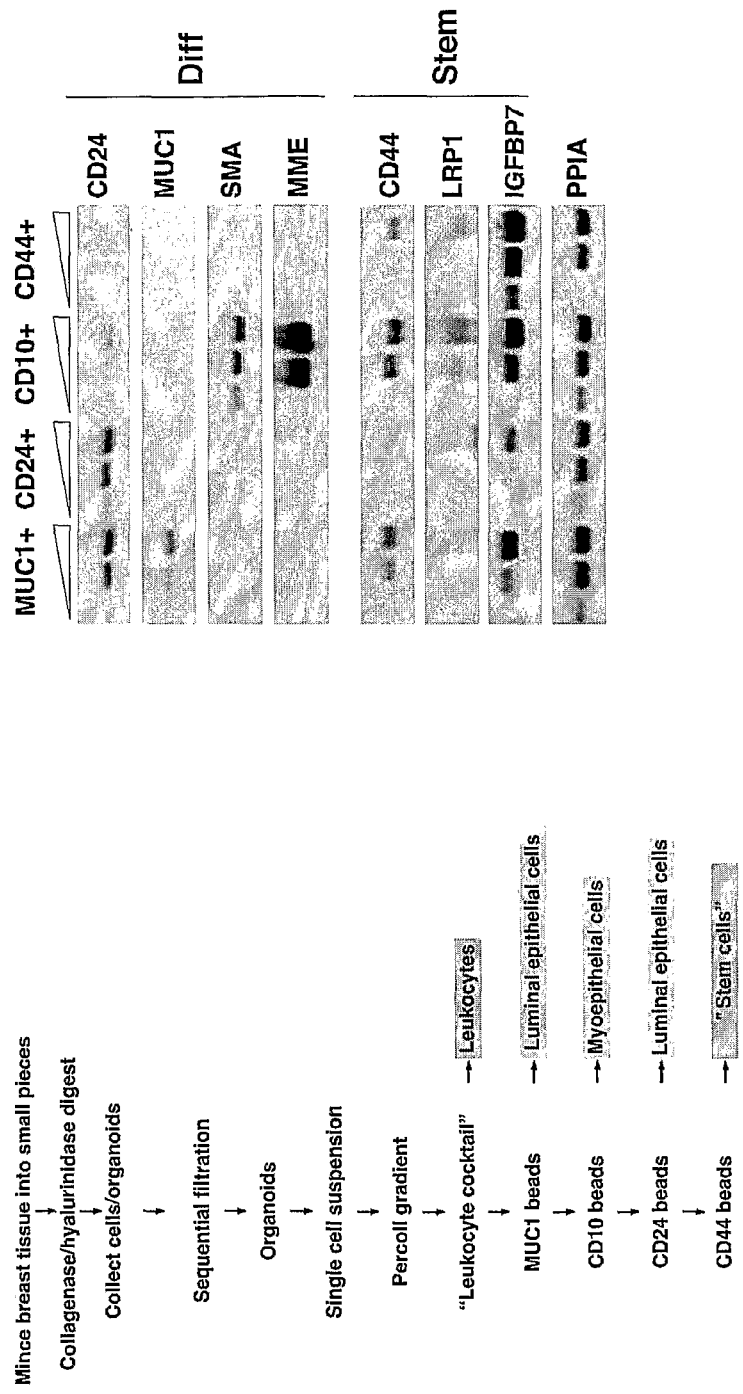
FIG. 26A is a schematic representation of the procedure used for tissue fractionation and purification of the various cell types from normal breast tissue. Cells were captured by antibody-coupled magnetic beads as indicated by the figure.
FIG. 26B is a series of photographs of ethidium bromide-stained electrophoretic gels of semi-quantitative RT-PCR analyses of selected genes from the purified cell fractions isolated from normal breast tissue. PPIA was used as a loading control. The triangles indicate an increasing number of PCR cycles (25, 30, and 35).

Determination of the Global DNA Methylation of Stem Cells and Their Differentiated Progeny To determine the global methylation profile of putative normal mammary epithelial stem cells and their differentiated progeny, cells were purified from normal human breast tissue using known cell type specific cell surface markers (see FIG. 26A). Mammary epithelial stem cells were identified as lineage$^-$/CD24$^{-/low}$/CD44$^+$ cells, while differentiated luminal epithelial cells were purified using anti-MUC1 and anti-CD24 antibodies, and myoepithelial cells were isolated using anti-CD10 antibodies. Hereafter, the putative normal mammary epithelial stem cells are referred to as CD44+ cells, the luminal epithelial cells as MUC1+ or CD24+ cells, and myoepithelial cells as CD10+ cells. The purity and differentiation status of the cells was confirmed by analyzing the expression of known differentiated (e.g., MUC1, MME) and mammary stem cell (e.g., IGFBP7, LRP1) markers by semi-quantitative RT-PCR (see FIG. 26B). SAGE (Serial Analysis of Gene Expression) libraries were also generated from each cell fraction to analyze their global expression profile. The SAGE data further confirmed the hypothesis that CD44+ cells represent stem cells while MUC1+, CD24+, and CD10+ cells represent a differentiated lineage of committed cells, since known luminal and myoepithelial lineage specific and stem markers were found mutually exclusively in the respective SAGE libraries.

Example 8

Analysis of MSDK Data Obtained from Isolated Stem Cells and Their Differentiated Progeny MSDK libraries were generated using genomic DNA isolated from CD44+, CD24+, MUC1+, and CD10+ cells purified as described above (see FIGS. 26A and 26B). By comparing the actual number of MSDK tags obtained in each library to the expected or predicted number of MSDK tags, normal mammary epithelial stem cells (CD44+) were found to be hypomethylated compared to luminal epithelial (CD24+ or MUC1+) and myoepithelial (CD10+) cells (see Table 14). Table 15 lists tags statistically significantly ($p<0.05$) differentially present in the four MSDK libraries.

TABLE 14

Chromosomal location and analysis of the frequency of MSDK tags in Stem and Differentiated Cells.

| | | | CD10 | | CD24 | | CD44 | | MUC1 | |
|---|---|---|---|---|---|---|---|---|---|---|
| Chr | Virtual Tag | Observed Tag | Variety | Copies | Variety | Copies | Variety | Copies | Variety | Copies |
| 1 | 588 | 182 | 134 | 811 | 95 | 363 | 145 | 1004 | 147 | 854 |
| 2 | 470 | 135 | 98 | 848 | 75 | 393 | 112 | 1005 | 107 | 826 |
| 3 | 354 | 119 | 83 | 760 | 61 | 329 | 103 | 1007 | 91 | 824 |
| 4 | 298 | 86 | 63 | 469 | 40 | 181 | 68 | 535 | 65 | 449 |
| 5 | 352 | 108 | 75 | 702 | 64 | 275 | 89 | 910 | 92 | 719 |
| 6 | 352 | 101 | 70 | 411 | 43 | 120 | 85 | 543 | 79 | 421 |
| 7 | 418 | 146 | 100 | 608 | 76 | 261 | 126 | 781 | 128 | 672 |
| 8 | 343 | 107 | 80 | 474 | 66 | 210 | 89 | 598 | 80 | 437 |
| 9 | 382 | 131 | 95 | 770 | 80 | 365 | 116 | 980 | 102 | 724 |
| 10 | 403 | 134 | 92 | 573 | 66 | 282 | 107 | 811 | 106 | 666 |
| 11 | 392 | 130 | 94 | 526 | 68 | 224 | 106 | 677 | 100 | 550 |
| 12 | 318 | 98 | 73 | 587 | 51 | 272 | 82 | 822 | 79 | 635 |
| 13 | 149 | 44 | 32 | 228 | 26 | 97 | 35 | 296 | 39 | 264 |

TABLE 14-continued

Chromosomal location and analysis of the frequency of MSDK tags in Stem and Differentiated Cells.

| Chr | Virtual Tag | Observed Tag | CD10 Variety | CD10 Copies | CD24 Variety | CD24 Copies | CD44 Variety | CD44 Copies | MUC1 Variety | MUC1 Copies |
|---|---|---|---|---|---|---|---|---|---|---|
| 14 | 242 | 64 | 47 | 368 | 35 | 149 | 50 | 472 | 45 | 345 |
| 15 | 270 | 82 | 55 | 252 | 43 | 117 | 70 | 340 | 66 | 270 |
| 16 | 350 | 108 | 69 | 485 | 49 | 179 | 86 | 585 | 78 | 520 |
| 17 | 421 | 138 | 109 | 795 | 69 | 328 | 117 | 1043 | 103 | 756 |
| 18 | 186 | 65 | 46 | 248 | 26 | 111 | 52 | 368 | 53 | 256 |
| 19 | 483 | 140 | 101 | 561 | 69 | 250 | 113 | 660 | 112 | 598 |
| 20 | 246 | 69 | 55 | 373 | 39 | 167 | 56 | 434 | 54 | 372 |
| 21 | 78 | 21 | 18 | 80 | 9 | 24 | 16 | 92 | 18 | 55 |
| 22 | 232 | 69 | 47 | 371 | 32 | 144 | 56 | 494 | 56 | 387 |
| X | 192 | 52 | 40 | 259 | 27 | 93 | 43 | 372 | 36 | 236 |
| Y | 12 | 0 | 0 | 0 | 0 | 0 | 0 | 0 | 0 | 0 |
| Mapped | 7531 | 2329 | 1676 | 11559 | 1209 | 4934 | 1922 | 14829 | 1836 | 11836 |
| Not Mapped | 339 | 123 | 86 | 608 | 76 | 458 | 95 | 773 | 100 | 726 |
| No Match | 0 | 3934 | 1218 | 6224 | 2174 | 7428 | 1181 | 6909 | 1202 | 6043 |
| Total | 7870 | 6386 | 2980 | 18391 | 3459 | 12820 | 3198 | 22511 | 3138 | 18605 |

The column headings are as indicated for Table 1, for the indicated purified cell populations, CD10, CD24, CD44, and MUC1.

TABLE 15

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| TAAGGCTAGACAGAAGA | 1319 | 50 | 83 | 39 | 32 | 4.22E-16 | | | | |
| GAAACTCCACAAAAAGA | 1320 | 25 | 61 | 31 | 34 | 4.11E-11 | | | | |
| GCCTTTCATAGAGCAGG | 1321 | 42 | 88 | 62 | 58 | 4.73E-11 | | | | |
| GGGCCCCGCCCAGCCAG | 1322 | 0 | 7 | 0 | 23 | 1.06E-09 | 10 | 126841258 | CTBP2 | C10orf137 |
| TTTAGTGCTTCCTTCAG | 1323 | 40 | 63 | 34 | 36 | 8.56E-09 | 2 | 192452398 | FLJ22833 | SDPR |
| TCGCCGGGCGCTTGCCC | | 90 | 18 | 7 | 66 | 26 | 9.55E-08 | 5 | 134391719 | PITX1 | PITX1 |
| GTCCTTGTTCCCATAGG | | 97 | 6 | 0 | 35 | 9 | 1.21E-07 | 6 | 1550618 | FOXF2 | |
| AGCCACCACGCCCAGCC | 1326 | 0 | 8 | 0 | 0 | 1.69E-07 | | | | |
| CCCCTGCCCTGTCACCC | 226 | 30 | 9 | 1 | 25 | 7.76E-07 | 17 | 70268314 | | SLC9A3R1, NAT9 |
| AAAAAAACCCGTTTCCA | 1328 | 17 | 29 | 6 | 19 | 1.07E-06 | | | | |
| CGCGTCACTAATTAGAT | 1329 | 261 | 173 | 384 | 384 | 1.58E-06 | | | | |
| GGGGCGAAGAAAGCAGA | 1330 | 45 | 15 | 83 | 29 | 6.56E-06 | X | 122819716 | BIRC4 | STAG2 |
| CCCCCGCGACGCGGCGG | | 34 | 28 | 1 | 20 | 7 | 2.01E-05 | 1 | 200773326 | C1orf157 | |
| GCCCGCCTGAGCAAGGG | 1332 | 92 | 33 | 143 | 83 | 5.46E-05 | 9 | 101328287 | C9orf125 | C9orf125 |
| TTGCTCAGGCTGGTCTC | 1333 | 98 | 23 | 93 | 69 | 6.04E-05 | | | | |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| GAAAAGTTGAACTCCTG | 1334 | 0 | 0 | 14 | 2 | 8.81E-05 | 18 | 13631664 | C18orf1 | C18orf1 |
| CCTGTAATCCCAGCTAC | 1335 | 7 | 25 | 15 | 22 | 0.000193 | 11, 14, 16, 17, 1, 20, 4 | 65171573, 74149211, 220738, 16224677, 8872811, 3641578, 6737623 | | |
| CTGACCGCGCTCGCCCC | 91 | 15 | 2 | 30 | 7 | 0.0001559 | 5 | 138757992 | | DNAJC18 |
| CCCACCAGGCACGTGGC | 1337 | 79 | 21 | 98 | 55 | 0.0001752 | 22 | 37564888 | NPTXR | CBX6 |
| TTCTAACCCAATGCAAG | 1338 | 1 | 10 | 0 | 4 | 0.0001769 | | | | |
| CAACCCACGGGCAGGTG | 110 | 2 | 1 | 21 | 5 | 0.0001798 | 6 | 159560410 | TAGAP | |
| TGAAGATATACCCGTTT | 1340 | 14 | 28 | 13 | 20 | 0.0001807 | | | | |
| GCCTGGCTTCCCCCCAG | 1341 | 65 | 13 | 46 | 42 | 0.000191 | 5 | 176814399 | PRR7, GRK6 | PRR7, DBN1 |
| GCCCGCGGGGCTGTCCC | 1342 | 13 | 0 | 25 | 24 | 0.0002373 | 18 | 73090569 | MBP | GALR1 |
| GCTATGGGTCGGGGAG | 215 | 45 | 13 | 79 | 41 | 0.0002564 | 17 | 39188537 | SOST | SOST, DUSP3 |
| AGCTCTGGCAGTAGTTG | 1344 | 41 | 6 | 51 | 23 | 0.0002667 | 14 | 63874915 | ESR2 | MTHFD1 |
| CACAGCCAGCCTCCCAG | 213 | 27 | 0 | 39 | 30 | 0.0002871 | 17 | 32372307 | | |
| AAGCAGTCTTCGAGGGG | 1346 | 89 | 27 | 105 | 60 | 0.00042 41 | 2 | 96903463 | CNNM4 | CNNM3 |
| TTCTGCTAGACAGAAGA | 1347 | 23 | 34 | 21 | 20 | 0.00047 64 | | | | |
| GGGGATTCTACCCTGGG | 1348 | 27 | 12 | 66 | 41 | 0.0005416 | 20 | 46877884 | PREX1 | ARFGEF2 |
| TCGGACGTACATCGTTA | 1349 | 316 | 282 | 401 | 285 | 0.0006099 | | | | |
| GTGGCTCACATCTGTAC | 1350 | 24 | 4 | 46 | 21 | 0.000654 | | | | |
| GCTGCCCCAAGTGGTCT | 180 | 1 | 7 | 22 | 9 | 0.0007181 | 12 | 47677137 | | |
| GCGCTGCCCTATATTGG | 1352 | 11 | 2 | 24 | 24 | 0.0010304 | 11 | 33018089 | TCP11L1, LOC91614 | TCP11L1 |
| TGGAGATTTCAATCGCT | 1353 | 18 | 34 | 27 | 22 | 0.00122 94 | | | | |
| AAGATCTTGAGCTTGGG | 1354 | 92 | 26 | 84 | 78 | 0.001288 | 22, 2, 22 | 18834687, 20063861, 20228651 | | |
| CGGGCCGGGTCGGGCTC | 1355 | 7 | 0 | 5 | 14 | 0.0014107 | 16 | 4683601 | MGRN1 | NUDT16L1, KIAA1977 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| TGGCAAACCCATTCTTG | 1356 | 79 | 20 | 82 | 66 | 0.0015245 | 7 | 43682173 | MRPS24 | MRPS24, URG4 |
| GTCCGTGGAATAGAAGG | 1357 | 0 | 4 | 1 | 10 | 0.001566 | 4 | 37979694 | TBC1D1 | FLJ13197 |
| AGTATCAAAACGGCAGC | 1358 | 8 | 2 | 20 | 22 | 0.0016076 | 7 | 122120649 | CADPS2 | TAS2R16 |
| CCACTGCACTCCAGCCT | 1359 | 7 | 25 | 16 | 12 | 0.001797 | 15, 2, 3, 6, 7, X | 43372896, 112885413, 172123633, 158701197, 127563622, 16561976 | | |
| CCTGACAGGAACCACCC | 1360 | 12 | 0 | 8 | 2 | 0.0018558 | | | | |
| TGGGAAGGCGTGGGGTG | 1361 | 67 | 20 | 66 | 36 | 0.0018849 | | | | |
| TTCGGCCCCATCCCTCG | 313 | 10 | 0 | 1 | 9 | 0.0019823 | 19 | 59668209 | | |
| GTGATAAAGGGAATATC | 1363 | 35 | 34 | 23 | 22 | 0.0020368 | | | | |
| GCCACCGTCCTGCTGAC | 1364 | 2 | 11 | 3 | 1 | 0.0020456 | | | | |
| GAGATGCGCCTACGCCC | 1365 | 28 | 3 | 42 | 24 | 0.0020914 | X | 17153468 | NHS | NHS |
| ACCCGCACCATCCCGGG | 229 | 89 | 46 | 140 | 72 | 0.0021761 | 17 | 75432403 | CBX4 | TBC1D16 |
| CGTGTGAGCTCTCCTGC | 1367 | 85 | 37 | 131 | 76 | 0.002228 | 3 | 185762859 | EPHB3 | EPHB3 |
| AACCCCGAAACTGGAAG | 1368 | 16 | 1 | 25 | 14 | 0.0022405 | 3 | 69064539 | FAM19A4 | AER61 |
| GCCTCAGCATCCTCCTC | 1369 | 19 | 7 | 8 | 2 | 0.002242 | 22 | 44777822 | FLJ10945 | FLJ27365 |
| ACCCTGAAAGTCTAGCC | 1370 | 7 | 2 | 22 | 6 | 0.0024548 | | | | |
| TGGCCTCTGACACCTGC | 1371 | 5 | 1 | 0 | 10 | 0.0025666 | 15, 18, 21 | 19241095, 14440489, 13999446 | | |
| TTTGCTTAGAGCCCAGC | 1372 | 7 | 0 | 9 | 15 | 0.0026357 | 16 | 66856002 | SLC7A6, LYPLA3 | SLC7A6, LOS |
| TCTTCTATTGCCTGATT | 1373 | 10 | 1 | 5 | 0 | 0.0028799 | 9 | 112017089 | SUSD1 | SUSD1 |
| GCTCGCCGAGGAGGGGC | 1374 | 26 | 12 | 56 | 47 | 0.0030451 | 3 | 28591784 | AZI2 | RBMS3 |
| TTGCCCAGGCTGGTCCC | 1375 | 0 | 6 | 0 | 1 | 0.0032534 | | | | |
| ACGGCCACTGAAACGGA | 1376 | 18 | 1 | 14 | 18 | 0.0032851 | 11 | 198846 | RIC8A, BET1L, ODF3 | SIRT3, RIC8A |
| CCTCAGATCAGGATGGG | 1377 | 25 | 5 | 33 | 39 | 0.003369 | X | 41058142 | DDX3X | NYX |
| CGCGCAGCTCGCTGAGG | 1378 | 17 | 2 | 4 | 14 | 0.0034725 | 20 | 34924764 | C20orf117 | C20orf118 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| GGCGTTAATAGAGAGGC | 1379 | 15 | 2 | 25 | 10 | 0.00348 | 9 | 130564512 | ASS | PRDM12 |
| TTGCCCAGGCTGGTCTC | 1380 | 2 | 14 | 5 | 6 | 0.00348 | 9 | 131187973 | FAM78A | PPAPDC3 |
| TTGGCTAGGCTGGTCTC | 1381 | 0 | 6 | 0 | 0 | 0.00350 | | | | |
| CCGCTGGGAGAGGGTTC | 1382 | 19 | 9 | 49 | 26 | 0.00355 | 11 | 133331480 | LOC283174 | JAM3 |
| CCGCTTGCCCCGAAACC | 1383 | 0 | 7 | 1 | 3 | 0.00356 | 9 | 109621801 | PALM2 | PALM2-AKAP2 |
| ACCCTGAAAGCCTAGCC | 266 | 6 | 3 | 24 | 9 | 0.00368 | 21 | 45176032 | ITGB2 | C21orf69, C21orf67, C21orf70 |
| CCCTGTCCTAGTAACGC | 1385 | 16 | 1 | 6 | 9 | 0.00379 | 8 | 38208799 | DDHD2 | DDHD2 |
| TCTCTTGGGGAGATGGG | 1386 | 15 | 1 | 10 | 3 | 0.00402 | 5 | 138757992 | PACAP, SLC23A1 | DNAJC18 |
| ACCCTCGCGTGGGCCCC | 1387 | 25 | 3 | 35 | 16 | 0.00435 | 19 | 12134824 | ZNF625 | ZNF136 |
| ACACCTGTGTCACCTGG | 1388 | 2 | 0 | 10 | 1 | 0.00435 | 15 | 26015921 | OCA2 | OCA2 |
| CACACACACACCCGGGC | 1389 | 0 | 3 | 9 | 0 | 0.00442 | 8 | 37774040 | GPR124 | BRF2 |
| TATTTGCCAAGTTGTAC | 113 | 4 | 0 | 14 | 6 | 0.00460 | 7 | 26997443 | | |
| TCAAGTGTGAGGGGAAG | 1391 | 28 | 3 | 25 | 13 | 0.00460 | 12 | 117004568 | FLJ20674 | PBP |
| TGCACGCACACTCTTCC | 1392 | 22 | 3 | 16 | 8 | 0.00460 | 4 | 147216331 | LOC152485 | LOC152485 |
| TCACAAGGACAGATGCC | 1393 | 0 | 0 | 3 | 8 | 0.00468 | 16 | 68353990 | WWP2, NOB1P | WWP2 |
| TCGAAGGCGGCCGGAGG | 1394 | 0 | 0 | 1 | 7 | 0.00494 | 2 | 56323579 | EFEMP1 | VRK2 |
| AAGAAATGCCGTTTCCA | 1395 | 0 | 6 | 1 | 1 | 0.00539 | | | | |
| TCACATTTCAGTTTGGG | 1396 | 33 | 7 | 46 | 22 | 0.00563 | 2 | 227854436 | COL4A4 | COL4A4, COL4A3 |
| GGGTGCGGAACCCGGCC | 1397 | 35 | 5 | 31 | 20 | 0.00583 | 20 | 26137059 | C20orf91 | FLJ45832 |
| GCAGAGGGCCTGCCCTT | 1398 | 8 | 0 | 1 | 2 | 0.00583 | 12 | 111958064 | OAS2 | DTX1 |
| TGGGAAAGGTCTTGTGG | 1399 | 40 | 12 | 65 | 47 | 0.00596 | 10 | 102749640 | LZTS2, PEO1 | LZTS2 |
| GGCAGGAAGACGGTGGA | 1400 | 3 | 0 | 13 | 7 | 0.00602 | 22 | 49403345 | ARSA | ACR |
| ACTGTCAAGGTTTCAGG | 1401 | 11 | 0 | 12 | 4 | 0.00609 | 4 | 185018413 | FLJ12716 | STOX2 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| CAGCCACACCAGTTGCC | 1402 | 5 | 1 | 7 | 15 | 0.006122 | 1, 1 | 120323448, 142699053 | | |
| GGCTTCACCATTGACTC | 1403 | 20 | 2 | 23 | 18 | 0.006576 | | | | |
| AAGCAGTCTCCCAGGGG | 1404 | 7 | 0 | 0 | 2 | 0.0067705 | 10 | 101079937 | HPSE2 | CNNM1 |
| TGGGACCCCAGCACGAC | 1405 | 2 | 0 | 6 | 10 | 0.0068417 | | | | |
| GCCCGTTCTCAATGAGC | 1406 | 2 | 7 | 0 | 7 | 0.0069278 | 10, 1 2, 15, 15, 1, 1, 1, 1, 22_random, 2, 3, 3, 3, 4, 5, 5, 7, 7, 9 | 120645025, 68533541, 43372896, 50365101, 157811972, 189557275, 223626710, 227896663, 222794, 188246276, 380694 28, 109228289, 114248945, 70807980, 37452235, 151074465, 127697694, 138662914, 26653797 | | |
| TATAAAATGTGTAAAGT | 1407 | 6 | 4 | 0 | 10 | 0.00705 | 15, 1 5, 15, 15, 1 5, 15, 15_random, 15_random, 15_random | 80434892, 80584867, 80742379, 80821379, 80979445, 82689354, 428294, 490281, 685562 | | |
| CTACTGCACTCCAGCCT | 1408 | 0 | 0 | 0 | 6 | 0.0074164 | | | | |
| CAACCCCAACCGCGTTC | 1409 | 13 | 5 | 17 | 27 | 0.0076309 | 3 | 126257049 | MUC13 | SLC12A8 |
| AGCTCATTTACATTTTA | 1410 | 9 | 0 | 2 | 4 | 0.0076883 | 6 | 35561523 | TEAD3 | TEAD3 |
| TGTCACAGACTCCCAGC | 1411 | 32 | 8 | 22 | 12 | 0.0076921 | 21 | 15359515 | NRIP1 | USP25 |
| GAAGCTTCGGGGTTCCC | 1412 | 8 | 0 | 13 | 13 | 0.0077771 | | | | |
| GACCCCACAAGGGCTTG | 1413 | 22 | 6 | 23 | 5 | 0.0081109 | 15 | 73922730 | ODF3L1 | UBE2Q2 |
| TGTGTCCTCGGCCCAGG | 1414 | 16 | 2 | 22 | 10 | 0.00857 32 | 6 | 90177921 | RRAGD | RRAGD |
| TTCCAGTGGCAAGTTGA | 1415 | 71 | 25 | 77 | 43 | 0.0087743 | 14 | 104557983 | CDCA4 | CDCA4 |
| CCCAGCAGAGAAGTCTG | 1416 | 4 | 0 | 6 | 11 | 0.0087872 | 11 | 129824700 | ADAMTS15 | ADAMTS15 |
| TATGTCAGTGTCTGGGA | 1417 | 0 | 1 | 8 | 1 | 0.008896 | 19 | 35411442 | C19orf2 | ZNF536 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| GCCTTCGACCCCCAGGC | 1418 | 8 | 2 | 4 | 16 | 0.0089053 | 9 | 136311861 | BTBD14A | LHX3 |
| CCCGCGCTCACTGCCAA | 1419 | 9 | 1 | 2 | 12 | 0.0095113 | 12 | 121990010 | ARL6IP4, FLJ13491, ABCB9 | ARL6IP4, PITPNM2 |
| CCAGGCAGGGGTGGGGG | 1420 | 18 | 6 | 30 | 9 | 0.0095478 | 16, 16 | 32804836, 33685485 | | |
| ATGAGTCCATTTCCTCG | 1421 | 23 | 5 | 40 | 20 | 0.0097631 | 7 | 1479529 | MGC10911 | LOC401296 |
| GGGGTAACTCTTGAGTC | 1422 | 1 | 0 | 3 | 8 | 0.0097789 | 8 | 145230748 | SHARPIN, CYC1 | SHARPIN, MAF1, KIAA1875 |
| AGTGAGCCACCACACCC | 1423 | 1 | 0 | 1 | 7 | 0.0098852 | 10 | 116518059 | ABLIM1 | KIAA1600 |
| GCCAAGCCAAATGAAGG | 1424 | 1 | 0 | 1 | 7 | 0.0098852 | 10 | 72642515 | UNC5B | UNC5B |
| GATTATGAAAGCCCATC | 1425 | 26 | 5 | 16 | 13 | 0.0099399 | 11 | 128748605 | RICS | BARX2 |
| ATGATTCCTTGCGATTC | 1426 | 0 | 5 | 0 | 1 | 0.0100684 | | | | |
| GTAGGGGTAAAAGGAGG | 1427 | 0 | 5 | 0 | 1 | 0.0100684 | | | | |
| TTGCCCAGGCTGGTCTT | 1428 | 0 | 5 | 0 | 1 | 0.0100684 | | | | |
| TTGGCCAGACTGGTCTG | 1429 | 0 | 5 | 0 | 1 | 0.0100684 | | | | |
| CCTAACAAGATTGCATA | 1430 | 47 | 12 | 62 | 41 | 0.0102573 | 16 | 68890570 | AARS | DDX19B, DDX19-DDX19L |
| TCTGAGGGTCGACCAGC | 1431 | 0 | 5 | 0 | 0 | 0.010276 | | | | |
| TCTTCATCCCCAAGCGG | 1432 | 0 | 5 | 0 | 0 | 0.010276 | | | | |
| GACGAGAGCGCCGCCGC | 1433 | 1 | 0 | 7 | 0 | 0.0105013 | 2 | 106269374 | UXS1 | ST6GAL2 |
| GTGCCGCCGCGGGCGCC | 1434 | 5 | 15 | 30 | 18 | 0.0105168 | 1 | 22215644 | WNT4 | ZBTB40 |
| GTGGATAAGTTTTTTGA | 1435 | 0 | 5 | 1 | 0 | 0.010527 | | | | |
| AGCCACCTGCGCCTGGC | 1436 | 50 | 16 | 37 | 26 | 0.0118729 | 4 | 80217832 | PAQR3 | GK2 |
| CCCCCAAGACACATCAA | 1437 | 7 | 4 | 24 | 10 | 0.0122468 | 14 | 95052535 | C14orf49 | GLRX5 |
| ACAAAAATGATCGTTCT | 1438 | 46 | 10 | 41 | 31 | 0.0122819 | 7 | 29841681 | PLEKHA8, FKBP14 | PLEKHA8 |
| AGAACGGGAACCGTCCA | 1439 | 39 | 21 | 29 | 52 | 0.0123784 | 12 | 56418555 | CENTG1 | CENTG1, TSPAN31, CDK4 |
| ACCATAGCAACCCTGCC | 1440 | 2 | 0 | 2 | 8 | 0.0124154 | 15 | 65920063 | LBXCOR1 | PIAS1 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| TGCCCTGGGCTGCCCGC | 1441 | 7 | 1 | 4 | 13 | 0.012724 5 | 7 | 35070597 | TBX20 | FLJ22313 |
| ATGGCCAGGCTGGTTTC | 1442 | 2 | 5 | 0 | 0 | 0.0131292 | 18 | 7106956 | LAMA1 | LAMA1 |
| CGCCAGCGCCCGCGACC | 1443 | 2 | 5 | 0 | 0 | 0.0131292 | | | | |
| GGTTTGCTGAAGTGGGG | 1444 | 9 | 3 | 23 | 10 | 0.0131729 | 9 | 137486498 | FLJ20433 | FLJ20433 |
| AGCCGCGGGCAGCCGCC | 1445 | 8 | 0 | 2 | 3 | 0.0134184 | 9 | 132487454 | FLJ46082 | BARHL1, DDX31 |
| GCGGGCGCGGCTCTGCG | 1446 | 9 | 0 | 6 | 2 | 0.0134888 | 18 | 12297562 | CIDEA | TUBB6 |
| TGGAGCTGGTCGGGGAG | 1447 | 16 | 4 | 27 | 12 | 0.0140481 | | | | |
| GCGCCAACCGGGGCTGC | 1448 | 12 | 1 | 16 | 6 | 0.0141907 | 8 | 145605854 | CPSF1 | SLC39A4 |
| GCCCTGGGGCTTAACC | 1449 | 21 | 3 | 14 | 12 | 0.014371 | 12 | 69602321 | TMEM16A | TMEM16A |
| ACCCACCAACACACGCC | 679 | 9 | 2 | 19 | 17 | 0.0144372 | 5 | 170221996 | RANBP17 | RANBP17 |
| GGCCGGTGCCGCCAGTC | 1451 | 19 | 5 | 14 | 27 | 0.0152514 51 | | 99266585 | CYP46A1 | EML1 |
| GCGGGGCAGCAGACGC | 1452 | 22 | 4 | 36 | 28 | 0.015363 | 8 | 71145343 | PRDM14 | PRDM14 |
| AGGCAGGAGATGGTCTG | 1453 | 22 | 5 | 32 | 12 | 0.0172091 | 9 | 130564512 | ASS | PRDM12 |
| AGAGAGAAGTTTCTGAG | 1454 | 1 | 5 | 1 | 0 | 0.017309 | | | | |
| TAAAAACTAGACAGAAG | 1455 | 1 | 5 | 1 | 0 | 0.017309 | | | | |
| AACTTGGGGCTGACCGG | 1456 | 4 | 0 | 2 | 8 | 0.0173746 | 7 | 69604814 | AUTS2 | AUTS2 |
| CCACTGCACTCCAGTCT | 1457 | 0 | 5 | 1 | 1 | 0.0173956 | | | | |
| GACAGACCCGGTCCCTG | 1458 | 5 | 0 | 0 | 0 | 0.0175720 96 | | 17610446 | RRBP1 | RRBP1 |
| AAAAGATGTGGTTTGGC | 1459 | 24 | 6 | 38 | 17 | 0.0185847 | | | | |
| TGTTGAGAATGGGGTAG | 1460 | 14 | 1 | 13 | 7 | 0.0186181 | 7 | 121538886 | LOC389549 | CADPS2 |
| AAGCGGGGAGGCTGAGG | 1461 | 5 | 1 | 14 | 12 | 0.0188420 3 | | 60247223 | OSBPL2, FLJ44790 | OSBPL2 |
| GAAACTGAACAACCTGC | 1462 | 13 | 19 | 8 | 22 | 0.0192181 | | | | |
| TCAGCCCAGCGGTATCC | 1463 | 15 | 4 | 32 | 24 | 0.0195120 4 | | 17610446 | RRBP1 | RRBP1 |
| GCCCTGTGTGTCAGCCT | 1464 | 3 | 3 | 4 | 15 | 0.0196416 67 | | 22733582 | HS3ST2 | HS3ST2 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| GGAACGCCCCACCCCGA | 1465 | 12 | 1 | 4 | 8 | 0.0201714 | | 551070 | C11orf35, LRRC56 | RASSF7 |
| AACTGGCAGAGCAGCAG | 1466 | 0 | 1 | 7 | 1 | 0.0202297 | 5 | 52811829 | MOCS2 | FST |
| GTTTATTCCAAACACTG | 1467 | 13 | 1 | 8 | 12 | 0.0203504 | 19 | 53638755 | GRIN2D | GRIN2D, GRWD1, KCNJ14 |
| CAGCCGAAGTGGCGCTC | 1468 | 8 | 1 | 4 | 12 | 0.0207811 98 | | 270514 | NALP6 | NALP6, ATHL1 |
| GGGTAGGCACAGCCGTC | 1469 | 4 | 0 | 4 | 9 | 0.0212363 | 16 | 30010789 | TBX6, PPP4C | YPEL3 |
| CCTGTAATCCCAGCTGC | 1470 | 1 | 1 | 0 | 6 | 0.02132 66 | | | | |
| CGTAGGGCCGTTCACCC | 1471 | 2 | 4 | 6 | 14 | 0.0221714 | 19 | 63765961 | ZNF42, UBE2M, CHMP2A | ZNF42 |
| CCTGCGCCGCCGCCCGG | 1472 | 5 | 1 | 8 | 13 | 0.0224732 | 20 | 48241223 | CEBPB | CEBPB |
| CCTGCGCCGGGGGAGGC | 1473 | 118 | 48 | 139 | 113 | 0.0227399 | 4 | 3804825 | FLJ35424 | ADRA2C |
| TACGCGGGTGGGGAAG | 1474 | 67 | 27 | 62 | 37 | 0.0229019 | | | | |
| GCCACGAAGAACCGGCT | 1475 | 1 | 0 | 1 | 6 | 0.0232111 49 | | 69298861 | FGF4 | FGF4 |
| TGAGGTGTCAGTCTGCC | 1476 | 1 | 8 | 2 | 3 | 0.023234 | 9 | 110077301 | C9orf152 | TXN |
| TCCCCATCGGTGGACCC | 1477 | 0 | 1 | 6 | 0 | 0.0237515 | 11 | 33847748 | LMO2 | LMO2 |
| CTGCCCGCCTGCTTTCC | 1478 | 1 | 0 | 6 | 0 | 0.024199 51 | 9 | 95352998 | PTCH | LOC375748 |
| TGAAACGCTGAAGGGAG | 1479 | 1 | 0 | 6 | 0 | 0.024199 51 | | | | |
| CGATTCCATTAGATGAT | 1480 | 1 | 5 | 0 | 2 | 0.0247046 | | | | |
| CTGGGTTGCGATTAGCT | 1481 | 44 | 15 | 29 | 40 | 0.0254225 | 5 | 122462500 | PPIC | FLJ36090 |
| AGGTTGTTGTTCTTGCC | 1482 | 0 | 1 | 0 | 5 | 0.0256876 | | | | |
| CAGCTGCCTGGGGAGG | 1483 | 0 | 1 | 0 | 5 | 0.0256876 | 2, 2 | 87000649, 106562389 | | |
| GGAATTATCTCTTCCTT | 1484 | 0 | 2 | 6 | 8 | 0.0257667 | 15 | 66133874 | PIAS1 | PIAS1 |
| CTATACTGGCTCGTCCT | 1485 | 18 | 4 | 9 | 5 | 0.0260243 | 3 | 10724319 | ATP2B2 | SLC6A11 |
| TAACTGTCCTTTCCGTA | 1486 | 29 | 10 | 49 | 25 | 0.0262064 | 8 | 92066919 | EFCBP1 | TMEM55A |
| GTCCGCACTACGAATCT | 1487 | 0 | 0 | 7 | 4 | 0.0262606 | 2 | 74668534 | HTRA2, AUP1, DQX1 | AUP1, LOXL3, HTRA2 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| ATCTGCCCGCCTCAGCC | 1488 | 1 | 2 | 7 | 0 | 0.026545 | 19 | 60289933 | EPS8L1 | EPS8L1, PPP1R12C |
| AATTTGTTGCAGGGTCT | 1489 | 10 | 1 | 5 | 1 | 0.0269431 | | | | |
| TACCCTAAAACTTAAAG | 1490 | 6 | 11 | 2 | 8 | 0.0274392 | 12, 2 | 120525394, 21544337 | | |
| AAACGAATTACACGGTG | 1491 | 1 | 0 | 0 | 5 | 0.0276621 | | | | |
| GCAGCCCCTTGGTGGAG | 1492 | 46 | 12 | 50 | 46 | 0.0278752 | 16 | 88518083 | TUBB3, MC1R | TUBB3 |
| CACAGCAGCCCGTCAGG | 1493 | 1 | 0 | 4 | 7 | 0.0280968 | 9 | 10603198 | PTPRD | TYRP1 |
| CCAGTGCACTCCAGCCT | 1494 | 11 | 1 | 3 | 6 | 0.0284294 | 1 | 39767910 | HEYL | HEYL |
| TGAGGTGTCAGTGTGCC | 1495 | 0 | 0 | 1 | 5 | 0.0289863 | | | | |
| ACGCCGGGGCCGCTCGC | 1496 | 0 | 4 | 0 | 0 | 0.028993 | 4 | 38487591 | FLJ13197 | KLF3, FLJ13197 |
| AGCCACCCCGCCTGGCC | 1497 | 0 | 4 | 0 | 0 | 0.028993 | | | | |
| AGCCCTGGGGAAAGGGG | 1498 | 0 | 4 | 0 | 0 | 0.028993 | | | | |
| AGTCCTGCACAGAAACT | 1499 | 0 | 4 | 0 | 0 | 0.028993 | | | | |
| ATGCTCCTAAGCCAAAA | 1500 | 0 | 4 | 0 | 0 | 0.028993 | | | | |
| ATTTGAGGGTTTGGGAC | 1501 | 0 | 4 | 0 | 0 | 0.028993 | | | | |
| CATAACCTAAGGTGAAG | 1502 | 0 | 4 | 0 | 0 | 0.028993 | | | | |
| CCCTATGCCTACCCAAG | 1503 | 0 | 4 | 0 | 0 | 0.028993 | | | | |
| CTCGGAAGGAAGCACCA | 1504 | 0 | 4 | 0 | 0 | 0.028993 | | | | |
| CTGGACAGAAGGGACTG | 1505 | 0 | 4 | 0 | 0 | 0.028993 | | | | |
| GCCTTTCATAGAGCAGC | 1506 | 0 | 4 | 0 | 0 | 0.028993 | | | | |
| GCGAAACCCCTCCCCCC | 1507 | 0 | 4 | 0 | 0 | 0.028993 | | | | |
| GCTAAACCCTCAACAAG | 1508 | 0 | 4 | 0 | 0 | 0.028993 | | | | |
| GGAAACTGAGGCAGAAG | 1509 | 0 | 4 | 0 | 0 | 0.028993 | | | | |
| GGAGCTGGCAGCAGAGG | 1510 | 0 | 4 | 0 | 0 | 0.028993 | | | | |
| GTGGCTTGCGCCTGTAC | 1511 | 0 | 4 | 0 | 0 | 0.028993 | | | | |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| GTGGTACCACAGATGGG | 1512 | 0 | 4 | 0 | 0 | 0.028993 | | | | |
| GTGGTGTGAGCCTGTAA | 1513 | 0 | 4 | 0 | 0 | 0.028993 | | | | |
| TAAGGCTAGACAGGAGA | 1514 | 0 | 4 | 0 | 0 | 0.028993 | | | | |
| TATCTGTAACTTACTAA | 1515 | 0 | 4 | 0 | 0 | 0.028993 | | | | |
| TGAAGATATACCCGTTC | 1516 | 0 | 4 | 0 | 0 | 0.028993 | | | | |
| GCCAGGGCCCAGGGGTC | 1517 | 6 | 2 | 12 | 1 | 0.0291436 | 7, 7 | 56827509, 62532332 | | |
| CGAACTTCCCGGTTCCG | 1518 | 45 | 13 | 49 | 28 | 0.0292354 | 12 | 127277890 | SPRR2G | SLC15A4 |
| GTGGCTTGCGCCTGTAG | 1519 | 15 | 5 | 15 | 24 | 0.029257 | 14 | 103407981 | PPP1R13B | C14orf2 |
| CACTCCACGTTTATAGA | 1520 | 1 | 0 | 7 | 7 | 0.0294868 | 4 | 146760778 | SMAD1 | SMAD1 |
| AGCAGTGGAAGCTTGAG | 1521 | 11 | 2 | 4 | 13 | 0.0301548 | 3 | 148597613 | ZIC4 | ZIC4 |
| GCCTGACCCTTTTCTGC | 1522 | 0 | 2 | 6 | 0 | 0.0303522 | 17 | 75366221 | ENPP7 | CBX2 |
| GCCGGGCGGGCTCCTC | 1523 | 6 | 1 | 12 | 2 | 0.0305549 | | | | |
| CAGAGGGAATAACCAGT | 1524 | 3 | 1 | 5 | 11 | 0.0306269 | 19 | 40183199 | GRAMD1A | GRAMD1A |
| AGCCACTGTGCCCAGCC | 1525 | 3 | 5 | 0 | 1 | 0.0306796 | | | | |
| AGCCACCACACCTGGCT | 1526 | 1 | 4 | 0 | 0 | 0.0311759 | | | | |
| ATTATAAGTTTCCTGAG | 1527 | 1 | 4 | 0 | 0 | 0.0311759 | | | | |
| GGCTACAGAGTGAGAGC | 1528 | 1 | 4 | 0 | 0 | 0.0311759 | | | | |
| AGCCATCACGCCCGGCC | 1529 | 0 | 4 | 0 | 1 | 0.0314057 | | | | |
| CAGCAGTTTCTGAGAAT | 1530 | 0 | 4 | 0 | 1 | 0.0314057 | | | | |
| TACATTTCTATTTGTGG | 1531 | 0 | 4 | 0 | 1 | 0.0314057 | | | | |
| CAGAATCTTCAAAAAGA | 1532 | 0 | 0 | 5 | 0 | 0.0316432 | | | | |
| TACACCAGCGTGGAGGG | 1533 | 0 | 0 | 5 | 0 | 0.0316432 | 2 | 47660006 | KCNK12 | KCNK12 |
| CGGAGCCGCCCCAGGGG | 1534 | 1 | 0 | 6 | 7 | 0.0326511 | 11 | 496887 | RNH1 | RNH1 |
| TATCCCAGAACTTAAAG | 1535 | 0 | 5 | 1 | 4 | 0.0327276 | 6 | 117609989 | RFXDC1 | VGLL2 |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| TGCAAATTGTGGGGTG | 1536 | 37 | 13 | 39 | 17 | 0.0329563 | | | | |
| CAGCCGACTCTCTGGCT | 1537 | 44 | 12 | 33 | 34 | 0.0329584 | 3 | 2115478 | CNTN6 | CNTN4 |
| GGCACCGTCCTGCTGTC | 1538 | 10 | 1 | 4 | 2 | 0.032995 | | | | |
| TGCAAGTGGACATTTGG | 1539 | 5 | 2 | 0 | 0 | 0.0331888 | | | | |
| ACAAAGTACCGTGGTTC | 1540 | 16 | 3 | 28 | 23 | 0.0331911 | 12 | 121784028 | TSP-NY, DENR | TSP-NY |
| CCAAATCCTACCCAGCC | 1541 | 0 | 2 | 0 | 5 | 0.0339817 | 14 | 70178138 | MED6 | MAP3K9 |
| ATGGTGTCGCTGGACAG | 1542 | 11 | 1 | 5 | 10 | 0.0346632 | 2 | 218907280 | IL8RA | ARPC2 |
| TTCGGGCCGGGCCGGGA | 1325 | 27 | 12 | 47 | 20 | 0.0351055 | 1 | 162057422 | LMX1A | RXRG |
| ATGTATCTACTCAGCTA | 934 | 0 | 5 | 3 | 1 | 0.0358045 | | | | |
| TATCAACTTGCAAATTC | 1208 | 0 | 5 | 3 | 1 | 0.0358045 | | | | |
| TCCATAGATTGACAAAG | 1327 | 26 | 5 | 31 | 16 | 0.0366297 | 6 | 114288310 | MARCKS | MARCKS |
| CCAGCGGACTGCGCTGC | 35 | 0 | 1 | 2 | 6 | 0.0366966 | 5 | 176169485 | TSPAN17 | UNC5A |
| AGCAACTTTCCTGGGTC | 302 | 25 | 4 | 30 | 27 | 0.0370664 | 20 | 30259008 | PLAGL2, POFUT1 | PLAGL2, |
| GGCTCTCTGGATTCCCC | 303 | 6 | 0 | 2 | 1 | 0.0371474 | 6 | 19800086 | IBRDC2 | ID4 |
| CAGCAGCAGTGGGGCTG | 1331 | 2 | 0 | 6 | 0 | 0.0375165 | 3 | 13566249 | FBLN2 | FBLN2 |
| GGTCCATCTGCAAAGGG | 677 | 4 | 1 | 12 | 3 | 0.0377136 | 19, 19 | 43952443, 43975229 | | |
| AATGAACGACCAGACCC | 250 | 32 | 17 | 63 | 43 | 0.0380187 | 10 | 70386398 | DDX21, DDX50 | DDX21 |
| TAATCTCCCTAAATACC | 1336 | 23 | 12 | 38 | 42 | 0.0383005 | 7 | 75592300 | HSPB1 | YWHAG |
| CTCCGGGTGGGAGGCC | 700 | 1 | 0 | 2 | 6 | 0.0387389 | 14 | 104187893 | FLJ42486 | C14orf151 |
| AACCCAGGAGGCGGAGC | 1163 | 0 | 5 | 2 | 2 | 0.0403961 | 8 | 74877871 | UBE2W | UBE2W |
| GCGTTTGGGGGTGTCGG | 1339 | 2 | 0 | 0 | 5 | 0.0407787 | 4 | 147216331 | LOC152485 | LOC152485 |
| GCGAAACCCCGTCTCTA | 481 | 5 | 5 | 1 | 10 | 0.0408821 | 12, 17, 17, 19, 4, 8, 9 | 74400342, 2626651, 5262441, 34250652, 7171443, 1168514781802, 6671656 | | |
| AAACGAAAGGTTCAAGT | 1345 | 10 | 21 | 15 | 10 | 0.0409508 | | | | |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | Asci Position | Up-Gene | Dn-Gene |
|---|---|---|---|---|---|---|---|---|---|---|
| CAGATTCTACAAAAGGA | 843 | 0 | 4 | 0 | 2 | 0.0413442 | | | | |
| AGCCACTGCACCTGGCC | 1351 | 1 | 7 | 1 | 4 | 0.0423153 | 1, 1, 20 | 231516029, 231648771, 44807423 | | |
| CCGGACGTACATCGTTA | 1362 | 5 | 0 | 0 | 5 | 0.0430657 | | | | |
| GCAGCGGCGCTCCGGGC | 1215 | 19 | 2 | 25 | 20 | 0.0432248 | 1 | 151836629 | DCST1 | ADAM15 |
| TTTCCAGTGCAATTCCG | 707 | 3 | 2 | 9 | 13 | 0.0438402 | | | | |
| TTTCTTCTAACAAAGGC | 676 | 0 | 0 | 2 | 5 | 0.0439943 | 5 | 65257128 | NLN | ERBB2IP |
| ACCCTCTCACACGCACC | 1324 | 4 | 0 | 0 | 0 | 0.0444093 | | | | |
| AGGCTGGGGCACAGGAC | 926 | 4 | 0 | 0 | 0 | 0.0444019 | 19 | 51834661 | GNG8 | MGC15476 |
| CCAACGCCTGAAGCTCT | 1203 | 4 | 0 | 0 | 0 | 0.0444010 | 10 | 30064273 | SVIL | SVIL |
| TCTCTGTAGCTCACCCG | 300 | 4 | 0 | 0 | 0 | 0.0444019 | 19 | 2376268 | TMPRSS9 | TIMM13, TMPRSS9, LMNB2 |
| TGCAACCACCTGAGGTT | 1343 | 4 | 0 | 0 | 0 | 0.0444093 | 2, 2_random | 242462672, 167214 | | |
| GAAATGCTAAGGGGTTG | 296 | 10 | 6 | 25 | 9 | 0.0448212 | 1 | 9646024 | RP13-15M17.2 | PIK3CD |
| AGCCACTGCGCCCGGCC | 544 | 3 | 8 | 5 | 1 | 0.0449333 | 7 | 150438654 | SMARCD3 | NYREN18 |
| CCCCGGCAGGCGGCGGC | 227 | 40 | 13 | 51 | 27 | 0.0450711 | 11 | 124175712 | FLJ23342 | ROBO3 |
| GCCACCGTCCTGCTGTC | 1205 | 1284 | 912 | 1467 | 1184 | 0.0454591 | | | | |
| CAGCCAGCTTTCTGCCC | 139 | 47 | 20 | 56 | 26 | 0.0455906 | 9 | 136323041 | LHX3 | QSGN6L1 |
| TTGGCCAGGCTGGTCTC | 812 | 45 | 51 | 52 | 47 | 0.0461099 | 10, 10, 14, 14, 17, 19, 19, 1, 1, 1, 1, 20, 4, 5, 5, 7, 7, 7, 8, 8, 8 | 102269169, 119125579, 104353395, 104838293, 2574777, 951525, 54391626, 672837 6, 9576680, 200773326, 239591215, 44814870, 3623233, 149090483, 149717373,6 89386, 655378 21, 1042663 33, 4225145 5, 42603361, 68020728 | | |
| CCATTGCATTCCATTCC | 789 | 0 | 0 | 0 | 4 | 0.0465406 | | | | |

TABLE 15-continued

List of tags statistically significantly (p < 0.05) differentially present in the four Stem and Differentiated Cell MSDK libraries.

| MSDK-Tag | SEQ ID NO: | CD10 | CD24 | CD44 | Muc1 | pValue | Chr | AscI Position | Up-Gene | Dn-Gene |
|---|---|---|---|---|---|---|---|---|---|---|
| CCTGGCTAATTTTTGT | 1078 | 0 | 0 | 0 | 4 | 0.04654 06 | | | | |
| CCTTTGGGTGGAGCAGT | 271 | 0 | 0 | 0 | 4 | 0.04654 06 | | | | |
| CTACAGGCTGGAGGGCA | 937 | 0 | 0 | 0 | 4 | 0.04654 06 | 19 | 1464508 | THSD6 | RKHD1 |
| GCCATAACTTTTAAGTC | 488 | 0 | 0 | 0 | 4 | 0.04654 06 | 14 | 74418552 | DLST | DLST |
| GGGTGGGGGTGCAGGC | 939 | 0 | 0 | 0 | 4 | 0.04654 06 | 2 | 241695521 | FLJ22671 | MTERFD2 |
| GTCTCGCTGGCTTCAGG | 1113 | 0 | 0 | 0 | 4 | 0.04654 06 | 15 | 91055991 | LOC400451 | CHD2 |
| GTGACTTTCTTCGGGGG | 1366 | 0 | 0 | 0 | 4 | 0.04654 06 | 10 | 79066844 | KCNMA1 | KCNMA1 |
| TGGGGACCCGAGAAGGG | 592 | 0 | 0 | 0 | 4 | 0.04654 06 | 22 | 36239821 | CARD10 | CDC42EP1 |
| TTGATTTGTGAATACCC | 1002 | 0 | 0 | 0 | 4 | 0.04654 06 | | | | |
| GCAGGGAAGAGAGGAGC | 1129 | 0 | 1 | 5 | 0 | 0.04942 05 | 12 | 117004568 | FLJ20674 | PBP |
| ATGCGAGGGCGCGGTA | 1162 | 37 | 9 | 44 | 32 | 0.04991 62 | 2 | 37811338 | CDC42EP3 | FAM82A |

P value, the significance of the difference in the raw abundances of the relevant MSDK tag between the four libraries.
SEQ ID NO:, refers to the Sequence Identification Number assigned to each MSDK-tag nucleotide sequence
CD10, CD24, CD44, MUC1, refer to the different cell populations used in the MSDK analysis.
AscI position, refers to the bp position within the corresponding chromosome(s) where the AscI site is located.
Chr, chromosome in which MSDK tag sequence is located.
UpGene, refers to nearest gene 5' to the AscI site.
DnGene, refers to the nearest gene 3' to the AscI site.

Figure 26C:
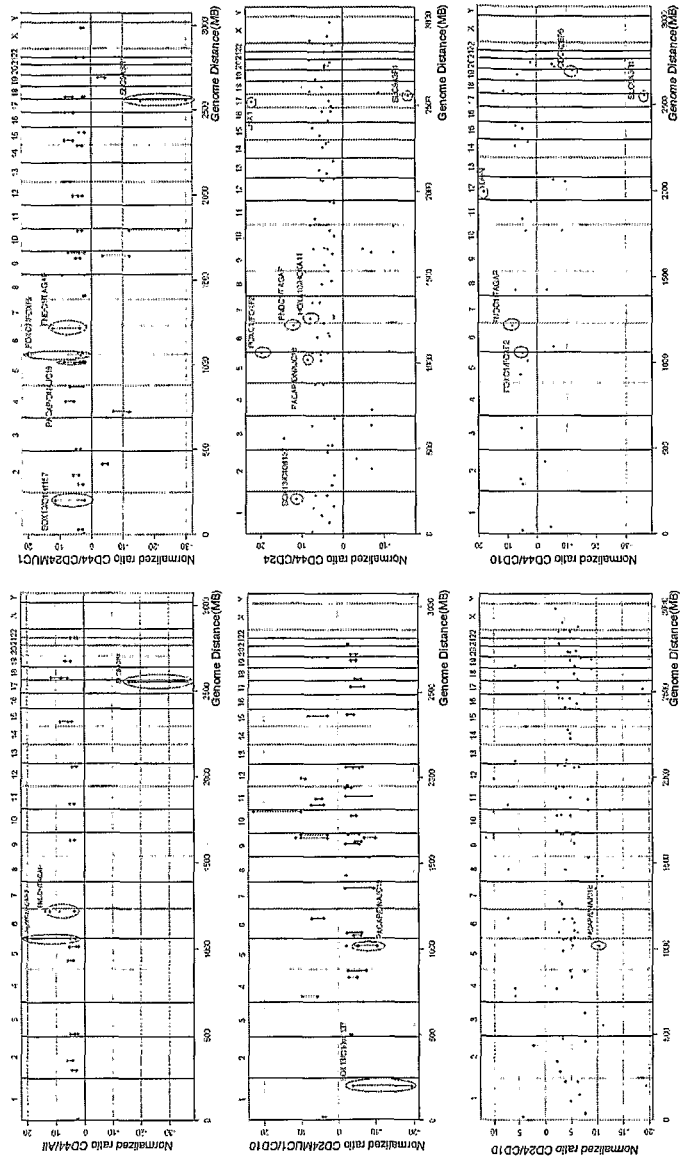
FIG. 26C is a series of graphs showing the ratio and location of statistically significant (p<0.05) tags, generated by MSDK, that are differentially methylated in different cell types isolated from normal mammary tissue. Dots corresponding to genes selected for further validation are circled.

In addition, CD10+ and MUC1+ cells were also found to be hypomethylated compared to CD24+ cells. This latter observation raised the hypothesis (also suggested by SAGE data on these cells) that CD10+ and MUC1+ cells may represent a mix of terminally differentiated myoepithelial and luminal epithelial cells, respectively, and their lineage committed progenitors, while CD24+ cells are mostly terminally differentiated luminal epithelial cells. To identify loci specifically methylated in stem or differentiated cells of a specific lineage (luminal or myoepithelial), pair-wise as well as combined comparisons of the MSDK libraries were performed. Statistically significant (p<0.05) differences were found in each of these comparisons and led to the identification of tags that were specifically methylated in differentiated (luminal or myoepithelial) cells (see FIG. 26C). Interestingly, many of the genes hypomethylated in CD44+ cells encode homeogenes, polycomb (chromo domain containing) proteins, or proteins involved in pathways known to be important for stem cell function. A detailed summary of these genes is shown in Table 16.

TABLE 16

Selected Differentially Methylated Genes in the CD44+ and CD24+ Libraries

| Tag | SEQ ID NO: | CD24 | CD44 | p value | Ratio | Chr | Gene | Distance | Position | Strand | Function |
|---|---|---|---|---|---|---|---|---|---|---|---|
| CACAGCCAGCCTCCCAG | 213 | 0 | 39 | 5.47E-07 | 22 | 17 | LHX1 | 3696 | inside | + | Homeobox gene |
| TATTTGCCAAGTTGTAC | 113 | 0 | 14 | 0.00205972 | 8 | 7 | HOXA10 | -4360 | upstream | − | Homeobox gene |
| TATTTGCCAAGTTGTAC | 113 | 0 | 14 | 0.00205972 | 8 | 7 | HOXA11 | 627 | inside | − | Homeobox gene |

TABLE 16-continued

Selected Differentially Methylated Genes in the CD44+ and CD24+ Libraries

| Tag | SEQ ID NO: | CD24 | CD44 | p value | Ratio | Chr | Gene | Distance | Position | Strand | Function |
|---|---|---|---|---|---|---|---|---|---|---|---|
| ACCCACCAACACACGCC | 679 | 2 | 19 | 0.00311433 | 5 | 5 | TLX3 | -446896 | upstream | + | Homeobox gene |
| TCGCCGGGCGCTTGCCC | 90 | 7 | 66 | 9.33E-08 | 5 | 5 | PITX1 | 6168 | inside | - | Homeobox gene |
| ACAATAGCGCGATCGAG | 904 | 2 | 14 | 0.0178476 | 4 | 16 | IRX3 | -644272 | upstream | - | Homeobox gene |
| ACAATAGCGCGATCGAG | 904 | 2 | 14 | 0.0178476 | 4 | 16 | IRX5 | -460 | upstream | + | Homeobox gene |
| TTAAGAGGGCCCCGGGG | 1384 | 0 | 7 | 0.0241671 | 4 | 14 | NKX2-8 | 1823 | inside | - | Homeobox gene |
| GAAGGGAATCACAAAAC | 1390 | 0 | 7 | 0.0241671 | 4 | 4 | PHOX2B | -124519 | upstream | - | Homeobox gene |
| GCTATGGGTCGGGGGAG | 215 | 13 | 79 | 2.60E-07 | 3 | 17 | MEOX1 | -94080 | upstream | - | Homeobox gene |
| AGCCCTCGGGTGATGAG | 29 | 5 | 24 | 0.0106181 | 3 | 1 | LMX1A | -747 | upstream | - | Homeobox gene |
| CCCCGTTTTTGTGAGTG | 221 | 6 | 22 | 0.0355276 | 2 | 17 | HOXB9 | -20615 | upstream | - | Homeobox gene |
| AGCAGCAGCCCCATCCC | 811 | 19 | 55 | 0.0136901 | 2 | 10 | EMX2 | -166366 | upstream | + | Homeobox gene |
| CAGCCAGCTTTCTGCCC | 139 | 20 | 56 | 0.0169362 | 2 | 9 | LHX3 | -141 | upstream | - | Homeobox gene |
| CCCCAGGCCGGGTGTCC | 303 | 9 | 37 | 0.0070473 | 2 | 17 | CBX8 | -16725 | upstream | - | Polycomb protein |
| ACCCGCACCATCCCGGG | 229 | 46 | 140 | 5.96E-06 | 2 | 17 | CBX4 | -4595 | upstream | - | Polycomb protein |
| CACCAAACCTAGAAGGC | 591 | 10 | 33 | 0.0383201 | 2 | 2 | GLI2 | -56233 | upstream | + | Shh pathway |
| ACCCTGAAAGCCTAGCC | 266 | 3 | 24 | 0.00179963 | 4 | 21 | ITGB2 | -10800 | upstream | - | stem cell marker |
| TGGTTTACCTTGGCATA | 252 | 0 | 13 | 0.00977299 | 7 | 6 | FOXF2 | -6378 | upstream | + | Development/ differentiation |
| GTCCTTGTTCCCATAGG | 97 | 0 | 35 | 2.40E-06 | 19 | 6 | FOXC1 | -5061 | upstream | + | Development/ differentiation |
| CCCCCGCGACGCGGCGG | 34 | 0 | 20 | 0.000800427 | 11 | 1 | SOX13 | -576 | upstream | + | Development/ differentiation |
| TGCTTGGATCGTGGGGA | | 0 | 11 | 0.0187511 | 6 | 17 | SOX15 | -24267 | upstream | - | Development/ differentiation |
| CACTCCACGTTTATAGA | 1520 | 0 | 7 | 0.0241671 | 4 | 4 | SMAD1 | -783 | upstream | + | TGFb signaling |
| GTTTTGGGGGAATGGCA | 1450 | 2 | 14 | 0.0178476 | 4 | 6 | WISP3 | -180585 | upstream | + | WNT/APC/BCTN pathway |
| CACAGCCAGCCTCCCAG | 213 | 44 | 113 | 0.00118262 | 1 | 2 | TCF7L1 | 854 | inside | + | WNT/APC/BCTN pathway |

P value, the significance of the difference in the raw abundances of the relevant MSDK tag between the four libraries.
SEQ ID NO:, refers to the Sequence Identification Number assigned to each MSDK-tag nucleotide sequence
CD24 and CD44, refer to the different cell populations (e.g., stem cell and differentiated cell populations) used in the MSDK analysis.
Chr, chromosome in which MSDK tag sequence is located.
Gene, refers to nearest gene to the AscI site.
Position, refers to the location of the AscI site within the associated gene, (i.e., Upstream (5') or inside (within the intronic or exonic portion of the gene).
Distance, refers to the distance of the AscI site from the start site of transcription for the associated gene.
Function, refers to the putative function associated with each gene located near the respective AscI site.

Example 9

Confirmation of Stem and Differentiated Cell MSDK Results by Bisulfite Sequencing Analysis To confirm the MSDK results, sets of statistically significantly differentially methylated genes from each comparison were selected and their methylation status was analyzed by sequence analysis of bisulfite treated genomic DNA from the same sample that was used for MSDK. These genes included FNDC1 and FOXC1 (hypomethylated in CD44+ cells compared to all others), PACAP (hypomethylated in CD44+ and CD10+ cells compared to others), SLC9A3R1 (hypomethylated in CD24+ MUC1+ and CD10+ cells compared to CD44+), DDN1 (hypomethylated in CD44+ compared to CD10+ cells), and DTX1 and CDC42EP5 (hypomethylated in CD10+ compared to CD44+ cells). In all these cases, bisulfite sequencing analysis confirmed the MSDK results (see FIG. 27A).

Example 10

Determination of the Frequency and Consistency of Methylation Difference Between Stem and Differentiated Cells by qMSP To determine how consistently the selected genes of FIG. 27A are differentially methylated in stem and differentiated cells from multiple independent women, the quantitative methylation specific PCR (qMSP) assay (described above) was utilized to analyze methylation in a larger set of samples. qMSP confirmed MSDK and bisulfite sequencing data and demonstrated that cell lineage specific methylation is consistent among samples derived from women of different ages (18-58 years old) and reproductive history, although some variability in the degree of methylation was observed (see FIG. 27B).

Example 11

Analysis of Gene Expression of Selected Genes Differentially Methylated in Stem and Differentiated Cells by qRT-PCR To characterize the effect of methylation changes on gene expression, the expression of the selected genes was analyzed by quantitative RT-PCR in the same cells that were analyzed by qMSP in Example 10. FIG. 28 shows the relative expression of the selected genes differentially methylated in CD44+, CD10+, MUC1+, and CD24+ cell subsets. Overall, an association between the methylation status and expression of the genes was observed. However, methylation did not have the same effect on expression of all the genes. The expression of FNDC1, DDN, LHX1, and HOXA10 was lower in methylated samples, while PACAP and CDC42EP5 were expressed at higher levels in hypermethylated cells. In the case of FOXC1 and SOX13 in the CD44+, MUC1+, and CD24+ samples, there was an inverse association between methylation and gene expression, but FOXC1 was expressed in CD10+ cells despite being methylated and SOX13 was not highly expressed in CD10+ cells despite being hypomethylated. These variations could result if the CD10+ cell fraction is a mix of myoepithelial progenitor and committed myoepithelial cells, and thus, has both progenitor and differentiated cell properties.

Example 12

Correlation of Methylation Status to Clinico-Pathologic Characteristics of Breast Carcinomas To determine if the methylation of the most highly cell lineage specifically methylated genes would correlate with clinico-pathologic characteristics of breast carcinomas, the methylation of PACAP, FOXC1 (both unmethylated in CD44+ cells compared to MUC1, CD24+ and CD10+ cells), and SLC9A3R1 (hypermethylated in CD44+ cells compared to all three other cell types) were analyzed in 149 sporadic invasive ductal carcinomas, 11 BRCA1$^+$ tumors, 21 BRCA2$^+$ tumors, and 14 phyllodes tumors. Based on this analysis, the methylation of PACAP and FOXC1 were found to be statistically significantly associated with hormone receptor (estrogen receptor-ER, progesterone receptor-PR) and HER2 status of the tumors and with tumor subtypes. Basal-like tumors (defined as ER$^-$/PR$^-$/HER2$^-$) and BRCA1 tumors exhibited the same methylation profile as normal CD44+ stem cells, while ER$^+$ and HER2$^+$ tumors were more similar to differentiated cells. These results supported the hypothesis that either (a) different tumor subtypes have distinct cells of origin or (b) cancer stem cells in different tumors have different differentiation potential.

To evaluate these two hypotheses, qMSP analyses of putative cancer stem (lin$^-$/CD24$^{-/low}$/CD44$^+$/EPCR$^+$) and differentiated cells (CD24+) cells were performed using genes that were highly cell type specifically methylated in normal breast tissue (see FIG. 29A). This analysis demonstrated that the DNA methylation profiles of tumor stem (CD44+) and CD24+ cells were the same as their corresponding normal counterparts, suggesting that regardless of the tumor subtype, cancer stem cells are likely to be more similar to each other and to normal stem cells than to more differentiated (CD24+) cells from the same tumor.

Example 13

Correlation of Methylation Status to Clinico-Pathologic Characteristics of Breast Carcinomas Based on the hypothesis that cancer stem cells are responsible for the metastatic spread and recurrence of tumors, the number of cancer stem cells would be expected to be higher in distant metastases compared to primary tumors. To test this hypothesis, the methylation status of four of the most highly cell type specifically methylated genes in primary tumors and matched distant metastases (collected from the same patient) was analyzed. Unexpectedly, the methylation of HOXA10, FOXC1, and LHX1 was higher in distant metastases compared to primary tumors, approaching or even exceeding levels detected in differentiated CD24+ cells, while no clear pattern was observed for PACAP (see FIG. 29B). This suggested that the number of CD24+ cells is increased in the distant metastasis, a finding reinforced by immunohistochemical analyses of these samples using stem and differentiated cell markers. Of the several plausible explanations of these results, the most likely is cell plasticity and different selection conditions in the primary tumor and distant metastases. Indeed, analysis of E-cadherin methylation and expression demonstrated that cell differentiation is a dynamic process and could occur during the metastatic progression. Thus, it is possible that the CD44+ cancer stem cells were the ones that metastasize, but they differentiate at the site of metastasis. Analysis of the genetic composition of CD24+ and CD44+ cells at the single cell level in primary tumors and matched metastases would be necessary to decipher this question.

In summary, the genome-wide DNA methylation profile of human putative mammary epithelial stem cells and differentiated luminal and myoepithelial cells was determined. Genes that were found to be methylated in a cell type specific manner demonstrated that cancer stem and differentiated cells are epigenetically distinct and are more similar to their corresponding normal counterparts than to each other, and the methylation status of selected genes classified breast tumors into cell subtypes.

What is claimed is:

1. A method of determining, in a human test tissue fibroblast, the level of methylation of one methylation site in a region of the TMEM39A gene, the C7orf3 gene, or the IRX5 gene that is 5' of the transcription start site, the method comprising
    determining the level of methylation of a methylation site in a section of a gene by experimentally assaying, in a test fibroblast from test breast tissue, the degree of methylation of a cytosine residue in a CpG sequence in the section of the gene, wherein
    (i) the gene is TMEM39A gene, the section of the gene is 5' of the transcription start site of the gene, and the CpG sequence is in the AscI restriction site (A) that is in the region of the gene 5' of the transcription start site of the gene and (B) that was identified by the Methylation Specific Digital Karyotyping (MSDK) tag consisting of SEQ ID NO:621;
    (ii) the gene is the C7orf3 gene, the section of the gene is 5' of the transcription start site of the gene, and the CpG sequence is in the AscI restriction site (A) that is in the region of the gene 5' of the transcription start site of the gene and (B) that was identified by the MSDK tag consisting of SEQ ID NO:731; or
    (iii) the gene is the IRX5 gene, the section of the gene is 5' of the transcription start site of the gene, and the CpG sequence is in the AscI restriction site (A) that is in the region of the gene 5' of the transcription start site of the gene and (B) that was identified by the MSDK tag consisting of SEQ ID NO:904.

2. The method of claim 1, wherein the gene is the TMEM39A gene.

3. The method of claim 1, wherein the gene is the C7orf3 gene.

4. The method of claim 1, wherein the gene is the IRX5 gene.

* * * * *

SEQUENCE LISTING

<160> NUMBER OF SEQ ID NOS: 1559

<210> SEQ ID NO 1
<211> LENGTH: 660
<212> TYPE: DNA
<213> ORGANISM: Homo sapiens

<400> SEQUENCE: 1

| | | | | | |
|---|---|---|---|---|---|
| caacccggtt | cctgcaaaac | ccattgaagt | tccctttcct | tccttcttct | cagtcctaca | 60 |
| aaactcgttg | gtagggtctg | tgggagccgc | ggggccctgc | caacctcggg | gctgggccgg | 120 |
| gagccgagcg | caggcggtcg | gagggcaatg | agcaagcga | cagctccagg | cgctcctggg | 180 |
| ccctcggctg | ggagggaaga | gccgaggacc | ctgggtcgca | ccgcgcagat | ggagacgcgc | 240 |
| tcccagagcc | cccgggcagg | tccagggacc | ccgcgacctg | ctctggccca | gcggtgtgac | 300 |
| cccgcgggtc | ctggcggtcc | tgactgcccg | caggggaggg | gcgcgccact | tttggctgcc | 360 |
| ctaggatgcg | ccgcctgaac | ctcttttccc | tcgcgggcag | cgtccgccac | attccccggg | 420 |
| ttcctcggaa | actccaatca | ttctaccagg | actattgggg | cctggggtag | ccctcggga | 480 |
| gccgcgtgga | cgagccctgg | ccaggtggga | gcgaagagcc | tcggcgactg | ccagtcctcc | 540 |
| cgcccccgca | ccgccgggaa | aggatggcgt | tttaatagac | aggcagcaag | ttcaccgagg | 600 |
| ctgaagaatg | aagcccttc | agggccggcg | ggtcttgaga | tcaatgagcc | caataagaaa | 660 |

<210> SEQ ID NO 2
<211> LENGTH: 660
<212> TYPE: DNA
<213> ORGANISM: Homo sapiens

<400> SEQUENCE: 2

| | | | | | |
|---|---|---|---|---|---|
| ggcggaggct | tgggatgtac | ggtggaggct | tggagaggtg | gggcacacat | ttggggtgcg | 60 |
| acatagaggc | ttaggatggg | gcttgggata | cgggctgggg | gctcgtggtg | caggttggag | 120 |
| acctgggtgg | gagctctcag | tgcaggctgg | aggcgtgggt | cggggggtcg | cggtgcaggc | 180 |
| tggaggcttg | gagtgcagag | ttggggatgc | agacttgggg | tacagggcag | agctcggggc | 240 |
| gggcacgcac | cttgtggcag | gctgggcaag | tgggcagcgc | gccgcccggc | ccgggcgcgc | 300 |
| ccttgccgcc | gtggccccg | ccgccgttca | ggctgctctg | gatctgcgtg | agctcctggc | 360 |
| gcagcacctg | cttctggtgg | aagctgaagg | ccgggtggtt | ggaggccatg | gtgaacagca | 420 |
| gcaggaactc | atcgcccgtg | cggccctcgt | taagctgcag | cccgtagttg | tggatgatgg | 480 |
| agtcgatgtg | cgtgagcgtg | cggtagagca | cgcccgccgc | ctcgcgctgc | tccgagccca | 540 |
| gcagcgccag | cgacaccagc | agcttgctgc | gcaccacctc | gtccgtcagg | ttggtgaggc | 600 |
| tgcccaggtc | ggccgggttg | ttggccttga | tctccgagtc | gcgcagcgag | tggtagtcct | 660 |

<210> SEQ ID NO 3
<211> LENGTH: 1246
<212> TYPE: DNA
<213> ORGANISM: Homo sapiens

<400> SEQUENCE: 3

| | | | | | |
|---|---|---|---|---|---|
| catgcagcca | gctttctgcc | ccttcacttt | gcacagcact | tgttacccaa | gaagggccag | 60 |
| ggcaaggaca | cgcgggtgca | aagccgagtg | tgtgcgggct | gtgctgggtg | caggtggctg | 120 |
| agtgtcagct | gctgccgaag | cgatcagggg | tcgtgtgtgg | caggactggg | aaggggcgg | 180 |
| cggcaggtta | aggaggcggc | ccaccctgct | ggcatctggc | cagccctcca | acaatgcctc | 240 |
| cattatttcc | cagcgtccgt | ggtgatggaa | tggcccttgg | ggagggtggt | tcaggcggga | 300 |

```
gacacaggct tgggtcccct gctgtggggt ccagagacct gggccgggct gtgtgcaaga      360
gctgacgggc actggtcacc gggggaacct agcacccctt ggtcggcccc atcgcccccc      420
agctgtgcct gcgatgcccc cttttttct  aggggcctcc actccaaccg ctgtcccgca      480
ctcttgcagg ccagcgtcag gccctccccg ccacccctgg atctggaaac tcactctctg      540
cagtttccat ctctgtgtcc cgcctgcaga gcggcgggac tttctttgcc tggccgctgg      600
ccctgcacgc acccccttcc tcgcgcctct gccgcccttg ccgtttctgt cctcagtgtc      660
ctgctggggc ttaccccgag tcccgcccaa ggtgcagacg gcggcggccc cgggcctcgc      720
tcggtcgcgc tcgagcccg  tttcagcag  catcgcggcc accaggccga gtggcgcgag      780
acgcgctcct cctaggtcag cgtccctgg  agggttcggg gctcccaagt cccgccgcgt      840
cgtgcggggc agggagcccg ggagccactg ggcctggcgc tgtccgcggt gctgaaggag      900
gcgcccgctg cccgccccgc ccgcgcgccc gcccacctcc cggggcccct ctcgtcgccc      960
cggtccccac ccccgcctct gcccgtgtc  gggcgcgcct ccctccctgg ctgggttggg      1020
ccgcactcaa ggcagccccc gccctcaccc ctctgagacc cagggtggcc gtgcccgctc      1080
ctccctaagc tccaggccct gctgaggcgc tgggattcgc cgagtttcgc agcaagcggg      1140
tcgtccagcc gcagggcagg aggacactga ccctacccct ctggcgtgca gcctctggaa      1200
ggcagtgccc aggccgtgcc ccggggcagc cccatgcgtg atcaac                    1246

<210> SEQ ID NO 4
<211> LENGTH: 1030
<212> TYPE: DNA
<213> ORGANISM: Homo sapiens

<400> SEQUENCE: 4
catgccccag ctcggcggcg ggggcggcgg cggcggcggc ggcagcgggg gaggcggcgg       60
ctccacgccg gggcggccgg cggaggggac gacctcgggg cgaacgacga gctgatcccc      120
ttccaggacg agggggggcga ggagcaggag ccgagcagcg atagcgcctc ggcgcagcgg     180
gacctagacg aggtcaagtc gtccctggtc aacgagtcgg agaaccagag cagcagctcg      240
gactcggagg taaggaagca ccgcggccac ccccggggga tcccggccct gcgtccgctc      300
acccgctctt gcctttgtgt ctcctccgca ggcggagagg cgcccgcagc ccgtccggga      360
cactttccag aagccgcggg actatttcgc cgaaggtatg tgcccgctgg acagccccc      420 cactctcgat tcccgctgcg ctccgctgct cagcccgggc ggccaccgt  ccccttgct      480 tgggtggacg caccccttgcc ctccgccttt attggcggca gccccgtgg  ggcgcgcgtg     540 gggggcgctg gggtcccag  ctccgcctc  gagcccctg  ccgcggcgct gtcagtcccg      600
ggggcctggg cctcacctcg ccttggtctt gttcgcagtg agaaggcctc aggacagcgc      660
gttctttaaa ggaccccgt  accctgggta ccccttcctg atgatcccgg acctgagcag      720
cccgtacctc tccaacggac ccctgtctcc cggaggagcg cgcaccgtga gtgcccgtcg      780
ggcgcgccgg ggagggtggg aggccgcggc ccgcaggatg cgcccccggg cttggccatg      840
gagtggggga tggggccttc tgcgccgatc ccaagcagaa cttgtttgcg gagttgaact      900
actctctggc ggccgagcgc gaggctgcgc tggccagtgc ctggatgaaa gtaaagttac      960
tttaactttt ccctcttgc  gggttgaggt tttggagtcc acctctggga tcttccttgg     1020
cctccagaat                                                           1030

<210> SEQ ID NO 5
```

<211> LENGTH: 1197
<212> TYPE: DNA
<213> ORGANISM: Homo sapiens

<400> SEQUENCE: 5

```
catgttcggg ccgggccggg aggacctgta gaggagaaga aacgatgcgt ctgacgtccg      60
tgcccgctgg gactcggcgc cagcagccac cgcactcctg ggaaagaact gagggagtgt     120
ccagggcgac cagaatcagc caggaggata gggtccagcc aagagaatgt agggtgggag     180
gagagatcag tcacagcgaa ctgctctggc tgatctgatt tcacttgaag tcaacacgtt     240
atgtacttag gcctccgccc cccaactgcg tttctccttc tcctgccccc ctcaccccca     300
cctacatccc ttgccccagg ttttccatcc cgaatccgac tccgcccaa cctatacgaa      360
ggtgggccct cgggacgtct ctgcaggaac gcagctactg gggtatattg gtatataaa      420
gagtgggtac cctccctcga cgaccgggt ccaggcacgc gggacgatgg ggtttgcaat      480
cccgcgtccc agccgccccg ttgcggcct cacctgcccc aggtcgagaa ggggcactgt      540
aagggacccg gagggcgtcc cgcccgcttc tggactcctg gcgctgcgct ctgttggggt     600
gcgcgcagga gccggtgtgc ggggcgcgcg gggaggtcct cccgccagtc ggccagtgcc     660
gggaatgtct gcagaagcaa aagagtcgcc tcggggagga gccccggctg gcccggctca     720
ctcttggatg catttcaagt caactttcag aaacacgccc gcccgagcca cagcctaggc     780
acgggcagcc ttacttacct ggtaggcgag ctctctccca gtgactggag cagagagaag     840
ttgcggagcg ctgctggaag cttctgcccg ggaaggcgtc gccccgaga ctgcagccgg      900
aggagccgcc ctcggcttcg gagcgccggg gaggagccg gagcgaacgc cggccgctgg     960
ctctgctcct cggcgcgccc aggctgggcc gggacgtggt cgcgagctgc cggccttccc    1020
gggacgtcct accagcccgc gtcgctcctc agcgggagga gagggccagt tgcttctcca    1080
aggctaggag ggaaggcaga ggcccagggt cctgggtgcg agtcggccct gcttcgccgg    1140
ggcggatcct gcagcttctg acaggggccg cggcgctgcg tgcgcggcgg cggagag       1197
```

<210> SEQ ID NO 6
<211> LENGTH: 659
<212> TYPE: DNA
<213> ORGANISM: Homo sapiens

<400> SEQUENCE: 6

```
gcaggtcagg accatgtggc tggctgctcg gctgtgggcg caaaagggg tggggatggg       60
ggggtggggg aggactccat tttcagagca gggggaaggc tgtggaggag cggggggattt    120
ccaaaatgct tgagggttcc ggacctggtg gtgggcccag aagaaggagc acatttgggg    180
atcccgcaag cctggggtat gtgggtgtgt ttgaggaggt gggtgggagt gagcgtgtgc    240
gccggggaga gggcgggagg gaggaagcaa gcgagcttgg gagcgcgcgg ggagggccgc    300
gggcctcggg gcgcgccagg aagtgagcgg cggaggcgag gggcctaact agtggccggg    360
cgctgacctg cctgtcctgt ctgttttgtc tcgcagtgaa ccccaactac accggtgggg    420
aacccaagcg gtcccgaacg gcctacaccc ggcagcaagt cctagaactg gaaaaagaat    480
ttcattttaa caggtatctg acaaggcgcc gtcggattga aatcgctcac accctgtgtc    540
tgtcggagcg ccagatcaag atctggttcc agaaccggag gatgaagtgg aaaaaagatc    600
ataagctgcc caacactaaa ggcaggtcat cgtcctcatc ttcctcctca cttgctcct     659
```

<210> SEQ ID NO 7
<211> LENGTH: 660

<212> TYPE: DNA
<213> ORGANISM: Homo sapiens

<400> SEQUENCE: 7

```
gaactagctg ggagtgggcc ctgcagtgag gcaggggtg ggccagggag aacaaggcaa    60
gaggagcttc attcagggtt cctgagcctt tgtgagccac tcacgttttt accactcact   120
taaccgtctt tgttgttggg gtgaggggtc ctcgagcctg gatttgggta tgaaaaccca   180
ggcaagaaag acctgcccaa gcctttaaag gaatgcaaag tcatcctcta gccacccca    240
gagatcgaaa ggctggggat tgagtctcct gcagatggtg gcggcctcct ggggctggca   300
agttgggaca gaggcccata agccctcctg ggcgcgcctt cccacccctc tcggccctct   360
ccactcccag ctggggattt gggtttcaga gcagcctggc acacacaccc ccaccccacc   420
agaatctcac tcccagcttc ctatgactat tcattagtat tcacaacaat gggaaagtct   480
gggtgtgcac agggattttt tacagttaga aagtgtttaa gtcaatgacc tcactgggcc   540
tcagcaaccc tggaggcag atggcagtca gaatgatcca taaatgacct gccccaggtc    600
acacagctcc taaacagggg agctggaacc tggctgggag ccttgactat ccactgctca   660
```

<210> SEQ ID NO 8
<211> LENGTH: 660
<212> TYPE: DNA
<213> ORGANISM: Homo sapiens

<400> SEQUENCE: 8

```
gcaccgcctg gccacgccct cgggctctct taaaggagcc gcaccccac cccagggcaa    60
tcatcggacc cggaccaggc ctccgggtga cacatccggc tctcagaggc gccaggaccc   120
tatcattcat ccctttccac gtgcaaagtg aaaagtcaga gcccgggcac acaccttggc   180
cgtttatgta tacagaagtg gggtgccggg cgggaagggc gcggggaatg agggaaccta   240
gaggccgatg acgtcgttca gctcgaggtc cgcgttgggg cggcagcggg cctgggggg    300
ctgcgtcccg gggcggggtt ccgcgtcggg cttggcggca gccgcctccg ggcgcgccgc   360
gtccatgacg cccagcaccg cgtccagcat ggagggcccc agatccaggt ggaaggacag   420
cagcgggtcg gcaggcgagg gcgctgcgga ctgcgggacg gcgggcggcg gcggggagcg   480
cggggccccc gcgggggggcg cccgggggctc gggggcggc ccgccgccgt ggcggctcag   540
gaacgaggtg tccccgaagg cgtcgccgcc gcgcccccacg tgcagcgtgt gccggaagtc   600
gccgagcggc gcggagatgg acagggcgcc gcgatcaggc cgcttcttgg gctgcgcggg   660
```

<210> SEQ ID NO 9
<211> LENGTH: 450
<212> TYPE: DNA
<213> ORGANISM: Homo sapiens

<400> SEQUENCE: 9

```
catggcggca gcggcgccgg cggtcgggcg aggaggcgga gccgggtgac gtcaccgctt    60
ccccccactc gccctcgcac cgcttcgccc ctgggcccaa gcctcttaaa ggacccctgc   120
gctgcctcgc ggcgggggtg ggggtcggcg ctgccgcgcg ctgggctaaa gctcgagtcg   180
cgctcagatc aggtgcaggc gcaggcgcgc cccgccccac ggccccccca ccgggcgagc   240
ctccacgcct ccgccctggg agccgccatc ttgccacttc ccctcgcccg gccgtccgcg   300
ggcgtcaata gcgactttca gcacaaaaca aagatggcgg cggcggcatc tcggaaatgc   360
ccggatgaga ctgctaaccc ctccgacgcg ctcggccccg ccccttggg aacggtctct    420
```

```
cgggttgata agggacgcac gcccgaagaa                                      450

<210> SEQ ID NO 10
<211> LENGTH: 660
<212> TYPE: DNA
<213> ORGANISM: Homo sapiens

<400> SEQUENCE: 10
gcggctccgt cccgggcgca ggcttgtcgc gccgaatcgc gcgctcgcgg aggctgggcc     60
acggcctcgg ggccttggcg ggggccgaat tatctcgtac gcgaagtggc cgagacttag    120
ccttctccag gaccacgtgg gtgctgcggg ccgtttcccg ggtctcaggt tccgaccgcc    180
ccgtggaccc gaaggtggcg ctgctcgggg ccggggcctc ggggctcagt tttctggcca    240
acgccgtctg cacgaagccc gcggcggcct gcaggggcc cagcgactcg tccagggaac     300
cggtgcgcag gagcagccgg gggcgcggcg cgccggccgc ccttggggga ctctggggcc    360
gggggcgcag ctcgatctga cgcttgggca ctgtccgggg cctggcggcc gcggcgccct    420
cctccagagc cacctccaca cactcgaact gcgctggggg ggcaggactt ggcccacggg    480
gccgcagctc taggtaggtg cccagcgggg agccaccatc ggggacctgg gactggcgtg    540
ggaccgcggc gggagacgct ggccccgcg gcaaggggct gatgaaggcc ggctccgtga    600
actgttgttg cgcctcgcga tcgtctgcgc cggagcagcc gaacaggggt ccgacgccga    660

<210> SEQ ID NO 11
<211> LENGTH: 329
<212> TYPE: DNA
<213> ORGANISM: Homo sapiens

<400> SEQUENCE: 11
tggggcagtg ttacaattac agaaaaggga gaggcgaggt ccgctgagtc cttggcctgg     60
gcaacaaggc acactgaaaa ctgggttcct tttcgacccg catcgtgcgc gccctagaaa    120
tgacagccag acgagcagg gtctaaggac gctgaaaacc cctgacgtgg gcgcgccggg     180
tgcgggtagg gacgtggaag gactgggcta gccacaggaa ctacagcgct gcggaccggg    240
tgaggggtcc cggcccgagt ccccacttgg ggcgcagagg tgtttctgta aggggacaaa    300
gggcactcct cggcgcgatg ggcgacttc                                       329

<210> SEQ ID NO 12
<211> LENGTH: 275
<212> TYPE: DNA
<213> ORGANISM: Homo sapiens

<400> SEQUENCE: 12
acggggcaaa gcctttcttc ccacacccac agccaaggcg cgtccgtgca ggggcacacg     60
ccttctgctc cagccccagg aaggcgcttt cgccctgcag tcctccgacg gccggctccc    120
gccgcaccgc gcaccctggc tccggcagac tctggggcct ggggactcgc ccaccctgcg    180
cggcgcgccc cccacatgag ccgaggttgg gaggctgcgg ggcctctgtc ctcccaggcc    240
gtggagtgcg gcggccgctc tgagtccgct gggga                                275

<210> SEQ ID NO 13
<211> LENGTH: 332
<212> TYPE: DNA
<213> ORGANISM: Homo sapiens

<400> SEQUENCE: 13
aacgccgtct gcacgaagcc cgcggcggcc tgcaggggc ccagcgactc gtccagggaa     60
```

```
ccggtgcgca ggagcagccg ggggcgcggc gcgccggccg cccttggggg actctggggc      120
cgggggcgca gctcgatctg acgcttgggc actgtccggg gcctggcggg cgcggcgccc      180
tcctccagag ccacctccac acactcgaac tgcgctgggg cggcaggact tggcccacgg      240
ggccgcagct ctaggtaggt ggcccagcgg gagccaccat cggggacctg ggactggcgt      300
gggaccgcgg cgggagacgc tggccccggc gg                                    332
```

<210> SEQ ID NO 14
<211> LENGTH: 282
<212> TYPE: DNA
<213> ORGANISM: Homo sapiens

<400> SEQUENCE: 14

```
ttaggcccag cagcttcggg agcccagggc agagccgagg ggtcggaagt ggcggtggtc       60
cagcggcgcg ccggccgggg ctgggcgcgg accccagggc cctacgccgg ggccctgcga      120
gaagccgtgt cccgtatccg ccgccacaca gcccctgact cggacacgga cgaagctgag      180
gagctcagcg tccatagcgg ctcctctgat ggaagcgaca cagaagcccc gggcgcctcc      240
tggcggaatg agaggaccct gcccgaggtt ggaaacagtt cg                         282
```

<210> SEQ ID NO 15
<211> LENGTH: 210
<212> TYPE: DNA
<213> ORGANISM: Homo sapiens

<400> SEQUENCE: 15

```
ctctggactc catctctcac ttctctctgg attctgggct ctcctggctc ggcctgggtg       60
cccaaagtgg cagtgtgggc ctctgtggga tggagaggcg cgccggggcc tgacctgaat      120
gacgcgcatg ttgaggccgg tctcctgcgc cagctgctcg cggatgtggc gggtgggctt      180
gggtgtagca gcgaaggcgg ccttcagcgt                                       210
```

<210> SEQ ID NO 16
<211> LENGTH: 295
<212> TYPE: DNA
<213> ORGANISM: Homo sapiens

<400> SEQUENCE: 16

```
aatggcgcga tctcggccca ctgcaacctc ccactcccgg gttcaagcga ttctcctgcc       60
tcagcctccc gagtaggggg ttacaggcgc gccaccacgc ccggctaatt ttttgtattt      120
ttagtagaga cggggtttca ccgtgttagc caggattgtc tccatctcct gacctcgtga      180
tccgcccccg tcggcctccc aaagtgctgg gattacaggc gtgagccacc gcgcccggca      240
gagatcaggt tcttaaggga agtccggaga aatgggcttt ttaaaaaacc cgagt           295
```

<210> SEQ ID NO 17
<211> LENGTH: 324
<212> TYPE: DNA
<213> ORGANISM: Homo sapiens

<400> SEQUENCE: 17

```
tgctgctcct gcggctctca gccagccctt tgcactccca actgcgtccc agaccctgcg       60
cccggcttca gtgggcttc tcgcctcccct ccggtctggg cccccttctc cgacggctcc      120
tgccgaaggg ggcgtccctg ccccccttgtt ccctctccac ggtgtcctgg aaggcctggg      180
tggccgcaga acgcacgggg gagggtgcg gcgtggaccc tcgggcggcg cgcctggact       240
```

```
gcggctccgg agctgggctg ggggacgagg gggacgaggg gggcgggggc ccgtgggcac    300
gccccacccc actcgtgctc gcga                                          324
```

<210> SEQ ID NO 18
<211> LENGTH: 364
<212> TYPE: DNA
<213> ORGANISM: Homo sapiens

<400> SEQUENCE: 18

```
tcggggcgcc gccgccgctc tttctcctct gctgccgccg ccgtctcccg gcagccgccg     60
ccgccgccgc tgtccgaact tgaagttgcc ggcgcgcccg ttgcagccgc cgccgccgcc    120
gcggaggtcg ccgtggccgc cgggggcccc ttctcggcgc tcttgtcccc ggggtagtcg    180
gaggaggcga ggttttccgg ggtgccgtag gctgtctcga aaaactggtc gaaagcctgt    240
ggcaggacgc cgttcctgcc cacggtgcta tagaaattgg acgagactgc gggggtgggg    300
tggtggtaga cgttggccga gctcttggcc agcacgtcgc caggcacgcc ggccgcgctg    360
ggcg                                                                364
```

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
gtgccgccgc gggcgcc                                                   17
```

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
gtgccgccgc gggcgcc                                                   17
```

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
gcacaatgaa agcattt                                                   17
```

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
gctggacaca atgggtc                                                   17
```

```
<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgtgagggcg agtgtga                                                   17

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agcacccgcc tggaacc                                                   17

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gctcacctac ccaggtg                                                   17

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcctctctgc gcctgcc                                                   17

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cccggacttg gccaggc                                                   17

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttcgggccgg gccggga                                                   17

<210> SEQ ID NO 29
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agccctcggg tgatgag                                                    17

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cttatgttta cagcatc                                                    17

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cttatgttta cagcatc                                                    17

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gttctcaaac agctttc                                                    17

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tccaggcagg gcctctg                                                    17

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cccccgcgac gcggcgg                                                    17

<210> SEQ ID NO 35
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccagcggact gcgctgc                                                     17

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtgaacttcc aagatgc                                                     17

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atgcgccccg cagcccc                                                     17

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atgcgccccg cagcccc                                                     17

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtccccgcgc cgcggcc                                                     17

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtccccgcgc cgcggcc                                                     17

<210> SEQ ID NO 41
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 41
atgcgagggg cgcggta                                                    17

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atgcgagggg cgcggta                                                    17

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gcagcattgc ggctccg                                                    17

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcattgcata ctgaagg                                                    17

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcattgcata ctgaagg                                                    17

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcgctacacg ccgctcc                                                    17

<210> SEQ ID NO 47
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 47
gcgctacacg ccgctcc                                                    17

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccccagctcg gcggcgg                                                    17

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctggccctg ttgtgtc                                                    17

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aagcagtctt cgagggg                                                    17

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggagggctgg agtgagg                                                    17

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
agaccatcct tggaccc                                                    17

<210> SEQ ID NO 53
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 53
ggcgccagag gaagatc                                                        17

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cccacccgag gggaaga                                                        17

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttaatctgct tatgaaa                                                        17

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aaattccata gacaacc                                                        17

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggtgacagag tgcgact                                                        17

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cagccgactc tctggct                                                        17

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 59
ggaggcaaac gggaacc                                               17

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gctcgccgag gaggggc                                               17

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gctcgccgag gaggggc                                               17

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gatcgctggg gttttgg                                               17

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gatcgctggg gttttgg                                               17

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ctaatctctc catctga                                               17

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 65
ctaatctctc catctga                                                17

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cggcgcgtcc ctgccgg                                                17

<210> SEQ ID NO 67
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aaccccgaaa ctggaag                                                17

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gaagagtccc agccggt                                                17

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gaagagtccc agccggt                                                17

<210> SEQ ID NO 70
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gaggagagag atggtcc                                                17

<210> SEQ ID NO 71
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 71
cctgcctctg gcagggg                                                    17

<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gcctagaaga agccgaa                                                    17

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gggccgagtc cggcagc                                                    17

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cgtgtgagct ctcctgc                                                    17

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cacttcccag ctctgag                                                    17

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cacatcccag cccgggg                                                    17

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
```
cctgcgccgg gggaggc                                                              17

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tacaatgaag gggtcag                                                              17

<210> SEQ ID NO 79
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tacaatgaag gggtcag                                                              17

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ttggtaagca ttatctc                                                              17

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gtccgtggaa tagaagg                                                              17

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tttacattta atctatg                                                              17

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tgcggagaag acccggg							17

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggaggtctca ggatccc							17

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaagcgatcc aaacaca							17

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
acccgggccg cagcggc							17

<210> SEQ ID NO 87
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ctgggttgcg attagct							17

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
acacatttat ttttcag							17

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtgggagtca aagagct							17

```
<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tcgccgggcg cttgccc                                                  17

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctgaccgcgc tcgcccc                                                  17

<210> SEQ ID NO 92
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cgtctcccat cccgggc                                                  17

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgccacccgg agtcgca                                                  17

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctgcccttat cctcgga                                                  17

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cgctgaccac caggagg                                                  17
```

```
<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gcagaaaaag cacaaag                                                     17

<210> SEQ ID NO 97
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtccttgttc ccatagg                                                     17

<210> SEQ ID NO 98
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tcaatgctcc ggcgggg                                                     17

<210> SEQ ID NO 99
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcagccgctt cggcgcc                                                     17

<210> SEQ ID NO 100
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agctctgaag ccagaag                                                     17

<210> SEQ ID NO 101
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
agctctgaag ccagaag                                                     17
```

```
<210> SEQ ID NO 102
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ccctccgatt ctactat                                                      17

<210> SEQ ID NO 103
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaggagaccg cacaggg                                                      17

<210> SEQ ID NO 104
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aaggagaccg cacaggg                                                      17

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
attgtcagat ctggaat                                                      17

<210> SEQ ID NO 106
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tggtgataac tgaaccc                                                      17

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tccatagatt gacaaag                                                      17

<210> SEQ ID NO 108
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tacaaggcac tatgctg                                                  17

<210> SEQ ID NO 109
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gttatggcca gaacttg                                                  17

<210> SEQ ID NO 110
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
caacccacgg gcaggtg                                                  17

<210> SEQ ID NO 111
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atgagtccat ttcctcg                                                  17

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
acctggaata aaccctg                                                  17

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tatttgccaa gttgtac                                                  17

<210> SEQ ID NO 114
<211> LENGTH: 17
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
acaaaaatga tcgttct                                                    17

<210> SEQ ID NO 115
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggctctccgt ctctgcc                                                    17

<210> SEQ ID NO 116
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gtccccagca cgcggtc                                                    17

<210> SEQ ID NO 117
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ccttgactgc ctccatc                                                    17

<210> SEQ ID NO 118
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tctgagtcgc cagcgtc                                                    17

<210> SEQ ID NO 119
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggggcctatt cacagcc                                                    17

<210> SEQ ID NO 120
<211> LENGTH: 17
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 120
ggggcctatt cacagcc                                                  17

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ccagacgccg gctcggc                                                  17

<210> SEQ ID NO 122
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtgacgatgg aggagct                                                  17

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctcctccttc ttttgcg                                                  17

<210> SEQ ID NO 124
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124 gcggggcag cagacgc                                                   17

<210> SEQ ID NO 125
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
taactgtcct ttccgta                                                  17

<210> SEQ ID NO 126
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 126
aagaggcaga acgtgcg                                                          17

<210> SEQ ID NO 127
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cttgcctctc atccttc                                                          17

<210> SEQ ID NO 128
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
aaatgaaact agtcttg                                                          17

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tctgtgtgct gtgtgcg                                                          17

<210> SEQ ID NO 130
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
taaataggcg agaggag                                                          17

<210> SEQ ID NO 131
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
taaataggcg agaggag                                                          17

<210> SEQ ID NO 132
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 132
gcgggcggcg cggtccc                                                  17

<210> SEQ ID NO 133
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aggcaggaga tggtctg                                                  17

<210> SEQ ID NO 134
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ggcgttaata gagaggc                                                  17

<210> SEQ ID NO 135
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aggttgttgt tcttgca                                                  17

<210> SEQ ID NO 136
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
aaggagccta cgttaat                                                  17

<210> SEQ ID NO 137
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gataagaagg atgagga                                                  17

<210> SEQ ID NO 138
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 138
gccttcgacc cccaggc                                                    17

<210> SEQ ID NO 139
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cagccagctt tctgccc                                                    17

<210> SEQ ID NO 140
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tccgcctgtg actcaag                                                    17

<210> SEQ ID NO 141
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gtcctgctcc tcaaggg                                                    17

<210> SEQ ID NO 142
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ggggaagctt cgagcgc                                                    17

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
aaaatagagg ttcctcc                                                    17

<210> SEQ ID NO 144
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 144
aaaatagagg ttcctcc                                                 17

<210> SEQ ID NO 145
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
aatgaacgac cagaccc                                                 17

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
agttagttcc caactca                                                 17

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
agttagttcc caactca                                                 17

<210> SEQ ID NO 148
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tggatttggg ttttcag                                                 17

<210> SEQ ID NO 149
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gggacaggtg gcaggcc                                                 17

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 150
gagctaatca ataggca                                                  17

<210> SEQ ID NO 151
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gtttccttat taataga                                                  17

<210> SEQ ID NO 152
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ccccgtggcg ggagcgg                                                  17

<210> SEQ ID NO 153
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ccccgtggcg ggagcgg                                                  17

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gaggtagtgc cctgtcc                                                  17

<210> SEQ ID NO 155
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ttgtgtgtac ataggcc                                                  17

<210> SEQ ID NO 156
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
```
gcaggacggc ggggcca                                                    17

<210> SEQ ID NO 157
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gcaggacggc ggggcca                                                    17

<210> SEQ ID NO 158
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gggccccgcc cagccag                                                    17

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gggccccgcc cagccag                                                    17

<210> SEQ ID NO 160
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cctggaagga atttagg                                                    17

<210> SEQ ID NO 161
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggagttccat ctccgag                                                    17

<210> SEQ ID NO 162
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ggagttccat ctccgag                                                 17

<210> SEQ ID NO 163
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gaaaactcca gatagtg                                                 17

<210> SEQ ID NO 164
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ctttgaaata agcgaat                                                 17

<210> SEQ ID NO 165
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggcaggagga tgcgggg                                                 17

<210> SEQ ID NO 166
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tctaggacct ccaggcc                                                 17

<210> SEQ ID NO 167
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tctaggacct ccaggcc                                                 17

<210> SEQ ID NO 168
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ccctgccctt agtgctt                                                 17

<210> SEQ ID NO 169
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gccaacctga agacccc                                                  17

<210> SEQ ID NO 170
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gccaacctga agacccc                                                  17

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171 gcccccctagg ccctttg                                                 17

<210> SEQ ID NO 172
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ctgcaaaatc tgctcct                                                  17

<210> SEQ ID NO 173
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gctcgaccca gctggga                                                  17

<210> SEQ ID NO 174
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gctcgaccca gctggga                                                  17

<210> SEQ ID NO 175
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gattatgaaa gcccatc                                                    17

<210> SEQ ID NO 176
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gattatgaaa gcccatc                                                    17

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gaacaaaccc agggatc                                                    17

<210> SEQ ID NO 178
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tgtgttcaga gggcgga                                                    17

<210> SEQ ID NO 179
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cctgccggtg gagggca                                                    17

<210> SEQ ID NO 180
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gctgccccaa gtggtct                                                    17

```
<210> SEQ ID NO 181
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
agaacgggaa ccgtcca                                                        17

<210> SEQ ID NO 182
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tctccgtgta tgtgcgc                                                        17

<210> SEQ ID NO 183
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tttcagcggg agccgcc                                                        17

<210> SEQ ID NO 184
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gaggccagat tttctcc                                                        17

<210> SEQ ID NO 185
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aaggctggga gttttct                                                        17

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cgaacttccc ggttccg                                                        17

<210> SEQ ID NO 187
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cagcggccaa agctgcc                                                    17

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cagcggccaa agctgcc                                                    17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cactgcctga tggtgtg                                                    17

<210> SEQ ID NO 190
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ccaccagcct ccctcgg                                                    17

<210> SEQ ID NO 191
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
agctctgcca gtagttg                                                    17

<210> SEQ ID NO 192
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
agctctgcca gtagttg                                                    17

<210> SEQ ID NO 193
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cctctaggac caagcct                                                 17

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ctacctaagg agagcag                                                 17

<210> SEQ ID NO 195
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gagtcgcagt attttgg                                                 17

<210> SEQ ID NO 196
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cggcgcagct ccaggtc                                                 17

<210> SEQ ID NO 197
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ggccggtgcc gccagtc                                                 17

<210> SEQ ID NO 198
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gggacccgga aaggtgg                                                 17

<210> SEQ ID NO 199
<211> LENGTH: 17
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 199
gctctgcccc cgtggcc                                                17

<210> SEQ ID NO 200
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
agagctgagt ctcaccc                                                17

<210> SEQ ID NO 201
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tcaggcttcc ccttcgg                                                17

<210> SEQ ID NO 202
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
cctgtggaca ggatacc                                                17

<210> SEQ ID NO 203
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tggggactga tgcaccc                                                17

<210> SEQ ID NO 204
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gcagtaaacc gtgactt                                                17

<210> SEQ ID NO 205
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 205
cgcactcaca cggacga                                                        17

<210> SEQ ID NO 206
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
atccggccaa gccctag                                                        17

<210> SEQ ID NO 207
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
atccggccaa gccctag                                                        17

<210> SEQ ID NO 208
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
cgattcgaag ggagggg                                                        17

<210> SEQ ID NO 209
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cctaacaaga ttgcata                                                        17

<210> SEQ ID NO 210
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cctaacaaga ttgcata                                                        17

<210> SEQ ID NO 211
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 211
tcccgcgccc aggcccc                                                    17

<210> SEQ ID NO 212
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gcaacagcct ccggagg                                                    17

<210> SEQ ID NO 213
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cacagccagc ctcccag                                                    17

<210> SEQ ID NO 214
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
cctacctatc cctggac                                                    17

<210> SEQ ID NO 215
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gctatgggtc gggggag                                                    17

<210> SEQ ID NO 216
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gatgctcgaa cgcagag                                                    17

<210> SEQ ID NO 217
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 217
gtgaaattcc cgtctct                                                  17

<210> SEQ ID NO 218
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gaggctggca cccaggc                                                  17

<210> SEQ ID NO 219
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
cccccagagt gactaag                                                  17

<210> SEQ ID NO 220
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ttgagaactg ccccct                                                   17

<210> SEQ ID NO 221
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ccccgttttt gtgagtg                                                  17

<210> SEQ ID NO 222
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gggcggtggc aagggc                                                   17

<210> SEQ ID NO 223
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cttagcccac agagaac					17

<210> SEQ ID NO 224
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
catttcctgg gctattt					17

<210> SEQ ID NO 225
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gtgaccagcc tggagag					17

<210> SEQ ID NO 226
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
cccctgccct gtcaccc					17

<210> SEQ ID NO 227
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ctgaatgggg caaggag					17

<210> SEQ ID NO 228
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
cctcttccca gaccgaa					17

<210> SEQ ID NO 229
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 229
acccgcacca tcccggg                                                    17

<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gctgcgggca ccgggcg                                                    17

<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gctgcgggca ccgggcg                                                    17

<210> SEQ ID NO 232
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
cctcggtgag tgtctcg                                                    17

<210> SEQ ID NO 233
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tccctcattc gccccgg                                                    17

<210> SEQ ID NO 234
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gaaaagttga actcctg                                                    17

<210> SEQ ID NO 235
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
``` gtggaggggga ggtactg                                                17

<210> SEQ ID NO 236
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tgaagaaaag gcctttg                                                 17

<210> SEQ ID NO 237
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gcccgcgggg ctgtccc                                                 17

<210> SEQ ID NO 238
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gcccgcgggg ctgtccc                                                 17

<210> SEQ ID NO 239
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
tcctgtctca tctgcga                                                 17

<210> SEQ ID NO 240
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tctcggcgca agcaggc                                                 17

<210> SEQ ID NO 241
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241

```
tccggagttg ggacctc                                                    17
```

<210> SEQ ID NO 242
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242

```
gcaaacatca ggaccac                                                    17
```

<210> SEQ ID NO 243
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243

```
aacgggatcc gcacggg                                                    17
```

<210> SEQ ID NO 244
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244

```
gccttcctgt cccccaa                                                    17
```

<210> SEQ ID NO 245
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245

```
gtgccaggaa gcaagtc                                                    17
```

<210> SEQ ID NO 246
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246

```
agcctgcaaa ggggagg                                                    17
```

<210> SEQ ID NO 247
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247

```
gggtagaacc tggggga                                                    17
```

<210> SEQ ID NO 248
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
cccgctcctt cggttcg                                                  17

<210> SEQ ID NO 249
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
cccgctcctt cggttcg                                                  17

<210> SEQ ID NO 250
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
cgtgggaaac ctcgatg                                                  17

<210> SEQ ID NO 251
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
cgtgggaaac ctcgatg                                                  17

<210> SEQ ID NO 252
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
agactaaacc cccgagg                                                  17

<210> SEQ ID NO 253
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ctagaagggg tcggga                                                   17

<210> SEQ ID NO 254
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ctagaagggg tcgggga                                                        17

<210> SEQ ID NO 255
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tacagctgct gcagcgc                                                        17

<210> SEQ ID NO 256
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
gtttattcca aacactg                                                        17

<210> SEQ ID NO 257
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
cggggtttct atggtaa                                                        17

<210> SEQ ID NO 258
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
cccaaccaat ctctacc                                                        17

<210> SEQ ID NO 259
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cgtagggccg ttcaccc                                                        17

```
<210> SEQ ID NO 260
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ctcacgacgc cgtgaag                                                    17

<210> SEQ ID NO 261
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tcagcccagc ggtatcc                                                    17

<210> SEQ ID NO 262
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gtttaccctc tgtctcc                                                    17

<210> SEQ ID NO 263
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gggtgcggaa cccggcc                                                    17

<210> SEQ ID NO 264
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ccagctttag agtcaga                                                    17

<210> SEQ ID NO 265
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gggaataggg gggcggg                                                    17

<210> SEQ ID NO 266
```

<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
accctgaaag cctagcc                                                   17

<210> SEQ ID NO 267
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ttccaaaaag gggcagg                                                   17

<210> SEQ ID NO 268
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cccaccaggc acgtggc                                                   17

<210> SEQ ID NO 269
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gcctcagcat cctcctc                                                   17

<210> SEQ ID NO 270
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gcctcagcat cctcctc                                                   17

<210> SEQ ID NO 271
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gccctggggt gttatgg                                                   17

<210> SEQ ID NO 272
<211> LENGTH: 17

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gccctggggt gttatgg                                                    17

<210> SEQ ID NO 273
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ggcaggaaga cggtgga                                                    17

<210> SEQ ID NO 274
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ggcaggaaga cggtgga                                                    17

<210> SEQ ID NO 275
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ggggcgaaga aagcaga                                                    17

<210> SEQ ID NO 276
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gaagcaagag tttggcc                                                    17

<210> SEQ ID NO 277
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
caacggaaac aaaaaca                                                    17

<210> SEQ ID NO 278
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 278
caacggaaac aaaaaca                                                       17

<210> SEQ ID NO 279
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
cccgccacgc cgccccg                                                       17

<210> SEQ ID NO 280
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ctccaaaaat cccttga                                                       17

<210> SEQ ID NO 281
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ctccaaaaat cccttga                                                       17

<210> SEQ ID NO 282
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gtgccgccgc gggcgcc                                                       17

<210> SEQ ID NO 283
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
gtgccgccgc gggcgcc                                                       17

<210> SEQ ID NO 284
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 284
ctgcaacttg gtgcccc                                                   17

<210> SEQ ID NO 285
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gcctctctgc gcctgcc                                                   17

<210> SEQ ID NO 286
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ctccgttttc ttttgtt                                                   17

<210> SEQ ID NO 287
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
agcgcttggc gctccca                                                   17

<210> SEQ ID NO 288
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tctggggccg ggtagcc                                                   17

<210> SEQ ID NO 289
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
cacccgcggg ggtgggg                                                   17

<210> SEQ ID NO 290
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 290
cgtgtgtatc tggggggt                                                 17

<210> SEQ ID NO 291
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gcagcggcgc tccgggc                                                  17

<210> SEQ ID NO 292
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
tgttcagagc cagcttg                                                  17

<210> SEQ ID NO 293
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ccaggctggc tcaccct                                                  17

<210> SEQ ID NO 294
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ccagggcctg gcactgc                                                  17

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
ttcgggccgg gccggga                                                  17

<210> SEQ ID NO 296
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 296
gaaatgctaa ggggttg                                                  17

<210> SEQ ID NO 297
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
cattccagtt acagttg                                                  17

<210> SEQ ID NO 298
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
tccacagcgg acgttcc                                                  17

<210> SEQ ID NO 299
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
acattgtcct ttttgcc                                                  17

<210> SEQ ID NO 300
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
ccgaggggcc tggcgcc                                                  17

<210> SEQ ID NO 301
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tccaggcagg gcctctg                                                  17

<210> SEQ ID NO 302
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 302
agcaactttc ctgggtc                                            17

<210> SEQ ID NO 303
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
ggctctctgg attcccc                                            17

<210> SEQ ID NO 304
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tggatttggt cgtctcc                                            17

<210> SEQ ID NO 305
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305 gccccgtgg cgccccg                                             17

<210> SEQ ID NO 306
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306 gccccgtgg cgccccg                                             17

<210> SEQ ID NO 307
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
tcggtggtcg ctcgtgg                                            17

<210> SEQ ID NO 308
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 308
tcggtggtcg ctcgtgg                                                  17

<210> SEQ ID NO 309
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gctagggaaa aacaggc                                                  17

<210> SEQ ID NO 310
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
gctagggaaa aacaggc                                                  17

<210> SEQ ID NO 311
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gacgcgctcc cgcgggc                                                  17

<210> SEQ ID NO 312
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gacgcgctcc cgcgggc                                                  17

<210> SEQ ID NO 313
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
caaaggagct gtggagc                                                  17

<210> SEQ ID NO 314
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gagcggccgc ccagagc                                                    17

<210> SEQ ID NO 315
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gccaatgaca gcggcgg                                                    17

<210> SEQ ID NO 316
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
atgcgccccg cagcccc                                                    17

<210> SEQ ID NO 317
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
atgcgccccg cagcccc                                                    17

<210> SEQ ID NO 318
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
ctggaacccc gcacacc                                                    17

<210> SEQ ID NO 319
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gtccccgcgc cgcggcc                                                    17

<210> SEQ ID NO 320
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gtccccgcgc cgcggcc                                                  17

<210> SEQ ID NO 321
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
aacttttaaa gtttccc                                                  17

<210> SEQ ID NO 322
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
aacttttaaa gtttccc                                                  17

<210> SEQ ID NO 323
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gccacccaag cccgtcg                                                  17

<210> SEQ ID NO 324
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gccacccaag cccgtcg                                                  17

<210> SEQ ID NO 325
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
cctttgcttc cctttcc                                                  17

<210> SEQ ID NO 326
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
cctttgcttc cctttcc                                                  17

```
<210> SEQ ID NO 327
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
cacacaaggc gcccgcg                                                  17

<210> SEQ ID NO 328
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
taagagtcca gcaggca                                                  17

<210> SEQ ID NO 329
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tcattgcata ctgaagg                                                  17

<210> SEQ ID NO 330
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tcattgcata ctgaagg                                                  17

<210> SEQ ID NO 331
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gcgctacacg ccgctcc                                                  17

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gcgctacacg ccgctcc                                                  17
```

<210> SEQ ID NO 333
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gacgacagcg ccgccgc                                                  17

<210> SEQ ID NO 334
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
aaattccata gacaacc                                                  17

<210> SEQ ID NO 335
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
ggcgtgggga gaggggg                                                  17

<210> SEQ ID NO 336
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
gctgcaggca ctgggtt                                                  17

<210> SEQ ID NO 337
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gctgcaggca ctgggtt                                                  17

<210> SEQ ID NO 338
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
atggtgtcgc tggacag                                                  17

<210> SEQ ID NO 339
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
atggtgtcgc tggacag                                                    17

<210> SEQ ID NO 340
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gacttctggc aagggag                                                    17

<210> SEQ ID NO 341
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
actgcatccg gcctcgg                                                    17

<210> SEQ ID NO 342
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
cctagcatct cctcttg                                                    17

<210> SEQ ID NO 343
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gaggactggg ggctggg                                                    17

<210> SEQ ID NO 344
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
ctttggccga ggccgag                                                    17

<210> SEQ ID NO 345

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
cggcgcgtcc ctgccgg                                                    17

<210> SEQ ID NO 346
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gagaagccgc cagccgg                                                    17

<210> SEQ ID NO 347
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
cctgcctctg gcagggg                                                    17

<210> SEQ ID NO 348
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gtttcttctc aatagcc                                                    17

<210> SEQ ID NO 349
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
tccttgatga aatgcgc                                                    17

<210> SEQ ID NO 350
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gctggcgatc tggggct                                                    17

<210> SEQ ID NO 351
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
acccttggag gaagggg                                                17

<210> SEQ ID NO 352
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
gggcggtggc ggggacg                                                17

<210> SEQ ID NO 353
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
cctgcgccgg gggaggc                                                17

<210> SEQ ID NO 354
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
atttaggggt ctgtacc                                                17

<210> SEQ ID NO 355
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
gtccgtggaa tagaagg                                                17

<210> SEQ ID NO 356
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gtggcgcgct ggcgggg                                                17

<210> SEQ ID NO 357
<211> LENGTH: 17
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 357
gtggcgcgct ggcgggg                                                  17

<210> SEQ ID NO 358
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ctgcccagta cctgagg                                                  17

<210> SEQ ID NO 359
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
ccgcggatct cgccggt                                                  17

<210> SEQ ID NO 360
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
agccacctgc gcctggc                                                  17

<210> SEQ ID NO 361
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tgcggagaag acccggg                                                  17

<210> SEQ ID NO 362
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gctgtccgca cgcggcc                                                  17

<210> SEQ ID NO 363
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gctgtccgca cgcggcc                                                17

<210> SEQ ID NO 364
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
tgcacgcaca ctcttcc                                                17

<210> SEQ ID NO 365
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gcgtttgggg gtgtcgg                                                17

<210> SEQ ID NO 366
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gtggggaggc tggggcg                                                17

<210> SEQ ID NO 367
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gtggggaggc tggggcg                                                17

<210> SEQ ID NO 368
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
ctgcactaaa atattcg                                                17

<210> SEQ ID NO 369
<211> LENGTH: 17
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 369
cttagatcta gcgttcc                                                    17

<210> SEQ ID NO 370
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
ccatatttgc ccaagcc                                                    17

<210> SEQ ID NO 371
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tgacaggcgt gcgagcc                                                    17

<210> SEQ ID NO 372
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
tgacaggcgt gcgagcc                                                    17

<210> SEQ ID NO 373
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
ctagaaagac agattgg                                                    17

<210> SEQ ID NO 374
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
ctagaaagac agattgg                                                    17

<210> SEQ ID NO 375
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 375
ctgggttgcg attagct                                                    17

<210> SEQ ID NO 376
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
cgtggctcgg attcggg                                                    17

<210> SEQ ID NO 377
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ccagagggtc ttaagtg                                                    17

<210> SEQ ID NO 378
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
ctgcgggagc tgcggcc                                                    17

<210> SEQ ID NO 379
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
tccgacaaga agccgcc                                                    17

<210> SEQ ID NO 380
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
cgtctcccat cccgggc                                                    17

<210> SEQ ID NO 381
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 381
gcagaaaaag cacaaag                                                17

<210> SEQ ID NO 382
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
gtcagcgccg gccccag                                                17

<210> SEQ ID NO 383
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
atgagtccat ttcctcg                                                17

<210> SEQ ID NO 384
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gcgagggccc aggggtc                                                17

<210> SEQ ID NO 385
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385 ggggggggaac cggaccg                                               17

<210> SEQ ID NO 386
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
aacttggggc tgaccgg                                                17

<210> SEQ ID NO 387
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 387
ccttgactgc ctccatc                                                        17

<210> SEQ ID NO 388
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
cccaggcttg gaatccc                                                        17

<210> SEQ ID NO 389
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
tacttttaac tccctgc                                                        17

<210> SEQ ID NO 390
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tacttttaac tccctgc                                                        17

<210> SEQ ID NO 391
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
attgcattct tgagggc                                                        17

<210> SEQ ID NO 392
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
gagctggcaa gcctggg                                                        17

<210> SEQ ID NO 393
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
```
gatgccacca ggttgtg                                                    17

<210> SEQ ID NO 394
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gatgccacca ggttgtg                                                    17

<210> SEQ ID NO 395
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
tcccgccgcg cgttgcc                                                    17

<210> SEQ ID NO 396
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
ccctgtccta gtaacgc                                                    17

<210> SEQ ID NO 397
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
cgaggaagtg accctcg                                                    17

<210> SEQ ID NO 398
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398 gcggggcag cagacgc                                                     17

<210> SEQ ID NO 399
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
taactgtcct ttccgta                                                    17

<210> SEQ ID NO 400
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
tctgtatttt cccgggg                                                    17

<210> SEQ ID NO 401
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
aagaggcaga acgtgcg                                                    17

<210> SEQ ID NO 402
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gcctcagccc gcacccg                                                    17

<210> SEQ ID NO 403
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
gaccggggcg cagggcc                                                    17

<210> SEQ ID NO 404
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gaccggggcg cagggcc                                                    17

<210> SEQ ID NO 405
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gtgcgggcga cggcagc                                                    17

<210> SEQ ID NO 406
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gcccgcctga gcaaggg                                                  17

<210> SEQ ID NO 407
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ggtggaggca ggcgggg                                                  17

<210> SEQ ID NO 408
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ggcgttaata gagaggc                                                  17

<210> SEQ ID NO 409
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
aggttgttgt tcttgca                                                  17

<210> SEQ ID NO 410
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
agccgcgggc agccgcc                                                  17

<210> SEQ ID NO 411
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
agccaccgta caaggcc                                                  17

```
<210> SEQ ID NO 412
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
gcgggcagct cgaggcg                                                17

<210> SEQ ID NO 413
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
gcggccgcgg gcagggg                                                17

<210> SEQ ID NO 414
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ccccgtggcg ggagcgg                                                17

<210> SEQ ID NO 415
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
ccccgtggcg ggagcgg                                                17

<210> SEQ ID NO 416
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gcctggctct ccttcgc                                                17

<210> SEQ ID NO 417
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
aaaagtaaac aggtatt                                                17
```

```
<210> SEQ ID NO 418
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
ccgcgctgag gggggc                                                    17

<210> SEQ ID NO 419
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
tcagaggctg atggggc                                                   17

<210> SEQ ID NO 420
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
tcagaggctg atggggc                                                   17

<210> SEQ ID NO 421
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
cggagccgcc ccagggg                                                   17

<210> SEQ ID NO 422
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
atgccacccc aggttgc                                                   17

<210> SEQ ID NO 423
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
gcgctgccct atattgg                                                   17

<210> SEQ ID NO 424
```

```
<210> SEQ ID NO 424
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
tcgtcctggg tggaggg                                                    17

<210> SEQ ID NO 425
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
tcgtcctggg tggaggg                                                    17

<210> SEQ ID NO 426
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gcctctgcag ccaggtg                                                    17

<210> SEQ ID NO 427
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ccacagacca gtgggtg                                                    17

<210> SEQ ID NO 428
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
ccccggcagg cggcggc                                                    17

<210> SEQ ID NO 429
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
ccccggcagg cggcggc                                                    17

<210> SEQ ID NO 430
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gaacaaaccc agggatc                                                  17

<210> SEQ ID NO 431
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
tcggagtccc cgtctcc                                                  17

<210> SEQ ID NO 432
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
agaacgggaa ccgtcca                                                  17

<210> SEQ ID NO 433
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
gcctggacgg cctcggg                                                  17

<210> SEQ ID NO 434
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
gtgcggcgcg gctcagc                                                  17

<210> SEQ ID NO 435
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
ttgcaaagaa cggagcc                                                  17

<210> SEQ ID NO 436
<211> LENGTH: 17
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 436
tttcagcggg agccgcc                                                    17

<210> SEQ ID NO 437
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
cgaacttccc ggttccg                                                    17

<210> SEQ ID NO 438
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
cagcggccaa agctgcc                                                    17

<210> SEQ ID NO 439
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
cagcggccaa agctgcc                                                    17

<210> SEQ ID NO 440
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
gtaggtggcg gcgagcg                                                    17

<210> SEQ ID NO 441
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
ctgtacatcg gggcggc                                                    17

<210> SEQ ID NO 442
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 442
gctgctgccc ccagccc                                                        17

<210> SEQ ID NO 443
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
cgcagttcgg aaggacc                                                        17

<210> SEQ ID NO 444
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
cgcagttcgg aaggacc                                                        17

<210> SEQ ID NO 445
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
ctgaggctgc gcccgcc                                                        17

<210> SEQ ID NO 446
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
ggccggtgcc gccagtc                                                        17

<210> SEQ ID NO 447
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
gccccacgcc ccctggc                                                        17

<210> SEQ ID NO 448
<211> LENGTH: 17
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 448
gccccacgcc ccctggc                                                  17

<210> SEQ ID NO 449
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
ctcgtgcgag tcgcgcg                                                  17

<210> SEQ ID NO 450
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
gccccggccg ccgcgcc                                                  17

<210> SEQ ID NO 451
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
agagctgagt ctcaccc                                                  17

<210> SEQ ID NO 452
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
gagcctctta tggctcg                                                  17

<210> SEQ ID NO 453
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
tcaggcttcc ccttcgg                                                  17

<210> SEQ ID NO 454
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 454
gccgggcccc gccctgc					17

<210> SEQ ID NO 455
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
ccttgagagc agagagc					17

<210> SEQ ID NO 456
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
ctaagtgggc agcactg					17

<210> SEQ ID NO 457
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
ggccgggctg gcaccgg					17

<210> SEQ ID NO 458
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
ggtgcagctc tgaggcc					17

<210> SEQ ID NO 459
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
gagtgcccgg ctcgccc					17

<210> SEQ ID NO 460
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
cccgcgggag agaccgg					17

<210> SEQ ID NO 461
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
cccgcgggag agaccgg					17

<210> SEQ ID NO 462
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
cgcagtgtcc tagtgcc					17

<210> SEQ ID NO 463
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
gagctcagag ctcctcc					17

<210> SEQ ID NO 464
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
ccttcctgcg aacccct					17

<210> SEQ ID NO 465
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
cgggccgggt cggcctc					17

<210> SEQ ID NO 466
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
gtggcgctcg gggtgcg					17

<210> SEQ ID NO 467
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
ccgggtccgc gggcgag					17

<210> SEQ ID NO 468
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
atccggccaa gccctag					17

<210> SEQ ID NO 469
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
atccggccaa gccctag					17

<210> SEQ ID NO 470
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
gttaaaaact tccagcc					17

<210> SEQ ID NO 471
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
gggtaggcac agccgtc					17

<210> SEQ ID NO 472
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tgcgcgcgtc ggtggcg                                                    17

<210> SEQ ID NO 473
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
cggtgcccgg gaggccc                                                    17

<210> SEQ ID NO 474
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
cggtgcccgg gaggccc                                                    17

<210> SEQ ID NO 475
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gtgcagtctc ggcccgg                                                    17

<210> SEQ ID NO 476
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
tcccgcgccc aggcccc                                                    17

<210> SEQ ID NO 477
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gcagcccctt ggtggag                                                    17

<210> SEQ ID NO 478
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
ccgtgttgtc ctgcccg                          17

<210> SEQ ID NO 479
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
ccacacctct ctccagg                          17

<210> SEQ ID NO 480
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ggcaaccact caggacg                          17

<210> SEQ ID NO 481
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
gcgaaacccc gtctcta                          17

<210> SEQ ID NO 482
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
ccaaggaacc tgaaaac                          17

<210> SEQ ID NO 483
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
gcccaaaagg agaatga                          17

<210> SEQ ID NO 484
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
cacgccacca cccaccc                          17

<210> SEQ ID NO 485
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
gaaacccctc tgagccc                                                    17

<210> SEQ ID NO 486
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
gtgaccagcc tggagag                                                    17

<210> SEQ ID NO 487
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
ctgaatgggg caaggag                                                    17

<210> SEQ ID NO 488
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
gccataactt ttaagtc                                                    17

<210> SEQ ID NO 489
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
ccccgacccc aggcggg                                                    17

<210> SEQ ID NO 490
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
taaactcttt tcctgtt                                                    17

<210> SEQ ID NO 491
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 491
taaactcttt tcctgtt                                            17

<210> SEQ ID NO 492
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 492
accctcgcgt gggcccc                                            17

<210> SEQ ID NO 493
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 493
accctcgcgt gggcccc                                            17

<210> SEQ ID NO 494
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 494
tccggggccc cgccccc                                            17

<210> SEQ ID NO 495
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 495
cgccccggtg cccaacg                                            17

<210> SEQ ID NO 496
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 496
cgccccggtg cccaacg                                            17

<210> SEQ ID NO 497
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
agcctgcaaa ggggagg                                                 17

<210> SEQ ID NO 498
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
tccctgtccc tgcaatc                                                 17

<210> SEQ ID NO 499
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
cccgctcctt cggttcg                                                 17

<210> SEQ ID NO 500
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
cccgctcctt cggttcg                                                 17

<210> SEQ ID NO 501
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
ttgggttcgc tcagcgg                                                 17

<210> SEQ ID NO 502
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
ttgggttcgc tcagcgg                                                 17

<210> SEQ ID NO 503

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gctgcggccg gccgggg                                                  17

<210> SEQ ID NO 504
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
gacagacccg gtccctg                                                  17

<210> SEQ ID NO 505
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
cgctcccacg tccggga                                                  17

<210> SEQ ID NO 506
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
ctttcaaact ggacccg                                                  17

<210> SEQ ID NO 507
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ggggattcta ccctggg                                                  17

<210> SEQ ID NO 508
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ggggattcta ccctggg                                                  17

<210> SEQ ID NO 509
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
tgtcacagac tcccagc                                                    17

<210> SEQ ID NO 510
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tgtcacagac tcccagc                                                    17

<210> SEQ ID NO 511
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
tgggctgctg tcggggg                                                    17

<210> SEQ ID NO 512
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
cgcgcgcagc gggcgcc                                                    17

<210> SEQ ID NO 513
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
gccctggggt gttatgg                                                    17

<210> SEQ ID NO 514
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gccctggggt gttatgg                                                    17

<210> SEQ ID NO 515
<211> LENGTH: 17
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 515
ccccttctca gctccgg                                                  17

<210> SEQ ID NO 516
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
atttacacgg ggctcac                                                  17

<210> SEQ ID NO 517
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
agtccccagg gctggca                                                  17

<210> SEQ ID NO 518
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
attaaccttt gaagccc                                                  17

<210> SEQ ID NO 519
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
gggctgcctc gccgggc                                                  17

<210> SEQ ID NO 520
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
gggctgcctc gccgggc                                                  17

<210> SEQ ID NO 521
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
gaaatgctaa ggggttg                                                   17

<210> SEQ ID NO 522
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
taaattccac tgaaaat                                                   17

<210> SEQ ID NO 523
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gtgccgccgc gggcgcc                                                   17

<210> SEQ ID NO 524
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
gtgccgccgc gggcgcc                                                   17

<210> SEQ ID NO 525
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
aaaatgttct caaaccc                                                   17

<210> SEQ ID NO 526
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
agcacccgcc tggaacc                                                   17

<210> SEQ ID NO 527
<211> LENGTH: 17
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 527
gctcacctac ccaggtg                                                  17

<210> SEQ ID NO 528
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
gcaggtagac caggcct                                                  17

<210> SEQ ID NO 529
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
cagcttttga aatcagg                                                  17

<210> SEQ ID NO 530
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
gcctctctgc gcctgcc                                                  17

<210> SEQ ID NO 531
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
cgcagaatcc cggaggc                                                  17

<210> SEQ ID NO 532
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
cccggacttg gccaggc                                                  17

<210> SEQ ID NO 533
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 533
agcgcttggc gctccca                                                          17

<210> SEQ ID NO 534
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
gcccaacccc ggggagt                                                          17

<210> SEQ ID NO 535
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
tctggggccg ggtagcc                                                          17

<210> SEQ ID NO 536
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
cgtgtgtatc tgggggt                                                          17

<210> SEQ ID NO 537
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
gcagcggcgc tccgggc                                                          17

<210> SEQ ID NO 538
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
gatcctcgcc cgcgcct                                                          17

<210> SEQ ID NO 539
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ccggtttccc agcgccc                                                17

<210> SEQ ID NO 540
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
ctgctcgggg gaccccc                                                17

<210> SEQ ID NO 541
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
ggcgccgcca tcttgcc                                                17

<210> SEQ ID NO 542
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
ccagggcctg gcactgc                                                17

<210> SEQ ID NO 543
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ttcgggccgg gccggga                                                17

<210> SEQ ID NO 544
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
agccactgcg cccggcc                                                17

<210> SEQ ID NO 545
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 545
gaggggggca aaactac                                                     17

<210> SEQ ID NO 546
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
cttatgttta cagcatc                                                     17

<210> SEQ ID NO 547
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
cttatgttta cagcatc                                                     17

<210> SEQ ID NO 548
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
tatttggtgc tgccaca                                                     17

<210> SEQ ID NO 549
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
tctccttgct cgctccg                                                     17

<210> SEQ ID NO 550
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
tctccttgct cgctccg                                                     17

<210> SEQ ID NO 551
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
```
gttctcaaac agctttc                                                17

<210> SEQ ID NO 552
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
tccaggcagg gcctctg                                                17

<210> SEQ ID NO 553
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
tcagatagtt ctccagc                                                17

<210> SEQ ID NO 554
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
tcagatagtt ctccagc                                                17

<210> SEQ ID NO 555
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555 acgttttaa ctacaca                                                 17

<210> SEQ ID NO 556
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
ctgtccaact cccaggg                                                17

<210> SEQ ID NO 557
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
tggatttggt cgtctcc                                                        17

<210> SEQ ID NO 558
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
gcccccgtgg cgcccccg                                                       17

<210> SEQ ID NO 559
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gcccccgtgg cgcccccg                                                       17

<210> SEQ ID NO 560
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ccacaccagg attcgag                                                        17

<210> SEQ ID NO 561
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
gtgaacttcc aagatgc                                                        17

<210> SEQ ID NO 562
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
gctagggaaa aacaggc                                                        17

<210> SEQ ID NO 563
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
gctagggaaa aacaggc                                                        17

<210> SEQ ID NO 564
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
gacgcgctcc cgcgggc                                                  17

<210> SEQ ID NO 565
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
gacgcgctcc cgcgggc                                                  17

<210> SEQ ID NO 566
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
gagcggccgc ccagagc                                                  17

<210> SEQ ID NO 567
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
atgcgccccg cagcccc                                                  17

<210> SEQ ID NO 568
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
atgcgccccg cagcccc                                                  17

<210> SEQ ID NO 569
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
ctctcacccg aggagcg                                                  17

```
<210> SEQ ID NO 570
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
gttcctgctc tccacga                                                    17

<210> SEQ ID NO 571
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
gtccccgcgc cgcggcc                                                    17

<210> SEQ ID NO 572
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
gtccccgcgc cgcggcc                                                    17

<210> SEQ ID NO 573
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
cttttgtccc ttttgtc                                                    17

<210> SEQ ID NO 574
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
gccacccaag cccgtcg                                                    17

<210> SEQ ID NO 575
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
gccacccaag cccgtcg                                                    17
```

<210> SEQ ID NO 576
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 576
accttaggcc cttctct                                              17

<210> SEQ ID NO 577
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 577
atgcgagggg cgcggta                                              17

<210> SEQ ID NO 578
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 578
atgcgagggg cgcggta                                              17

<210> SEQ ID NO 579
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 579
gattctgtct atgcttc                                              17

<210> SEQ ID NO 580
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 580
gcagcattgc ggctccg                                              17

<210> SEQ ID NO 581
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 581
cacacaaggc gcccgcg                                              17

<210> SEQ ID NO 582

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
tcattgcata ctgaagg                                                  17

<210> SEQ ID NO 583
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
tcattgcata ctgaagg                                                  17

<210> SEQ ID NO 584
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
ctggagctca gcactga                                                  17

<210> SEQ ID NO 585
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
ttcaccccca cccactc                                                  17

<210> SEQ ID NO 586
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
ccccagctcg gcggcgg                                                  17

<210> SEQ ID NO 587
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
agggcaatcc agccctc                                                  17

<210> SEQ ID NO 588
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
aagcagtctt cgagggg                                                    17

<210> SEQ ID NO 589
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
cggtggggta ggcggtc                                                    17

<210> SEQ ID NO 590
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
agagtgacgt gctgtgg                                                    17

<210> SEQ ID NO 591
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
caccaaacct agaaggc                                                    17

<210> SEQ ID NO 592
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
tggggacccg agaaggg                                                    17

<210> SEQ ID NO 593
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
tccccatttc accaagg                                                    17

<210> SEQ ID NO 594
<211> LENGTH: 17
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 594 ggcgagggggg cctctgg                                                17

<210> SEQ ID NO 595
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
agaccatcct tggaccc                                                 17

<210> SEQ ID NO 596
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
ggcgccagag gaagatc                                                 17

<210> SEQ ID NO 597
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
tgtaaggcgg cggggag                                                 17

<210> SEQ ID NO 598
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
aaattccata gacaacc                                                 17

<210> SEQ ID NO 599
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
atggtgtcgc tggacag                                                 17

<210> SEQ ID NO 600
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 600
atggtgtcgc tggacag                                                    17

<210> SEQ ID NO 601
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
tcacatttca gtttggg                                                    17

<210> SEQ ID NO 602
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
actgcatccg gcctcgg                                                    17

<210> SEQ ID NO 603
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
cacccgcggt gccgggc                                                    17

<210> SEQ ID NO 604
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
gggtcttcat ctgatcc                                                    17

<210> SEQ ID NO 605
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
gggtgggggg tgcaggc                                                    17

<210> SEQ ID NO 606
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 606
cagccgactc tctggct                                                  17

<210> SEQ ID NO 607
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
cctagcatct cctcttg                                                  17

<210> SEQ ID NO 608
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
ctatactggc tcgtcct                                                  17

<210> SEQ ID NO 609
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
ctatactggc tcgtcct                                                  17

<210> SEQ ID NO 610
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
gaggactggg ggctggg                                                  17

<210> SEQ ID NO 611
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
ggaggcaaac gggaacc                                                  17

<210> SEQ ID NO 612
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 612
cccgacgggc ggcgcgg                                               17

<210> SEQ ID NO 613
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
cccgacgggc ggcgcgg                                               17

<210> SEQ ID NO 614
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
gatcgctggg gttttgg                                               17

<210> SEQ ID NO 615
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
gatcgctggg gttttgg                                               17

<210> SEQ ID NO 616
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
cggcgcgtcc ctgccgg                                               17

<210> SEQ ID NO 617
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ccacttcccc attggtc                                               17

<210> SEQ ID NO 618
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
cacaccccgc ccccagc                                                17

<210> SEQ ID NO 619
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
aaccccgaaa ctggaag                                                17

<210> SEQ ID NO 620
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
gaagagtccc agccggt                                                17

<210> SEQ ID NO 621
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
gaagagtccc agccggt                                                17

<210> SEQ ID NO 622
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622 caacccaac cgcgttc                                                 17

<210> SEQ ID NO 623
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
cctgcctctg gcagggg                                                17

<210> SEQ ID NO 624
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 624
gcgttgggca cccctgc                                                  17

<210> SEQ ID NO 625
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
gcctagaaga agccgaa                                                  17

<210> SEQ ID NO 626
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
gggccgagtc cggcagc                                                  17

<210> SEQ ID NO 627
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
gaaagggcag tcccgcc                                                  17

<210> SEQ ID NO 628
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
gaaagggcag tcccgcc                                                  17

<210> SEQ ID NO 629
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
ctcggtggcg ggaccgg                                                  17

<210> SEQ ID NO 630
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
```
gccgggccgg tgactcc                                                17

<210> SEQ ID NO 631
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
gccgggccgg tgactcc                                                17

<210> SEQ ID NO 632
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
cccagagact ttatcct                                                17

<210> SEQ ID NO 633
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
cccagagact ttatcct                                                17

<210> SEQ ID NO 634
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
cgtgtgagct ctcctgc                                                17

<210> SEQ ID NO 635
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
tctcaacacg ctaggca                                                17

<210> SEQ ID NO 636
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
ggtacctgca tcctctc                                                  17

<210> SEQ ID NO 637
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
ggaagcgccc tgccctc                                                  17

<210> SEQ ID NO 638
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
cacttcccag ctctgag                                                  17

<210> SEQ ID NO 639
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
cacctctgcc gtgctgc                                                  17

<210> SEQ ID NO 640
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
cacctctgcc gtgctgc                                                  17

<210> SEQ ID NO 641
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
gggcggtggc ggggacg                                                  17

<210> SEQ ID NO 642
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
gctctgggcg ccctttc                                                  17

<210> SEQ ID NO 643
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 643
cctgcgccgg gggaggc                                              17

<210> SEQ ID NO 644
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 644
tacaatgaag gggtcag                                              17

<210> SEQ ID NO 645
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 645
tacaatgaag gggtcag                                              17

<210> SEQ ID NO 646
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 646
gcattgattg ctgtccc                                              17

<210> SEQ ID NO 647
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 647
gcattgattg ctgtccc                                              17

<210> SEQ ID NO 648
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 648
gtccgtggaa tagaagg                                              17

<210> SEQ ID NO 649
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
acgccggcgc cgctcgc                                                 17

<210> SEQ ID NO 650
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
aaagcacagg ctctccc                                                 17

<210> SEQ ID NO 651
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
ccgcggatct cgccggt                                                 17

<210> SEQ ID NO 652
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
agccacctgc gcctggc                                                 17

<210> SEQ ID NO 653
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
caagggttca catatgc                                                 17

<210> SEQ ID NO 654
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
cgcttcgggg tgcatct                                                 17

```
<210> SEQ ID NO 655
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
cgcttcgggg tgcatct                                                    17

<210> SEQ ID NO 656
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
ccgggcagcc tcagagg                                                    17

<210> SEQ ID NO 657
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
gctgtccgca cgcggcc                                                    17

<210> SEQ ID NO 658
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
gctgtccgca cgcggcc                                                    17

<210> SEQ ID NO 659
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
tgcacgcaca ctcttcc                                                    17

<210> SEQ ID NO 660
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
gtggggaggc tggggcg                                                    17

<210> SEQ ID NO 661
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
gtggggaggc tggggcg                                                    17

<210> SEQ ID NO 662
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
tttttcatct tcccccc                                                    17

<210> SEQ ID NO 663
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
tttttcatct tcccccc                                                    17

<210> SEQ ID NO 664
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
cttagatcta gcgttcc                                                    17

<210> SEQ ID NO 665
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
taacgctccc gggcctc                                                    17

<210> SEQ ID NO 666
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
tctgcacgcc ggggtct                                                    17

<210> SEQ ID NO 667
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
ggaggtctca ggatccc                                                   17

<210> SEQ ID NO 668
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
cccactttca aaggggg                                                   17

<210> SEQ ID NO 669
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
cccactttca aaggggg                                                   17

<210> SEQ ID NO 670
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
acccgggccg cagcggc                                                   17

<210> SEQ ID NO 671
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
ctgggttgcg attagct                                                   17

<210> SEQ ID NO 672
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
acacatttat ttttcag                                                   17

<210> SEQ ID NO 673
<211> LENGTH: 17
<212> TYPE: DNA
```

<213> ORGANISM: Artificial Sequence
<220> FEATURE:
<223> OTHER INFORMATION: Description of Artificial Sequence: Synthetic
     oligonucleotide

<400> SEQUENCE: 673
gtgggagtca aagagct                                                17

<210> SEQ ID NO 674
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 674
ccgctggtgc actccgg                                                17

<210> SEQ ID NO 675
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 675
gtttcttccc gcccatc                                                17

<210> SEQ ID NO 676
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 676
tttcttctaa caaaggc                                                17

<210> SEQ ID NO 677
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 677
ggtccatctg caaaggg                                                17

<210> SEQ ID NO 678
<211> LENGTH: 17
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 678
ccagagggtc ttaagtg                                                17

<210> SEQ ID NO 679
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
acccaccaac acacgcc                                                    17

<210> SEQ ID NO 680
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
cgtctcccat cccgggc                                                    17

<210> SEQ ID NO 681
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
gcagcagcct gtaatcc                                                    17

<210> SEQ ID NO 682
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
gcctggcttc cccccag                                                    17

<210> SEQ ID NO 683
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
cgccagagct ctttgtg                                                    17

<210> SEQ ID NO 684
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
gtttcacgtc tctgagt                                                    17

<210> SEQ ID NO 685
<211> LENGTH: 17
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 685
ctttaggtcg caggaca                                                     17

<210> SEQ ID NO 686
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
tcaatgctcc ggcgggg                                                     17

<210> SEQ ID NO 687
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
ggtctccgaa gcgagcg                                                     17

<210> SEQ ID NO 688
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
gtgaaagcat accgtca                                                     17

<210> SEQ ID NO 689
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
gctctcacac aatagga                                                     17

<210> SEQ ID NO 690
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
aaggagaccg cacaggg                                                     17

<210> SEQ ID NO 691
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 691
aaggagaccg cacaggg                                                    17

<210> SEQ ID NO 692
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
gttggaaatg gtgcgaa                                                    17

<210> SEQ ID NO 693
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
attgtcagat ctggaat                                                    17

<210> SEQ ID NO 694
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
tccatagatt gacaaag                                                    17

<210> SEQ ID NO 695
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
tacaaggcac tatgctg                                                    17

<210> SEQ ID NO 696
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
gagaacggct cgggcgc                                                    17

<210> SEQ ID NO 697
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 697
gttatggcca gaacttg                                                 17

<210> SEQ ID NO 698
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
aacttgagag cgatttc                                                 17

<210> SEQ ID NO 699
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
gcagtgttct gcttggc                                                 17

<210> SEQ ID NO 700
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
ctccgggtgg ggaggcc                                                 17

<210> SEQ ID NO 701
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
ggcagacagg ccctatc                                                 17

<210> SEQ ID NO 702
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
gcaaacgtct agttatc                                                 17

<210> SEQ ID NO 703
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 703
atgagtccat ttcctcg                                                17

<210> SEQ ID NO 704
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704 ggggggaac cggaccg                                                 17

<210> SEQ ID NO 705
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
gggggtcttt cccctc                                                 17

<210> SEQ ID NO 706
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
catttcctcg ggtgtga                                                17

<210> SEQ ID NO 707
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
tttccagtgc aattccg                                                17

<210> SEQ ID NO 708
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
acaaaaatga tcgttct                                                17

<210> SEQ ID NO 709
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
```
tccgccctgc cccgggc                                              17

<210> SEQ ID NO 710
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
ggctctccgt ctctgcc                                              17

<210> SEQ ID NO 711
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
gaacgtgcgt ttgcttt                                              17

<210> SEQ ID NO 712
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
gtccccagca cgcggtc                                              17

<210> SEQ ID NO 713
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
tgccctgggc tgcccgc                                              17

<210> SEQ ID NO 714
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
tggcaaaccc attcttg                                              17

<210> SEQ ID NO 715
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
gccacactcc tgacttg                                                17

<210> SEQ ID NO 716
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
aacttggggc tgaccgg                                                17

<210> SEQ ID NO 717
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
cccagtctag ccaaggt                                                17

<210> SEQ ID NO 718
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
ccccgccgcg ctgattg                                                17

<210> SEQ ID NO 719
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
ccttccgccc gagcgtc                                                17

<210> SEQ ID NO 720
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
taatctccct aaatacc                                                17

<210> SEQ ID NO 721
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
cactagacct gcctgag                                                17

<210> SEQ ID NO 722
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
tttggaggag tggagtt                                                  17

<210> SEQ ID NO 723
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
ggcggcggcc acttctg                                                  17

<210> SEQ ID NO 724
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
tctgagtcgc cagcgtc                                                  17

<210> SEQ ID NO 725
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
agtatcaaaa cggcagc                                                  17

<210> SEQ ID NO 726
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
ccccggcccg ctctccc                                                  17

<210> SEQ ID NO 727
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
ttatttttac agcaaac                                                  17

<210> SEQ ID NO 728
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
gagctggcaa gcctggg                                                  17

<210> SEQ ID NO 729
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
gatgccacca ggttgtg                                                  17

<210> SEQ ID NO 730
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
gatgccacca ggttgtg                                                  17

<210> SEQ ID NO 731
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
cggaccacgc gtccctg                                                  17

<210> SEQ ID NO 732
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
cggaccacgc gtccctg                                                  17

<210> SEQ ID NO 733
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
ggggcctatt cacagcc                                                  17

```
<210> SEQ ID NO 734
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
ggggcctatt cacagcc                                                    17

<210> SEQ ID NO 735
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
ccagacgccg gctcggc                                                    17

<210> SEQ ID NO 736
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
gcttttcaac cgtagcg                                                    17

<210> SEQ ID NO 737
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
gtgacgatgg aggagct                                                    17

<210> SEQ ID NO 738
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
cacacacaca cccgggc                                                    17

<210> SEQ ID NO 739
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
cctcctgttc ctctgcc                                                    17

<210> SEQ ID NO 740
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
ccctgtccta gtaacgc                                                    17

<210> SEQ ID NO 741
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
ctcctccttc ttttgcg                                                    17

<210> SEQ ID NO 742
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
cttcaatttg gtgaggg                                                    17

<210> SEQ ID NO 743
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
cgaggaagtg accctcg                                                    17

<210> SEQ ID NO 744
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
gcgggggcag cagacgc                                                    17

<210> SEQ ID NO 745
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
caccagtctt cgcccgc                                                    17

<210> SEQ ID NO 746
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
caccagtctt cgcccgc                                                 17

<210> SEQ ID NO 747
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
taactgtcct ttccgta                                                 17

<210> SEQ ID NO 748
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
tgccattctg gagagct                                                 17

<210> SEQ ID NO 749
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
taattcgagc actttga                                                 17

<210> SEQ ID NO 750
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
aataggtaac tcacaaa                                                 17

<210> SEQ ID NO 751
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
aagttggcca cctcggg                                                 17

<210> SEQ ID NO 752
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 752
actgccttgc cccctcc                                                    17

<210> SEQ ID NO 753
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
cttgcctctc atccttc                                                    17

<210> SEQ ID NO 754
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
ggggtaactc ttgagtc                                                    17

<210> SEQ ID NO 755
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
gcctcagccc gcacccg                                                    17

<210> SEQ ID NO 756
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
ggcacgggag ctgctcc                                                    17

<210> SEQ ID NO 757
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
gcgccaaccc gggctgc                                                    17

<210> SEQ ID NO 758
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 758
gcacctcagg cggcagt                                                 17

<210> SEQ ID NO 759
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
gcacctcagg cggcagt                                                 17

<210> SEQ ID NO 760
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
gacctactgg attgctc                                                 17

<210> SEQ ID NO 761
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
aaatgaaact agtcttg                                                 17

<210> SEQ ID NO 762
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
tctgtgtgct gtgtgcg                                                 17

<210> SEQ ID NO 763
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
cacagcagcc cgtcagg                                                 17

<210> SEQ ID NO 764
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 764
cacagcagcc cgtcagg                                                    17

<210> SEQ ID NO 765
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
agggggctgc tccggag                                                    17

<210> SEQ ID NO 766
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
gggatacaca cagggga                                                    17

<210> SEQ ID NO 767
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
gtgcgggcga cggcagc                                                    17

<210> SEQ ID NO 768
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
gggtgccgcg gccacga                                                    17

<210> SEQ ID NO 769
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
taaataggcg agaggag                                                    17

<210> SEQ ID NO 770
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 770
taaataggcg agaggag					17

<210> SEQ ID NO 771
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
atcgagtgcg acgcctg					17

<210> SEQ ID NO 772
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
ccgcttgccc cgaaacc					17

<210> SEQ ID NO 773
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
tcttctattg cctgatt					17

<210> SEQ ID NO 774
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
aagtcagtgc gcaaacg					17

<210> SEQ ID NO 775
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
gcgggcggcg cggtccc					17

<210> SEQ ID NO 776
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
atttgtgcag ctaccgt                                                   17

<210> SEQ ID NO 777
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
aggcaggaga tggtctg                                                   17

<210> SEQ ID NO 778
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
ggcgttaata gagaggc                                                   17

<210> SEQ ID NO 779
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
aggttgttgt tcttgca                                                   17

<210> SEQ ID NO 780
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
agccctgggc tctctct                                                   17

<210> SEQ ID NO 781
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
agccctgggc tctctct                                                   17

<210> SEQ ID NO 782
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 782 ctcctttga gcccctg                                                    17

<210> SEQ ID NO 783
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783 ctcctttga gcccctg                                                    17

<210> SEQ ID NO 784
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
ctcccagtac aggagcc                                                   17

<210> SEQ ID NO 785
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
tacgcgggtg ggggaga                                                   17

<210> SEQ ID NO 786
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
cagggccctg ggtgctg                                                   17

<210> SEQ ID NO 787
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
aaggagccta cgttaat                                                   17

<210> SEQ ID NO 788
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
```
gaggacagcc ggctcgt				17

<210> SEQ ID NO 789
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
ccattgcatt ccattcc				17

<210> SEQ ID NO 790
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
ttttcccgag gccagag				17

<210> SEQ ID NO 791
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
aagagcaaat aagaggc				17

<210> SEQ ID NO 792
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
agccaccgta caaggcc				17

<210> SEQ ID NO 793
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
ccccaggcct cggccag				17

<210> SEQ ID NO 794
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
ctcagaggag gggcaga                                                  17

<210> SEQ ID NO 795
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795
aaaatagagg ttcctcc                                                  17

<210> SEQ ID NO 796
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
aaaatagagg ttcctcc                                                  17

<210> SEQ ID NO 797
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
acctcgaagc cgccaag                                                  17

<210> SEQ ID NO 798
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
aatgaacgac cagaccc                                                  17

<210> SEQ ID NO 799
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
ggtcgctcct cgttggg                                                  17

<210> SEQ ID NO 800
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
gagtttcttt agtaaag                                                  17

<210> SEQ ID NO 801
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
agttagttcc caactca                                                      17

<210> SEQ ID NO 802
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
agttagttcc caactca                                                      17

<210> SEQ ID NO 803
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
gggacaggtg gcaggcc                                                      17

<210> SEQ ID NO 804
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
gagctaatca ataggca                                                      17

<210> SEQ ID NO 805
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
tgggaaaggt cttgtgg                                                      17

<210> SEQ ID NO 806
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
gcggccgcgg gcagggg                                                      17

<210> SEQ ID NO 807
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
ctgcccgcag gtggcgc                                                      17

<210> SEQ ID NO 808
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
gaggtagtgc cctgtcc                                                      17

<210> SEQ ID NO 809
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
ttgtgtgtac ataggcc                                                      17

<210> SEQ ID NO 810
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
gctcattgcg tcccgct                                                      17

<210> SEQ ID NO 811
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
agcagcagcc ccatccc                                                      17

<210> SEQ ID NO 812
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
ttggccaggc tggtctc                                                      17

```
<210> SEQ ID NO 813
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
gggccccgcc cagccag                                                    17

<210> SEQ ID NO 814
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
gggccccgcc cagccag                                                    17

<210> SEQ ID NO 815
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
tgcgcttggc agccggg                                                    17

<210> SEQ ID NO 816
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
tcagaggctg atggggc                                                    17

<210> SEQ ID NO 817
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
tcagaggctg atggggc                                                    17

<210> SEQ ID NO 818
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
tggaggcagg tgcacag                                                    17

<210> SEQ ID NO 819
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
cagccgaagt ggcgctc                                              17

<210> SEQ ID NO 820
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820
gcctggcact gggtcca                                              17

<210> SEQ ID NO 821
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821
gcctggcact gggtcca                                              17

<210> SEQ ID NO 822
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822
gaaaactcca gatagtg                                              17

<210> SEQ ID NO 823
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
ctttgaaata agcgaat                                              17

<210> SEQ ID NO 824
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
gcgctgccct atattgg                                              17

<210> SEQ ID NO 825
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
tctaggacct ccaggcc                                                    17

<210> SEQ ID NO 826
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
tctaggacct ccaggcc                                                    17

<210> SEQ ID NO 827
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
ccctgccctt agtgctt                                                    17

<210> SEQ ID NO 828
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
ctctgggctg tgaggac                                                    17

<210> SEQ ID NO 829
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
ctctgggctg tgaggac                                                    17

<210> SEQ ID NO 830
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
cgccccttcc ctgcgcc                                                    17

<210> SEQ ID NO 831
<211> LENGTH: 17
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 831
ccacagacca gtgggtg                                               17

<210> SEQ ID NO 832
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 832
gccctgcata caaccct                                               17

<210> SEQ ID NO 833
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 833
gctcagaggc gctggaa                                               17

<210> SEQ ID NO 834
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 834
ccccggcagg cggcggc                                               17

<210> SEQ ID NO 835
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 835
ccccggcagg cggcggc                                               17

<210> SEQ ID NO 836
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 836
gattatgaaa gcccatc                                               17

<210> SEQ ID NO 837
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 837
gattatgaaa gcccatc                                                    17

<210> SEQ ID NO 838
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
cgacatatca gggatca                                                    17

<210> SEQ ID NO 839
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
ctccagccct gtgtcct                                                    17

<210> SEQ ID NO 840
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
cctgccggtg gagggca                                                    17

<210> SEQ ID NO 841
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
ccacgtctta gcactct                                                    17

<210> SEQ ID NO 842
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
ccacgtctta gcactct                                                    17

<210> SEQ ID NO 843
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 843
cagattctac aaaagga                                                      17

<210> SEQ ID NO 844
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
gcggcctcag gtgagcg                                                      17

<210> SEQ ID NO 845
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
tccccacccc tggtacc                                                      17

<210> SEQ ID NO 846
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 846
tctccgtgta tgtgcgc                                                      17

<210> SEQ ID NO 847
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
ttgacaggca gacaagt                                                      17

<210> SEQ ID NO 848
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
ccttcctccc cacgcag                                                      17

<210> SEQ ID NO 849
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 849
ttgcaaagaa cggagcc                                               17

<210> SEQ ID NO 850
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 850
tcaagtgtga ggggaag                                               17

<210> SEQ ID NO 851
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
tcaagtgtga ggggaag                                               17

<210> SEQ ID NO 852
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
acaaagtacc gtggttc                                               17

<210> SEQ ID NO 853
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
gaggccagat tttctcc                                               17

<210> SEQ ID NO 854
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
aaggctggga gttttct                                               17

<210> SEQ ID NO 855
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 855
gggcggccgg cggggc                                                    17

<210> SEQ ID NO 856
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 856
cgaacttccc ggttccg                                                   17

<210> SEQ ID NO 857
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
cagcggccaa agctgcc                                                   17

<210> SEQ ID NO 858
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 858
cagcggccaa agctgcc                                                   17

<210> SEQ ID NO 859
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
cgcaggctac cagtgca                                                   17

<210> SEQ ID NO 860
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
cactgcctga tggtgtg                                                   17

<210> SEQ ID NO 861
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 861
aaggtctcta ccgcgcc                                                    17

<210> SEQ ID NO 862
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 862
aaggtctcta ccgcgcc                                                    17

<210> SEQ ID NO 863
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
tttgctacgt gtacatc                                                    17

<210> SEQ ID NO 864
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
ccaccagcct ccctcgg                                                    17

<210> SEQ ID NO 865
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 865
cagtggcctc catctgg                                                    17

<210> SEQ ID NO 866
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
ggttcgaagg gcagcgg                                                    17

<210> SEQ ID NO 867
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 867
```
agctctgcca gtagttg                                                17

<210> SEQ ID NO 868
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868
agctctgcca gtagttg                                                17

<210> SEQ ID NO 869
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
tgcccagccc tcagcac                                                17

<210> SEQ ID NO 870
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
cctctaggac caagcct                                                17

<210> SEQ ID NO 871
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
gagtcgcagt attttgg                                                17

<210> SEQ ID NO 872
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 872
cggcgcagct ccaggtc                                                17

<210> SEQ ID NO 873
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 873
gccttcaggt tgcgggt					17

<210> SEQ ID NO 874
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 874
gccccacgcc ccctggc					17

<210> SEQ ID NO 875
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
gccccacgcc ccctggc					17

<210> SEQ ID NO 876
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
gaggccagcc tgagggc					17

<210> SEQ ID NO 877
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 877
gaggccagcc tgagggc					17

<210> SEQ ID NO 878
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
ttccagtggc aagttga					17

<210> SEQ ID NO 879
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
tcgagccgcg cggtcgt					17

<210> SEQ ID NO 880
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 880
gctctgcccc cgtggcc                                                   17

<210> SEQ ID NO 881
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
gcagaggctg agcggcc                                                   17

<210> SEQ ID NO 882
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
gccgcccccc gaccgaa                                                   17

<210> SEQ ID NO 883
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
tttctcctga tggagtc                                                   17

<210> SEQ ID NO 884
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
tcaggcttcc ccttcgg                                                   17

<210> SEQ ID NO 885
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
gccccaaccg gtccttc                                                   17

```
<210> SEQ ID NO 886
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 886
gaccccacaa gggcttg                                                      17

<210> SEQ ID NO 887
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
ccttgagagc agagagc                                                      17

<210> SEQ ID NO 888
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
tggggactga tgcaccc                                                      17

<210> SEQ ID NO 889
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
cacgtgaggg ggtggta                                                      17

<210> SEQ ID NO 890
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
cccgcgggag agaccgg                                                      17

<210> SEQ ID NO 891
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
cccgcgggag agaccgg                                                      17
```

<210> SEQ ID NO 892
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
ccgggtccgc gggcgag                                                    17

<210> SEQ ID NO 893
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
atccggccaa gccctag                                                    17

<210> SEQ ID NO 894
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
atccggccaa gccctag                                                    17

<210> SEQ ID NO 895
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
ttcctacccc ctacacc                                                    17

<210> SEQ ID NO 896
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
gagggagctt gacattc                                                    17

<210> SEQ ID NO 897
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
gcctataggg tcctggg                                                    17

<210> SEQ ID NO 898

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
gggtaggcac agccgtc                                                    17

<210> SEQ ID NO 899
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
tgcgcgcgtc ggtggcg                                                    17

<210> SEQ ID NO 900
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
aactatccag ggacctg                                                    17

<210> SEQ ID NO 901
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 901
aactatccag ggacctg                                                    17

<210> SEQ ID NO 902
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 902
gttggggaag gcaccgc                                                    17

<210> SEQ ID NO 903
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 903
gttggggaag gcaccgc                                                    17

<210> SEQ ID NO 904
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 904
acaatagcgc gatcgag                                                    17

<210> SEQ ID NO 905
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
tgcttggatc gtggga                                                     17

<210> SEQ ID NO 906
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
gggcgcgccg cgccgcg                                                    17

<210> SEQ ID NO 907
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907
gggcgcgccg cgccgcg                                                    17

<210> SEQ ID NO 908
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
cgattcgaag ggagggg                                                    17

<210> SEQ ID NO 909
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
gtgcagtctc ggcccgg                                                    17

<210> SEQ ID NO 910
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 910
gggatcctct tgcaaag                                                  17

<210> SEQ ID NO 911
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 911
gggatcctct tgcaaag                                                  17

<210> SEQ ID NO 912
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 912
agccaccaca cccttcc                                                  17

<210> SEQ ID NO 913
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 913
aacaccctca gccagcc                                                  17

<210> SEQ ID NO 914
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 914
ccgtgttgtc ctgcccg                                                  17

<210> SEQ ID NO 915
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
caaagccaca cagttta                                                  17

<210> SEQ ID NO 916
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 916
gcggagccca gtcccga                                                      17

<210> SEQ ID NO 917
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 917
ccacacctct ctccagg                                                      17

<210> SEQ ID NO 918
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 918
tgggagtcac gtcctca                                                      17

<210> SEQ ID NO 919
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
cgcttttgac acattgg                                                      17

<210> SEQ ID NO 920
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
gctgccgccg gcgcagc                                                      17

<210> SEQ ID NO 921
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
ctggtctgcg gcctccg                                                      17

<210> SEQ ID NO 922
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 922
gccgcgcaca ggccggt                                                  17

<210> SEQ ID NO 923
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 923
caccagaaac ctcgggg                                                  17

<210> SEQ ID NO 924
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 924
ccaaggaacc tgaaaac                                                  17

<210> SEQ ID NO 925
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 925
cctacctatc cctggac                                                  17

<210> SEQ ID NO 926
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
aggctggggc acaggac                                                  17

<210> SEQ ID NO 927
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 927
gatgctcgaa cgcagag                                                  17

<210> SEQ ID NO 928
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 928
gaggctggca cccaggc                                                    17

<210> SEQ ID NO 929
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 929
aacacgctgg ctcttgc                                                    17

<210> SEQ ID NO 930
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 930
gagctgatca ccattct                                                    17

<210> SEQ ID NO 931
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
tgtgtctgcg tagaaat                                                    17

<210> SEQ ID NO 932
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
gtcctgcggg gcgagag                                                    17

<210> SEQ ID NO 933
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
catttcctgg gctattt                                                    17

<210> SEQ ID NO 934
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
atgtatctac tcagcta                                                17

<210> SEQ ID NO 935
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 935
ctgcccggca gccagcc                                                17

<210> SEQ ID NO 936
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
ttgactcgcc gcttccc                                                17

<210> SEQ ID NO 937
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
ctacaggctg gagggca                                                17

<210> SEQ ID NO 938
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
cctcttccca gaccgaa                                                17

<210> SEQ ID NO 939
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
gggtgggggg tgcaggc                                                17

<210> SEQ ID NO 940
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
tccctcattc gccccgg                                                17

<210> SEQ ID NO 941
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
cacacgcacg ggagcgc                                                17

<210> SEQ ID NO 942
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
tgaagaaaag gcctttg                                                17

<210> SEQ ID NO 943
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
gaactatctt ctaccaa                                                17

<210> SEQ ID NO 944
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
cgcataaggg gtgtggc                                                17

<210> SEQ ID NO 945
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
gagaataaat tactggg                                                17

<210> SEQ ID NO 946
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
tccggagttg ggacctc					17

<210> SEQ ID NO 947
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
ctccggcttc agtggcc					17

<210> SEQ ID NO 948
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
aacgggatcc gcacggg					17

<210> SEQ ID NO 949
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
gccatctctt cgggcgc					17

<210> SEQ ID NO 950
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
acagtagcgc cccctct					17

<210> SEQ ID NO 951
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 951
acagtagcgc cccctct					17

<210> SEQ ID NO 952
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
ctccgaggcg gccaccc                                                    17

<210> SEQ ID NO 953
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 953
ctccgaggcg gccaccc                                                    17

<210> SEQ ID NO 954
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
ccctctgcaa gcaccac                                                    17

<210> SEQ ID NO 955
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 955
atcgtagctc gctgcag                                                    17

<210> SEQ ID NO 956
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 956
aaggacggga gggagaa                                                    17

<210> SEQ ID NO 957
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 957
aaggacggga gggagaa                                                    17

<210> SEQ ID NO 958
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 958
cagactttag ttttgaa                                                    17

<210> SEQ ID NO 959
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 959
cagactttag ttttgaa                                                17

<210> SEQ ID NO 960
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 960
gtcgttcagg ggcgtct                                                17

<210> SEQ ID NO 961
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 961
gctccagcga tgattgt                                                17

<210> SEQ ID NO 962
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
accctcgcgt gggcccc                                                17

<210> SEQ ID NO 963
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 963
accctcgcgt gggcccc                                                17

<210> SEQ ID NO 964
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964
cctcccgccc ggcccgg                                                17

<210> SEQ ID NO 965
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 965
agcctgcaaa ggggagg                                                    17

<210> SEQ ID NO 966
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 966
cagagggaat aaccagt                                                    17

<210> SEQ ID NO 967
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967
acctcaagca cgcggtc                                                    17

<210> SEQ ID NO 968
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
tgattgtgtg tgaggct                                                    17

<210> SEQ ID NO 969
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 969
acgagcacac tgaaaag                                                    17

<210> SEQ ID NO 970
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
ttgggttcgc tcagcgg                                                    17

<210> SEQ ID NO 971
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 971
ttgggttcgc tcagcgg                                                17

<210> SEQ ID NO 972
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 972
cgtgggaaac ctcgatg                                                17

<210> SEQ ID NO 973
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 973
cgtgggaaac ctcgatg                                                17

<210> SEQ ID NO 974
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 974
agactaaacc cccgagg                                                17

<210> SEQ ID NO 975
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 975
ctggtgggga aggtggc                                                17

<210> SEQ ID NO 976
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 976
tacagctgct gcagcgc                                                17

<210> SEQ ID NO 977

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 977
gtttattcca aacactg                                                17

<210> SEQ ID NO 978
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978
ctcacgacgc cgtgaag                                                17

<210> SEQ ID NO 979
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
tcagcccagc ggtatcc                                                17

<210> SEQ ID NO 980
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 980
gtttaccctc tgtctcc                                                17

<210> SEQ ID NO 981
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 981
gaaaagactg ccctctg                                                17

<210> SEQ ID NO 982
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
gacaacgcgg ggaagga                                                17

<210> SEQ ID NO 983
<211> LENGTH: 17
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 983
gcaaggggca gagaaag                                                    17

<210> SEQ ID NO 984
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
gctgagagct gcgggtg                                                    17

<210> SEQ ID NO 985
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 985
agcaactttc ctgggtc                                                    17

<210> SEQ ID NO 986
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 986
cgctcccacg tccggga                                                    17

<210> SEQ ID NO 987
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 987
ctttcaaact ggacccg                                                    17

<210> SEQ ID NO 988
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 988
cgcgcagctc gctgagg                                                    17

<210> SEQ ID NO 989
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 989
ggataggcgt ggccggg                                                     17

<210> SEQ ID NO 990
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 990
cgcaaccctg gcgacgc                                                     17

<210> SEQ ID NO 991
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 991
gggaataggg gggcggg                                                     17

<210> SEQ ID NO 992
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
ggggattcta ccctggg                                                     17

<210> SEQ ID NO 993
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 993
ggggattcta ccctggg                                                     17

<210> SEQ ID NO 994
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 994
cctgcgccgc cgcccgg                                                     17

<210> SEQ ID NO 995
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 995
atccccgagc tgctgga                                                          17

<210> SEQ ID NO 996
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
tccagaggcc cgagctc                                                          17

<210> SEQ ID NO 997
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
aagcggggag gctgagg                                                          17

<210> SEQ ID NO 998
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
tgtcacagac tcccagc                                                          17

<210> SEQ ID NO 999
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999
tgtcacagac tcccagc                                                          17

<210> SEQ ID NO 1000
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
gaaatgtggc cagtgca                                                          17

<210> SEQ ID NO 1001
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1001
agtccttgct ggggtcc                                                        17

<210> SEQ ID NO 1002
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1002
ttgatttgtg aataccc                                                        17

<210> SEQ ID NO 1003
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1003
aatggaactg accactg                                                        17

<210> SEQ ID NO 1004
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1004
gggggcctgc agggtgg                                                        17

<210> SEQ ID NO 1005
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1005
cccaccaggc acgtggc                                                        17

<210> SEQ ID NO 1006
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1006
gtggccgtgg accctga                                                        17

<210> SEQ ID NO 1007
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1007
gcctcagcat cctcctc                                                  17

<210> SEQ ID NO 1008
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1008
gcctcagcat cctcctc                                                  17

<210> SEQ ID NO 1009
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1009
gccctggggt gttatgg                                                  17

<210> SEQ ID NO 1010
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1010
gccctggggt gttatgg                                                  17

<210> SEQ ID NO 1011
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1011
aagagccagg ccacggg                                                  17

<210> SEQ ID NO 1012
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1012
gtttcgaaat gagctcc                                                  17

<210> SEQ ID NO 1013
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1013
gagatgcgcc tacgccc                                                    17

<210> SEQ ID NO 1014
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1014
tagttcacta tcgcttc                                                    17

<210> SEQ ID NO 1015
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1015
ggtctcctga ggaccag                                                    17

<210> SEQ ID NO 1016
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1016
actcatccct gaagagt                                                    17

<210> SEQ ID NO 1017
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1017
cctcagatca ggatggg                                                    17

<210> SEQ ID NO 1018
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1018
gtctggtcga tgttgcg                                                    17

<210> SEQ ID NO 1019
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1019
gtctggtcga tgttgcg                                                    17

<210> SEQ ID NO 1020
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1020
tagtactttc aggtagg                                                    17

<210> SEQ ID NO 1021
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1021
atttacacgg ggctcac                                                    17

<210> SEQ ID NO 1022
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1022
ggggcgaaga aagcaga                                                    17

<210> SEQ ID NO 1023
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1023
atcctgtccc tggcctc                                                    17

<210> SEQ ID NO 1024
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1024
gcggcagcgg cgccggc                                                    17

<210> SEQ ID NO 1025
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1025
```
gcggcagcgg cgccggc                                              17

<210> SEQ ID NO 1026
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1026
gaagcaagag tttggcc                                              17

<210> SEQ ID NO 1027
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1027
aagctgctgc ggcgggc                                              17

<210> SEQ ID NO 1028
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1028
gcgcgggaag gggtgga                                              17

<210> SEQ ID NO 1029
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1029
gtggtcttca gaggtag                                              17

<210> SEQ ID NO 1030
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1030
tccgaacttc cggaccc                                              17

<210> SEQ ID NO 1031
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1031
gcccaacccc ggggagt                                                       17

<210> SEQ ID NO 1032
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1032
tctggggccg ggtagcc                                                       17

<210> SEQ ID NO 1033
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1033
gcagcggcgc tccgggc                                                       17

<210> SEQ ID NO 1034
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1034
ctctcacccg aggagcg                                                       17

<210> SEQ ID NO 1035
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1035
gcagcattgc ggctccg                                                       17

<210> SEQ ID NO 1036
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1036
tcattgcata ctgaagg                                                       17

<210> SEQ ID NO 1037
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1037
tcattgcata ctgaagg                                                       17

```
<210> SEQ ID NO 1038
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1038
ccccagctcg gcggcgg                                                         17

<210> SEQ ID NO 1039
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1039
aagcagtctt cgagggg                                                         17

<210> SEQ ID NO 1040
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1040
cccccacccc ccagccc                                                         17

<210> SEQ ID NO 1041
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1041
tgtaaggcgg cggggag                                                         17

<210> SEQ ID NO 1042
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1042
actgcatccg gcctcgg                                                         17

<210> SEQ ID NO 1043
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1043
ggaggcaaac gggaacc                                                         17
```

<210> SEQ ID NO 1044
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1044
cggcgcgtcc ctgccgg                                                    17

<210> SEQ ID NO 1045
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1045
ccacttcccc attggtc                                                    17

<210> SEQ ID NO 1046
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1046
cctgcctctg gcagggg                                                    17

<210> SEQ ID NO 1047
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1047
ctcggtggcg ggaccgg                                                    17

<210> SEQ ID NO 1048
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1048
cgtgtgagct ctcctgc                                                    17

<210> SEQ ID NO 1049
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1049
cctgcgccgg gggaggc                                                    17

```
<210> SEQ ID NO 1050
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1050
aaagcacagg ctctccc                                                  17

<210> SEQ ID NO 1051
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1051
tgcggagaag acccggg                                                  17

<210> SEQ ID NO 1052
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1052
ggaggtctca ggatccc                                                  17

<210> SEQ ID NO 1053
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1053
gcaggctgca ggttccg                                                  17

<210> SEQ ID NO 1054
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1054
gcaggctgca ggttccg                                                  17

<210> SEQ ID NO 1055
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1055
cccactttca aaggggg                                                  17

<210> SEQ ID NO 1056
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1056
cccactttca aaggggg                                                      17

<210> SEQ ID NO 1057
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1057
ccgctggtgc actccgg                                                      17

<210> SEQ ID NO 1058
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1058
cgtctcccat cccgggc                                                      17

<210> SEQ ID NO 1059
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1059
gctgcggccc tccgggg                                                      17

<210> SEQ ID NO 1060
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1060
gctgcggccc tccgggg                                                      17

<210> SEQ ID NO 1061
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1061
ggtctccgaa gcgagcg                                                      17

<210> SEQ ID NO 1062
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1062
gcagccgctt cggcgcc                                                      17

<210> SEQ ID NO 1063
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1063
tccatagatt gacaaag                                                      17

<210> SEQ ID NO 1064
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1064
gcgagggccc aggggtc                                                      17

<210> SEQ ID NO 1065
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1065
gtccccagca cgcggtc                                                      17

<210> SEQ ID NO 1066
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1066
aacttggggc tgaccgg                                                      17

<210> SEQ ID NO 1067
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1067
ggacgcgctg agtggtg                                                      17

<210> SEQ ID NO 1068
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1068
ggacgcgctg agtggtg                                                     17

<210> SEQ ID NO 1069
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1069
taattcgagc actttga                                                     17

<210> SEQ ID NO 1070
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1070
aagaggcaga acgtgcg                                                     17

<210> SEQ ID NO 1071
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1071
agaggagcag gaagcga                                                     17

<210> SEQ ID NO 1072
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1072
taaataggcg agaggag                                                     17

<210> SEQ ID NO 1073
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1073
taaataggcg agaggag                                                     17

<210> SEQ ID NO 1074
<211> LENGTH: 17
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 1074
atcgagtgcg acgcctg                                                  17

<210> SEQ ID NO 1075
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1075
ggcgttaata gagaggc                                                  17

<210> SEQ ID NO 1076
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1076
ctcccagtac aggagcc                                                  17

<210> SEQ ID NO 1077
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1077
gaggacagcc ggctcgt                                                  17

<210> SEQ ID NO 1078
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1078
cctggctaat tttttgt                                                  17

<210> SEQ ID NO 1079
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1079
agccaccgta caaggcc                                                  17

<210> SEQ ID NO 1080
<211> LENGTH: 17
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 1080
tgacggcaaa agccgcc                                                        17

<210> SEQ ID NO 1081
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1081
tgggaaaggt cttgtgg                                                        17

<210> SEQ ID NO 1082
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1082
ccccgtggcg ggagcgg                                                        17

<210> SEQ ID NO 1083
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1083
ccccgtggcg ggagcgg                                                        17

<210> SEQ ID NO 1084
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1084
ttgtgtgtac ataggcc                                                        17

<210> SEQ ID NO 1085
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1085
cggagccgcc ccagggg                                                        17

<210> SEQ ID NO 1086
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1086
tctaggacct ccaggcc                                                17

<210> SEQ ID NO 1087
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1087
tctaggacct ccaggcc                                                17

<210> SEQ ID NO 1088
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1088
gaggcctctg aggagcg                                                17

<210> SEQ ID NO 1089
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1089
gaggcctctg aggagcg                                                17

<210> SEQ ID NO 1090
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1090
cgccccttcc ctgcgcc                                                17

<210> SEQ ID NO 1091
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1091
tcggagtccc cgtctcc                                                17

<210> SEQ ID NO 1092
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1092
gcctggacgg cctcggg                                                          17

<210> SEQ ID NO 1093
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1093
actgtctccg cgaagag                                                          17

<210> SEQ ID NO 1094
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1094
cgaacttccc ggttccg                                                          17

<210> SEQ ID NO 1095
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1095
cagcggccaa agctgcc                                                          17

<210> SEQ ID NO 1096
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1096
cagcggccaa agctgcc                                                          17

<210> SEQ ID NO 1097
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1097
tttgctacgt gtacatc                                                          17

<210> SEQ ID NO 1098
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1098
gcggacgagg ccccgcg                                                17

<210> SEQ ID NO 1099
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1099
cccccaagac acatcaa                                                17

<210> SEQ ID NO 1100
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1100
cccccaagac acatcaa                                                17

<210> SEQ ID NO 1101
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1101
ggccggtgcc gccagtc                                                17

<210> SEQ ID NO 1102
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1102
gaggccagcc tgagggc                                                17

<210> SEQ ID NO 1103
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1103
gaggccagcc tgagggc                                                17

<210> SEQ ID NO 1104
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1104

-continued acacctgtgt cacctgg                                        17

<210> SEQ ID NO 1105
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1105
gctctgcccc cgtggcc                                        17

<210> SEQ ID NO 1106
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1106 cccacccccca cacccccc                                      17

<210> SEQ ID NO 1107
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1107
gcagcccctt ggtggag                                        17

<210> SEQ ID NO 1108
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1108
ccgtgttgtc ctgcccg                                        17

<210> SEQ ID NO 1109
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1109
aaggtgaaga agggcgg                                        17

<210> SEQ ID NO 1110
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1110
gccgcgcaca ggccggt                                                    17

<210> SEQ ID NO 1111
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1111
cctacctatc cctggac                                                    17

<210> SEQ ID NO 1112
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1112
gcctgaccct tttctgc                                                    17

<210> SEQ ID NO 1113
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1113
gtctcgctgg cttcagg                                                    17

<210> SEQ ID NO 1114
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1114
cgctatattg gaccgca                                                    17

<210> SEQ ID NO 1115
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1115
gcccgcgggg ctgtccc                                                    17

<210> SEQ ID NO 1116
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1116
gcccgcgggg ctgtccc                                                    17

<210> SEQ ID NO 1117
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1117
tctcggcgca agcaggc                                                17

<210> SEQ ID NO 1118
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1118
gcgggtcggg ccggggc                                                17

<210> SEQ ID NO 1119
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1119
ctagaagggg tcggga                                                 17

<210> SEQ ID NO 1120
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1120
ctagaagggg tcgggga                                                17

<210> SEQ ID NO 1121
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1121
gcggccgctc ggcagcc                                                17

<210> SEQ ID NO 1122
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1122
gcggccgctc ggcagcc                                                17

<210> SEQ ID NO 1123
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1123
gctgcggccg gccgggg                                                  17

<210> SEQ ID NO 1124
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1124
tcagcccagc ggtatcc                                                  17

<210> SEQ ID NO 1125
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1125
ggggattcta ccctggg                                                  17

<210> SEQ ID NO 1126
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1126
ggggattcta ccctggg                                                  17

<210> SEQ ID NO 1127
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1127
cctgcgccgc cgcccgg                                                  17

<210> SEQ ID NO 1128
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1128
ctggccgccg tgctggc                                                  17

<210> SEQ ID NO 1129
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1129
gcagggaaga gaggagc                                                    17

<210> SEQ ID NO 1130
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1130
ctggacagag ccctcgg                                                    17

<210> SEQ ID NO 1131
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1131
ctgcctgcgg aggcaca                                                    17

<210> SEQ ID NO 1132
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1132
aagagccagg ccacggg                                                    17

<210> SEQ ID NO 1133
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1133
gcggccgagg cgacagc                                                    17

<210> SEQ ID NO 1134
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1134
cggggtgccg agccccg                                                    17

<210> SEQ ID NO 1135

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1135
cggggtgccg agccccg                                                  17

<210> SEQ ID NO 1136
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1136
tgcaagatac gcggggc                                                  17

<210> SEQ ID NO 1137
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1137
attaaccttt gaagccc                                                  17

<210> SEQ ID NO 1138
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1138
gcctctctgc gcctgcc                                                  17

<210> SEQ ID NO 1139
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1139
cgcaaaagcg ggcagcc                                                  17

<210> SEQ ID NO 1140
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1140
cgcaagaggc gcaggca                                                  17

<210> SEQ ID NO 1141
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1141
cgcaagaggc gcaggca                                                  17

<210> SEQ ID NO 1142
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1142
gagcggccgc ccagagc                                                  17

<210> SEQ ID NO 1143
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1143
ccccagctcg gcggcgg                                                  17

<210> SEQ ID NO 1144
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1144
agagtgacgt gctgtgg                                                  17

<210> SEQ ID NO 1145
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1145
aaattccata gacaacc                                                  17

<210> SEQ ID NO 1146
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1146
tgtattgctt cttccct                                                  17

<210> SEQ ID NO 1147
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1147
gggccgagtc cggcagc                                                  17

<210> SEQ ID NO 1148
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1148
ctcggtggcg ggaccgg                                                  17

<210> SEQ ID NO 1149
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1149
gcggcgccct ctgctgg                                                  17

<210> SEQ ID NO 1150
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1150
gcggcgccct ctgctgg                                                  17

<210> SEQ ID NO 1151
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1151
tggcccccgc tgcccgc                                                  17

<210> SEQ ID NO 1152
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1152
tggcccccgc tgcccgc                                                  17

<210> SEQ ID NO 1153
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1153
agccacctgc gcctggc                                                17

<210> SEQ ID NO 1154
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1154
cttagatcta gcgttcc                                                17

<210> SEQ ID NO 1155
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1155
ggaggtctca ggatccc                                                17

<210> SEQ ID NO 1156
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1156
tgacaggcgt gcgagcc                                                17

<210> SEQ ID NO 1157
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1157
tgacaggcgt gcgagcc                                                17

<210> SEQ ID NO 1158
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1158
cctacggcta cggcccc                                                17

<210> SEQ ID NO 1159
<211> LENGTH: 17
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 1159
ccactactta agtttac                                                        17

<210> SEQ ID NO 1160
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1160
ctgggttgcg attagct                                                        17

<210> SEQ ID NO 1161
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1161
gtttcttccc gcccatc                                                        17

<210> SEQ ID NO 1162
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1162
atgcgagggg cgcggta                                                        17

<210> SEQ ID NO 1163
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1163
aacccaggag gcggagc                                                        17

<210> SEQ ID NO 1164
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1164
aaacaggcgt gcgggag                                                        17

<210> SEQ ID NO 1165
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1165
acaaaaatga tcgttct                                                 17

<210> SEQ ID NO 1166
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1166
gtccccagca cgcggtc                                                 17

<210> SEQ ID NO 1167
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1167
cactagacct gcctgag                                                 17

<210> SEQ ID NO 1168
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1168
tctgggggca aatacgt                                                 17

<210> SEQ ID NO 1169
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1169
agtatcaaaa cggcagc                                                 17

<210> SEQ ID NO 1170
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1170
cgaggaagtg accctcg                                                 17

<210> SEQ ID NO 1171
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1171
cggcttccca ggcccac                                                17

<210> SEQ ID NO 1172
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1172
cagcgctacg cgcgggg                                                17

<210> SEQ ID NO 1173
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1173 gtgggggcg acctgtc                                                 17

<210> SEQ ID NO 1174
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1174
tacgcgggtg ggggaga                                                17

<210> SEQ ID NO 1175
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1175 agcccccat tgaaaag                                                 17

<210> SEQ ID NO 1176
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1176
aagagcaaat aagaggc                                                17

<210> SEQ ID NO 1177
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1177
cttttttttt cttttaa                                                  17

<210> SEQ ID NO 1178
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1178
cttttttttt cttttaa                                                  17

<210> SEQ ID NO 1179
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1179
gaagcgctga cgctgtg                                                  17

<210> SEQ ID NO 1180
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1180
gttacgcgcc tgcctcc                                                  17

<210> SEQ ID NO 1181
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1181
ccagcccggg cccgggg                                                  17

<210> SEQ ID NO 1182
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1182
ccagcccggg cccgggg                                                  17

<210> SEQ ID NO 1183
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1183
```
gctcagaggc gctggaa                                                  17

<210> SEQ ID NO 1184
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1184
ccacgtctta gcactct                                                  17

<210> SEQ ID NO 1185
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1185
ccacgtctta gcactct                                                  17

<210> SEQ ID NO 1186
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1186
aaggctggga gttttct                                                  17

<210> SEQ ID NO 1187
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1187
cagcattgtt ttcacca                                                  17

<210> SEQ ID NO 1188
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1188
ggcttcggcc cagggtg                                                  17

<210> SEQ ID NO 1189
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1189

```
ggcttcggcc cagggtg                                                        17
```

<210> SEQ ID NO 1190
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1190

```
cattccttgc gtggctc                                                        17
```

<210> SEQ ID NO 1191
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1191

```
gtgaccccg ccctcc                                                          17
```

<210> SEQ ID NO 1192
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1192

```
tttgctacgt gtacatc                                                        17
```

<210> SEQ ID NO 1193
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1193

```
gccacgagcc ctagcgg                                                        17
```

<210> SEQ ID NO 1194
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1194

```
gccccacgcc ccctggc                                                        17
```

<210> SEQ ID NO 1195
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1195

```
gccccacgcc ccctggc                                                        17
```

<210> SEQ ID NO 1196
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1196
agagctgagt ctcaccc                                                17

<210> SEQ ID NO 1197
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1197
gagctgcctg cttcccc                                                17

<210> SEQ ID NO 1198
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1198
caggacgact caaaggc                                                17

<210> SEQ ID NO 1199
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1199
cgattcgaag ggagggg                                                17

<210> SEQ ID NO 1200
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1200
gtgcagtctc ggcccgg                                                17

<210> SEQ ID NO 1201
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1201
tttgcttaga gcccagc                                                17

<210> SEQ ID NO 1202
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1202
cctacctatc cctggac                                                   17

<210> SEQ ID NO 1203
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1203
ccaacgcctg aagctct                                                   17

<210> SEQ ID NO 1204
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1204
ctgacgggca ccgagcc                                                   17

<210> SEQ ID NO 1205
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1205
gccaccgtcc tgctgtc                                                   17

<210> SEQ ID NO 1206
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1206
gcccaaaagg agaatga                                                   17

<210> SEQ ID NO 1207
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1207
gcccggcggg cctccgg                                                   17

```
<210> SEQ ID NO 1208
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1208
tatcaacttg caaattc                                                   17

<210> SEQ ID NO 1209
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1209
gaaaagttga actcctg                                                   17

<210> SEQ ID NO 1210
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1210
gtggagggga ggtactg                                                   17

<210> SEQ ID NO 1211
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1211
cgtgcgcccg ggctggc                                                   17

<210> SEQ ID NO 1212
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1212
cgtgcgcccg ggctggc                                                   17

<210> SEQ ID NO 1213
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1213
atcgtagctc gctgcag                                                   17

<210> SEQ ID NO 1214
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1214
cacgaagccg ccgggcc                                              17

<210> SEQ ID NO 1215
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1215
gcagcggcgc tccgggc                                              17

<210> SEQ ID NO 1216
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1216
gacagacccg gtccctg                                              17

<210> SEQ ID NO 1217
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1217
tccagaggcc cgagctc                                              17

<210> SEQ ID NO 1218
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1218
cttcgactcc ggaggcc                                              17

<210> SEQ ID NO 1219
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1219
caatcacgaa tttgtta                                              17

<210> SEQ ID NO 1220
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1220
caccgggcgc agtagcg                                                    17

<210> SEQ ID NO 1221
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1221
ggtctcctga ggaccag                                                    17

<210> SEQ ID NO 1222
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1222
ctcgcataaa ggccacc                                                    17

<210> SEQ ID NO 1223
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1223
agcacccgcc tggaacc                                                    17

<210> SEQ ID NO 1224
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1224
tccgaacttc cggaccc                                                    17

<210> SEQ ID NO 1225
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1225
tctggggccg ggtagcc                                                    17

<210> SEQ ID NO 1226
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1226
gcagcggcgc tccgggc                                                17

<210> SEQ ID NO 1227
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1227
ccccggcagg cggcggc                                                17

<210> SEQ ID NO 1228
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1228 acgttttaa ctacaca                                                 17

<210> SEQ ID NO 1229
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1229
gccacccaag cccgtcg                                                17

<210> SEQ ID NO 1230
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1230
gccacccaag cccgtcg                                                17

<210> SEQ ID NO 1231
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1231
gcagcattgc ggctccg                                                17

<210> SEQ ID NO 1232
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1232
cacacaaggc gcccgcg                                                        17

<210> SEQ ID NO 1233
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1233
ctggagctca gcactga                                                        17

<210> SEQ ID NO 1234
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1234
ccccagctcg gcggcgg                                                        17

<210> SEQ ID NO 1235
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1235
cgtggccggt cagtgcc                                                        17

<210> SEQ ID NO 1236
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1236
ggcgccagag gaagatc                                                        17

<210> SEQ ID NO 1237
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1237
cggcggggca gccgacg                                                        17

<210> SEQ ID NO 1238
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1238
cggcgcgtcc ctgccgg                                                       17

<210> SEQ ID NO 1239
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1239 cacacccgc ccccagc                                                        17

<210> SEQ ID NO 1240
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1240
tgcggcgcgg ggcggcc                                                       17

<210> SEQ ID NO 1241
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1241
gtccgtggaa tagaagg                                                       17

<210> SEQ ID NO 1242
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1242
tttcttttat gcagttc                                                       17

<210> SEQ ID NO 1243
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1243
atttagttct tgttttg                                                       17

<210> SEQ ID NO 1244
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1244
tgacaggcgt gcgagcc                                                   17

<210> SEQ ID NO 1245
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1245
tgacaggcgt gcgagcc                                                   17

<210> SEQ ID NO 1246
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1246
acccgggccg cagcggc                                                   17

<210> SEQ ID NO 1247
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1247
cggccgctca gcaactt                                                   17

<210> SEQ ID NO 1248
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1248
acacatttat ttttcag                                                   17

<210> SEQ ID NO 1249
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1249
tctcttgggg agatggg                                                   17

<210> SEQ ID NO 1250
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1250
aatgaacgac cagaccc                                                  17

<210> SEQ ID NO 1251
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1251
tccgacaaga agccgcc                                                  17

<210> SEQ ID NO 1252
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1252
tggtttacct tggcata                                                  17

<210> SEQ ID NO 1253
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1253
aaggagaccg cacaggg                                                  17

<210> SEQ ID NO 1254
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1254
aaggagaccg cacaggg                                                  17

<210> SEQ ID NO 1255
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1255
gggggggaac cggaccg                                                  17

<210> SEQ ID NO 1256
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1256
gtgcggccgc cgcggcc                                                  17

<210> SEQ ID NO 1257
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1257
aacttggggc tgaccgg                                                  17

<210> SEQ ID NO 1258
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1258
ccttgactgc ctccatc                                                  17

<210> SEQ ID NO 1259
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1259
taaaataaac tcaggac                                                  17

<210> SEQ ID NO 1260
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1260
cactagacct gcctgag                                                  17

<210> SEQ ID NO 1261
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1261
agtatcaaaa cggcagc                                                  17

<210> SEQ ID NO 1262
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1262
```

```
ggggcctatt cacagcc                                                17

<210> SEQ ID NO 1263
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1263
ggggcctatt cacagcc                                                17

<210> SEQ ID NO 1264
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1264
cccatccccc acccgga                                                17

<210> SEQ ID NO 1265
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1265
aagttggcca cctcggg                                                17

<210> SEQ ID NO 1266
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1266
tctgtgtgct gtgtgcg                                                17

<210> SEQ ID NO 1267
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1267
atcgagtgcg acgcctg                                                17

<210> SEQ ID NO 1268
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1268
```
ggtggaggca ggcgggg                                                        17

<210> SEQ ID NO 1269
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1269 gtgggggcg acctgtc                                                         17

<210> SEQ ID NO 1270
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1270
gccttcgacc cccaggc                                                        17

<210> SEQ ID NO 1271
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1271
cctttgggtg gagcagt                                                        17

<210> SEQ ID NO 1272
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1272
ggggaagctt cgagcgc                                                        17

<210> SEQ ID NO 1273
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1273
aggcaacagg caggaag                                                        17

<210> SEQ ID NO 1274
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1274
aaaatagagg ttcctcc                                                        17

<210> SEQ ID NO 1275
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1275
aaaatagagg ttcctcc                                                   17

<210> SEQ ID NO 1276
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1276
aatgaacgac cagaccc                                                   17

<210> SEQ ID NO 1277
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1277
caactggccc caactag                                                   17

<210> SEQ ID NO 1278
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1278
agttagttcc caactca                                                   17

<210> SEQ ID NO 1279
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1279
agttagttcc caactca                                                   17

<210> SEQ ID NO 1280
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1280
ccgcgctgag gggggc                                                    17

```
<210> SEQ ID NO 1281
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1281
gggccccgcc cagccag                                                    17

<210> SEQ ID NO 1282
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1282
gggccccgcc cagccag                                                    17

<210> SEQ ID NO 1283
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1283
tctaggacct ccaggcc                                                    17

<210> SEQ ID NO 1284
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1284
tctaggacct ccaggcc                                                    17

<210> SEQ ID NO 1285
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1285
tccagcccac ctgacag                                                    17

<210> SEQ ID NO 1286
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1286
gagcagccag ggccgga                                                    17
```

```
-continued

<210> SEQ ID NO 1287
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1287
agccacgcac ccagact                                                  17

<210> SEQ ID NO 1288
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1288
agggaagcag aaaggcc                                                  17

<210> SEQ ID NO 1289
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1289
gccgccactg cctcagg                                                  17

<210> SEQ ID NO 1290
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1290
gtaggtggcg gcgagcg                                                  17

<210> SEQ ID NO 1291
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1291
gatatcaagg tcgcaga                                                  17

<210> SEQ ID NO 1292
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1292
ggccggtgcc gccagtc                                                  17

<210> SEQ ID NO 1293
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1293
gccccggccg ccgcgcc                                                    17

<210> SEQ ID NO 1294
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1294
gtgcagtctc ggcccgg                                                    17

<210> SEQ ID NO 1295
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1295
gggatcctct tgcaaag                                                    17

<210> SEQ ID NO 1296
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1296
gggatcctct tgcaaag                                                    17

<210> SEQ ID NO 1297
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1297
ccgtgttgtc ctgcccg                                                    17

<210> SEQ ID NO 1298
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1298
ccacacctct ctccagg                                                    17

<210> SEQ ID NO 1299
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1299
ggcaaccact caggacg                                                        17

<210> SEQ ID NO 1300
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1300
tctctgtagc tcacccg                                                        17

<210> SEQ ID NO 1301
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1301
gccgctgcgg ctgcagc                                                        17

<210> SEQ ID NO 1302
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1302
gccgctgcgg ctgcagc                                                        17

<210> SEQ ID NO 1303
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1303
ccccaggccg ggtgtcc                                                        17

<210> SEQ ID NO 1304
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1304
gcgggcgcgg ctctgcg                                                        17

<210> SEQ ID NO 1305
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1305
cgagggatct aggtagc                                                    17

<210> SEQ ID NO 1306
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1306
gtggagggga ggtactg                                                    17

<210> SEQ ID NO 1307
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1307
tgcttttctg ccccact                                                    17

<210> SEQ ID NO 1308
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1308
tgcttttctg ccccact                                                    17

<210> SEQ ID NO 1309
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1309
gatttgttgc agggtct                                                    17

<210> SEQ ID NO 1310
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1310
ggccccgccc acagccc                                                    17

<210> SEQ ID NO 1311
<211> LENGTH: 17
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 1311
taggttctat gctcagt                                                          17

<210> SEQ ID NO 1312
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1312
gtttattcca aacactg                                                          17

<210> SEQ ID NO 1313
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1313
ttcggcccca tccctcg                                                          17

<210> SEQ ID NO 1314
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1314
gctgcggccg gccgggg                                                          17

<210> SEQ ID NO 1315
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1315
cgctcccacg tccggga                                                          17

<210> SEQ ID NO 1316
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1316
ctttcaaact ggacccg                                                          17

<210> SEQ ID NO 1317
<211> LENGTH: 17
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 1317
ttccaaaaag gggcagg                                                    17

<210> SEQ ID NO 1318
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1318
tagtactttc aggtagg                                                    17

<210> SEQ ID NO 1319
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1319
taaggctaga cagaaga                                                    17

<210> SEQ ID NO 1320
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1320
gaaactccac aaaaaga                                                    17

<210> SEQ ID NO 1321
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1321
gcctttcata gagcagg                                                    17

<210> SEQ ID NO 1322
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1322
gggccccgcc cagccag                                                    17

<210> SEQ ID NO 1323
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1323
tttagtgctt ccttcag                                                    17

<210> SEQ ID NO 1324
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1324
accctctcac acgcacc                                                    17

<210> SEQ ID NO 1325
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1325
ttcgggccgg gccggga                                                    17

<210> SEQ ID NO 1326
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1326
agccaccacg cccagcc                                                    17

<210> SEQ ID NO 1327
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1327
tccatagatt gacaaag                                                    17

<210> SEQ ID NO 1328
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1328
aaaaaaaccc gtttcca                                                    17

<210> SEQ ID NO 1329
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1329
cgcgtcacta attagat                17

<210> SEQ ID NO 1330
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1330
ggggcgaaga aagcaga                17

<210> SEQ ID NO 1331
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1331
cagcagcagt ggggctg                17

<210> SEQ ID NO 1332
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1332
gcccgcctga gcaaggg                17

<210> SEQ ID NO 1333
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1333
ttgctcaggc tggtctc                17

<210> SEQ ID NO 1334
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1334
gaaaagttga actcctg                17

<210> SEQ ID NO 1335
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1335
cctgtaatcc cagctac                                                    17

<210> SEQ ID NO 1336
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1336
taatctccct aaatacc                                                    17

<210> SEQ ID NO 1337
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1337
cccaccaggc acgtggc                                                    17

<210> SEQ ID NO 1338
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1338
ttctaaccca atgcaag                                                    17

<210> SEQ ID NO 1339
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1339
gcgtttgggg gtgtcgg                                                    17

<210> SEQ ID NO 1340
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1340
tgaagatata cccgttt                                                    17

<210> SEQ ID NO 1341
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1341
```
gcctggcttc cccccag                                                        17

<210> SEQ ID NO 1342
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1342
gcccgcgggg ctgtccc                                                        17

<210> SEQ ID NO 1343
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1343
tgcaaccacc tgaggtt                                                        17

<210> SEQ ID NO 1344
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1344
agctctgcca gtagttg                                                        17

<210> SEQ ID NO 1345
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1345
aaacgaaagg ttcaagt                                                        17

<210> SEQ ID NO 1346
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1346
aagcagtctt cgagggg                                                        17

<210> SEQ ID NO 1347
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1347
ttctgctaga cagaaga 17

<210> SEQ ID NO 1348
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1348
ggggattcta ccctggg 17

<210> SEQ ID NO 1349
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1349
tcggacgtac atcgtta 17

<210> SEQ ID NO 1350
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1350
gtggctcaca tctgtac 17

<210> SEQ ID NO 1351
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1351
agccactgca cctggcc 17

<210> SEQ ID NO 1352
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1352
gcgctgccct atattgg 17

<210> SEQ ID NO 1353
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1353
tggagatttc aatcgct 17

<210> SEQ ID NO 1354
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1354
aagatcttga gcttggg                                                  17

<210> SEQ ID NO 1355
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1355
cgggccgggt cggcctc                                                  17

<210> SEQ ID NO 1356
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1356
tggcaaaccc attcttg                                                  17

<210> SEQ ID NO 1357
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1357
gtccgtggaa tagaagg                                                  17

<210> SEQ ID NO 1358
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1358
agtatcaaaa cggcagc                                                  17

<210> SEQ ID NO 1359
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1359
ccactgcact ccagcct                                                  17

```
<210> SEQ ID NO 1360
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1360
cctgacagga accaccc                                                      17

<210> SEQ ID NO 1361
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1361
tgggaaggcg tggggtg                                                      17

<210> SEQ ID NO 1362
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1362
ccggacgtac atcgtta                                                      17

<210> SEQ ID NO 1363
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1363
gtgataaagg gaatatc                                                      17

<210> SEQ ID NO 1364
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1364
gccaccgtcc tgctgac                                                      17

<210> SEQ ID NO 1365
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1365
gagatgcgcc tacgccc                                                      17
```

-continued

<210> SEQ ID NO 1366
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1366
gtgactttct tcggggg                                                    17

<210> SEQ ID NO 1367
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1367
cgtgtgagct ctcctgc                                                    17

<210> SEQ ID NO 1368
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1368
aaccccgaaa ctggaag                                                    17

<210> SEQ ID NO 1369
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1369
gcctcagcat cctcctc                                                    17

<210> SEQ ID NO 1370
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1370
accctgaaag tctagcc                                                    17

<210> SEQ ID NO 1371
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1371
tggcctctga cacctgc                                                    17

<210> SEQ ID NO 1372

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1372
tttgcttaga gcccagc                                                    17

<210> SEQ ID NO 1373
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1373
tcttctattg cctgatt                                                    17

<210> SEQ ID NO 1374
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1374
gctcgccgag gaggggc                                                    17

<210> SEQ ID NO 1375
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1375
ttgcccaggc tggtccc                                                    17

<210> SEQ ID NO 1376
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1376
acggccactg aaacgga                                                    17

<210> SEQ ID NO 1377
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1377
cctcagatca ggatggg                                                    17

<210> SEQ ID NO 1378
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1378
cgcgcagctc gctgagg                                                  17

<210> SEQ ID NO 1379
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1379
ggcgttaata gagaggc                                                  17

<210> SEQ ID NO 1380
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1380
ttgcccaggc tggtctc                                                  17

<210> SEQ ID NO 1381
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1381
ttggctaggc tggtctc                                                  17

<210> SEQ ID NO 1382
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1382
ccgctgggag agggttc                                                  17

<210> SEQ ID NO 1383
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1383
ccgcttgccc cgaaacc                                                  17

<210> SEQ ID NO 1384
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1384
ttaagagggc cccgggg                                                    17

<210> SEQ ID NO 1385
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1385
ccctgtccta gtaacgc                                                    17

<210> SEQ ID NO 1386
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1386
tctcttgggg agatggg                                                    17

<210> SEQ ID NO 1387
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1387
accctcgcgt gggcccc                                                    17

<210> SEQ ID NO 1388
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1388
acacctgtgt cacctgg                                                    17

<210> SEQ ID NO 1389
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1389
cacacacaca cccgggc                                                    17

<210> SEQ ID NO 1390
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1390
gaagggaatc acaaaac                                                       17

<210> SEQ ID NO 1391
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1391
tcaagtgtga ggggaag                                                       17

<210> SEQ ID NO 1392
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1392
tgcacgcaca ctcttcc                                                       17

<210> SEQ ID NO 1393
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1393
tcacaaggac agatgcc                                                       17

<210> SEQ ID NO 1394
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1394
tcgaaggcgg ccggagg                                                       17

<210> SEQ ID NO 1395
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1395
aagaaatccc gtttcca                                                       17

<210> SEQ ID NO 1396
<211> LENGTH: 17
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 1396
tcacatttca gtttggg                                                        17

<210> SEQ ID NO 1397
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1397
gggtgcggaa cccggcc                                                        17

<210> SEQ ID NO 1398
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1398
gcagagggcc tgccctt                                                        17

<210> SEQ ID NO 1399
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1399
tgggaaaggt cttgtgg                                                        17

<210> SEQ ID NO 1400
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1400
ggcaggaaga cggtgga                                                        17

<210> SEQ ID NO 1401
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1401
actgtcaagg tttcagg                                                        17

<210> SEQ ID NO 1402
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1402
cagccacacc agttgcc                                                    17

<210> SEQ ID NO 1403
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1403
ggcttcacca ttgactc                                                    17

<210> SEQ ID NO 1404
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1404
aagcagtctc ccagggg                                                    17

<210> SEQ ID NO 1405
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1405
tgggacccca gcacgac                                                    17

<210> SEQ ID NO 1406
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1406
gcccgttctc aatgagc                                                    17

<210> SEQ ID NO 1407
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1407
tataaaatgt gtaaagt                                                    17

<210> SEQ ID NO 1408
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1408
ctactgcact ccagcct                                                      17

<210> SEQ ID NO 1409
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1409 caacccaac cgcgttc                                                       17

<210> SEQ ID NO 1410
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1410
agctcattta cattta                                                       17

<210> SEQ ID NO 1411
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1411
tgtcacagac tcccagc                                                      17

<210> SEQ ID NO 1412
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1412
gaagcttcgc ggttccc                                                      17

<210> SEQ ID NO 1413
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1413
gaccccacaa gggcttg                                                      17

<210> SEQ ID NO 1414
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1414
tgtgtcctcg gcccagc                                                  17

<210> SEQ ID NO 1415
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1415
ttccagtggc aagttga                                                  17

<210> SEQ ID NO 1416
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1416
cccagcagag aagtctg                                                  17

<210> SEQ ID NO 1417
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1417
tatgtcagtg tctggga                                                  17

<210> SEQ ID NO 1418
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1418
gccttcgacc cccaggc                                                  17

<210> SEQ ID NO 1419
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1419
cccgcgctca ctgccaa                                                  17

<210> SEQ ID NO 1420
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1420
```

-continued ccaggcaggg gtggggg                                                  17

<210> SEQ ID NO 1421
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1421
atgagtccat ttcctcg                                                  17

<210> SEQ ID NO 1422
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1422
ggggtaactc ttgagtc                                                  17

<210> SEQ ID NO 1423
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1423
agtgagccac cacaccc                                                  17

<210> SEQ ID NO 1424
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1424
gccaagccaa atgaagg                                                  17

<210> SEQ ID NO 1425
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1425
gattatgaaa gcccatc                                                  17

<210> SEQ ID NO 1426
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1426
atgattcctt gcgattc                                              17

<210> SEQ ID NO 1427
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1427 gtagggtaa aaggagg                                               17

<210> SEQ ID NO 1428
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1428
ttgcccaggc tggtctt                                              17

<210> SEQ ID NO 1429
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1429
ttggccagac tggtctg                                              17

<210> SEQ ID NO 1430
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1430
cctaacaaga ttgcata                                              17

<210> SEQ ID NO 1431
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1431
tctgagggtc gaccagc                                              17

<210> SEQ ID NO 1432
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1432
tcttcatccc caagcgg                                              17

<210> SEQ ID NO 1433
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1433
gacgacagcg ccgccgc                                                 17

<210> SEQ ID NO 1434
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1434
gtgccgccgc gggcgcc                                                 17

<210> SEQ ID NO 1435
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1435
gtggataagt tttttga                                                 17

<210> SEQ ID NO 1436
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1436
agccacctgc gcctggc                                                 17

<210> SEQ ID NO 1437
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1437
cccccaagac acatcaa                                                 17

<210> SEQ ID NO 1438
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1438
acaaaaatga tcgttct                                                 17

<210> SEQ ID NO 1439
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1439
agaacgggaa ccgtcca                                                    17

<210> SEQ ID NO 1440
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1440
accatagcaa ccctgcc                                                    17

<210> SEQ ID NO 1441
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1441
tgccctgggc tgcccgc                                                    17

<210> SEQ ID NO 1442
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1442
atggccaggc tggtttc                                                    17

<210> SEQ ID NO 1443
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1443
cgccagcgcc cgcgacc                                                    17

<210> SEQ ID NO 1444
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1444
ggtttgctga agtgggg                                                    17

```
<210> SEQ ID NO 1445
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1445
agccgcgggc agccgcc                                                  17

<210> SEQ ID NO 1446
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1446
gcgggcgcgg ctctgcg                                                  17

<210> SEQ ID NO 1447
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1447
tggagctggt cggggag                                                  17

<210> SEQ ID NO 1448
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1448
gcgccaaccc gggctgc                                                  17

<210> SEQ ID NO 1449
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1449
gcccctgggg cttaacc                                                  17

<210> SEQ ID NO 1450
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1450 gttttgpggg aatggca                                                  17

<210> SEQ ID NO 1451
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1451
ggccggtgcc gccagtc                                                  17

<210> SEQ ID NO 1452
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1452 gcggggcag cagacgc                                                   17

<210> SEQ ID NO 1453
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1453
aggcaggaga tggtctg                                                  17

<210> SEQ ID NO 1454
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1454
agagagaagt ttctgag                                                  17

<210> SEQ ID NO 1455
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1455
taaaaactag acagaag                                                  17

<210> SEQ ID NO 1456
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1456
aacttggggc tgaccgg                                                  17

<210> SEQ ID NO 1457
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1457
ccactgcact ccagtct                                                  17

<210> SEQ ID NO 1458
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1458
gacagacccg gtccctg                                                  17

<210> SEQ ID NO 1459
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1459
aaaagatgtg gtttggc                                                  17

<210> SEQ ID NO 1460
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1460
tgttgagaat ggggtag                                                  17

<210> SEQ ID NO 1461
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1461
aagcggggag gctgagg                                                  17

<210> SEQ ID NO 1462
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1462
gaaactgaac aacctgc                                                  17

<210> SEQ ID NO 1463
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1463
tcagcccagc ggtatcc                                                        17

<210> SEQ ID NO 1464
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1464
gccctgtgtg tcagcct                                                        17

<210> SEQ ID NO 1465
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1465
ggaacgcccc accccga                                                        17

<210> SEQ ID NO 1466
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1466
aactggcaga gcagcag                                                        17

<210> SEQ ID NO 1467
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1467
gtttattcca aacactg                                                        17

<210> SEQ ID NO 1468
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1468
cagccgaagt ggcgctc                                                        17

<210> SEQ ID NO 1469
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1469
gggtaggcac agccgtc                                                        17

<210> SEQ ID NO 1470
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1470
cctgtaatcc cagctgc                                                        17

<210> SEQ ID NO 1471
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1471
cgtagggccg ttcaccc                                                        17

<210> SEQ ID NO 1472
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1472
cctgcgccgc cgcccgg                                                        17

<210> SEQ ID NO 1473
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1473
cctgcgccgg gggaggc                                                        17

<210> SEQ ID NO 1474
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1474
tacgcgggtg ggggaag                                                        17

<210> SEQ ID NO 1475
<211> LENGTH: 17
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 1475
gccacgaaga accggct                                                   17

<210> SEQ ID NO 1476
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1476
tgaggtgtca gtctgcc                                                   17

<210> SEQ ID NO 1477
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1477
tccccatcgg tggaccc                                                   17

<210> SEQ ID NO 1478
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1478
ctgcccgcct gctttcc                                                   17

<210> SEQ ID NO 1479
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1479
tgaaacgctg aagggag                                                   17

<210> SEQ ID NO 1480
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1480
cgattccatt agatgat                                                   17

<210> SEQ ID NO 1481
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1481
ctgggttgcg attagct                                                        17

<210> SEQ ID NO 1482
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1482
aggttgttgt tcttgcc                                                        17

<210> SEQ ID NO 1483
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1483
cagctgcctg ggggagg                                                        17

<210> SEQ ID NO 1484
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1484
ggaattatct cttcctt                                                        17

<210> SEQ ID NO 1485
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1485
ctatactggc tcgtcct                                                        17

<210> SEQ ID NO 1486
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1486
taactgtcct ttccgta                                                        17

<210> SEQ ID NO 1487
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1487
gtccgcacta cgaatct                                                  17

<210> SEQ ID NO 1488
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1488
atctgcccgc ctcagcc                                                  17

<210> SEQ ID NO 1489
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1489
aatttgttgc agggtct                                                  17

<210> SEQ ID NO 1490
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1490
taccctaaaa cttaaag                                                  17

<210> SEQ ID NO 1491
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1491
aaacgaatta cacggtg                                                  17

<210> SEQ ID NO 1492
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1492 gcagccccttt ggtggag                                                 17

<210> SEQ ID NO 1493
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1493
cacagcagcc cgtcagg                                                    17

<210> SEQ ID NO 1494
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1494
ccagtgcact ccagcct                                                    17

<210> SEQ ID NO 1495
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1495
tgaggtgtca gtgtgcc                                                    17

<210> SEQ ID NO 1496
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1496
acgccggcgc cgctcgc                                                    17

<210> SEQ ID NO 1497
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1497
agccaccccg cctggcc                                                    17

<210> SEQ ID NO 1498
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1498
agccctgggg aaagggg                                                    17

<210> SEQ ID NO 1499
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1499
```
agtcctgcac agaaact					17

<210> SEQ ID NO 1500
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1500
atgctcctaa gccaaaa					17

<210> SEQ ID NO 1501
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1501
atttgagggt ttgggac					17

<210> SEQ ID NO 1502
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1502
cataacctaa ggtgaag					17

<210> SEQ ID NO 1503
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1503
ccctatgcct acccaag					17

<210> SEQ ID NO 1504
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1504
ctcggaagga agcacca					17

<210> SEQ ID NO 1505
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1505
ctggacagaa gggactg                                          17

<210> SEQ ID NO 1506
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1506
gcctttcata gagcagc                                          17

<210> SEQ ID NO 1507
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1507
gcgaaacccc tcccccc                                          17

<210> SEQ ID NO 1508
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1508
gctaaaccct caacaag                                          17

<210> SEQ ID NO 1509
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1509
ggaaactgag gcagaag                                          17

<210> SEQ ID NO 1510
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1510
ggagctggca gcagagg                                          17

<210> SEQ ID NO 1511
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1511
gtggcttgcg cctgtac                                          17

<210> SEQ ID NO 1512
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1512
gtggtaccac agatggg                                                    17

<210> SEQ ID NO 1513
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1513
gtggtgtgag cctgtaa                                                    17

<210> SEQ ID NO 1514
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1514
taaggctaga caggaga                                                    17

<210> SEQ ID NO 1515
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1515
tatctgtaac ttactaa                                                    17

<210> SEQ ID NO 1516
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1516
tgaagatata cccgttc                                                    17

<210> SEQ ID NO 1517
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1517
gccagggccc agggtc                                                     17

<210> SEQ ID NO 1518
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1518
cgaacttccc ggttccg                                                     17

<210> SEQ ID NO 1519
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1519
gtggcttgcg cctgtag                                                     17

<210> SEQ ID NO 1520
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1520
cactccacgt ttataga                                                     17

<210> SEQ ID NO 1521
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1521
agcagtggaa gcttgag                                                     17

<210> SEQ ID NO 1522
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1522
gcctgaccct tttctgc                                                     17

<210> SEQ ID NO 1523
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1523
gccggggcgg gctcctc                                                     17

```
<210> SEQ ID NO 1524
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1524
cagagggaat aaccagt                                                      17

<210> SEQ ID NO 1525
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1525
agccactgtg cccagcc                                                      17

<210> SEQ ID NO 1526
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1526
agccaccaca cctggct                                                      17

<210> SEQ ID NO 1527
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1527
attataagtt tcctgag                                                      17

<210> SEQ ID NO 1528
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1528
ggctacagag tgagagc                                                      17

<210> SEQ ID NO 1529
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1529
agccatcacg cccggcc                                                      17

<210> SEQ ID NO 1530
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1530
cagcagtttc tgagaat                                                    17

<210> SEQ ID NO 1531
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1531
tacatttcta tttgtgg                                                    17

<210> SEQ ID NO 1532
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1532
cagaatcttc aaaaaga                                                    17

<210> SEQ ID NO 1533
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1533
tacaccagcg tggaggg                                                    17

<210> SEQ ID NO 1534
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1534
cggagccgcc ccagggg                                                    17

<210> SEQ ID NO 1535
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1535
tatcccagaa cttaaag                                                    17

<210> SEQ ID NO 1536
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1536
tgcaaattgt gggggtg                                                   17

<210> SEQ ID NO 1537
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1537
cagccgactc tctggct                                                   17

<210> SEQ ID NO 1538
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1538
ggcaccgtcc tgctgtc                                                   17

<210> SEQ ID NO 1539
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1539
tgcaagtgga catttgg                                                   17

<210> SEQ ID NO 1540
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1540
acaaagtacc gtggttc                                                   17

<210> SEQ ID NO 1541
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1541
ccaaatccta cccagcc                                                   17

<210> SEQ ID NO 1542
<211> LENGTH: 17
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 1542
atggtgtcgc tggacag                                                17

<210> SEQ ID NO 1543
<211> LENGTH: 266
<212> TYPE: DNA
<213> ORGANISM: Homo sapiens

<400> SEQUENCE: 1543
tcacgttttt accactcact taaccgtctt tgttgttggg gtgaggggtc ctcgagcctg    60
gatttgggta tgaaaaccca ggcaagaaag acctgcccaa gcctttaaag gaatgcaaag   120
tcatcctcta gccacccca gagatcgaaa ggctggggat tgagtctcct gcagatggtg    180
gcggcctcct ggggctggca agttgggaca gaggcccata agccctcctg ggcgcgcctt   240
cccacccctc tcggccctct ccactc                                        266

<210> SEQ ID NO 1544
<211> LENGTH: 203
<212> TYPE: DNA
<213> ORGANISM: Homo sapiens

<400> SEQUENCE: 1544
cgtttatgta tacagaagtg gggtgccggg cgggaagggc gcggggaatg agggaaccta    60
gaggccgatg acgtcgttca gctcgaggtc cgcgttgggg cggcagcggg cctgggggg    120 ctgcgtcccg gggcgggtt ccgcgtcggg cttgcggca ccgcctccg ggcgcgccgc      180 gtccatgacg cccagcaccg cgt                                           203

<210> SEQ ID NO 1545
<211> LENGTH: 369
<212> TYPE: DNA
<213> ORGANISM: Homo sapiens

<400> SEQUENCE: 1545
cgagtcccgc caaggtgca gacggcggcg gccccgggcc tcgctcggtc gcgctcgagc     60 cccgttttcca gcagcatcgc ggccaccagg ccgagtggcg cgagacgcgc tcctcctagg   120
tcagcgtccc ctggagggtt cggggctccc aagtcccgcc gcgtcgtgcg gggcagggag   180
cccgggagcc actgggcctg gcgctgtccg cggtgctgaa ggaggcgccc gctgcccgcc   240
ccgcccgcgc gcccgcccac ctcccggggc ccctctcgtc gccccggtcc ccaccccgc    300 ctctgccccg tgtcgggcgc gcctccctcc ctggctgggt tgggccgcac tcaaggcagc   360
ccccgccct                                                          369

<210> SEQ ID NO 1546
<211> LENGTH: 234
<212> TYPE: DNA
<213> ORGANISM: Homo sapiens

<400> SEQUENCE: 1546
agagagaagt tgcggagcgc tgctggaagc ttctgcccgg gaaggcgtcg cccccgagac    60
tgcagccgga ggagccgccc tcggcttcgg agcgccgggg agggagccgg agcgaacgcc   120
ggccgctggc tctgctcctc ggcgcgccca ggctgggccg gacgtggtc gcgagctgcc   180

| | |
|---|---|
| ggccttcccg ggacgtccta ccagcccgcg tcgctcctca gcgggaggag aggg | 234 |

<210> SEQ ID NO 1547
<211> LENGTH: 222
<212> TYPE: DNA
<213> ORGANISM: Homo sapiens

<400> SEQUENCE: 1547

| | |
|---|---|
| cggacctgag cagcccgtac ctctccaacg gacccctgtc tcccggagga gcgcgcaccg | 60 |
| tgagtgcccg tcgggcgcgc cggggagggt gggaggccgc ggcccgcagg atgcgccccc | 120 |
| gggcttggcc atggagtggg ggatggggcc ttctgcgccg atcccaagca gaacttgttt | 180 |
| gcggagttga actactctct ggcggccgag cgcgaggctg cg | 222 |

<210> SEQ ID NO 1548
<211> LENGTH: 174
<212> TYPE: DNA
<213> ORGANISM: Homo sapiens

<400> SEQUENCE: 1548

| | |
|---|---|
| cgcgacctgc tctggcccag cggtgtgacc ccgcgggtcc tggcggtcct gactgcccgc | 60 |
| aggggagggg cgcgccactt ttggctgccc taggatgcgc cgcctgaacc tcttttccct | 120 |
| cgcgggcagc gtccgccaca ttccccgggt tcctcggaaa ctccaatcat tcta | 174 |

<210> SEQ ID NO 1549
<211> LENGTH: 214
<212> TYPE: DNA
<213> ORGANISM: Homo sapiens

<400> SEQUENCE: 1549

| | |
|---|---|
| tggaggcgtg ggtcggggggg tcgcggtgca ggctggaggc ttggagtgca gagttgggga | 60 |
| tgcagacttg gggtacaggg cagagctcgg ggcgggcacg caccttgtgg caggctgggc | 120 |
| aagtgggcag cgcgccgccc ggcccggggcg cgcccttgcc gccgtggccc ccgccgccgt | 180 |
| tcaggctgct ctggatctgc gtgagctcct ggcg | 214 |

<210> SEQ ID NO 1550
<211> LENGTH: 204
<212> TYPE: DNA
<213> ORGANISM: Homo sapiens

<400> SEQUENCE: 1550

| | |
|---|---|
| agaagaagga gcacatttgg ggatcccgca agcctggggt atgtgggtgt gtttgaggag | 60 |
| gtgggtggga gtgagcgtgt gcgccgggga gagggcggga gggaggaagc aagcgagctt | 120 |
| gggagcgcgc ggggaggggcc gcgggcctcg gggcgcgcca ggaagtgagc ggcggaggcg | 180 |
| aggggcctaa ctagtggccg ggcg | 204 |

<210> SEQ ID NO 1551
<211> LENGTH: 266
<212> TYPE: DNA
<213> ORGANISM: Homo sapiens

<400> SEQUENCE: 1551

| | |
|---|---|
| tcacgttttt accactcact taaccgtctt tgttgttggg gtgagggggtc ctcgagcctg | 60 |
| gatttgggta tgaaaaccca ggcaagaaag acctgcccaa gccttttaaag gaatgcaaag | 120 |
| tcatcctcta gccaccccca gagatcgaaa ggctggggat tgagtctcct gcagatggtg | 180 |
| gcggcctcct ggggctggca agttgggaca gaggcccata agccctcctg ggcgcgcctt | 240 | cccacccctc tcggccctct ccactc 266

<210> SEQ ID NO 1552
<211> LENGTH: 245
<212> TYPE: DNA
<213> ORGANISM: Homo sapiens

<400> SEQUENCE: 1552
aacgccgtct gcacgaagcc cgcggcggcc tgcaggggc ccagcgactc gtccagggaa    60
ccggtgcgca ggagcagccg ggggcgcggc gcgccggccg cccttggggg actctggggc   120 cggggcgca gctcgatctg acgcttgggc actgtccggg gcctggcggg cgcggcgccc   180
tcctccagag ccacctccac acactcgaac tgcgctgggg cggcaggact tggcccacgg   240
ggccg                                                              245

<210> SEQ ID NO 1553
<211> LENGTH: 203
<212> TYPE: DNA
<213> ORGANISM: Homo sapiens

<400> SEQUENCE: 1553
cgtttatgta tacagaagtg gggtgccggg cgggaagggc gcggggaatg agggaaccta    60
gaggccgatg acgtcgttca gctcgaggtc cgcgttgggg cggcagcggg cctggggggg   120
ctgcgtcccg gggcggggtt ccgcgtcggg cttggcggca ccgcctccg ggcgcgccgc    180 gtccatgacg cccagcaccg cgt                                          203

<210> SEQ ID NO 1554
<211> LENGTH: 200
<212> TYPE: DNA
<213> ORGANISM: Homo sapiens

<400> SEQUENCE: 1554
ccctgcgctg cctcgcggcg ggggtggggg tcggcgctgc cgcgcgctgg gctaaagctc    60
gagtcgcgct cagatcaggt gcaggcgcag gcgcgccccg ccccacggcc ccccaccgg   120 gcgagcctcc acgcctccgc cctgggagcc gccatcttgc cacttcccct cgcccggccg   180
tccgcgggcg tcaatagcga                                              200

<210> SEQ ID NO 1555
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1555
tttgcagagg ttcgtaatcg agttgggtgg                                    30

<210> SEQ ID NO 1556
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1556
cgcgccaccc aactcgatta cgaacctctg c                                  31

```
<210> SEQ ID NO 1557
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1557

Asp Glu Ala Asp
1

<210> SEQ ID NO 1558
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1558

Lys Asp Glu Leu
1

<210> SEQ ID NO 1559
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1559

Asp Glu Ala His
1
```

UNITED STATES PATENT AND TRADEMARK OFFICE
CERTIFICATE OF CORRECTION

| | |
|---|---|
| PATENT NO. | : 9,556,430 B2 |
| APPLICATION NO. | : 11/915645 |
| DATED | : January 31, 2017 |
| INVENTOR(S) | : Kornelia Polyak et al. |

Page 1 of 1

It is certified that error appears in the above-identified patent and that said Letters Patent is hereby corrected as shown below:

In the Specification

In Column 1, delete Lines 17-21, and insert the following new paragraph:
-- This invention was made with government support under grant numbers P50 CA089393 and CA094074 awarded by the National Institutes of Health and DAMD17-02-1-0692 and W81XWH-04-1-0452 awarded by The Department of The Army. The government has certain rights in the invention. --

Signed and Sealed this
Third Day of October, 2017

Joseph Matal
*Performing the Functions and Duties of the*
*Under Secretary of Commerce for Intellectual Property and*
*Director of the United States Patent and Trademark Office*